United States Patent
Birkett et al.

(10) Patent No.: US 11,787,906 B2
(45) Date of Patent: Oct. 17, 2023

(54) BIODEGRADABLE DRUG-POLYMER CONJUGATE

(71) Applicant: POLYACTIVA PTY LTD, Melbourne (AU)

(72) Inventors: Stephen Lonsdale Birkett, Langwarrin (AU); Andrew Craig Donohue, Bentleigh East (AU); Asha Marina D'Souza, Carnegie (AU); Sarah Man Yee Ng, Berwick (AU); Adrian Sulistio, Glen Iris (AU); Russell John Tait, Balwyn (AU); David Valade, Glenroy (AU); Alan Naylor, Harston (GB); Jason Watling, Cheltenham (AU); Carmen Vittoria Scullino, Moonee Ponds (AU)

(73) Assignee: POLYACTIVA PTY LTD, Melbourne (AU)

( * ) Notice: Subject to any disclaimer, the term of this patent is extended or adjusted under 35 U.S.C. 154(b) by 702 days.

(21) Appl. No.: 16/493,252

(22) PCT Filed: Mar. 14, 2018

(86) PCT No.: PCT/AU2018/050234
§ 371 (c)(1),
(2) Date: Sep. 11, 2019

(87) PCT Pub. No.: WO2018/165711
PCT Pub. Date: Sep. 20, 2018

(65) Prior Publication Data
US 2020/0123322 A1 Apr. 23, 2020

Related U.S. Application Data

(63) Continuation-in-part of application No. 15/458,546, filed on Mar. 14, 2017, now Pat. No. 10,113,033.

(30) Foreign Application Priority Data

Mar. 14, 2017 (AU) ................................. 2017900888

(51) Int. Cl.
*C08G 73/08* (2006.01)
*A61K 47/59* (2017.01)
(Continued)

(52) U.S. Cl.
CPC .......... *C08G 73/08* (2013.01); *A61K 31/5377* (2013.01); *A61K 31/5575* (2013.01); *A61K 47/59* (2017.08)

(58) Field of Classification Search
None
See application file for complete search history.

(56) References Cited

U.S. PATENT DOCUMENTS

| 4,228,152 A | 10/1980 | Ferruti et al. |
| 5,120,719 A | 6/1992 | Iwamoto et al. |

(Continued)

FOREIGN PATENT DOCUMENTS

| EP | 0 369 463 A2 | 5/1990 |
| JP | 2004-059439 A | 2/2004 |

(Continued)

OTHER PUBLICATIONS

Office Action dated Jan. 8, 2021, in U.S. Appl. No. 16/493,258 (US 2020-0121798).

(Continued)

*Primary Examiner* — Samantha L Shterengarts
(74) *Attorney, Agent, or Firm* — Foley & Lardner LLP

(57) ABSTRACT

A drug-polymer conjugate, which is a copolymer of at least one monomer of formula (I): (I) where: X may be the same or different at each occurrence and represents a terminal functional group comprising an alkyne or an azide; Q is independently selected at each occurrence and may be present or absent and when present, represents a linking group; R is selected from the group consisting of linear or branched hydrocarbon, optionally substituted aryl and optionally substituted heteroaryl; D is a releasable drug selected from prostaglandins, β-blockers and mixtures thereof; L is a linker group group; and at least one co-monomer of Formula III III J represents a linking functional group, n is 2 to 8, preferably 3 to 8; Y comprises a polyether of formula (ORa)m wherein Ra is independently ethylene, propylene and butylene and m is from 1 to 300 (preferably 2 to 300) and the polyether is in chain with one or more groups which are preferably selected from one or more of optionally substituted straight or branched C1 to do alkylene, amino, ether, ester, amide, carbonate and carbamate; A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

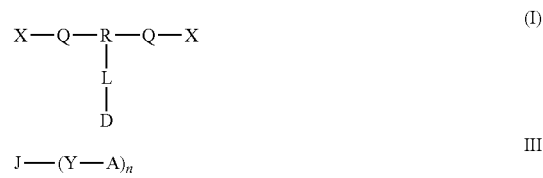

20 Claims, 11 Drawing Sheets

(51) Int. Cl.
*A61K 31/5377* (2006.01)
*A61K 31/5575* (2006.01)

(56) References Cited

U.S. PATENT DOCUMENTS

| 9,572,892 | B2 | 2/2017 | Ng et al. |
| 10,111,886 | B2 | 10/2018 | Ng et al. |
| 10,113,033 | B2 | 10/2018 | Ng et al. |
| 2010/0104654 | A1 | 4/2010 | Robinson et al. |
| 2011/0319487 | A1 | 12/2011 | Mercier |
| 2014/0120058 | A1 | 5/2014 | O'Shea et al. |
| 2016/0000929 | A1 | 1/2016 | Ng et al. |
| 2020/0121798 | A1 | 4/2020 | Birkett et al. |

FOREIGN PATENT DOCUMENTS

| JP | 2013-035802 A | 2/2013 |
| WO | WO-2007/018431 A2 | 2/2007 |
| WO | WO-2010/040187 A1 | 4/2010 |
| WO | WO 2010/040188 A1 | 4/2010 |
| WO | WO 2010/141507 A1 | 12/2010 |
| WO | WO 2012/075117 A2 | 6/2012 |
| WO | WO-2012/139164 A1 | 10/2012 |
| WO | WO-2014/134689 A1 | 9/2014 |

OTHER PUBLICATIONS

IUPAC: "Prostaglandins: Gold Book" In "IUPAC Compendium of Chemical Technology", Research Triangle Park, NC, XP055733523, ISBN:978-0-9678550-9-7 p. 1, (Jun. 2009) DOI:1351/goldbook.P04891.
U.S. Appl. No. 16/493,258, filed Sep. 11, 2019, Birkett et al.
Gao et al., "Linear Cationic Click Polymer for Gene Delivery: Synthesis, Biocompatibility, and In Vitro Transfection," Biomacromolecules, vol. 11, No. 11, pp. 3102-3111, Nov. 2010.
Meudtner et al., "Responsive Backbones Based on Alternating Triazole-Pyridine/Benzene Copolymers: From Helically Folding Polymers to Metallosupramolecularly Crosslinked Gels," Macromolecular Rapid Communications, vol. 29, No. 4, pp. 347-351, Feb. 2008.
Efthymiou et al., "Efficient synthesis and cell-based silencing activity of siRNAs that contain triazole backbone linkages," Bioorganic & Medicinal Chemistry Letters, vol. 22, No. 4, pp. 1722-1726, Feb. 2012.
Supplementary European Search Report dated Oct. 20, 2016 in application No. EP 14 76 0322.
International Search Report dated May 26, 2014 in application No. PCT/AU2014/000231.
Gao et al., "Linear Cationic Click Polymers/DNA Nanoparticles: In Vitro Structure—Activity Relationship and In Vivo Evaluation for Gene Delivery," Bioconjugate Chemistry, vol. 22, pp. 1153-1161, May 2011.
International Search Report dated May 17, 2012 in application No. PCT/AU2012/00376.
Miller et al., "Feasibility of Using a 1-4, 7, 8 Bone Targeted, Macromolecular Delivery System Couples with Prostaglandin E1 to Promote Bone Formation in Aged, Estrogen-Deficient Rats," Pharmaceutical Research, vol. 25, No. 12, pp. 2889-2895, (Aug. 2008).
Pan et al., "Proceeding published 2009 by the American Chemical Society: Bone Targeting HPMA Copolymer—Prostaglandin Conjugates", Polymer Preprints, vol. 50, No. 1, pp. 294-295 (Jan. 2009).
Pan et al., "Release of Progstaglandin E 1 from N-(2-Hydroxypropyl)methacrulamide Copolymer Conjugates by Bone Cells," Macromolecular Bioscience, vol. 8, No. 7, pp. 559-605 (Jul. 2008).
Pan et al., "Water-soluble HPMA copolymer-prostaglandin E1 conjugates containing a cathepsin K sensitive spacer," Journal of Drug Targeting, vol. 14, No. 6, pp. 425-435, (Jan. 2006).
Pan et al., "Stability in Plasmas of Various Species of HPMA Copolymer-PGE$_1$ Conjugates," Pharmaceutical Research, vol. 24, No. 12, pp. 2270-2280, (Dec. 2007).
Supplementary European Search Report issued in application No. EP 12 77 0802 dated Sep. 4, 2014.
International Search Report dated May 9, 2018 in application No. PCT/AU2018/050234.
International Search Report dated Apr. 24, 2018 in application No. PCT/AU2018/050233.

BIODEGRADABLE DRUG-POLYMER CONJUGATE

CROSS-REFERENCE TO RELATED APPLICATIONS

The present application is the U.S. National Stage of International Application No. PCT/AU2018/050234, filed Mar. 14, 2018, which claims priority to Australian Patent Application No. 2017900888, filed Mar. 14, 2017, and U.S. application Ser. No. 15/458,546, filed Mar. 14, 2017.

FIELD

The invention relates to a drug-polymer conjugate, to a drug-monomer conjugate for use in preparation thereof and to an implant containing the drug-polymer conjugate.

BACKGROUND

Polymer-drug conjugates containing a drug covalently bound to a polymer are of interest for the targeted and controlled delivery of therapeutic agents. In the treatment of many different conditions, the site-specific delivery of a drug directly to or near a desired site of action in the body of a subject can be highly desirable to improve the efficacy and/or safety of the drug. Certain sites in a subject may require sophisticated delivery vehicles to overcome barriers for effective drug delivery. For example, the eye has a limited volume for administration and requires a pharmaceutical product with a high drug loading to ensure that adequate doses of drug can be delivered while keeping product volume to a minimum. Despite the limited volume it is desirable to be able to deliver drug to the site continuously and in a controlled manner over an extended period of time. Administration to the target site generally involves injection of the product. Consequently it is both an advantage and desirable for the product to biodegrade and disappear at the target site after treatment is provided, obviating the need for removal at the end of therapy. Such removal typically requires surgical intervention.

β-blockers are antagonists of β-adrenoreceptor sites and are used to treat or manage a range of conditions, including cardiac arrhythmias, hypertension, hypotension and glaucoma. Elevated intraocular pressure (ocular hypertension) is a risk factor for glaucoma. β-blockers can reduce intraocular pressure and exert an ocular hypotensive effect by reducing the production of aqueous humour in the eye.

ProstaglandinProstaglandins are molecules designed to bind to a prostaglandin receptor and are used to treat gastro-intestinal acid related disorders such as duodenal and gastric ulcers, as abortifacients or uterotonics to induce labour or prevent past partum haemorrhage, and to treat ocular hypertension. ProstaglandinProstaglandins exert an ocular hypotensive effect by increasing uveoscleral outflow of aqueous humour.

ProstaglandinProstaglandins and β-blockers used in the treatment of glaucoma are presently formulated as eye drops, which if administered conscientiously to the affected eye will lower intraocular pressure. This in turn can slow the progression of glaucoma. The prostaglandinprostaglandins and β-blockers are administered as eye drops, either alone (i.e. as a single agent) or in combination. It is postulated that combining prostaglandins with β-blockers that exert their effect through a different mechanism, may provide an additive effect in reducing intraocular pressure. For example, some pharmaceutical preparations used in the treatment of glaucoma, such as Xalacom™ eye drops marketed by Pfizer and Ganfort™ eye drops marketed by Allergan, contain a prostaglandin in combination with a β-blocker.

Unfortunately, as glaucoma is an asymptomatic disease many patients do not use their drops conscientiously, compromising therapy. A recent study by Friedman et al. (Friedman et al. *IOVS* 2007:48, 5052-5057) showed that adherence to glaucoma treatment options is poor with only 59% of patients in possession of an ocular hypotensive agent at 12 months, and only 10% of patients used such medication continuously. Patient compliance in glaucoma therapy is therefore an issue.

Unfortunately, as ocular surgery is more prevalent in the elderly many patients do not have the drop competence to administer their drops effectively, compromising therapy. A recent study by An et al showed that drop competence in the elderly is poor with only 7.4% of patients capable of administering their drops effectively following cataract surgery (An J A, Kasner O, Samek D A, Levesque V. *Evaluation of eye drop administration by inexperienced patient after cataract surgery*. J Cataract Refract Surg. 2014; 40:1857-1861). Drop competence in post-surgical drop therapy is therefore an issue.

Drug delivery systems have been developed to aid in the administration and/or sustained delivery of agents (such as drugs) to a desired site of action. One mode of delivering a drug to a subject involves the use of a polymer in association with the drug so that it can be delivered to and/or retained at a specific location.

One form of a polymer/drug delivery system utilises an admixture of a polymer with a drug, where the drug is blended with the polymer matrix. However, such admixtures generally result in poor control over the release of the drug, with a "burst effect" often occurring immediately after administration and significant changes in the physical properties of the admixture occurring as the drug is released (Sjoquist, B.; Basu, S.; Byding, P.; Bergh, K.; Stjernschantz, J. *Drug Metab. Dispos.* 1998, 26, 745). In addition, such admixtures have limited dose loading capacity, resulting in a prohibitively large device for convenient administration to some sites in a subject.

Another form of a polymer/drug delivery system is based on the polymerisation of a drug so as to incorporate the drug molecule as part of the backbone of a polymer chain. Such a system is described in U.S. Pat. No. 6,613,807, WO2008/128193, WO94/04593 and U.S. Pat. No. 7,122,615. However, such polymer systems generally provide inefficient delivery of the drug, as release of the drug relies on breakdown of the polymer backbone. Furthermore, breakdown of the polymer backbone produces inactive intermediates. Such intermediates can complicate regulatory approval, which may require the safety of the intermediates to be demonstrated.

Another approach for preparing polymer-drug conjugates involves the covalent attachment of drug molecules to a pre-formed polymer backbone. Examples of such polymer conjugates have been reviewed in *Nature Reviews: Drug Discovery* 2003:2, 347-360. However, this approach can also be problematic. In particular, steric and thermodynamic constraints can affect the amount of drug that can be covalently attached, and also impact on the distribution of the drug along the polymer backbone. These factors can, in turn, reduce control over the release of the drug. Furthermore, the use of a pre-formed polymer backbone provides limited scope for modification of the polymer conjugate after attachment of the drug, should the properties of the conjugate need to be adjusted to improve drug release and/or to aid patient comfort, particularly in the eye.

A further consideration with a polymer/drug delivery system is the safety and tolerability of the polymer system. Poor tolerability can come about from the chemistry of the polymer (e.g. acidic by-products with PLA or PLGA systems) or the physical properties of the polymer (e.g. non-biodegradable systems, hard materials with sharp edges). The polymer systems most commonly recognised as safe and well tolerated are the polyether class, such as polyethylene glycol, or polypropylene glycol. Such polymers are chemically inert, metabolically stable and produce soft, deformable materials. They also have low immunogenicity. All features that make them an excellent candidate for polymer/drug delivery systems. All such polymers are typically hydrophilic, which contributes to their good safety and tolerability also limits their use as a base polymer for a polymer/drug delivery system. Hydrophilic polymers, such as polyethers, provide little or no diffusivity barrier for control of drug release, particularly over longer periods of weeks or months. Furthermore, hydrophilic polymers are often water soluble so are rapidly cleared from the site. The chemical and metabolic stability of polyethers is another barrier to their use in polymer/drug delivery systems. Such stable systems are cleared from the body intact, so need to be soluble in water to be cleared. Hydrogels have generally been found to be of limited use as drug delivery systems as there is still little or no diffusivity barrier to control rate of release of a drug.

It would be desirable to provide new polymer-drug conjugates, which address or ameliorate one or more disadvantages or shortcomings associated with existing materials and/or their method of manufacture, or to at least provide a useful alternative to such materials and their method of manufacture.

SUMMARY

In one aspect the invention provides a drug-polymer conjugate, which is a copolymer of at least one monomer of formula (I):

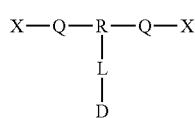

(I)

where:

X may be the same or different at each occurrence and represents a terminal functional group comprising an alkyne or an azide;

Q is independently selected at each occurrence and may be present or absent and when present, represents a linking group;

R is selected from the group consisting of linear or branched hydrocarbon, optionally substituted aryl and optionally substituted heteroaryl;

D is a releasable drug;

L is a linker group group;

and at least one co-monomer of Formula III

 III

J represents a linking functional group, n is 2 to 8, preferably 3 to 8;

Y comprises a polyether of formula $(OR^a)_m$ wherein $R^a$ is independently ethylene, propylene and butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate;

A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

The presence of at least 3 groups of three (Y-A) arranged about J provides a three dimensional network structure to the polymer. This network structure provides a solid polymeric scaffold for delivery of the active which can be moulded into suitable shapes for introduction to localised sites within the body so as to deliver the drug payload to the required site. The polymer conjugate may be adapted to remain at the site of the body to which it is introduced. Despite the solid nature of the polymer network the structure including the multi-arm cores of the network comprising oxyalkylene polymer segments $(OR^a)_m$ provides controlled release of the active agent over a period of time which may avoid the need for repeated administration of the active agent. The polymer backbone may be adapted to biodegrade. In this way the solid polymer-conjugate may be adapted to biodegrade to smaller segments after the desired treatment period to provide clearance of the polymer from the site of delivery.

In one embodiment the drug-polymer conjugate comprises a polymer backbone with a plurality of biodegradable groups. Specific examples of the biodegradable groups are backbone segments of Formula (II):

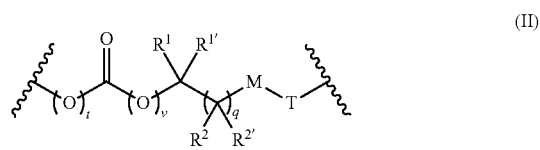

(II)

wherein each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and

T is a triazole moiety.

In one embodiment and at least one of $R^1$, $R^{1'}$, $R^2$ and $R^{2'}$ is not hydrogen. We have found that the presence of the substituents moderates biodegradation to allow controlled release over an extended period where prolonged treatment of for example over 15 days such as over 30 days or over 60 days is desirable.

The biodegradable group may be present as Q in the drug-monomer conjugate of formula (I), in the comonomer of as part of the group Y in formula (III) or in both the drug monomer and the comonomer.

Examples of the group Q which may be present in the drug monomer include groups of formula:

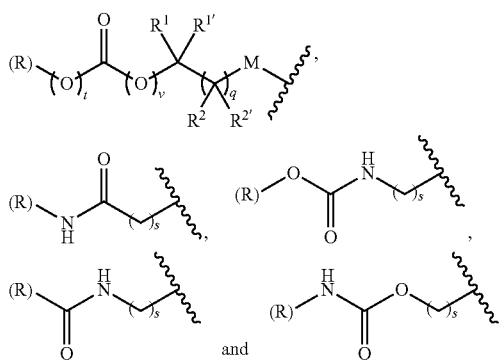

wherein
each of t and v are independently 0 or 1 and at least one of t and v is 1 (preferably one of t and v is 1 and the other is 0);

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$, and $R^2$, $R^{2'}$, may between the members of the pair form a carbocycle or heterocycle of 3 to 6 constituent ring members wherein the heterocycle may comprise from 1 to 3 constituent oxygen heteroatom ring members; and M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and

S is from 0 to 10, preferably 0 to 6.

More specific examples of Q may be selected from the group consisting of:

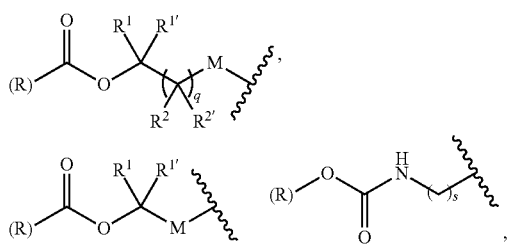

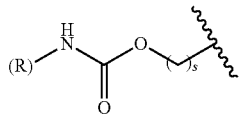

In one aspect the drug-polymer conjugate is a co-polymer of a drug-monomer conjugate of formula (I) is of formula (IV)

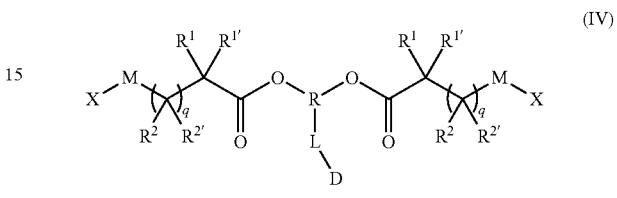

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

X may be the same or different at each occurrence and is a terminal functional group comprising an alkyne or an azide;

R is selected from the group consisting of optionally substituted linear or branched hydrocarbon, optionally substituted aryl and optionally substituted heteroaryl;

L is a linker group; and

D is a releasable drug selected from prostaglandins, β-blockers and mixtures thereof.

It will be understood by those skilled in the art that reaction of the alkyne group and azide provides a triazole link in the backbone of the polymer.

In one embodiment the monomer of formula (I) is of formula IVa

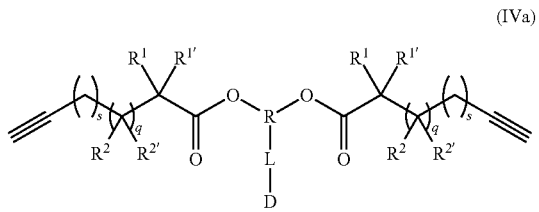

Wherein R, $R^1$, $R^{1'}$, $R^2$, $R^{2'}$, R, L, D and q are as defined above and s is from 0 to 10 preferably 0 to 6 such as 0, 1, 2 or 3.

The drug-polymer conjugate of any one of claims 1 to 5, wherein the co-monomer of Formula III has the formula IIIa $$J\text{-}((OR^a)_m\text{—}B\text{-}A)_n \qquad (IIIa)$$

wherein
A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (I);

J represents a bond, oxygen or linking functional group, $R^a$ is selected from ethylene, propylene, butylene and mixtures thereof;

m is 1 to 300;

n is 3 to 8;

B is a bond, oxygen, the group of formula -MOC(O)N(H)M'-, -MOC(O)OM'-MC(O)NHM'-, the group formula selected from (VIa), (VIb), (VIc) and (VId):

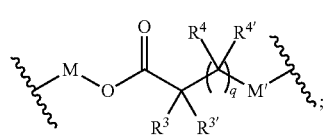
(VIa)

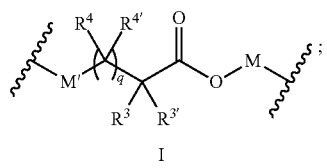
(VIb)

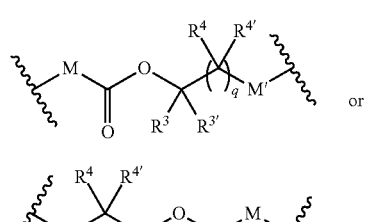
(VIc)

or

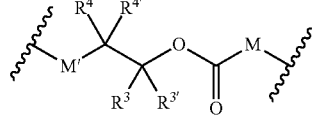
(VIc)

wherein M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula, (VIa), (VIb), (VIc) and (VId) the groups R3, R3', R4 and R4' are independently selected from the group consisting of hydrogen, alkyl, alkoxy, alkoxy-alkyl, amino, alkyl amino, dialkylamino, amino-alkyl, alkylamino-alkyl, dialkylamino-alkyl wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

The functional group B in formula IIIa in one embodiment is selected from the group consisting a bond, oxygen, the group of formula -MOC(O)N(H)M' and the group formula selected from (VIa) and (VIb).

In one aspect the conjugate is a copolymer of monomers of formula II and IIIa wherein at least one of $R^1$, $R^{1'}$, $R^2$, $R^{2'}$, $R^3$, $R^{3'}$, $R^4$ and $R^{4'}$ present in the monomers is not hydrogen. Without wishing to be bound by theory the presence of the substituents in a position alpha or beta to the ester (particularly alpha) is believed to moderate the susceptibility of the ester to hydrolysis and accordingly moderates biodegradation of the drug-polymer conjugate The drug-polymer conjugate in one set of embodiments comprises network branched segments of formula (XXX):

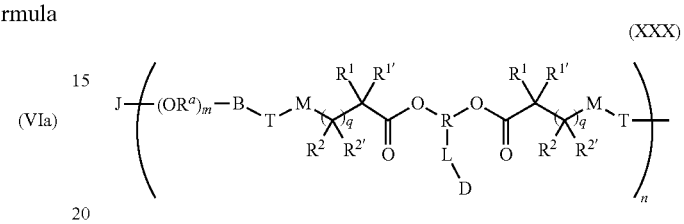
(XXX)

wherein n is 3 to 8 and is the number of branches of the bracketed group about J and the groups J, R, $R^a$, $R^1$, $R^{1'}$, $R^2$, $R^{2'}$, T, M, L and D and the integers m, q and n are as above defined and B is as defined for formula (IIIa).

The drug-polymer may contain a range of different groups R in the polymer backbone which are the group in the backbone to which the drug D is tethered via linking group L. The group R may in one set of embodiments be selected from the group consisting of straight and branched chain hydrocarbon of from 1 to 12 carbon atoms,

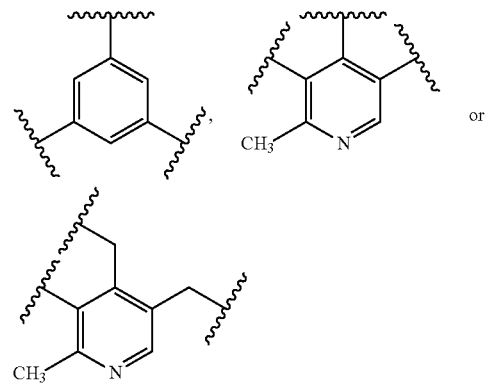

or

In one set of embodiments the drug-polymer conjugate is a co-polymer of a drug conjugate monomer of formula (IV)

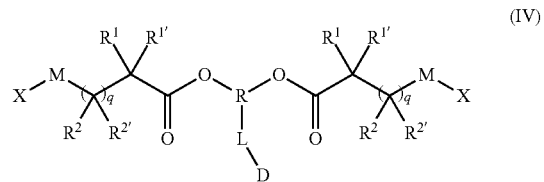
(IV)

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group $N(R^w)$ wherein Fe is selected from hydrogen and $C_1$ to $C_4$ alkyl;

X is a terminal functional group comprising an alkyne or an azide;

R is selected from the group consisting of optionally substituted linear or branched hydrocarbon, optionally substituted aryl and optionally substituted heteroaryl;

L is a linker group; and

D is a releasable drug selected from prostaglandins, β-blockers and mixtures thereof;

and a co-monomer of Formula IIIa

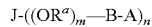
    J-((OR$^a$)$_m$—B-A)$_n$      IIIa where:

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (II);

J represents a linking functional group, preferably an optionally substituted hydrocarbon or hydrocarbon ether or polyether of from 2 to 4 hydrocarbon units; $R^a$ at each occurrence may be ethylene, propylene or butylene;

m is from 1 to 300;

n is from 3 to 8 (preferably 3 or 4);

B is a bond, oxygen, the group of formula -MOC(O)N(H)M'- or the group formula (VIa)

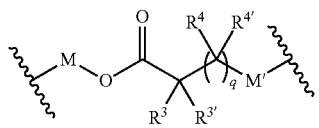
(VIa)

wherein

M and M' M are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N(R$^w$)—($C_1$ to $C_{10}$ straight or branched chain aliphatic) and an amine linking group comprising $C_1$ to $C_{10}$ straight or branched chain aliphatic interrupted by the group N(R$^w$) wherein R$^w$ is selected from hydrogen and $C_1$ to $C_4$ alkyl;

q is 0 or 1;

wherein in the monomers of formula (IV) and (III) the groups $R^1$, $R^{1'}$, $R^2$, $R^{2'}$, $R^3$, $R^{3'}$, $R^4$ and $R^{4'}$ are independently selected from the group consisting of hydrogen, alkyl, alkoxy, alkoxy-alkyl and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and one of the pairs of $R^3$, $R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members I.

The drug D is generally selected from Prostaglandins and β-blockers. The drug-polymer conjugate may comprise a prostaglandin linked to the backbone via an ester in which the acid residue is the 1-position acid of the prostaglandin and the alcohol portion of the ester is provided by the linker. A prostaglandin acid portion is shown in formula Xb

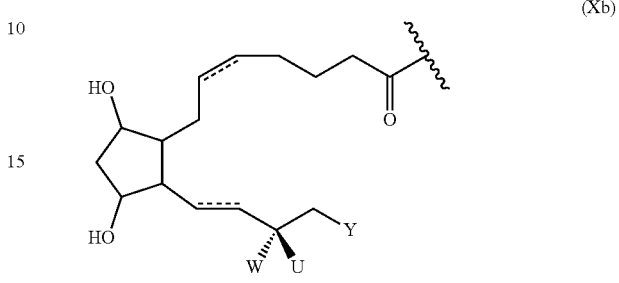
(Xb)

wherein:

~~~~ represents the point of attachment of the prostaglandin to linking group L;

------ represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo.

The drug (D) may be a β-blocker of formula (XV):

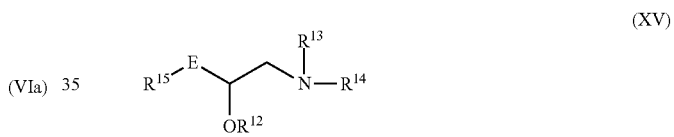
(XV)

wherein:

E is a bond or —OCH$_2$— (preferably —OCH$_2$—);

$R^{12}$ is hydrogen in the parent compound and is the linker L in formula I when the β-blocker is linked to the polymer backbone and is the alcohol residue (—O—) of an ester formed with an acid residue present in L or together with L forms a carbonate linking group;

$R^{13}$ and $R^{14}$ are each independently selected from the group consisting of H, and linear or branched $C_1$-$C_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl; (preferably $R^{13}$ is H and $R^{14}$ is isopropyl or tert-butyl); and $R^{15}$ in formula (XV) is an optionally substituted cycloalkyl or aryl moiety (including polycyclic moieties).

Biodegradation of the polymer in vivo is controlled by the presence of substituents when at least one of $R^1$, $R^{1'}$, $R^2$, $R^{2'}$, $R^3$, $R^{3'}$, $R^4$ and $R^{4'}$ present in the monomers is not hydrogen and/or when the comonomer of formula (IIIa) is present and n is from 3 to 8 (preferably 3 or 4. This biodegradation chemistry introduced in the polymer backbone in formula (I) and (II) can be used to ensure the in-use life of the product is greater than the treatment period controlled by the pendant linker chemistry. Conversely, the backbone substitution and resultant biodegradation chemistry can be used to control the treatment period independently of the pendant linker chemistry by ensuring the rate of biodegradation is faster than the rate of drug release. Such a system ensures no loss of potency near the end of the in-use life of the product.

The invention further allows the product to maintain its integrity and have minimal loss of function during the treatment period, yet biodegrade and dissolve as soon as possible thereafter. Such a system may be used to provide a non-linear loss of mass with respect to time during its in-use lifetime with minimal mass loss attributable to the polymer backbone during the treatment period and rapid mass loss of the polymer backbone after the treatment period. A cross-linked or hyperbranched polymer architecture provided by co-monomer (111a) where n is 3 or more with biodegradation chemistry incorporated into the polymer architecture provides such a mass loss profile.

In the drug-polymer conjugates of the invention we have found that the polyether segments particularly in the network polymers (where n is 3 to 8) delivery would retains the hydrophilic, low immunogenic properties typical of such polyether, but the drug-polymer is rendered insoluble for the desired treatment period and is then able to biodegrade into soluble fragments thereafter.

Modification of the polyethers segments $(OR^a)_m$ into a network architecture provides a polymer conjugate that is insoluble in water but still generally sufficiently hydrophilic to form a hydrogel. The use of a multi-valent monomer component (III) in the reaction allows preparation of the insoluble polymer. By weight, such hydrogels are mostly liquid, yet they behave like solids due to a three-dimensional cross-linked network within the liquid. Covalent attachment the drug pendant to the polymer network chain of the hydrogel together with the chemistry of the linker provides a means for controlling the rate of drug release.

The combination of the linkage chemistry of the pendant drug to the polymer chain and the biodegradation chemistry incorporated into the polymer chain of the network provides a means to separately control the rate of drug release from the rate of biodegradation of the polymer. The treatment period of the product can then be determined by either the period of controlled drug release or the period its takes for the polymer to biodegrade, whichever comes sooner.

The modification of the branched polyether to introduce chemistry susceptible to hydrolysis (e.g. ester, amides, carbonates or carbamates) at points within the polymer chain facilitates polymer biodegradation. The introduction of such chemistry into any of the monomers used to produce a hydrogel may be used to provide efficient biodegradation of the hydrogel at the end of the treatment period.

The cross-linked hydrogel offers a further advantage by providing a non-linear loss of product mass compared with an equivalent linear polymer system. The underlying hydrolysis of a common biodegradation chemistry (e.g. ester) is the same, whether contained in a liner polymer or a cross-linked hydrogel. However, in the case of the hydrogel, the cross-linked architecture ensures no significant loss of product mass occurs until a critical proportion of all the biodegradation moieties within the polymer chain are cleaved. Rapid mass loss occurs once that critical level is achieved. Hence, the mass loss profile is non-linear with very little loss of mass until the critical proportion of cleavage occurs after which there is a rapid loss of mass.

Such a system allows a product to be produced that has little or no mass loss during the treatment period and rapid mass loss after the treatment period.

BRIEF DESCRIPTION OF DRAWINGS

Examples of the invention are described with reference to the attached drawings.

In the drawings:

FIG. 4A: cumulative release (μg/10 mg) of latanoprost free acid; and FIG. 4B: % mass loss with time exposed to isotonic phosphate buffer (pH 7.4) at 37.0° C. and 55.0° C., respectively, from drug-polymer conjugates.

FIG. 7A: cumulative release (μg/10 mg) of latanoprost free acid; and FIG. 7B: % mass loss with time exposed to rabbit aqueous humour in vivo from drug-polymer conjugates, Example 160, Example 164, Example 163, Example 166 and Example 231.

FIG. 8A: cumulative release (μg/10 mg) of latanoprost free acid; and FIG. 8B: % mass loss with time exposed to isotonic phosphate buffer (pH 7.4) at 37.0° C. and 55.0° C., respectively, from drug-polymer conjugate Examples, Example 160 and Example 196.

FIG. 11A: cumulative release (μg/10 mg) of latanoprost free acid, and FIG. 11B: % mass loss with time exposed to isotonic phosphate buffer (pH 7.4) at 37.0° C. from drug-polymer conjugates of Example 156, Example 232, Example 161 and Example 162.

FIG. 12A: cumulative release (μg/10 mg) of latanoprost free acid, and FIG. 12B: % mass loss with time exposed to isotonic phosphate buffer (pH 7.4) at 37.0° C. and 55.0° C., respectively, from drug-polymer conjugates of Example 160, Example 173, Example 170, Example 177, Example 179, Example 195, Example 180, Example 181 and Example 186.

from drug-polymer conjugates Example 221, Example 222, Example 223 and Example 224.

Figure 14A:
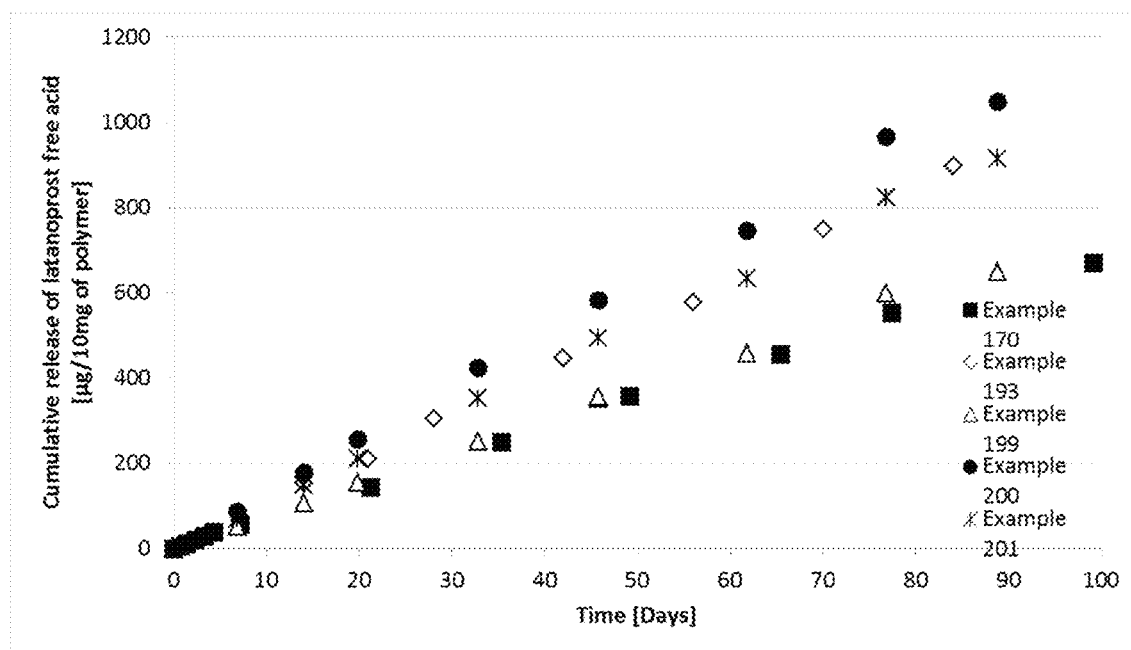
Figure 14B:
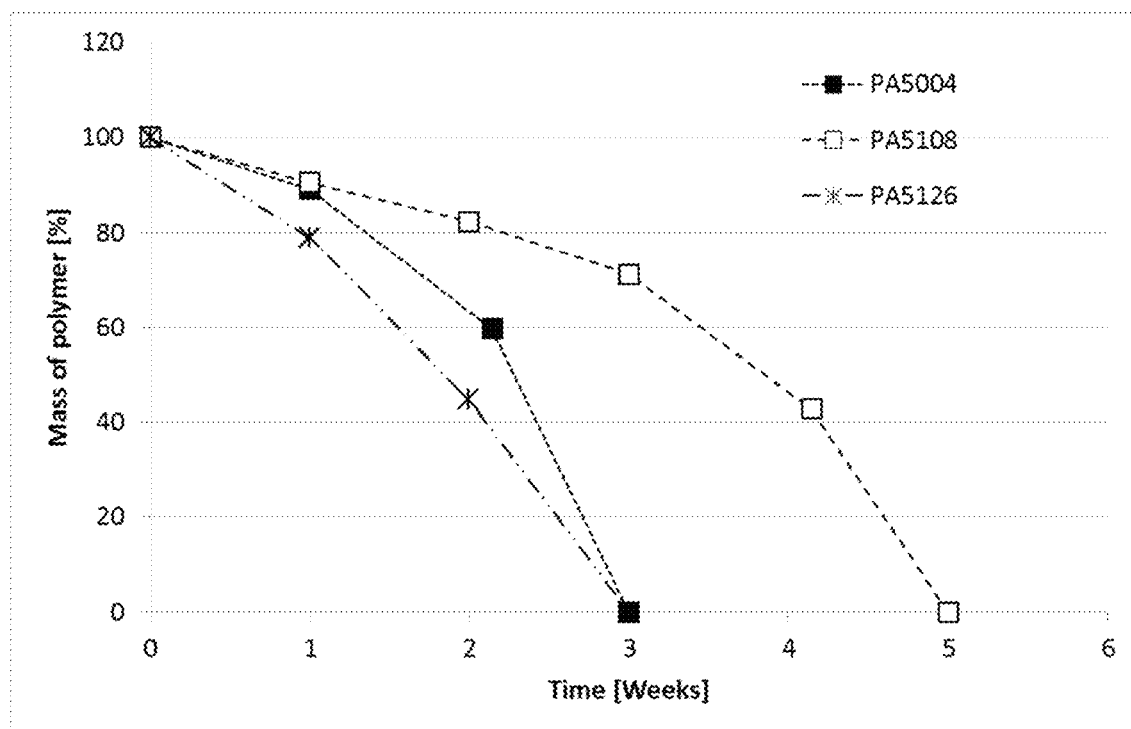

FIG. 14A and FIG. 14B are two graphs each having five plots showing FIG. 14A: cumulative release (μg/10 mg) of latanoprost free acid, and FIG. 14B: % mass loss with time exposed to isotonic phosphate buffer (pH 7.4) at 37.0° C. and 55.0° C., respectively, from drug-polymer conjugates of Example 170, Example 193, Example 199, Example 200 and Example 201.

Figure 15:
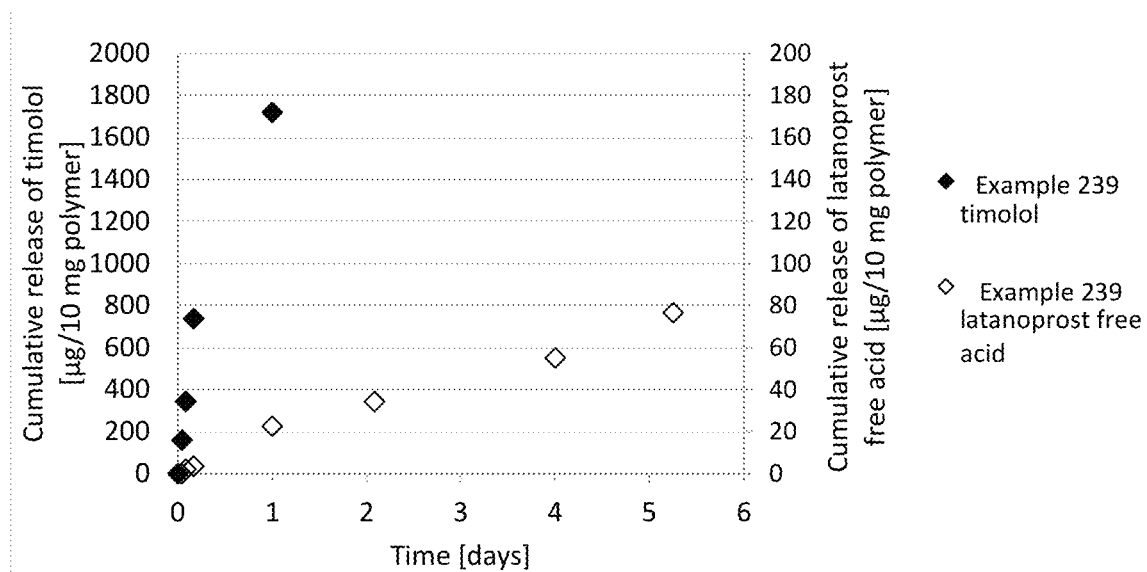

FIG. 15 is a graph having a plot showing cumulative release (μg/10 mg) of latanoprost free acid and timolol with time exposed to isotonic phosphate buffer (pH 7.4) at 37.0° C. from Example 239.

DETAILED DESCRIPTION

The term "drug" refers to a substance for therapeutic use whose application (or one or more applications) involves: a chemical interaction, or physico-chemical interaction, with a subject's physiological system; or an action on an infectious agent, or on a toxin or other poison in a subject's body, or with biological material such as cells in vitro.

As used herein, the term "prodrug" refers to a derivative of the drug moiety, wherein the derivative may have little or none of the activity of the drug moiety per se yet is capable of being converted in vivo or in vitro into a drug moiety. An example of such derivatisation is the acetylation of one or more hydroxyl groups on a drug moiety, such that subsequent to being released in vivo the released prodrug is deactylated to produce the drug moiety.

As used herein, the term "pharmaceutically acceptable salt" means those salts that are safe and effective for use in pharmaceutical preparations. Pharmaceutically acceptable salts include salts of acidic groups present in compounds of the invention. Suitable salts may include sodium, potassium, ammonium, calcium, diethylamine and piperazine salts and the like. Pharmaceutically acceptable salts are described in Stahl PH, Wermuth CG, editors. 2002. Handbook of pharmaceutical salts: Properties, selection and use. Weinheim/Zurich: Wiley-VCH/VHCA.

As used herein, it is contemplated that the term "prostaglandin" includes, without limitation, natural prostaglandins and prostaglandin analogs. The prostaglandins are generally present in the polymer-prostaglandin conjulates and monomer prostaglandin conjugates as the acid residue portion of an ester forned at the (D) end of the linker.

Polymers having drug s covalently attached thereto are sometimes referred to in the art as "polymer-drug conjugates". In some instances, it may be convenient to refer to a polymer-drug agent conjugate of the invention as a "drug-polymer conjugate", "drug-polymer conjugate", "drug-polymer conjugate", "polymer conjugate", "polymeric prodrug" or simply a "conjugate".

A hydrogel is a macromolecular polymer gel constructed of a network of cross-linked polymer chains. Hydrogels are synthesized hydrophilic monomers by either chain or step growth polymerisation, along with a functional crosslinker to promote network formation.

In one aspect, the present invention relates to a polymer-drug agent conjugate comprising a polymer backbone and a plurality of releasable drugs covalently bonded to and pendant from the polymer backbone. In accordance with this aspect, the polymer backbone comprises a plurality of triazole moieties.

Triazole moieties present in the polymer backbone of the polymer-drug conjugates, which are the product of an azide/alkyne coupling, are 1,2,3-triazole moieties.

1,2,3-Triazole moieties can be produced through the reaction of co-monomers having appropriate complementary terminal functional groups comprising alkyne and/or azide functionalities, under click reaction conditions. The terms "complementary terminal functionality" and "complementary terminal functional group" as used in the context of the present invention means a terminal chemical group that is capable of reacting with another chemical group to form a covalent intermolecular bond there between.

An appropriate click reaction for the formation of 1,2,3-triazoles is the Huisgen 1,3-dipolar cycloaddition of azides and alkynes (thermal) which gives a mixture of the 1,4 and 1,5 regioisomers of the 1,2,3-triazole. Click reactions suitable for forming triazole moieties may also be metal catalysed. For example, a Copper(I)-catalyzed Azide-Alkyne Cycloaddition (CuAAC) variant of the Huisgen cycloaddition of azides and terminal alkynes forms 1,2,3-triazoles. Use of a copper catalyst in the Huisgen cycloaddition reaction results in formation of a 1,4-substituted 1,2,3-triazole from azides and terminal alkynes, while use of a ruthenium catalyst enables use of terminal or internal alkynes and results in the formation of the alternate 1,5-regiosiomer. The use of a silver catalyst also results in the 1,4-substituted 1,2,3-triazole. Other metals that can be used include, but are not limited to, Ni, Pt, Pd, Rh, and Ir; the regiochemistry of the 1,2,3 triazole resulting from the use of these metal catalysts is less well defined Some exemplary click functional groups have been described by W. H. Binder and R. Sachsenhofer in Macromol. Rapid Commun., 2007, 28, 15-54, the disclosure of which is incorporated herein by reference.

In one aspect the invention provides a drug-polymer conjugate, which is a copolymer of at least one monomer of formula (I):

(I)

where:

X may be the same or different at each occurrence and represents a terminal functional group comprising an alkyne or an azide;

Q is independently selected at each occurrence and may be present or absent and when present, represents a linking group;

R is selected from the group consisting of linear or branched hydrocarbon, optionally substituted aryl and optionally substituted heteroaryl;

D is a releasable drug;

L is a linker group group;

and at least one co-monomer of Formula III

   III

J represents a linking functional group, n is 2 to 8, preferably 3 to 8;

Y comprises a polyether of formula $(OR^a)_m$ wherein $R^a$ is independently ethylene, propylene and butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate;

A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

The embodiment in which n is 3 to 8 provides particular advantages in controlling biodegradation of the polymer backbone while also providing a sold polymer which can be formed into a relatively dense article such as a pellet for placement at a site in the body of the subject where effective treatment with a prostaglandin and/or β-blocker is required over a period of time such as at least 10 days, at least 20 days or at least 30 days.

Examples of the group Q which may be present in the drug monomer of formula (I) include groups of formula:

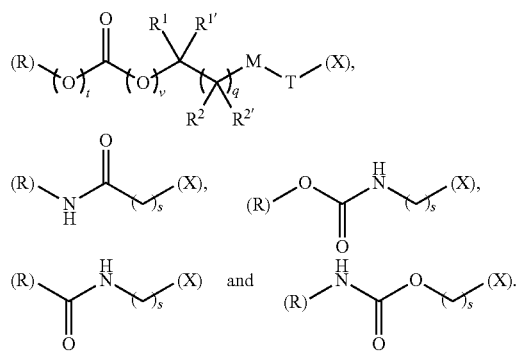

wherein
each of t and v are independently 0 or 1 and at least one of t and v is 1 (preferably one of t and v is 1 and the other is 0);
$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
s is from 0 to 10, preferably 0 to 6 such as 0, 1, 2 or 3.

More specific examples of Q may be selected from the group consisting of:

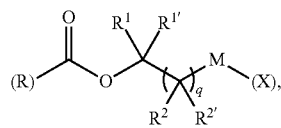

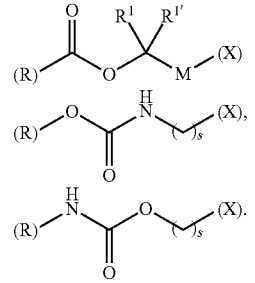

In one aspect the invention provides a drug-polymer conjugate comprising a polymer backbone and a plurality of drugs covalently bound to and pendant from the polymer backbone wherein the polymer backbone comprises a plurality of biodegradable groups of Formula (II):

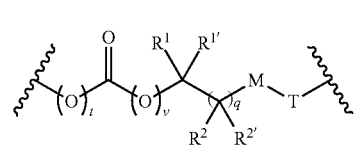

(II)

wherein:
each of t and v are independently 0 or 1 and at least one of t and v is 1 (preferably one oft and v is 1 and the other is 0); $R^1$, $R^{1'}$,'$R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and
q is 0 or 1; and
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
and
T is a triazole moiety.

The unit of formula (II) may be provided by the monomer of formula (I), the comonomer of formula III.

In one embodiment at least one of $R^1$, $R^{1'}$, $R^2$ and $R^{2'}$ is preferably not hydrogen. The presence of substituents has been found to regulate the rate of biodegradation and their use can allow the period of effective delivery to be determined in combination with the Network structure provided when n in the comonomer of formula (III) or (IIIa) is 3 to 8.

The compound of formula I includes a number of variables and may be in the form of any one of formulae (Ia), (Ib), (Ic), (Id) or combinations of two or more thereof in the polymer backbone:

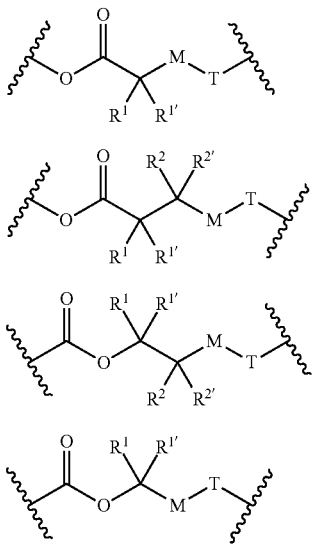

(IIa)

(IIb)

(IIc)

(IId)

wherein the groups $R^1$, $R^{1'}$, $R^2$, $R^{2'}$, M and T are as herein defined in respect of formula II.

In one set of embodiments the drug-polymer conjugate comprising a plurality of polymer segments of formula V

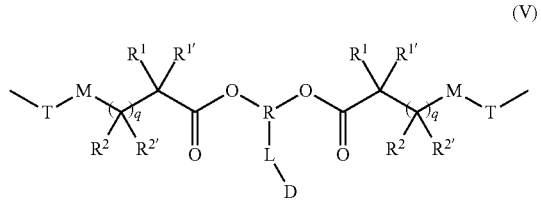

(V)

wherein $R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and at least one of $R^1$, $R^{1'}$, $R^2$ and $R^{2'}$ present in the polymer is not hydrogen;

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

R is selected from the group consisting of linear or branched hydrocarbon, optionally substituted aryl and optionally substituted heteroaryl;

L is a linker group; and

D is a releasable drug; and

T is a triazole moiety.

In some embodiments of the co-monomer of formula III the group B is a bond, oxygen, the group of formula -MOC(O)N(H)M'- or the group formula (VIa)

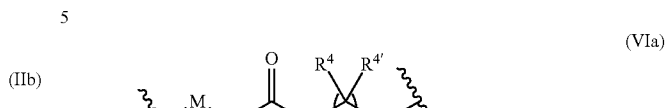

(VIa)

wherein

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$)

wherein $R^w$ is selected from hydrogen and $C_1$ to $C_4$ alkyl;

q is 0 or 1; and wherein the groups $R^3$, $R^{3'}$, $R^4$ and $R^{4'}$ are selected from the group consisting of hydrogen, $C_1$ to $C_6$ alkyl, $C_1$ to $C_6$ alkoxy and $C_1$ to $C_6$ alkoxy-($C_1$ to $C_6$ alkyl) and wherein one of the pairs of $R^3$, $R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members.

In some embodiments at least one of the groups R3, R3', R4 and R4' is other than hydrogen.

The segment of formula (VIa) may be oriented between the groups $(OR^a)_m$ and A and this may be of orientation (VIa) or (VIb):

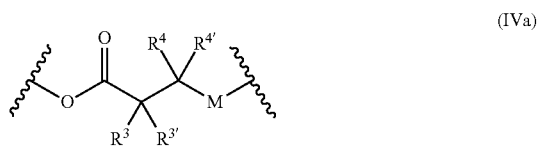

(IVa)

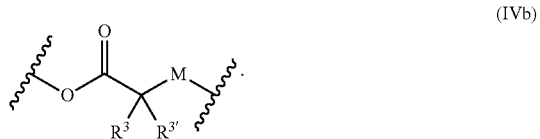

(IVb)

In this embodiment the resulting polymer comprises substituents $R^1$, $R^{1'}$, $R^2$, $R^{2'}$, $R^3$, $R^{3'}$, (and in the case of formula (IVa) $R^4$ and $R^{4'}$) at least one of which is not hydrogen. In some embodiments at least one of $R^1$, $R^{1'}$, $R^2$, $R^{2'}$ is other than hydrogen, in other embodiments at least one of $R^3$, $R^{3'}$, $R^4$ and $R^{4'}$ is other than hydrogen one in some embodiments at least one of the groups $R^1$, $R^{1'}$, $R^2$, $R^{2'}$ is other than hydrogen and at least one of $R^3$, $R^{3'}$, $R^4$ and $R^{4'}$ is other than hydrogen.

In some embodiments, the polymer backbone of the polymer-drug conjugate comprises at least one triazole moiety selected from the group consisting of formula (VIIa) and (VIIb)):

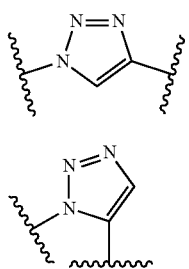

(VIIa)

(VIIb)

The backbone may comprise a multiplicity of triazole moiety such as (VIIa), (VIIb) and combinations thereof.

Additional co-monomers useful for the preparation of polymer-drug conjugates of the invention comprise terminal functional groups comprising an alkyne and/or an azide. One skilled in the relevant art would understand that under appropriate reaction conditions, an alkyne and an azide containing functional groups can covalently react to form a triazole moiety. Click reaction conditions have been described in for example, Chem. Rev. 2008, 108, 2952, Angew Chem Int Ed 2001, 40, 2004, Angew Chem Int Ed Engl. 2002, Jul. 15, 41(14): 2596-9, Aldrichimica Acta 2010, 43 (1) 15 and *Accounts of Chemical Research* 44 (9): 666-676.

In one aspect of the invention the drug conjugated with the polymer backbone of the drug-polymer conjugate and in the monomer is selected from prostaglandins, β-blockers and combinations of two or more thereof. In some embodiments it is useful to have drugs from two or more of these drug classes for specific treatments or to optimise treatment. Combinations of drugs from the prostaglandin and β-blocker classes are therapies that may be provided by conjugation of these two drugs to the same polymer backbone by, for example forming the polymer with a mixture of monomers of formula I where D is selected from prostaglandins in at least one monomer and D is selected from β-blockers in at least one monomer.

In the monomer-drug conjugate of formula (I) each substituent X represents a group comprising a terminal functional group comprising an alkyne or azide functionality. The terminal functional group X may be the same or different at each occurrence. Where the terminal functional groups (X) are the same, the monomer will generally be a diazide or dialkynyl monomer.

One skilled in the relevant art would understand that the terms "alkyne" and "azide" represent the following structures:
Alkyne: —C≡CH
Azide: —N=N$^+$=N$^-$ In one embodiment the drug is conjugated to the polymer backbone via an ester linkage formed between the drug D and the linker L. For example in one embodiment the drug is covalently bonded to the linker by a carboxylic acid ester. The ester may comprise an acid portion —C(O)— derived from an acid functional group of the drug and an alcohol portion provided by the linker or an acid portion of the ester may be derived from the linker and the alcohol portion by the drug.

The drug moiety (D) in formula (I), (IV), (IVa) and (IVb) may be a prostaglandin.

Prostaglandins as described herein constitute an α-chain, an ω-chain and a 5-membered ring, numbered according to the C20 prostanoic acid as follows:

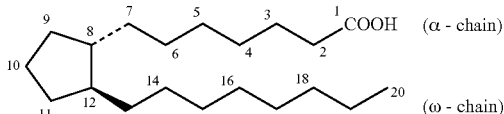

In one aspect, the present invention relates to a drug-polymer conjugate comprising a polymer backbone and a PGF2α class of prostaglandin conjugated to the polymer backbone.

Prostaglandins delivered by polymer-drug conjugates of the invention comprise at least one functional group selected from the group consisting of a carboxylic acid group at the 1 position, a hydroxy group at the 9 position, a hydroxy group at the 11 position, and a hydroxy group at the 15 position.

The carboxylic acid group at the 1 position, and the hydroxy groups at the 9, 11 and 15 position of the prostaglandin can serve as reactive functional groups for conjugation of the prostaglandin drug to a polymer. In conjugating the drug to the polymer backbone, the prostaglandin is conjugated to the polymer backbone via a selected group at the 1, 9, 11 or 15 position. The drug moiety (denoted D in formulae described herein) linked to the polymer is therefore an acid residue (in the case of conjugation at the 1 position) or an alcohol residue (in the case of conjugation at the 9, 11 or 15 positions) of the ester, anhydride or carbonate linking group conjugating the prostaglandin to the polymer backbone. The moiety represented by D may therefore be a releasable prostaglandin.

The prostaglandin may be conjugated to the polymer backbone via an ester (including [alkoxycarbonyl)oxy]alkyl ester), anhydride or carbonate linking group. Ester (including [alkoxycarbonyl)oxy]alkyl ester), anhydride and carbonate linking groups have been found to be hydrolytically labile in biological environments and can help to ensure that a sufficient amount of the drug is effectively released from the polymer conjugate to achieve therapeutic levels in the immediate vicinity of the polymer conjugate material.

When the prostaglandin is conjugated to the polymer backbone by an ester linking group, the ester linking group may link the drug at a position selected from the group consisting of the 1, 9, 11 and 15 position of the drug.

When the prostaglandin is conjugated to the polymer backbone by an [alkoxycarbonyl)oxy]alkyl ester linking group, the [alkoxycarbonyl)oxy]alkyl ester group may link the drug at the 1 position of the drug.

When the prostaglandin is conjugated to the polymer backbone by a carbonate linking group, the carbonate linking group may link the drug at a position selected from the group consisting of the 9, 11 and 15 position of the drug.

When the prostaglandin is conjugated to the polymer backbone by an anhydride linking group, the anhydride linking group may link the drug at the 1 position of the drug.

As used herein, the term "acid residue" is a reference to that part of an ester or anhydride linking group that is derived from a carboxylic acid functional group of a drug, after conjugation of the drug to the polymer backbone. The acid residue will generally have the structure —C(O)—. In the case of a prostaglandin, the carboxylic acid group is located at the 1 position.

As used herein the term "alcohol residue" is a reference to that part of an ester or carbonate linking group that is derived from a hydroxy functional group of a drug, after conjugation of the drug to the polymer backbone. The alcohol residue will generally have the structure —O—. In the case of a prostaglandin, the hydroxy group may be selected by located at the 9, 11 or 15 position.

In one set of embodiments, the drug (D) is a prostaglandin of formula (X):

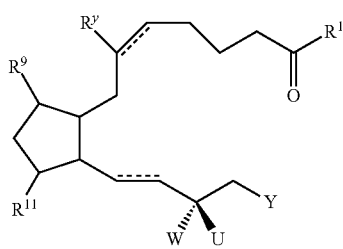
(X)

where:

------ represents a double or single bond;

W and U are selected from the group consisting of where W and U together form oxo (=O), where W and U are each halo, and where W is $R^{15}$ and U is hydrogen;

$R^y$ is an optional substituent selected from the group consisting of oxo and hydroxy;

Y is optionally substituted $C_4$ to $C_{10}$ hydrocarbyl or optionally substituted $C_4$ to $C_{10}$ hydrocarbyloxy; and one of $R^1$, $R^9$, $R^{11}$ and $R^{15}$ is linked to the polymer backbone and wherein:

$R^9$, $R^{11}$ and $R^{15}$ when linked to the polymer backbone are the alcohol residue of an ester or carbonate linking group and $R^1$ when linked to the polymer backbone forms the acid residue of an ester or anhydride linking group; and $R^1$ when not linked to the backbone is selected from the group consisting of —OH, —O($C_{1-6}$ alkyl), and —$NR^aR^b$ where $R^a$ and $R^b$ are each independently selected from the group consisting of H and $C_{1-6}$ alkyl;

$R^9$ and $R^{11}$ when not linked to the polymer backbone are both hydroxy and where one of $R^9$ and $R^{11}$ is linked to the backbone, the other is hydroxy; and when $R^{15}$ is not linked to the backbone then W is hydroxy and U is hydrogen, or W and U are each fluoro, or W and U together form oxo.

In some embodiments, the prostaglandin of formula (X) is selected from the group consisting of:

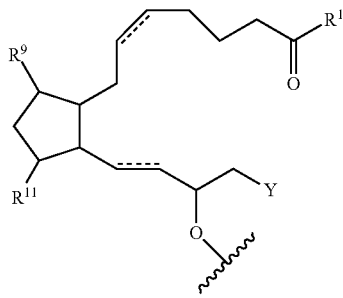
(Xa)

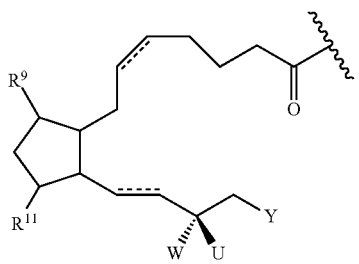
(Xb)

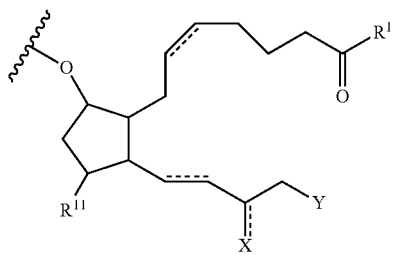
(Xc)

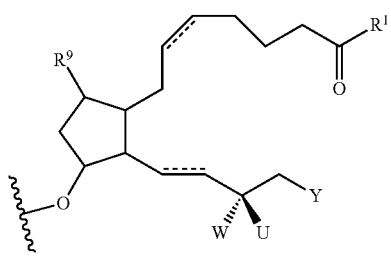
(Xd)

wherein:

⁓⁓⁓⁓ represents the point of attachment of the prostaglandin to L;

------ represents a double or single bond;

Y is optionally substituted $C_4$ to $C_{10}$ hydrocarbyl or optionally substituted $C_4$ to $C_{10}$ hydrocarbyloxy;

in formulae (Xa), (Xc) and (Xd) $R^1$ is hydroxy, $C_1$ to $C_6$ alkoxy or $C_1$ to $C_6$ alkylamino (preferably, isopropoxy or ethylamino);

in formulae (Xa) and (Xb) $R^9$ and $R^{11}$ are hydroxy;

in formula (Xc) $R^{11}$ is hydroxy and X is 0 or hydroxy;

in formula (Xd) $R^9$ is hydroxy; and in formulae (Xb) and (Xd) W is hydroxy and U is hydrogen, or W and U are both fluoro, or W and U together form oxo.

In general it is preferred that when drug is a prostaglandin the prostaglandin is linked to the backbone via an ester, including an [alkoxycarbonyl)oxy]alkyl ester, in which the 1-position of the prostaglandin forms the acid residue of the ester and is linked to the backbone via an alcohol residue on the linker L.

In this embodiment the group D is a prostaglandin according to formula Xb (Xb)

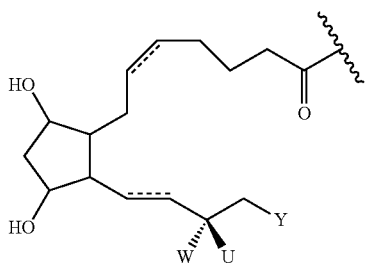

wherein:

~~~~ represents the point of attachment of the prostaglandin to linking group L;

------ represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo.

It will be understood that prostaglandin contains chiral centres and is preferably of formula X(e)

X(e)

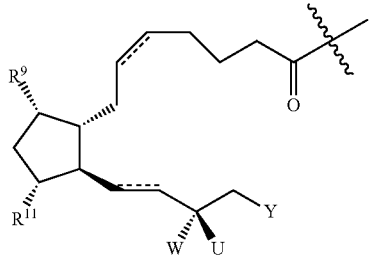

In preferred embodiments at least 80 mol % (more preferably at least 90 mol %) of the prostaglandin is present in the drug-polymer conjugate in the form of one optical isomer.

Examples of the drug monomer conjugate of formula II wherein the drug is a prostaglandin in acid residue form include monomers of formula (IVa) and (IVb):

(IVb)

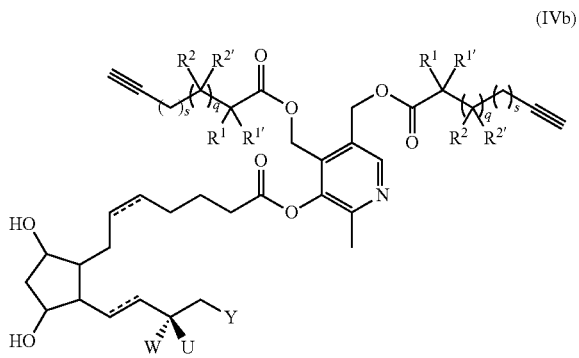

(IVc)

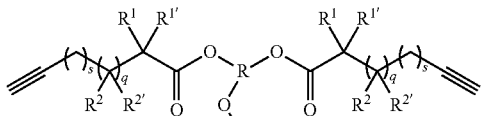

wherein:

the groups $R^1$, $R^{1'}$, $R^2$ and $R^{2'}$ are independently selected from the group consisting of hydrogen, $C_1$ to $C_6$ alkyl, $C_1$ to $C_6$ alkoxy, $C_1$ to $C_6$ alkoxy-($C_1$ to $C_6$ alkyl), and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and wherein at least one of $R^1$, $R^{1'}$, $R^2$ and $R^{2'}$ is preferably other than hydrogen;

s is from 0 to 6 (preferably 0 to 2);

$R^5$ is selected from hydrogen and $C_1$ to $C_6$ alkyl, preferably from the group consisting of hydrogen, methyl, ethyl, propyl, isopropyl, butyl, isobutyl, sec-butyl, and tert-butyl and wherein:

------ represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo.

Specific examples of the drug-polymer conjugate include conjugates of formula V (V)

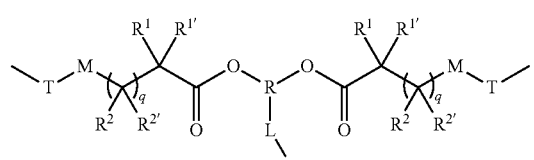

wherein the substituents are as hereinbefore defined except that D is selected from the specific prostaglandins in the form of the acid residue as shown in Table 1.

Specific drug-monomers are of formula (II):

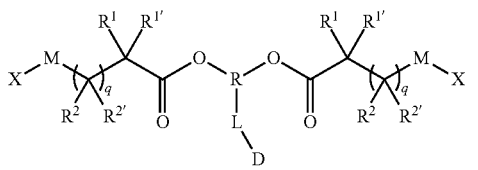

wherein the substituents are as hereinbefore defined except that D is selected from the specific prostaglandins in the form of the acid residue as shown in Table 1.

TABLE 1

| Drug | 1-COOH |
|---|---|
| PGF$_{2\alpha}$ | |
| Travoprost | |
| Carboprost | |
| Tafluprost | |

TABLE 1-continued

| Drug | 1-COOH |
|---|---|
| Latanoprost | |
| Unoprostone | |
| Bimatoprost | |

In this embodiment the linker L provides the alcohol portion of the ester formed with the acid residue of the prostaglandin.

In preferred embodiments the linker L is of formula selected from the group consisting of (R) —O-(D);
(R) —OC(O)—Ar—O-(D);
(R) —NHC(O)—Ar—O-(D);
(R) —C(O)O—C$_{1-12}$alkylene-O-(D);
(R) —OC(O)O—C$_{1-12}$alkylene-O— (D)
(R) —OC(O)—C$_1$-C$_{12}$alkylene-O-(D).

In more preferred embodiments L is selected from (R) —O-(D);

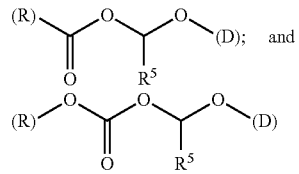

where R$^5$ is selected from hydrogen and C$_1$ to C$_6$ alkyl, preferably from the group consisting of hydrogen, methyl, ethyl, propyl, isopropyl, butyl, isobutyl, sec-butyl, and tert-butyl.

In one particularly preferred embodiment, L is
(R) —O-(D); and R is selected from the group consisting of

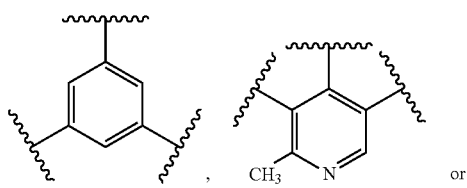

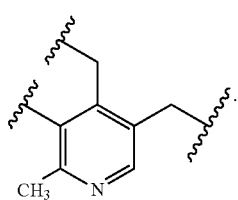

In a further particularly preferred embodiment, L is

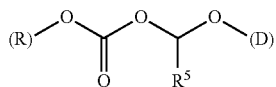

where $R^5$ is selected from hydrogen and $C_1$ to $C_6$ alkyl, preferably from the group consisting of hydrogen, methyl, ethyl, propyl, isopropyl, butyl, isobutyl, sec-butyl, and tert-butyl; and R is a saturated hydrocarbon of from 1 to 10 carbon atoms. More preferred $R^5$ are hydrogen and methyl.

In the most preferred embodiment the drug-polymer comprises a plurality of segments of formula Va, formula Vb or mixture thereof:

(Va)

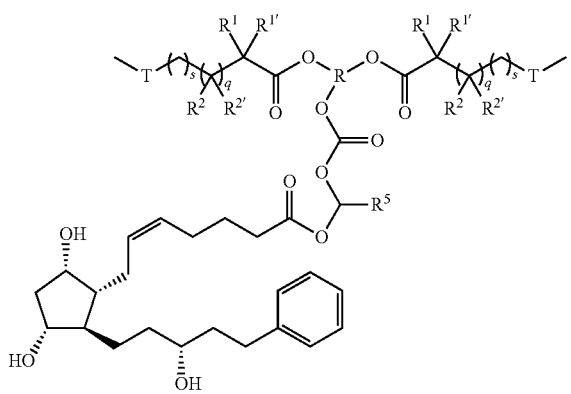

(Vb)

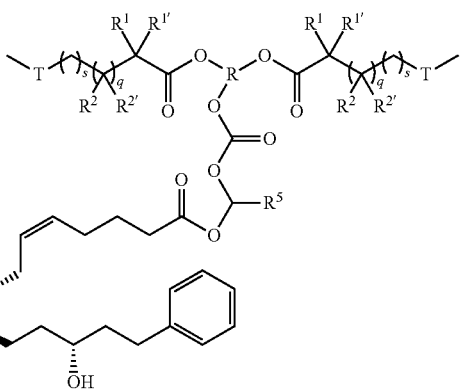

In a further set of embodiments there is provided a drug-monomer and co-polymer formed therefrom wherein the drug monomer is of formula IIc, IId or combination thereof:

(IVc)

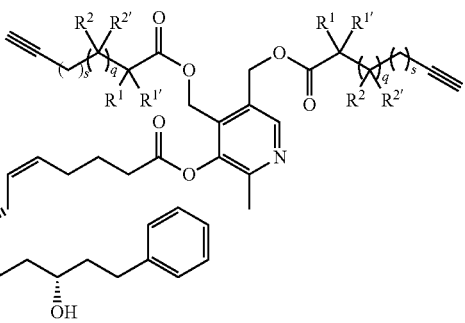

(IVd)

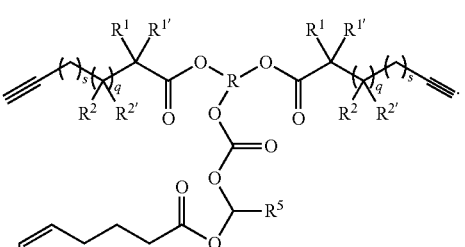

In another aspect, a polymer-drug conjugate according to the invention comprises a drug selected from β-blockers. A β-blocker is a drug that has pharmacological activity to block or antagonise β-adrenergic receptors. The β-blockers employed in the polymer conjugates of the invention are preferably β-amino alcohol β-adrenergic antagonists.

β-amino alcohol β-adrenergic antagonists comprise an alcohol (—OH) and an amino (—NH$_2$, —NHR or —NR$_2$) functional group. The β-blocker is conjugated to the polymer backbone via an ester or carbonate linking group formed with the alcohol moiety of the β-amino alcohol group.

The drug (D) may be a β-blocker of formula (XV):

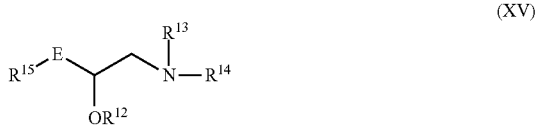

(XV)

wherein:

E is a bond or —OCH$_2$— (preferably —OCH$_2$—);

R$^{12}$ is hydrogen in the parent compound and is the linker L in formula I when the β-blocker is linked to the polymer backbone and is the alcohol residue (—O—) of an ester formed with an acid residue present in L or together with L forms a carbonate linking group;

R$^{13}$ and R$^{14}$ are each independently selected from the group consisting of H, and linear or branched C$_1$-C$_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl; (preferably R$^{13}$ is H and R$^{14}$ is isopropyl or tert-butyl); and R$^{15}$ in formula (XV) is an optionally substituted cycloalkyl or aryl moiety (including polycyclic moieties).

In one embodiment the group R$^{15}$ may be a group of formula (XVa)

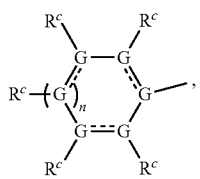

(XVa)

providing a drug (D) which is a β-blocker of formula (XVb):

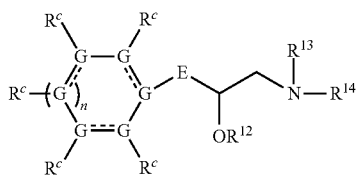

(XVb)

wherein:

R$^{12}$ is linked to the polymer backbone via linker L and is the alcohol residue of an ester or carbonate formed with linker l;

$\overline{\text{------}}$ represents a single bond or double bond;

E is a bond or —OCH$_2$—;

G at each occurrence is independently selected from the group consisting of carbon (C), nitrogen (N), oxygen (O) and sulphur (S), with the proviso that at least two G are carbon;

R$^{13}$ and R$^{14}$ are each independently selected from the group consisting of H, and linear or branched C$_1$-C$_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably R$^{13}$ is H and R$^{14}$ is isopropyl or tert-butyl);

R$^e$ at each occurrence is an optional substituent, or two R$^e$ can join together to form an optionally substituted cycloalkyl or aryl ring; and n is 0 or 1.

In one set of embodiments of formula (XV), R$^{15}$ may be selected from the group consisting of 4-morpholin-4-yl-1,2,5-thiadiazol-3-yl, [2-(cyclopropylmethoxy)ethyl]-phenyl, 3,4-dihydronaphthalen-1(2H)-one, 4-phenyl-acetamide, 1-napthyl, and 4-(2-methoxyethyl)phenyl.

In some embodiments, the drug (D) is β-blocker of formula (XVc):

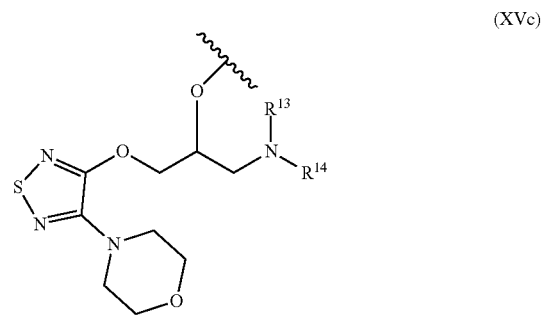

(XVc)

wherein:

∼∼∼∼ represents the point of attachment of the β-blocker to L;

R$^{13}$ and R$^{14}$ are each independently selected from the group consisting of H, and linear or branched C$_1$-C$_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably R$^{13}$ is H and R$^{14}$ is isopropyl or tert-butyl).

In some embodiments, the β-blocker is of formula (XVd):

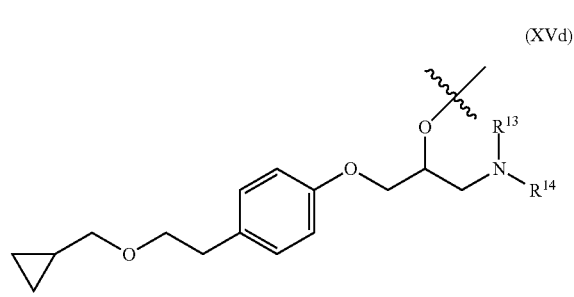

(XVd)

wherein:

∼∼∼∼ represents the point of attachment of the β-blocker to the ester or carbonate linking group conjugating the drug to the polymer backbone. Preferably the attachment is via an ester in which (XVd) forms the alcohol residue of the ester and linker L forms the acid residue of the ester.

R$^{13}$ and R$^{14}$ are each independently selected from the group consisting of H, and linear or branched C$_1$-C$_4$ alkyl optionally substituted by one or more substituents selected from the group consisting of hydroxy, optionally substituted alkoxy, optionally substituted aryloxy, optionally substituted amido, optionally substituted cycloalkyl, and optionally substituted aryl (preferably $R^{13}$ is H and $R^{14}$ is isopropyl or tert-butyl).

Some specific examples of releasable β-blockers of formulae described herein are betaxolol, carteolol, levobunolol, metripranolol, and timolol, preferably timolol. These β-blockers are shown in Table 2. The β-blockers are conjugated to the polymer backbone of the polymer-drug conjugate via the alcohol moiety of the beta-amino alcohol group of the drug.

TABLE 2

| Drug | Structure |
|---|---|
| betaxolol | 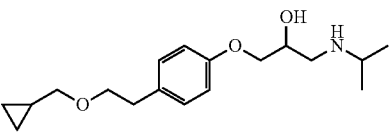 [SMILES: CC(C)NCC(O)COc1ccc(CCOCC2CC2)cc1] |
| levobunolol | 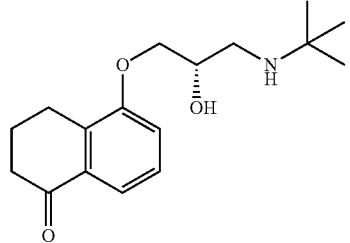 [SMILES: CC(C)(C)NC[C@H](O)COc1cccc2c1CCCC2=O] |
| Timolol | 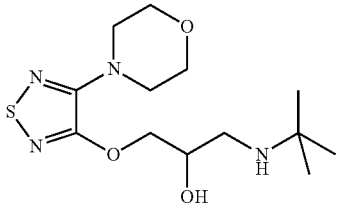 [SMILES: CC(C)(C)NCC(O)COc1nsnc1N1CCOCC1] |
| carteolol | 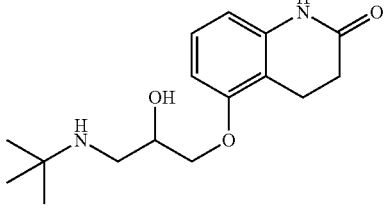 |
| metripranolol | 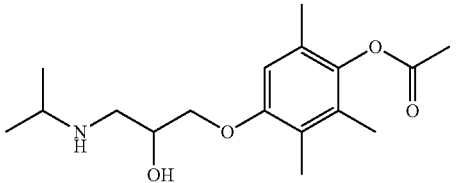 [SMILES: CC(=O)Oc1c(C)cc(OCC(O)CNC(C)C)c(C)c1C] |

Although not necessarily depicted, those skilled in the art will appreciate that drugs of general formulae described herein may have particular stereoisomeric structures and possibly, particular geometric isomeric structures. For avoidance of any doubt, the general formulae shown herein are intended to embrace all such structures. Stereoisomeric structures can include the (S)-enantiomer or the (R)-enantiomer of the drug, as well as racemic mixtures.

For example, the β-blocker timolol has (S) and (R) enantiomers of the following structures:

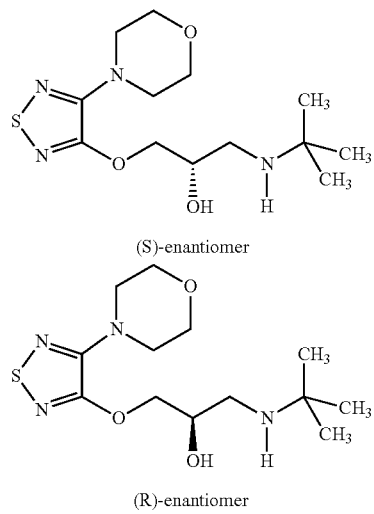

(S)-enantiomer (R)-enantiomer

When a drug can exist in different stereoisomers, the polymer-drug conjugate may be enriched in one stereoisomer. In one set of embodiments, the polymer-drug conjugate may comprise at least 70%, at least 80%, at least 90% or at least 95% of the drug as one enantiomer.

In one set of embodiments, where the polymer-drug conjugate comprises a β-blocker, it may comprise the (S)-enantiomer of the β-blocker, such as for example, the (S)-enantiomer of timolol.

Examples of suitable spacer moieties that may form part of L include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkyloxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present the or each —$CH_2$— group in any alkyl chain may be replaced by a divalent group independently selected from —O—, —OP(O)$_2$—, —OP(O)$_2$O—, —S—, —S(O)—, —S(O)$_2$O—, —OS(O)$_2$O—, —N=N—, —OSi(OR$^b$)$_2$O—, —Si(OR$^b$)$_2$O—, —OB(OR$^b$)O—, —B(OR$^b$)O—, —NR$^b$—, —C(O)—, —C(O)O—, —OC(O)O—, —OC(O)NR$^b$— and —C(O)NR$^b$—, where the or each R$^b$ may be independently selected from hydrogen, alkyl, alkenyl, alkynyl, aryl, carbocyclyl, heteroaryl, heterocyclyl, arylalkyl, and acyl. The one or more R$^b$ groups may also be independently selected from hydrogen, $C_{1-18}$alkyl, $C_{6-18}$aryl, $C_{3-18}$carbocyclyl, $C_{3-18}$heteroaryl, $C_{3-18}$heterocyclyl, and $C_{7-18}$arylalkyl.

In some embodiments the spacer moiety may be branched. Where the spacer moiety is branched, two or more releasable drugs may be appended to the spacer moiety.

In the lists above defining groups (generally divalent) from which each spacer moiety may be selected, each alkyl, alkenyl, alkynyl, aryl, carbocyclyl, heteroaryl, and heterocyclyl moiety may be optionally substituted. For avoidance of any doubt, where a given spacer moiety contains two or more of such moieties (e.g. alkylaryl), each of such moieties may be optionally substituted with one, two, three or more optional substituents as herein defined.

In the lists above defining groups (generally divalent) from which the or each spacer moiety may be selected, where a given spacer moiety contains two or more subgroups (e.g. [group A][group B]), the order of the subgroups is not intended to be limited to the order in which they are presented. Thus, a spacer moiety with two subgroups defined as [group A][group B] (e.g. alkylaryl) is intended to also be a reference to a spacer moiety with two subgroups defined as [group B][group A] (e.g. arylalkyl).

Some specific examples of spacer moieties that may form part of L include: —O—; —C(O)—; —OC(O)— and optionally substituted: —OC(O)—$C_{1-18}$alkylene-C(O)—; —C(O)O—$C_1$-$C_{18}$alkylene-C(O)O—; —O—Ar—C(O)O—; —O—Ar—C(O)—$NR^b$—; —O—Ar—; —C(O)O—Ar—C(O)O—; —C(O)O—Ar—C(O)—$NR^b$—; —C(O)O—Ar—; —C(O)O—Ar—; —$NR^b$C(O)—$C_1$-$C_{18}$alkylene-C(O)—; —C(O)O—$C_1$-$C_{18}$alkylene-O—; —OC(O)O—$C_1$-$C_{18}$alkylene-O—; —O—$C_1$-$C_{18}$alkylene-O—; —O—$C_1$-$C_{18}$alkylene-$NR^b$—; —OC(O)—$C_1$-$C_{18}$alkylene-$NR^b$—; —C(O)—$C_1$-$C_{18}$alkylene-$NR^b$—; —OC(O)—$C_1$-$C_{18}$alkylene-O—; —C(O)—$C_1$-$C_{18}$alkylene-O—; and —C(O)$NR^b$—$C_1$-$C_{18}$alkylene-$NR^b$— where $R^b$ is as defined above for the spacer moiety.

In one form of the invention, exemplary spacer moieties include: —O—; —C(O)—; —OC(O)O—$C_1$-$C_{18}$alkylene-O—; and —OC(O)—$C_{1-18}$alkylene-C(O)—, such as —OC(O)—$C_{2-3}$alkylene-C(O)—, —O—$C_{5-6}$Ar—C(O)O and —C(O)O—$C_{5-6}$Ar—C(O)O—.

The choice of spacer moieties will determine the spacing of the drugs from the polymer backbone. The skilled artisan would be capable of selecting the appropriate spacer moiety based on an evaluation of steric constraints, phase chemistry and surface chemistry. For example, larger drugs can be advantageously spaced from the monomer by the choice of a longer spacer moiety.

In the moieties of formulae (II), (V) and (XXX), the drug (D) is coupled to R through a cleavable linking group denoted by L. As used herein "linking group" refers to a generally divalent substituent group that couples D to R. The substituent group, generally the group linking L to D such as an ester, anhydride or carbonate, is cleavable so that the drug is releasable.

In some embodiments, the cleavable linking group represented by L is a cleavable covalent bond that directly couples the drug to the polymer backbone.

In other embodiments, the cleavable linking group represented by L comprises a spacer moiety and a cleavable covalent bond. The spacer moiety is attached to the polymer backbone while the cleavable covalent bond couples the spacer moiety to the drug. In some embodiments of a polymer-drug conjugate of the invention, it is a proviso that L does not include a triazole moiety. Thus, polymer conjugates of the invention do not include drugs coupled to the polymer backbone via a product of a click chemistry reaction.

The covalent bond coupling the drug (D) with the linking group (L) is not a carbon-carbon bond. Accordingly, the cleavable covalent bond will generally form part of a functional group selected from: esters; carbonates; and anhydrides. Of these functional groups, esters and carbonates are preferred. A skilled person would recognise that such groups are capable of being cleaved, for example hydrolytically, enzymatically, and/or by radical mechanisms, so as to release the drug.

The present invention preferably employs a group selected from ester, anhydride and carbonate linking groups to conjugate the drug to the polymer backbone as such linking groups have been found to be hydrolytically labile in biological environments. Such linking groups may also be generally more labile than other groups or moieties that may be present in the polymer-drug conjugate, such as for example, biodegradable moieties that may be present in the polymer backbone of polymer conjugates of some embodiments of the invention. Ester, anhydride and carbonate linking groups may further help to ensure that a sufficient amount of the drug is effectively released from the polymer conjugate to achieve therapeutic levels in the immediate vicinity of the polymer conjugate material.

Breakdown of the cleavable covalent bond can be promoted hydrolytically (i.e. hydrolytic cleavage) and may take place in the presence of water and an acid or a base. In some embodiments the cleavage may take place in the presence of one or more hydrolytic enzymes or other endogenous biological compounds that catalyze or at least assist in the cleavage process. For example, an ester bond may be hydrolytically cleaved to produce a carboxylic acid and an alcohol.

At the very least the drug will be releasable from the conjugate per se. However, as further described below, the polymer backbone may also biodegrade in vivo or in vitro such that the polymer backbone breaks into lower molecular weight fragments, with the drug remaining tethered to such a fragment(s) via L. In that case, the drug will nevertheless still be capable of being released or cleaved from L, which may or may not still be associated with the polymer conjugate per se.

As indicated above, drug as described herein may be coupled to a spacer moiety, which in turn is attached to the polymer backbone. As used herein, the terms "spacer", "spacer group" or "spacer moiety" refer to an atom or any straight chain or branched, symmetric or asymmetric compound capable of linking or coupling the drug to a polymer backbone.

In some embodiments, the "spacer", "spacer group" or "spacer moiety" refers to a substituent which is generally divalent. As outlined above, the covalent bond between the spacer moiety and the drug is cleavable so that the drug is releasable.

Examples of suitable spacer moieties that may form part of L include the divalent form of a group selected from oxy (—O—), alkyl, alkenyl, alkynyl, aryl, acyl (including —C(O)—), carbocyclyl, heterocyclyl, heteroaryl, alkyloxy, alkenyloxy, alkynyloxy, aryloxy, acyloxy, carbocyclyloxy, heterocyclyloxy, heteroaryloxy, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, alkylheterocyclyl, alkylheteroaryl, alkyloxyalkyl, alkenyloxyalkyl, alkynyloxyalkyl, aryloxyalkyl, alkylacyloxy, alkyloxyacylalkyl, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, arylalkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, arylacyloxy, arylcarbocyclyloxy, arylheterocyclyloxy, arylheteroaryloxy, alkylthioaryl, alkenylthioaryl, alkynylthioaryl, arylthioaryl, arylacylthio, arylcarbocyclylthio, arylheterocyclylthio, and arylheteroarylthio, wherein where present the or each —$CH_2$— group in any alkyl chain may be replaced by a divalent group independently selected from —O—, —$OP(O)_2$—, —$OP(O)_2O$—, —S—, —S(O)—, —$S(O)_2O$—, —$OS(O)_2O$—, —N=N—, —$OSi(OR^b)_2O$—, —$Si(OR^b)_2O$—, —$OB(OR^b)O$—, —$B(OR^b)O$—, —$NR^b$—, —C(O)—, —C(O)O—, —OC(O)O—, —OC(O)$NR^b$— and —C(O)$NR^b$—, where the or each $R^b$ may be independently selected from hydrogen, alkyl, alkenyl, alkynyl, aryl, carbocyclyl, heteroaryl, heterocyclyl, arylalkyl, and acyl. The one or more $R^b$ groups may also be independently selected from hydrogen, $C_{1-18}$alkyl, $C_{6-18}$aryl, $C_{3-18}$carbocyclyl, $C_{3-18}$heteroaryl, $C_{3-18}$heterocyclyl, and $C_{7-18}$arylalkyl.

In some embodiments the spacer moiety may be branched. Where the spacer moiety is branched, two or more releasable drugs may be appended to the spacer moiety.

In the lists above defining groups (generally divalent) from which each spacer moiety may be selected, each alkyl, alkenyl, alkynyl, aryl, carbocyclyl, heteroaryl, and heterocyclyl moiety may be optionally substituted. For avoidance of any doubt, where a given spacer moiety contains two or more of such moieties (e.g. alkylaryl), each of such moieties may be optionally substituted with one, two, three or more optional substituents as herein defined.

In the lists above defining groups (generally divalent) from which the or each spacer moiety may be selected, where a given spacer moiety contains two or more subgroups (e.g. [group A][group B]), the order of the subgroups is not intended to be limited to the order in which they are presented. Thus, a spacer moiety with two subgroups defined as [group A][group B] (e.g. alkylaryl) is intended to also be a reference to a spacer moiety with two subgroups defined as [group B][group A] (e.g. arylalkyl).

Some specific examples of spacer moieties that may form part of L include: —O—; —C(O)—; —OC(O)— and optionally substituted: —OC(O)—$C_{1-18}$alkylene-C(O)—; —C(O)O—$C_{1}$-$C_{18}$alkylene-C(O)—; —O—Ar—C(O)O—; —O—Ar—C(O)—$NR^b$—; —C(O)O—Ar—C(O)O—; —C(O)O—Ar—C(O)—$NR^b$—; —C(O)O—Ar—; —C(O)O—Ar—; —$NR^b$C(O)—$C_{1}$-$C_{18}$alkylene-C(O)—; —C(O)O—$C_{1}$-$C_{18}$alkylene-O—; —OC(O)O—$C_{1}$-$C_{18}$alkylene-O—; —$C_{18}$alkylene-O—; $C_{1}$-$C_{18}$alkylene-$NR^b$—; —OC(O)—$C_{1}$-$C_{18}$alkylene-$NR^b$—; —C(O)—$C_{1}$-$C_{18}$alkylene-$NR^b$—; —OC(O)—$C_{1}$-$C_{18}$alkylene-O—; —C(O)—$C_{1}$-$C_{18}$alkylene-O—; and —C(O)$NR^b$—$C_{1}$-$C_{18}$alkylene-$Nb^a$— where $R^b$ is as defined above for the spacer moiety.

In one form of the invention, exemplary spacer moieties include: —O—; —C(O)—; —OC(O)O—$C_{1}$-$C_{18}$alkylene-O—; and —OC(O)—$C_{1-18}$alkylene-C(O)—, such as —OC(O)—$C_{2-3}$alkylene-C(O)—, —O—$C_{5-6}$Ar—C(O)O and —C(O)O—$C_{5-6}$Ar—C(O)O—.

The choice of spacer moieties will determine the spacing of the drug as from the polymer backbone. The skilled artisan would be capable of selecting the appropriate spacer moiety based on an evaluation of steric constraints, phase chemistry and surface chemistry. For example, larger drug moieties can be advantageously spaced from the monomer by the choice of a longer spacer moiety.

In some embodiments of a drug-polymer conjugate of the invention, when the drug (D) is a carboxylic acid such as a prostaglandin linked to the polymer backbone, then L is of a formula selected from the group consisting of:
(R) —O-(D);
(R) —OC(O)—Ar—O-(D);
(R) —NHC(O)—Ar—O-(D);
(R) —C(O)O—$C_{1-12}$alkylene-O-(D);
(R) —OC(O)O—$C_{1-12}$alkylene-O— (D);
(R) —OC(O)—$C_{1}$-$C_{12}$alkylene-O-(D);
(R) —OC(O)—O-(D);
(R) —OC(O)—Ar—OC(O) —O-(D);
(R) —NHC(O)—Ar—OC(O)—O (D);
(R) —C(O)O—$C_{1}$-$C_{12}$alkylene-OC(O)—O (D); and
(R) —OC(O)—$C_{1}$-$C_{12}$alkylene-OC(O)-(D).

In one embodiment, when the drug is linked via an ester formed with a drug acid residue and an alcohol —O— portion of a linker L, then L may be selected from the group consisting of —O—; —OC(O)—; —OC(O)O—$C_{1}$-$C_{6}$alkylene-O—; —O—$C_{6}$-aryl-C(O)O—; —O—$C_{6}$-aryl-C(O)NH—; —O-Pyridoxine-; and —O-Phloroglucinol-.

In one embodiment R is an aromatic group selected from the group consisting of:

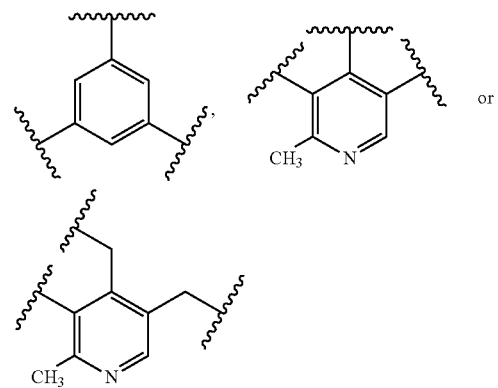

and linker L is of formula —O—.

In a further embodiment R is aliphatic of from 1 to 10 carbon atoms and L is of formula:

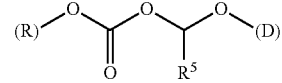

wherein $R^5$ is selected from the group consisting of hydrogen and $C_1$ to $C_6$ alkyl, preferably from the group consisting of hydrogen, methyl, ethyl, propyl, isopropyl, butyl, isobutyl, sec-butyl, and tert-butyl, more referably hydrogen or methyl.

In some embodiments of a polymer-drug conjugate of the invention, when the drug (D) comprises an alcohol such as in the case of a β-blocker of formula (XX), then L may be of a formula selected from the group consisting of:
(R) —C(O) (D);
(R) —OC(O)— (D);
(R) —OC(O)—$C_{1}$-$C_{12}$alkylene-C(O)-(D);
(R) —NHC(O)—$C_{1}$-$C_{12}$alkylene-C(O)-(D);
(R) —OC(O)—$C_{1}$-$C_{12}$alkylene-OC(O)-(D);
(R) —NHC(O)—$C_{1}$-$C_{12}$alkylene-OC(O)-(D);
(R) —OC(O)—Ar—C(O)-(D);

(R) —NHC(O)—Ar—C(O)-(D);
(R) —OC(O)—Ar—OC(O)-(D);
(R) —NHC(O)—Ar—OC(O)-(D).

In a specific embodiment, when the β-blocker is linked to the polymer backbone, then L is —C(O)—; —C(O)O—$C_1$-$C_5$alkylene-O—; —C(O)—$C_{1-5}$alkylene-C(O)O—; —C(O)—$C_{1-5}$alkylene-C(O)NH—; —C(O)O—; —C(O)O—$C_6$-aryl-C(O)O—; —C(O)O—$C_6$-aryl-C(O)NH—; —C(O)O-Pyridoxine-; and —C(O)O-Phloroglucinol-.

In another set of embodiments, the monomer of complementary functionality may be a further monomer of formula (I). In such embodiments at least two monomers of formula (IV) may react together, provided the monomers of formula (I) have complementary terminal functionality.

In some embodiments monomers of formula (I) having complementary terminal functionality may be homofunctional. That is, each of the co-monomers may comprise one type of terminal functional group. The terminal functional groups of the co-monomers would be complementary and capable of reacting with one another to form a triazole moiety. For example, one co-monomer of formula (II) may comprise a terminal functional group comprising an alkyne functionality while the other co-monomer of formula (II) comprises a terminal functional group comprising an azide functionality. These co-monomers would be able to copolymerise under appropriate conditions to form a polymer conjugate having triazole moieties in the polymer backbone.

Examples of complementary monomers of formula (I) that are capable of copolymerising to form a polymer-drug conjugate include a monomer of formula (I) where each group X is alkyne and a monomer of formula (I) wherein each group X is azide.

The monomers of formula (I) and (III) may react with one another in a mole ratio of 1:1.

The co-monomer for reaction with the drug-monomer conjugate is of formula III

J-(Y-A)$_n$           (III)

J represents a linking functional group,
n is 2 to 8, preferably 3 to 8;
Y comprises a polyether of formula $(OR^a)_m$ wherein $R^a$ is independently ethylene, propylene and butylene and m is from 1 to 300 (preferably 2 to 300) and the polyether is in chain with one or more groups which are preferably selected from one or more of optionally substituted straight or branched $C_1$ to $C_{10}$ alkylene, amino, ether, ester, amide, carbonate and carbamate;
A may be the same or different at each occurrence and represents a group comprising a terminal functional group comprising an alkyne or an azide functionality, wherein said terminal functional group is complementary to the terminal functional group X of formula (I) providing triazole moieties from reaction of X and A.

In the monomer of formula (III), A represents a group comprising a terminal functional group comprising an alkyne or an azide functionality. The azide or alkyne functionality present in terminal functional group of moiety "A" is complementary to the azide or alkyne functionality present in the terminal functional group of X in formula (I), such that upon reaction of the functional groups in A and X under click reaction conditions, a triazole moiety is formed.

In the monomer of formula (III) n is an integer and is at least 2. In some embodiments, n is an integer selected from the group consisting of 2, 3, 4, 5, 6, 7 and 8. Generally the network form of the copolymer is of particular advantage, in which case n is an integer from 3 to 8.

When n is 3 or more, the monomer of formula (III) is multifunctional and comprises 3 or more A moieties. In such embodiments, the monomer of formula (III) is a branched monomer. Monomers of formula (III) comprising at least three terminal functional groups provide branched or network architectures for the polymer conjugates of the invention.

As used herein, the term "group comprising a terminal functional group" encompasses embodiments where the group represents the terminal functional group per se, as well as embodiments where the terminal functional group is part of a larger chemical group.

The moiety "J" in formula (III) represents an optionally substituted linker group. In some embodiments J may be a divalent group. Alternatively, J may be multivalent and be a branched group. When a monomer of formula (I) and (III) copolymerise, J forms a linker segment in the polymer backbone of the conjugate.

In some embodiments, J may comprise a linker moiety selected from the group consisting of optionally substituted linear or branched aliphatic hydrocarbon, optionally substituted carbocyclyl, optionally substituted heterocyclyl, optionally substituted aryl, optionally substituted heteroaryl, an optionally substituted polymeric segment, and combinations thereof.

Optionally substituted linear or branched aliphatic hydrocarbon linker moieties may be selected from optionally substituted $C_1$ to $C_{20}$, $C_1$ to $C_{10}$ or $C_1$ to $C_6$ linear or branched aliphatic hydrocarbons. The aliphatic hydrocarbons may be saturated or unsaturated hydrocarbon.

Optionally substituted carbocyclyl linker moieties may have from 3 to 12, 3 to 8 or 5 to 6 carbon ring members.

Optionally substituted heterocyclyl linker moieties may have from 3 to 12, 3 to 8 or 5 to 6 ring members and 1, 2, 3, 4 or more heteroatoms as a part of the ring. The heterotoms may be independently selected from the group consisting of O, N and S.

Optionally substituted aryl linker moieties may have from 3 to 12, 3 to 8 or 5 to 6 carbon ring members and at least one unsaturation.

Optionally substituted heteroaryl linker moieties may have from 3 to 12, 3 to 8 or 5 to 6 ring members and 1, 2, 3, 4 or more heteroatoms as a part of the ring. The heterotoms may be independently selected from the group consisting of O, N and S. The heteroaryl linker moiety also has at least one unsaturation.

Exemplary polyethers include polymers of $C_2$ to $C_4$ alkylene diols, such as polyethylene glycol and polypropylene glycol, preferably polyethylene glycol.

Exemplary polyesters include polycaprolactone, poly(lactic acid), poly(glycolic acid) and poly(lactic-co-glycolic acid).

In one form, the polymeric linker moiety may comprise a biodegradable polymer. In general, biodegradable polymers comprise at least one biodegradable moiety.

Optionally substituted polymeric linker moieties may be of any suitable molecular weight, and the desired molecular weight may depend on the type of polymer and its properties. In some embodiments, J comprises a polymeric moiety having a molecular weight of not more than 1500.

In one set of embodiments, J comprises a polyether linker moiety derived from polyethylene glycol (PEG). The polyether segment may be derived from a PEG of suitable molecular weight. In some embodiments, the PEG has a molecular weight in the range of from about 200 to 10,000, preferably from about 200 to about 3000.

Typically J is selected from the group consisting of optionally substituted linear or branched aliphatic hydrocarbon, In one set of embodiments, J comprises a linker moiety derived from lysine, including the ethyl ester of lysine such as ethyl-2,6-bis(((3-azidopropoxy)carbonyl)amino)hexanoate (ELDN$_3$) the di(1-pentynol)urethane of the ethyl ester of lysine and the di(1-pentynol)urethane of the 1-pentynol ester of lysine.

In some embodiments, the group "J" in the formula (III) may comprise a functional group. The functional group may be selected from the group consisting of an amide, ether, ester, urethane, urea, and carbonate ester functional group. Such functional groups will generally be cleavable functional groups, which can degrade in a biological environment.

In a preferred embodiment the co-monomer is of formula III is of formula (IIIa)

 (IIIa)

wherein

A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (I);

J represents a bond, oxygen or linking functional group, $R^a$ is selected from ethylene, propylene, butylene and mixtures thereof;

m is 1 to 300;

n is 3 to 8;

B is a bond, oxygen, the group of formula -MOC(O)N(H)M'-, -MOC(O)OM'-MC(O)NHM'-, the group formula selected from (VIa), (VIb), (VIc) and (VId):

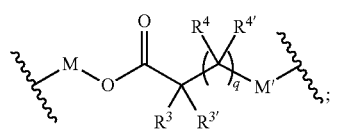 (VIa)

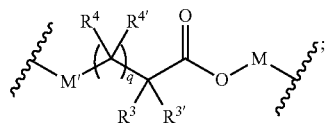 (VIb)

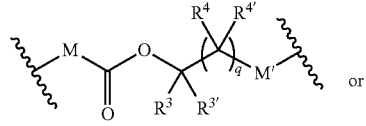 (VIc) or

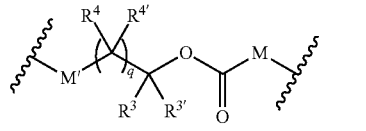 (VId)

wherein M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula, (VIa), (VIb), (VIc) and (VId) the groups $R^3$, $R^{3'}$, $R^4$ and $R^{4'}$ are independently selected from the group consisting of hydrogen, alkyl, alkoxy, alkoxy-alkyl, amino, alkyl amino, dialkylamino, amino-alkyl, alkylamino-alkyl, dialkylamino-alkyl wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl.

In one set of embodiments the comonomer of formula (III) is of formula (IIIa)

 (IIIa)

wherein

J is selected from an optionally substituted hydrocarbon or hydrocarbon ether or polyether of from 2 to 4 hydrocarbon units in each ether unit;

$R^a$ at each occurrence may be ethylene, propylene or butylene;

m is from 1 to 300, such as 1 to 100 or 1 to 50;

n is from 2 to 8 (preferably 2 to 4 such as 3 or 4);

B is a bond, oxygen, the group of formula -MOC(O)N(H)M'- or the group formula (IV)

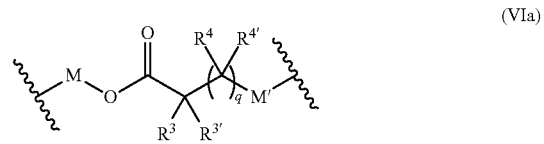 (VIa)

wherein

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and wherein in the monomers of formula (III) and (IIIa) the groups $R^3$, $R^{3'}$, $R^4$ and $R^{4'}$ are independently selected from the group consisting of hydrogen, alkyl, alkoxy and alkoxyalkyl and wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent oxygen heteroatom ring members.

In a preferred embodiment of the co-monomer of formula (III) the integer n is at least three, such as from 3 to 8 and most preferably is 3 or 4. In this embodiment the resulting co-monomer has 3 or more arms with reactive terminal group resulting in reaction with the drug-monomer of formula II to form a polymer network comprising pendent drug moieties covalently linked to the network of polymer backbone.

The moiety of formula (VIa) may be of either orientation with respect to $(OR^a)_m$ and A.

In some embodiments, specifically when n is 3 to 8 in the monomer of formula (I), Q is present and each Q-X is independently selected from the following group:

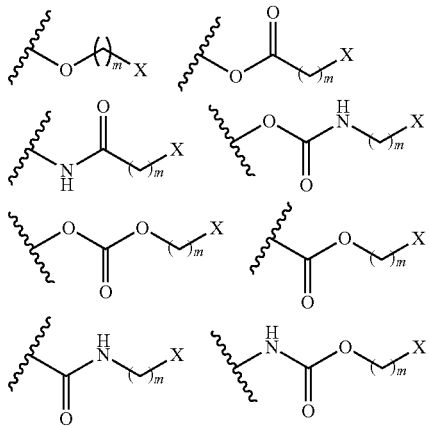

where m is from 0 to 10, preferably 0 to 6.

As described above specific example of the preferred group Q including in the monomer of formula (I) and the polymer segment of formula include:

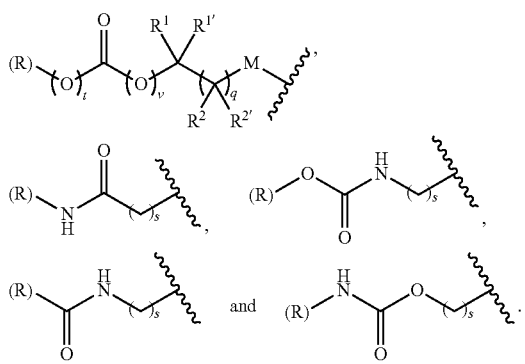

wherein
(R) indicates the end of the group attached to the group R and the opposite end is attached to (X);
each of t and v are independently 0 or 1 and at least one of t and v is 1 (preferably one of t and v is 1 and the other is 0);
$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1; and
s is from 0 to 10 preferably from 0 to 6.

Specific preferred examples of Q of this type include:

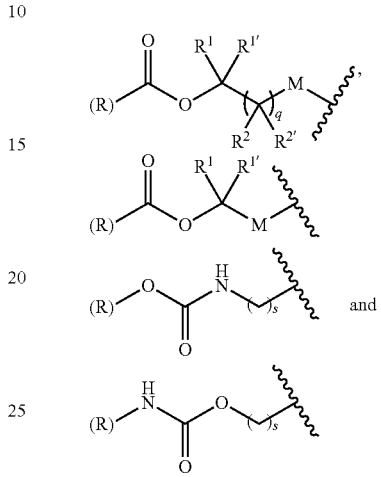

When a monomer-drug conjugate having a linking group Q is used to prepare polymer conjugates of the invention, the linking group Q becomes incorporated into the polymer backbone. Thus any linking moieties and functional groups present in Q become part of the backbone of the polymer conjugate.

When Q comprises a functional group such as an amide, ether, ester, urethane, urea, and carbonate ester functional group, such functional groups will generally be cleavable functional groups and can provide points for erosion or degradation in the polymer backbone when a monomer-bioactive agent conjugate comprising such groups is used to form the polymer conjugate. The presence of cleavable groups derived from the functional groups in the polymer backbone can facilitate breakdown of the polymer conjugate, allowing formation of lower molecular weight polymer fragments.

In a preferred set of embodiments the drug-polymer conjugate which is a co-polymer of a drug conjugate monomer of formula (IV)

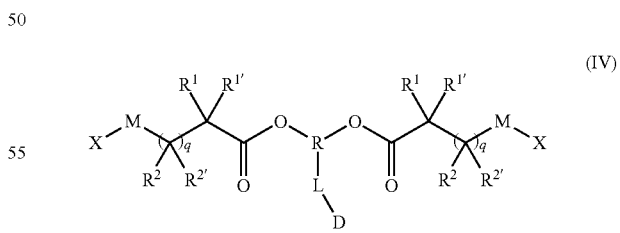

wherein
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group $N(R^w)$ wherein $R^w$ is selected from hydrogen and $C_1$ to $C_4$ alkyl;

q is 0 or 1;

X is a terminal functional group comprising an alkyne or an azide;

R is selected from the group consisting of linear or branched hydrocarbon, optionally substituted aryl and optionally substituted heteroaryl;

L is a linker group; and

D is a releasable drug;

and a co-monomer of Formula (IIIa)

$$J\text{-}((OR^a)_m\text{---}B\text{-}A)_n \quad \text{(IIIa)}$$

J is selected from an optionally substituted hydrocarbon or hydrocarbon ether or polyether of from 2 to 4 hydrocarbon units;

$R^a$ at each occurrence may be ethylene, propylene or butylene;

m is from 1 to 300;

n is from 3 to 8 (preferably 3 or 4);

B is a bond, oxygen, the group of formula -MOC(O)N(H)M'- or the group formula (IVa)

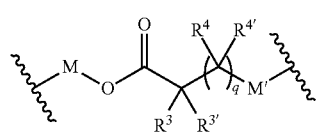

(IVa)

wherein

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —$N(R^w)$—($C_1$ to $C_{10}$ straight or branched chain aliphatic) and an amine linking group comprising $C_1$ to $C_{10}$ straight or branched chain aliphatic interrupted by the group $N(R^w)$ wherein $R^w$ is selected from hydrogen and $C_1$ to $C_4$ alkyl;

q is 0 or 1; and wherein in the monomers of formula (I) and (111a) the groups $R^1$, $R^{1'}$, $R^2$, $R^{2'}$, R3, R3', R4 and R4' are independently selected from the group consisting of hydrogen, alkyl, alkoxy, alkoxy-alkyl and wherein one of the pairs of $R^1$, R1' and $R^2$, R2', may between the members of the pair form a carbocycle or heterocycle of 3 to 6 constituent ring members wherein the heterocycle may comprise from 1 to 3 constituent oxygen heteroatom ring members; and one of the pairs of $R^3$, $R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members I.

In preferred embodiments the group B is of formula (IVa) or (IVb):

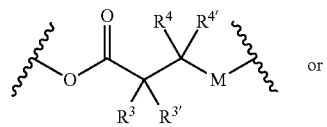

(VIa)

or

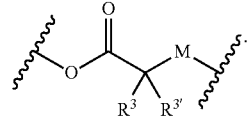

(VIb)

In this embodiment the co-monomer is branched and results in a network copolymer which we have found to provide a significant advantage in control of biodegradation.

Accordingly the invention further provides a drug-polymer conjugate, which is a hyperbranched polymer network comprising network segments of formula (XXX):

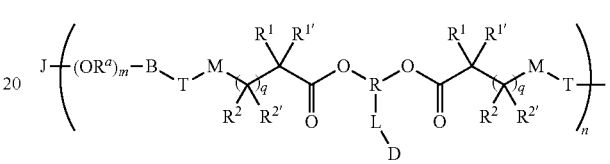

XXX wherein groups J, R, B, $R^a$, T, M, R, L and D and m and q are as hereinbefore defined for formulae (II) and (IIIa) and n is an integer of from 3 to 8 and preferably 3 or 4.

In one set of embodiments of formula (IIIa) and (XXX) the integer n is 3 to 8 and the branched linker J is a hydrocarbon of formula:

$$C_zH_{2z+2-n}$$

wherein z is from 1 to 8, preferably 3 to 8 and n is from 3 to 8 and preferably 3 or 4.

Specific examples of the linker J where n is 3 to 8 include:

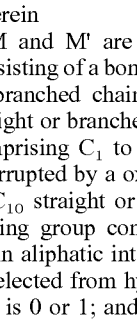

wherein n is 3; and

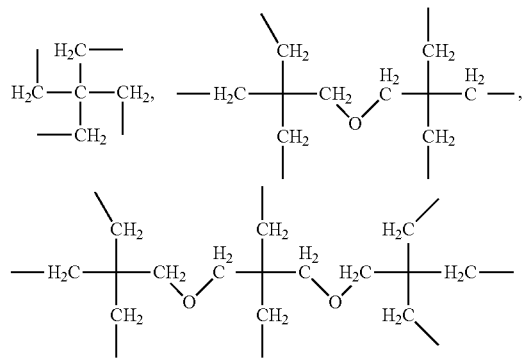

wherein n is from 4, 6 or 8.

In the formula IIIc the group $(OR^a)_m$ is a polymer of one or more of ethylene oxide, propylene oxide and butylene oxide.

In one set of embodiments the formula $(OR^a)_m$ in formula (III) or formula (XXX) is selected from poly(ethylene oxide), poly(propylene oxide), poly(butylene oxide), block copolymers of one or more of poly(ethylene oxide), poly (propylene oxide) and poly(butylene oxide), block copolymers of two or more of poly(ethylene oxide), poly(propylene oxide) and poly(butylene oxide), wherein $(OR^a)m$ has a molecular weight in the range of from 200 to 10,000.

Specific examples of the comonomer of formula (IIIa) include:

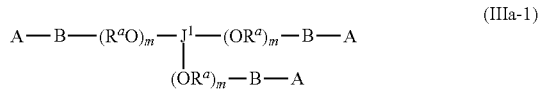
(IIIa-1)

wherein $J^1$ is of formula $C_zH_{2z-1}$ (straight or branched chain) and wherein z is an integer from 1 to 8, preferably 3 to 8; and

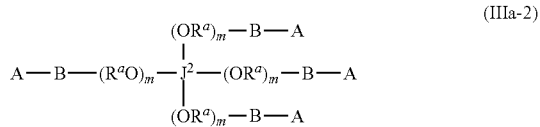
(IIIa-2)

wherein $J^2$ is of formula $C_zH_{2z-2}$ (straight or branched chain) and wherein z is an integer from 1 to 8, preferably 3 to 8.

In formulae (I), (II), (IIa), (IIb), (IIc), (IId) (IIIa), (IIIa-1), (IIIa-2), (IV), (IVa), (IVb), and (XXX) some or all of the substituents $R^1$, $R^{1'}$, $R^2$, $R^{2'}$, $R^3$, $R^{3'}$, $R^4$ and $R^{4'}$ are present.

The substituents $R^1$, $R^{1'}$, $R^2$, $R^{2'}$, $R^3$, $R^{3'}$, $R^4$ and $R^{4'}$ independently selected from the group consisting of hydrogen, alkyl, alkoxy and alkoxyalkyl and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent oxygen heteroatom ring members.

It is particularly preferred that at least one of the substituents on the carbon atom in a position alpha or beta to the carbonyl carbon, that is at least one of $R^1$, $R^{1'}$, $R^2$, $R^{2'}$, $R^3$, $R^{3'}$, $R^4$ and $R^{4'}$ (present in each of the compounds) is other than hydrogen.

The substituents other than hydrogen significantly improve the control of biodegradation of the backbone. The control allows the backbone of the drug-polymer conjugate to be degraded and any remaining drug active to be systemically diluted in the subject. The biodegradation allows the treatment term of the subject to be predetermined. This limitation on treatment term and biodegradation of the backbone are particularly advantageous in embodiments in which the drug polymer conjugate is used in localised treatment of tissue such as in the case of use of the drug-polymer conjugate in the form of an implant in treatment, for example of glaucoma.

In some embodiments at least one of $R^1$ and $R^{1'}$ is other than hydrogen and in further embodiments at least one of $R^2$ and $R^{2'}$ is other than hydrogen.

In embodiments of the invention where the monomer of formula (IIIa) and at least one of the segments of formula (VIa), (VIb), (VIc) (VId) is present, then substituents $R^3$, $R^{3'}$, $R^4$, $R^{4'}$ may be hydrogen where at least one of $R^1$, $R^{1'}$, $R^2$ and $R^{2'}$ are other than hydrogen or where $R^1$, $R^{1'}$, $R^2$ and $R^{2'}$ are hydrogen the control of biodegradation is significantly improved where at least one of $R^3$, $R^{3'}$, $R^4$ and $R^{4'}$ is other than hydrogen. In one set of embodiments at least one of $R^1$, $R^{1'}$, $R^2$ and $R^{2'}$ is other than hydrogen and at least one of $R^3$, $R^{3'}$, $R^4$, $R^{4'}$ is other than hydrogen.

It is generally preferred in order to enhance control of degradation that at least one of the groups on the carbon alpha to the carbonyl, that is $R^1$, $R^{1'}$, $R^3$ and $R^{3'}$, are other than hydrogen.

When one or more of $R^1$, $R^{1'}$, $R^2$, $R^{2'}$, $R^3$, $R^{3'}$, $R^4$ and $R^{4'}$ are other than hydrogen specific examples of the substituents other than hydrogen may be selected from the group selected from $C_1$ to $C_4$ alkyl such as methyl, ethyl, propyl, isopropyl, butyl, isobutyl, sec-butyl, and tert-butyl, $C_1$ to $C_4$ alkoxy such as methoxy, ethoxy, propyl, isopropoxy, butoxy, isobutoxy, sec-butoxy, and tert-butoxy; and $C_1$ to $C_4$ alkoxy substituted $C_1$ to $C_4$ alkyl such as one of the above $C_1$ to $C_4$ alkoxy examples substituted with one of the above $C_1$ to $C_4$ alkyl examples. Biodegradation may be enhanced by gemal-substitution with groups other than hydrogen. In cases where the carbon atom alpha or beta to the carbonyl carbon are di-substituted specific examples of the di-substitution pair may be selected from $C_1$ to $C_4$ alkyl such as methyl, ethyl, propyl, isopropyl, butyl, isobutyl, sec-butyl, and tert-butyl, $C_1$ to $C_4$ alkoxy such as methoxy, ethoxy, propyl, isopropoxy, butoxy, isobutoxy, sec-butoxy, and tert-butoxy; and C1 to C4 alkoxy substituted $C_1$ to $C_4$ alkyl such as one of the above $C_1$ to $C_4$ alkoxy examples substituted with one of the above $C_1$ to $C_4$ alkyl examples. Biodegradation is particularly enhanced where the carbon alpha to the carbonyl carbon is di-substituted, that is at least one or both of the pairs $R_1$, $R_{1'}$ and $R^3$, $R^{3'}$ are other than hydrogen.

The pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent oxygen heteroatom ring members.

Specific examples of carbocycles of this type include groups where one or more of the pairs $R^1$, $R^{1'}$; $R^2$, $R^{2'}$; $R^3$, $R^{3'}$ and; $R^4$, $R^{4'}$ between the pair form a spiro carbocycle via a linker selected from the group consisting of optionally substituted alkylene of from 2 to 5 methylene groups alkylene wherein the optional substituent is $C_1$ to $C_4$ alkyl or $C_1$ to $C_4$ alkoxy, and optionally substituted group of from 2 to 5 methylenes and from 1 to 3 oxygen heteroatoms wherein the optional substituents are $C_1$ to $C_4$ alkyl or $C_1$ to $C_4$ alkoxy.

Specific examples include the groups —$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—O—$CH_2$—$CH_2$—.

In formulas (I), (II), (IV), (IVa), (IVb) and (V) linking groups M or M and M' are present in the backbone portion of the monomer or polymer. The groups M and M' are independently selected and occurrences of M in portions of the drug-monomer conjugate and co-monomer are also independently selected. The drug-monomer conjugate contains two M linking groups which may be independently selected but in many embodiments it is convenient that they are the same. The groups M and M' are each selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N(R$^w$)—($C_1$ to $C_{10}$ straight or branched chain aliphatic) and an amine linking group comprising $C_1$ to $C_{10}$ straight or branched chain aliphatic interrupted by the group N(R$^w$) wherein is selected from hydrogen and $C_1$ to $C_4$ alkyl. Preferred examples of embodiments where M and M' are $C_1$ to $C_{10}$ aliphatic include —(CH$_2$)$_y$— where y is from 1 to 6, preferably 1 to 4 such as methylene or ethylene and wherein one or two hydrogens in the chain —(CH$_2$)$_y$— may be substituted by methylene to form an alkene branch or $C_1$ to $C_4$ alkyl. In embodiments where one or both of M and M' are selected from —O($C_1$ to $C_{10}$ straight or branched chain aliphatic) examples include —O—(CH$_2$)$_y$— where y is from 1 to 6, preferably 1 to 4 such as methylene or ethylene. In embodiments where one or both of M and M' are selected from ether linking group comprising $C_1$ to $C_{10}$ straight or branched chain aliphatic interrupted by a oxygen (—O—) examples include the group (CH2)-O—(CH2)y where y is from 1 to 6, preferably 1 to 4 such as methylene or ethylene. In embodiments where M and/or M' are the group —N(R$^w$)—($C_1$ to $C_{10}$ straight or branched chain aliphatic) and an ether linking group comprising $C_1$ to $C_{10}$ straight or branched chain aliphatic interrupted by the group N(R$^w$) wherein R$^w$ is selected from hydrogen and $C_1$ to $C_4$ alkyl examples include —N(R$^w$)—(CH2)y- where y is from 1 to 6, preferably 1 to 4 such as methylene or ethylene. In embodiments where one or both of M and M' are selected from amine linking group comprising $C_1$ to $C_{10}$ straight or branched chain aliphatic interrupted by a oxygen (—O—) examples include the group (CH2)-N(R$^w$)—(CH2)y where y is from 1 to 6, preferably 1 to 4 such as methylene or ethylene.

Specific examples of monomers of formula (I) comprising one or more groups $R^1$, $R^{1'}$; $R^2$, $R^{2'}$ other than hydrogen include the following:

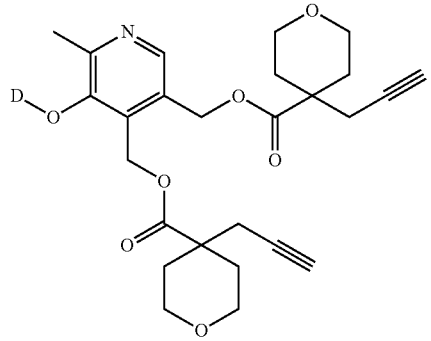

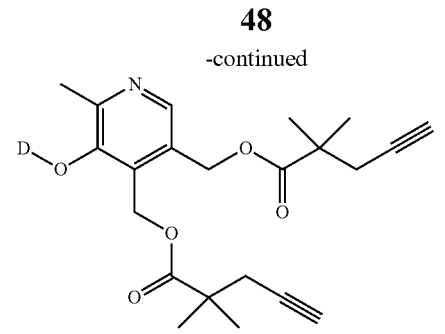

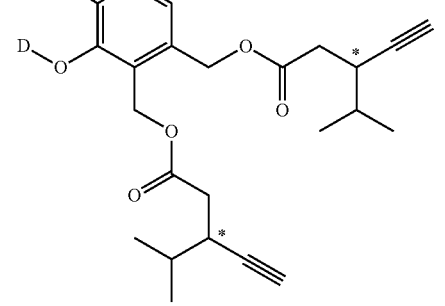

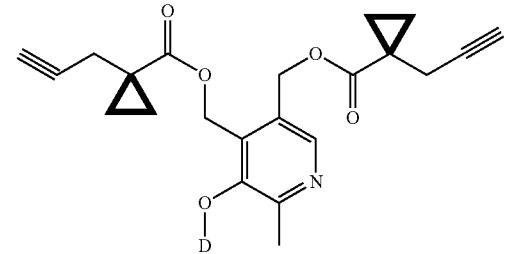

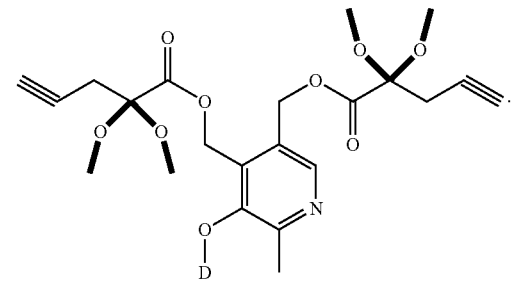

where D is the acid residue of a drug such as selected from the group consisting of the acid residue of a prostaglandin.

Examples of hyperbranched polymer networks include compounds of the following formula where the terminal crosses represent branching moieties provided by co-monomers of formula (IIIa-2):

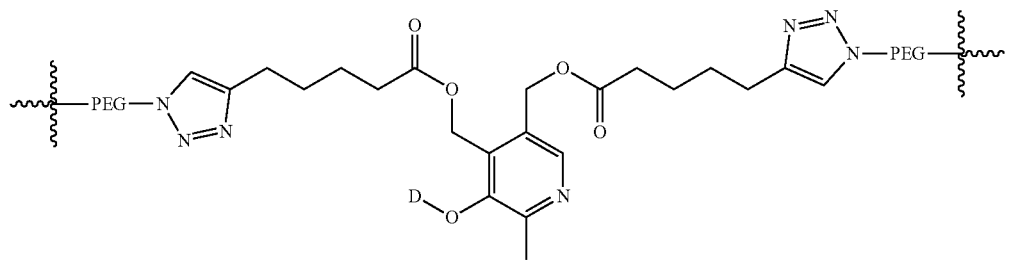

-continued
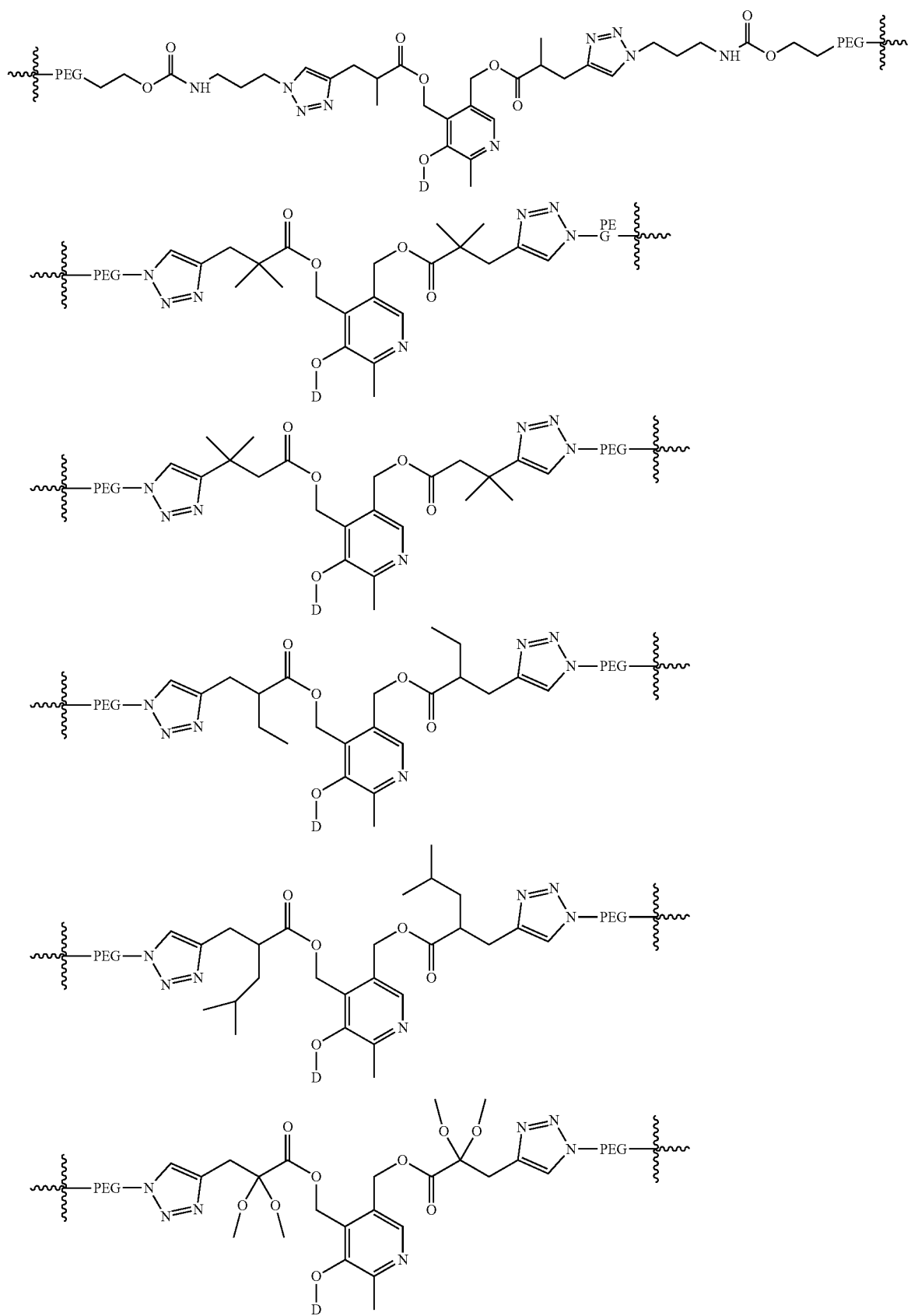

and wherein D is the acid residue of a drug such as selected from prostaglandins.

In a number of embodiments of formulae (IIa), (IIb), (IIc) and (IId) s is from 0 to 6 (preferably 0 to 2). The number s in some examples may be 0, 1 or 2.

According to one embodiment there is provided a method of delivering a drug to a subject, the method comprising administering to the subject a drug-polymer conjugate in accordance with the invention.

By the polymer conjugate being "suitable" for administration to a subject is meant that administration of the conjugate to a subject will not result in unacceptable toxicity, including allergenic responses and disease states. By the term "subject" is meant either an animal or human subject.

By "administration" of the conjugate to a subject is meant that the composition is transferred to the subject such that the drug will be released. The drug-polymer conjugate comprising prostaglandins β-blockers or mixtures thereof, may be used in the treatment of eye disorders associated with increased intraocular pressure, such as glaucoma, it is preferred that the polymer conjugate is administered to an affected eye of a subject. Administration to the eye may be by way of intracameral to either the anterior or posterior chamber, intravitreal, subchoroidal or subconjunctival administration.

The polymer conjugates may be provided in particulate form and blended with a pharmacologically acceptable carrier to facilitate administration. By "pharmacologically acceptable" is meant that the carrier is suitable for administration to a subject in its own right. In other words, administration of the carrier to a subject will not result in unacceptable toxicity, including allergenic responses and disease states. The term "carrier" refers to the vehicle with which the conjugate is contained prior to being administered.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans. Suitable pharmacologically acceptable carriers are described in Martin, Remington's Pharmaceutical Sciences, 18th Ed., Mack Publishing Co., Easton, Pa., (1990).

The polymer drug conjugates may also form part of or be formed into an article or device, or be applied as a coating on an article or device, and implanted in a subject. By being "implanted" is meant that the article or device is totally or partly introduced medically into a subject's body and which is intended to remain there after the procedure.

Suitable dosage amounts of the drug and dosing regimens of the polymer conjugates can be determined by a physician and may depend on the particular condition being treated, the rate of release of the form the polymer backbone, the severity of the condition as well the general age, health and weight of the subject.

The form of the drug-polymer conjugate may be adjusted to be suited to the required application such as a coating, film, pellet, capsule, fibres, laminate, foam etc. The difference in the form of the conjugate provides a means to alter the release profile of the drug. For example the amount of polymer and drug may be the same in two different structures however the differences in the surface area to volume, rates of hydration and diffusion paths from the different physical forms or structures can result in different rates of drug release from essentially the same polymer.

The adjustment of the form of the polymer conjugate to suit the application and further to adjust the form to further control drug release provides an additional advantage over purely compositional and polymer structural means to control the release profile of the drug.

Some of the compositional/structural means to control the release of the drug include: controlling the loading of the drug; composition of the other co-monomers to adjust criteria such as hydrophobicity, flexibility, susceptibility to degradation, ability of the fragments to autocatalyse the polymer degradation, thermal stability of the polymer, mouldability, polymer solubility to assist casting etc.

In one set of embodiments, the drug may be released from the polymer conjugate such that it provides for a sustained drug delivery system. Such a delivery system may in its simplest form be the polymer conjugate provided in a desired shape, for example a pellet or more intricate shape. To promote surface area contact of the polymer conjugate under physiological conditions or with a biological environment, it may also be provided in the form of a foamed product or a coating on substrate.

By "sustained drug moiety delivery" is meant that the drug is released from the conjugate over a period of time, for example over a period of 10 or more minutes, 30 or more minutes, 60 or more minutes, 2 or more hours, 4 or more hours, 12 or more hours, 24 or more hours, 2 or more days, 5 or more days, 10 or more days, 30 or more days, 2 or more months, 4 or more months or over 6 or more months.

Drug-polymer conjugates of the present invention may be incorporated into drug delivery systems, therapeutic articles, devices or preparations, and pharmaceutical products for the treatment of ocular hypertension.

The drug-polymer conjugates of the present invention may be blended with one or more other polymers (for example, biodegradable polymers).

Drug-polymer conjugates in accordance with the invention can be formed into an article or device. The article or device may be fabricated in a range of forms. Suitably, the article or device is a medical device, preferably an ocular implant. The polymer conjugates in accordance with the invention can also be incorporated or made into coatings for target in vitro and in vivo applications.

The drug-polymer conjugates in accordance with the invention can be formed into an article or device that is suitable for administration to the eye.

In some embodiments, a drug-polymer conjugate may be in the form of a solid article (such as a particle, rod, sphere or pellet), a semi-solid, a deformable solid, a gel, or a liquid, for placement in the eye of the subject.

In another aspect, the present invention provides an ocular implant for the treatment of glaucoma comprising a drug-polymer conjugate of any one of the embodiments described herein.

In another aspect, the present invention provides an ocular implant for the treatment or prevention of endophthalmitis or ocular inflammation glaucoma comprising a drug-polymer conjugate of any one of the embodiments described herein.

In one form, the implant is a rod-shaped or sphere-shaped and is able to be housed within the lumen of a needle, such as a 20 to 23 gauge needle. The outer diameter of the implant would be less than 0.5 mm, preferably about 0.4 mm and more preferably 0.3 mm. The length of the rod-shaped implant can be selected to deliver the required dose of drug.

The implant can be of a number of different structural forms. The ocular implant could be a solid, a semi-solid or even a gel. A solid implant would comprise material with a glass transition temperature (as measured by differential scanning calorimetry) above 37° C., a semi-solid would have a glass transition temperature at or just below 25-37° C. A gel could be formed by appropriate formulation of the polymer conjugate with an appropriate plasticiser. In one set of embodiments, the implant could be a hydrogel.

In yet another aspect the present invention provides an injectable article for placement in an eye of the subject, wherein the injectable article comprises a drug-polymer conjugate of any one of the embodiments described herein. In one form, the injectable article is an injectable gel.

It is contemplated that an ocular implant may be a bi-component polymer structure where the drug-polymer conjugate can either be incorporated in the outer or inner layers of the bi-component structure. Incorporating the drug-polymer conjugate in the outer layer could be done to give a measured dose. Additionally the inner polymer layer could be to provide structural integrity to allow the delivery via the needle. Additionally the inner polymer could be designed to degrade either faster or slower than the polymer conjugate layer. This could be to alter the rate of bioerosion or the implant.

Possible means for producing rod-shaped implants include:
   Melt extrusion of the drug-polymer conjugate or a material containing the drug-polymer conjugate through a shaped die.
   Simultaneous bi-component extrusion of the drug-polymer conjugate and other materials forming the outer or inner layers through an appropriate die.
   Sequential overcoating extrusion of one polymer later with another. For example a core polymer fibre of PLGA could be melt overcoated with a polymer containing the drug-polymer conjugate.
   It is also possible to solution coat an appropriate inner polymer carrier material (e.g. PLGA) with a solution containing the drug-polymer conjugate.

Possible means for producing rod-shaped or sphere-shaped implants include:
   Injection moulding of the drug-polymer conjugate or a material containing the drug-polymer conjugate.
   Solution casting in a mould of the drug-polymer conjugate or a material containing the drug-polymer conjugate.

In yet another aspect the present invention provides an injectable article for placement in an eye of the subject, wherein the injectable article comprises a drug-polymer conjugate of any one of the embodiments described herein. In one form, the injectable article is in the form of a gel.

In this specification "optionally substituted" is taken to mean that a group may or may not be substituted or fused (so as to form a condensed polycyclic group) with one, two, three or more of organic and inorganic groups (i.e. the optional substituent) including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocycloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups.

Preferred optional substituents include the aforementioned reactive functional groups or moieties, polymer chains and alkyl, (e.g. $C_{1-6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc.) alkoxy (e.g. $C_{1-6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1-6}$ alkyl, halo, hydroxy, hydroxy$C_{1-6}$ alkyl, $C_{1-6}$ alkoxy, halo$C_{1-6}$alkyl, cyano, nitro OC(O)$C_{1-6}$ alkyl, and amino), benzyl (wherein benzyl itself may be further substituted e.g., by $C_{1-6}$ alkyl, halo, hydroxy, hydroxy$C_{1-6}$alkyl, $C_{1-6}$ alkoxy, halo$C_{1-6}$ alkyl, cyano, nitro OC(O)$C_{1-6}$ alkyl, and amino), phenoxy (wherein phenyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), benzyloxy (wherein benzyl itself may be further substituted e.g., by $C_{1-6}$ alkyl, halo, hydroxy, hydroxy$C_{1-6}$ alkyl, $C_{1-6}$ alkoxy, halo$C_{1-6}$ alkyl, cyano, nitro OC(O)$C_{1-6}$ alkyl, and amino), amino, alkylamino (e.g. $C_{1-6}$ alkyl, such as methylamino, ethylamino, propylamino etc), dialkylamino (e.g. $C_{1-6}$ alkyl, such as dimethylamino, diethylamino, dipropylamino), acylamino (e.g. NHC(O)$CH_3$), phenylamino (wherein phenyl itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$alkyl, and amino), replacement of $CH_2$ with C=O, $CO_2H$, $CO_2$alkyl (e.g. $C_{1-6}$ alkyl such as methyl ester, ethyl ester, propyl ester, butyl ester), $CO_2$phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl amide, ethyl amide, propyl amide, butyl amide) CONHdialkyl (e.g. $C_{1-6}$ alkyl) aminoalkyl (e.g., HN $C_{1-6}$ alkyl-, $C_{1-6}$alkylHN-$C_{1-6}$ alkyl- and $(C_{1-6}$ alkyl$)_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkylO$_2$CC$_{1-6}$ alkyl-), amidoalkyl (e.g., $H_2N(O)CC_{1-6}$ alkyl-, H($C_{1-6}$ alkyl)N(O)CC$_{1-6}$ alkyl-), formylalkyl (e.g., OHCC$_{1-6}$alkyl-), acylalkyl (e.g., $C_{1-6}$ alkyl(O)CC$_{1-6}$ alkyl-), nitroalkyl (e.g., $O_2NC_{1-6}$ alkyl-), sulfoxidealkyl (e.g., $R^3$(O)SC$_{1-6}$ alkyl, such as $C_{1-6}$ alkyl(O)SC$_{1-6}$ alkyl-), sulfonylalkyl (e.g., $R^3(O)_2SC_{1-6}$ alkyl- such as $C_{1-6}$ alkyl(O)$_2$SC$_{1-6}$ alkyl-), sulfonamidoalkyl (e.g., 2HRN(O)SC$_{1-6}$ alkyl, H($C_{1-6}$ alkyl)N(O)SC$_{1-6}$ alkyl-).

It is understood that the compounds of the present invention (including monomers and polymers) may exist in one or more stereoisomeric forms (e.g. enantiomers, diastereomers). The present invention includes within its scope all of these stereoisomeric forms either isolated (in for example enantiomeric isolation), or in combination (including racemic mixtures).

The following Examples are intended to illustrate the scope of the invention and to enable reproduction and comparison. They are not intended to limit the scope of the disclosure in any way.

EXAMPLES

General Experimental Procedures

The following compounds necessary for the invention were prepared according to literature methods or unless otherwise described using techniques well known to those skilled in the art.

2-(Prop-2-yn-1-yl)pent-4-yn-1-ol (CAS 432027-96-8); (2-Hydroxypropane-1,3-diyl bis(hex-5-ynoate) (CAS1627101-87-4); 1,3-Bis(prop-2-yn-1-yloxy)propan-2-ol (CAS 16169-22-5) 2-(Prop-2-yn-1-yl)pent-4-yn-1-yl 4-hydroxybenzoate (CAS1627101-89-6) [2-(Prop-2-yn-1-yl)pent-4-yn-1-yl 3-hydroxybenzoate was prepared in the same manner]; 4-Hydroxy-N-(2-(prop-2-yn-1-yl)pent-4-yn-1-yl)benzamide (CAS1627101-91-0); 2-(Prop-2-yn-1-yl) pent-4-ynoic acid (CAS 65994-70-9) and 3-(Hex-5-ynoyloxy)-2-((hex-5-ynoyloxy)methyl)-2-methyl propanoic acid (CAS 1627101-95-4) were all prepared according to the procedures described in WO 2014134689 A1, Sep. 12, 2014. 2-(hydroxymethyl)-2-methylpropane-1,3-diyl bis(2,2-dim ethylpent-4-ynoate) and 2-(hydroxymethyl)-2-methylpropane-1,3-diyl bis(hex-5-ynoate) were prepared using standard literature methods from 1,1,1-Tris(hydroxymethyl)ethane and the corresponding carboxylic acid using DCC.

(5-Hydroxy-6-methylpyridine-3,4-diyl)bis(methylene) bis(alkanoates) were all prepared using (5-(benzyloxy)-6-methylpyridine-3,4-diyl)dimethanol (5-PMB pyridoxine) and the appropriate carboxylic acid in the same manner described in WO 2017/041142 A1, Mar. 16, 2017.

(Z)-Isopropyl 7-((1R,2R,3R,5S)-3,5-dihydroxy-2-((R)-5-phenyl-3-((2-(prop-2-yn-1-yl)pent-4-ynoyl)oxy)pentyl)cyclopentyl)hept-5-enoate; (CAS1627102-11-7); 2-((((R)-1-((1R,2R,3S,5R)-3,5-Dihydroxy-2-((Z)-7-isopropoxy-7-oxohept-2-en-1-yl)cyclopentyl)-5-phenylpentan-3-yl)oxy) carbonyl)-2-methylpropane-1,3-diyl bis(hex-5-ynoate); (CAS1672102-14-0); (R)-1-((1R,2R,3S,5R)-3,5-Dihydroxy-2-((Z)-7-isopropoxy-7-oxohept-2-en-1-yl)cyclopentyl)-5-phenylpentan-3-yl (2-(prop-2-yn-1-yl)pent-4-yn-1-yl) succinate; (CAS1627102-17-3); Z)-Isopropyl 7-((1R,2R, 3R,5S)-3,5-dihydroxy-2-((R)-5-phenyl-3-((((2-(prop-2-yn-1-yl)pent-4-yn-1-yl)oxy)carbonyl)oxy)pentyl)cyclopentyl) hept-5-enoate; (CAS 1627102-21-9); 2-(Prop-2-yn-1-yl) pent-4-yn-1-yl 4-(((((R)-1-((1R,2R,3S,5R)-3,5-dihydroxy-2-((Z)-7-isopropoxy-7-oxohept-2-en-1-yl)cyclopentyl)-5-phenylpentan-3-yl)oxy)carbonyl)oxy)benzoate; (CAS 1627102-25-3); (Z)-Isopropyl 7-((l R,2R,3R,5S)-3,5-dihydroxy-2-((R,E)-3-((2-(prop-2-yn-1-yl)pent-4-ynoyl)oxy)-4-(3-(trifluoromethyl)phenoxy)but-1-en-1-yl)cyclopentyl) hept-5-enoate (CAS 1627102-33-3); (S)-1-(tert-Butylamino)-3-((4-morpholino-1,2,5-thiadiazol-3-yl)oxy) propan-2-yl (2-(prop-2-yn-1-yl)pent-4-yn-1-yl) carbonate (CAS 1627102-47-9); (Z)-2-(Prop-2-yn-1-yl)pent-4-yn-1-yl 7-((1R,2R, 3R, 5S)-3,5-dihydroxy-2-((R,E)-3-hydroxy-4-(3-(trifluoromethyl)phenoxy)but-1-en-1-yl)cyclopentyl) hept-5-enoate (CAS 1627102-30-0); (Z)-7-((1R,2R,3R,5S)-3,5-Dihydroxy-2-((R)-3-hydroxy)-5 phenylpentyl) cyclopentyl)hept-5-enoic acid-2-prop-2-yn-1-yl)pent-4-ynoic anhydride. (CAS 1627102-35-5) were all prepared according to the procedures described in WO 2014134689 A1, Sep. 12, 2014

(5-Hydroxy-6-methylpyridine-3,4-diyl)bis(methylene) di(pent-4-yn-1-yl) bis(carbonate) was prepared using (5-(benzyloxy)-6-methylpyridine-3,4-diyl)dimethanol (5-PMB pyridoxine) and chloroformate of pent-4-yn-1-ol. The formation of the chloromate, followed by the formation of carbonate was prepared in the same manner described in WO20134689 A1, Sep. 12, 2014.

Unless otherwise described linear poly(ethylene glycol) bis(azides) of different molecular weights were purchase from commercial sources or prepared using standard literature methods. 4-Arm PEG-Azide, MW 2k, 4-Arm PEG-OH, MW 2k and 8-Arm PEG-Azide, MW 10k were purchased from Creative PEGWorks, Chapel Hill, N.C., USA.

Monomer Synthesis

Method 1A: Carbodiimide Mediated Ester Formation

To a solution of the carboxylic acid substrate (1.5 mol eq. to the hydroxyl group), the alcohol derivative (1.0 eq) and DMAP (0.1 mol. eq. of the carboxylic acid group) in anhydrous DCM, N,N'-dicyclohexylcarbodiimide (DCC) or N,N'-diisopropylcarbodiimide (DIC) (1 mol. eq. to the carboxylic acid group) is added at 0° C. The mixture is allowed to warm to room temperature and stirred for 16 h or until the reaction is complete. The reaction precipitate is removed by filtration. The filtrate is concentrated and dried in vacuo. Purification is by flash chromatography.

Method 1B: Carbodiimide Mediated Ester Formation

To a solution of the carboxylic acid substrate (1.0 eq), the alcohol derivative (1.1 eq) and DMAP (0.1 mol) in anhydrous DCM, is added dropwise a solution of N,N'-dicyclohexylcarbodiimide (DCC) or N,N'-diisopropylcarbodiimide (DIC) (1.1 eq) in anhydrous DCM at 0° C. The mixture is stirred at 0° C. for 1 h before allowing to warm to room temperature and stirring for 3 days, or until the reaction is complete. The mixture is concentrated under reduced pressure until most solvent is removed and the residue slurried with EtOAc. The resultant white precipitate is filtered through a short plug of silica, washing with EtOAc. The filtrate is dried in vacuo and the crude material purified by flash chromatography (10-100% EtOAc/petrol gradient elution) to give product.

Method 2: HBTU Mediated Ester Formation

A solution of the carboxylic acid substrate (1.0 eq.) in anhydrous THF or DCM is added to a stirring solution of HBTU (~1.2 eq.), the alcohol derivative (~1.6 eq.) and triethylamine (~4.3 eq.) in anhydrous THF or DCM under a nitrogen atmosphere. The mixture is stirred at room temperature for 3 days, with the exclusion of light, or until the reaction is complete. The reaction is quenched with 0.5 M or 1 M aqueous citric acid and extracted with DCM or ethyl acetate. The organic phase is then washed (sat. aq. $NaHCO_3$, and brine), dried ($Na_2SO_4$), filtered, concentrated, and dried in vacuo. Purification is by flash chromatography.

Method 3: Boc Anhydride Mediated Ester Formation

To a solution of the carboxylic acid substrate (1.0 eq.) in $CH_3CN$ stirred under a $N_2$ atmosphere, di-tert-butyl dicarbonate (1.3 eq.), the alcohol derivative (~1.3 eq.) and DMAP (0.1 eq.) was added. The mixture was stirred at room temperature for 16 h. Solvent was removed in vacuo. The solid was slurried with EtOAc and filtered through a plug of silica. The filtrate was dried in vacuo and the crude material purified by flash chromatography (0-100% EtOAc/petrol gradient elution) to give the product.

Method 4: Acid Chloride Mediated Ester Formation

A mixture of carboxylic acid (1 eq.) and thionyl chloride (~2 eq) is heated at 80° C. for 2 h with stirring. The reaction is allowed to cool to room temperature before the excess thionyl chloride is removed under reduced pressure to give the acid chloride.

A solution of acid chloride (3 eq) in DCM is added via cannula to a 0° C. solution of (5-((4-methoxybenzyl)oxy)-6-methylpyridine-3,4-diyl)dimethanol (1 eq) in DCM. $NEt_3$ (5.5 eq) is added and the reaction is heated at reflux for 15 h. DMAP (1 eq) is added and the mixture is heated at reflux for a further 24 h. The reaction is allowed to cool to room temperature and EtOAc and sat. aq. $NH_4Cl$ are added. The product is extracted (3× EtOAc), washed (3×$H_2O$, then brine), dried ($Na_2SO_4$), filtered and concentrated under reduced pressure. The crude material is purified by flash chromatography to provide the title compound.

Method 5: Esterification Using p-Nitrophenol Activated Esters

A solution of activated dialkyne (1.1 eq) in anhydrous DCM is slowly added to a stirring solution of boronated bimatoprost (1.0 eq) and DMAP (3.0 eq) in anhydrous DCM under a nitrogen atmosphere. The mixture is stirred at room temperature for 21 h, or until the reaction is complete. Solvent is removed in vacuo and the residue redissolved in MeOH. The mixture is then stirred at room temperature for 21 h, or until the reaction is complete. Solvent is removed in vacuo and the crude purified by flash chromatography (70-100% EtOAc/petrol gradient elution) to give the product.

Method 6: BOP-Cl Mediated Ester Formation

To a 0° C. solution of alcohol substrate (1.0 eq), carboxylic acid (1.0 eq) and triethylamine (2.0 eq) in anhydrous DCM was added BOP-Cl (1.0 eq) under a nitrogen atmosphere. The mixture is allowed to slowly warm to room temperature and stirred for 45 h or until the reaction is complete. The mixture was washed (sat. aq. $NH_4Cl$, then brine), dried ($Na_2SO_4$), filtered and concentrated under reduced pressure. The crude was purified by flash chromatography (10-100% EtOAc/petrol gradient elution) to give the title compound.

Method 7: Chloroformate Mediated Ester Formation

To a 0° C. solution of the carboxylic acid (1.0 eq) in $CH_2Cl_2$ was added $NEt_3$ (1.3 eq.) followed by ethyl chloroformate (1.2 eq.). The resulting mixture was stirred at 0° C. for 50 min before a solution of the alcohol 1.1 eq.) in $CH_2Cl_2$ was added via cannula. The mixture was stirred at 0° C. for 1 h before allowing to warm to rt and stirring for a further 18 h. The reaction was quenched ($H_2O$), extracted ($CH_2Cl_2$), washed ($H_2O$, then brine), dried ($Na_2SO_4$), filtered and concentrated under reduced pressure. Flash chromatography gave the title compound.

Method 8: PMB-Deprotection

To a solution of PMB-protected substrate (1.0 eq.) in $CH_2Cl_2$, triethylsilane ($Et_3SiH$) (1.1 eq.) is added. The resultant solution is stirred at ambient temperature for ~10 min before trifluroroacetic acid (TFA) (5 eq.) is added dropwise. The reaction mixture is stirred at room temperature for 18 h or until the reaction is complete. The reaction mixture is concentrated under reduced pressure. The residue is dissolved in DCM, washed (sat. aq $NaHCO_3$, water and brine), dried ($Na_2SO_4$), filtered, concentrated and dried in vacuo. Purification is by flash chromatography.

Method 9A: Formation of Chioroalkyl Reagents

Example 1-Chloroethyl (2-(prop-2-yn-1-yl)pent-4-yn-1-yl) carbonate

To a solution of 2-(prop-2-yn-1-yl)pent-4-yn-1-ol (2.649 g, 21.7 mmol) in anhydrous pyridine (50 mL), 1-chloroethyl chloroformate (4.70 mL, 43.4 mmol) was added dropwise at 0° C. The reaction mixture was allowed to warm to room temperature and stirred for a further 2 days. The solvent was removed under reduced pressure. The residue was extracted with ethyl acetate and washed with water and brine. The organic phase was then dried over $Na_2SO_4$, filtered and concentrated and dried in vacuo. The crude residue was purified by flash chromatography.

Method 9B

To an ice cold solution of 2-(prop-2-yn-1-yl)pent-4-yn-1-ol (2.0 g, 16.37 mmol) and DMAP (3.0 g, 24.55 mmol) in anhydrous dichloromethane (60 mL), was added 1-chloroethyl chloroformate (3.4 mL, 31.4 mmol). The reaction mixture was allowed to warm to room temperature and stirred for 18 h. The solvent was removed under reduced pressure. The crude was slurried with ethyl acetate and passed through a plug of silica. The title compound was isolated as a clear amber coloured liquid (3.01 g, 80% yield).

Method 10A: Formation of [Alkoxycarbonyl)Oxy]Alkyl Esters

Illustrated for 1-(((((2-(prop-2-yn-1-yl)pent-4-yn-1-yl)oxy)carbonyl)oxy)ethyl (Z)-7-((1R,2R,3R,5S)-3,5-dihydroxy-2-((R)-3-hydroxy-5-phenylpentyl)cyclopentyl)hept-5-enoate Example 65.

To a 0° C. solution of latanoprost free acid (1.80 mmol) in DMF (5 mL) was added $K_2CO_3$ (3.66 mmol). After 5 mins a solution of alkyl chloride (e.g. 1-chloroethyl (2-(prop-2-yn-1-yl)pent-4-yn-1-yl) carbonate 5.98 mmol) in DMF (20 mL) was added via cannula and the resultant solution was allowed to warm to room temperature and stirred for 5 days or until the reaction is complete. EtOAc and sat. aq. $NH_4Cl$ were added, the product was extracted (EtOAc), washed ($H_2O$, then brine), dried ($Na_2SO_4$) and concentrated under reduced pressure. Flash chromatography (20%-100% EtOAc/petrol gradient elution) gave 1-((((2-(prop-2-yn-1-yl)pent-4-yn-1-yl)oxy)carbonyl)oxy)ethyl (Z)-7-((1R,2R, 3R, 5S)-3,5-dihydroxy-2-((R)-3-hydroxy-5-phenylpentyl) cyclopentyl)hept-5-enoate (643.4 mg, 1.10 mmol, 61%) as a colourless viscous oil. $R_f$=0.60 (EtOAc).

Method 10B: Formation of [(Alkoxycarbonyl)Oxy]Alkyl Esters Using NaH

To a 0° C. solution of carboxylic acid or alcohol (1 eq) in THF is added NaH (1.1 eq) and the reaction stirred for 10-30 mins. A solution of alkyl chloride (2 eq) is added via cannula and the resultant solution is allowed to warm to room temperature and stirred until the reaction is complete. EtOAc and sat. aq. NH$_4$Cl are added, before the product is extracted (EtOAc), washed (H$_2$O then brine), dried (Na$_2$SO$_4$) filtered and concentrated under reduced pressure. Flash chromatography (EtOAc/petrol gradient elution) gived the [(alkoxycarbonyl)oxy]alkyl ester.

Method 11: Chloroformate Formation

To a –45° C. solution of alcohol (1 eq) and triphosgene (0.5 eq) in DCM is added DMAP (1.3 eq). The reaction is stirred at –45° C. for 1 h before allowing to warm to room temperature and stirring for 40 h. The mixture is filtered through a plug of silica before concentrating under reduced pressure.

Method 12: Carbonate Formation

To a 0° C. solution of alcohol (1 eq) and DMAP (3 eq) in DCM is added a solution of chloroformate (3 eq to the alcohol group) in DCM. The reaction is stirred at 0° C. for 1 h before allowing to warm to room temperature and stirring for 4 days, or until the reaction is complete. Silica is added and the mixture is concentrated under reduced pressure before purifying by flash chromatography (dry loaded, EtOAc/petrol gradient elution) to give the carbonate.

Method 13: Carbamate Formation

To a 0° C. solution of alcohol (1 eq) in THF is added CU (1.1 eq relative to the alcohol group). The reaction is allowed to warm to room temperature and stirred for 18 h before recooling to 0° C. Amine (2.5 eq) is added dropwise and the mixture is stirred at 0° C. for 1 h before allowing to warm to rt and stirring for 3 days, or until the reaction is complete. EtOAc and H$_2$O are added, the product is extracted (EtOAc), washed (H$_2$O, then brine), dried (Na$_2$SO$_4$), filtered and concentrated under reduced pressure. Flash chromatography (EtOAc/petrol gradient elution) provides the carbamate.

Method 14: Formation of α-Substituted Carboxylic Acids

Unless otherwise stated α-substituted carboxylic acids were prepared in the same manner as described in Org. Lett., 2010, 12(24), 5644. 5,5-dimethyl-2-(prop-2-ynyl)-1,3-dioxane-2-carboxylic acid was prepared from methyl 2,2-dimethoxypent-4-ynoate in the same manner as described in Tetrahedron: asymmetry 2008, 19(24), 2816. Ethyl 2-(prop-2-ynyloxy)propanoate was prepared in the same manner as described in WO/2007/026104 A1, Mar. 8, 2007 followed by basic hydrolysis (KOH/EtOH, 16 hours, room temperature).

Method 15: Formation of β Substituted Carboxylic Acids.

3-isopropylpent-4-ynoic acid was prepared starting from Meldrums acid and isobutyraldehdye following procedures described in Tetrahedron Letters 42 (2001) 5203-5205, Organic letters 2004, 6(13) 2281-3 and J. Am. Chem. Soc., 2003, 125, 6054-6055. 3-Methylpent-4-ynoic acid and 3,3-dimethylpent-4-ynoic acid were prepared from tert-butyl((1-ethoxyvinyl)oxy)dimethylsilane (Sigma Aldrich or J. Am. Chem. Soc 2002, 124(44), 12964-65) following methods described in U.S. Pat. No. 4,423,064, Dec. 27, 1983) followed by basic hydrolysis (KOH/EtOH, 3 days, room temperature).

Method 16: Formation of "Pyridoxine Building Blocks"

Preparation of Example 10

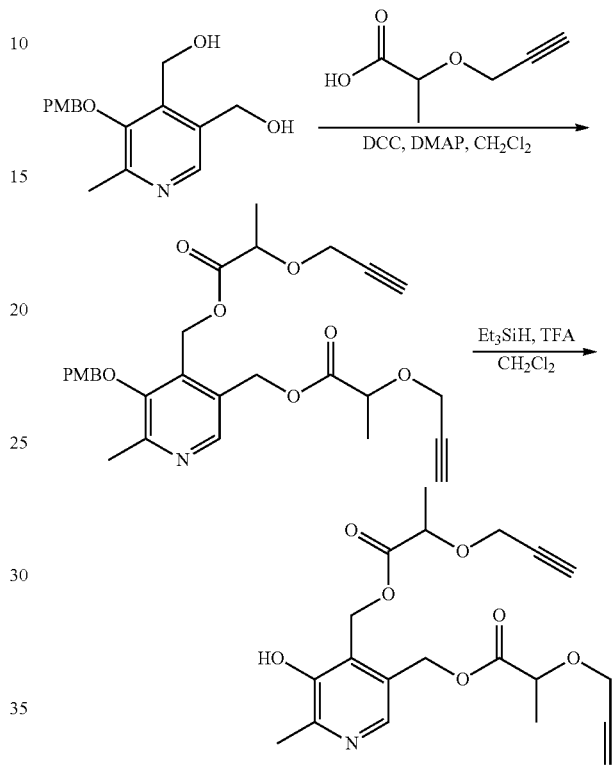

To a solution of (5-((4-methoxybenzyl)oxy)-6-methylpyridine-3,4-diyl)dimethanol (1.77 g, 6.12 mmol), 2-(prop-2-yn-1-yloxy)propanoic acid (1.93 g, 15.1 mmol) and DMAP (54.8 mg, 0.449 mmol) in CH$_2$Cl$_2$ (70 mL) was added DCC (3.06 g, 14.8 mmol) in one portion. The reaction was stirred at rt for 17 h before the resulting precipitate was removed by filtration. The filtrate was concentrated under reduced pressure and the residue purified by flash chromatography (20%-100% EtOAc/petrol gradient elution) to give (5-((4-methoxybenzyl)oxy)-6-methylpyridine-3,4-diyl)bis (methylene) bis(2-(prop-2-yn-1-yloxy)propanoate) (2.84 g, 5.57 mmol, 91%). $R_f$=0.40 (50% EtOAc/petrol)$^1$H NMR (400 MHz, CDCl$_3$) δ 8.35 (s, 1H), 7.38-7.31 (m, 2H), 6.94-6.89 (m, 2H), 5.31-5.24 (m, 4H), 4.84 (s, 2H), 4.33-4.13 (m, 6H), 2.58 (s, 3H), 2.44 (t, J=2.4 Hz, 1H), 2.40 (t, J=2.4 Hz, 1H), 1.42 (d, J=6.9 Hz, 3H), 1.40 (d, J=6.9 Hz, 3H). $^{13}$C NMR (100 MHz, CDCl$_3$) δ 172.4, 172.3, 160.1, 154.6, 152.1, 145.7, 135.7, 130.1, 129.2, 128.2, 114.3, 78.92, 78.89, 76.4, 75.4, 73.11, 73.07, 62.0, 57.9, 57.3, 55.5, 20.1, 18.59, 18.56.

Et$_3$SiH (1.0 mL, 6.3 mmol) was added to a stirred solution of (5-((4-methoxybenzyl)oxy)-6-methylpyridine-3,4-diyl) bis(methylene) bis(2-(prop-2-yn-1-yloxy)propanoate) (2.84 g, 5.57 mmol) in CH$_2$Cl$_2$ (100 mL). The resultant solution was stirred at rt for 10 min before TFA (2.4 mL, 31 mmol) was added dropwise. The reaction mixture was stirred at rt for 18 h before the volatiles were removed under reduced pressure. The residue was dissolved (CH$_2$Cl$_2$), washed (sat. aq. NaHCO$_3$, then H$_2$O, then brine), dried (Na$_2$SO$_4$), filtered and concentrated under reduced pressure. Flash chromatography (20%-100% EtOAc/petrol gradient elution) gave (5-hydroxy-6-methylpyridine-3,4-diyl)bis(methylene) bis (2-(prop-2-yn-1-yloxy)propanoate) (1.93 g, 4.96 mmol, 89%).

Preparation of Precursors for Drug-Monomers

Using the above methods and methods known to those skilled in the art, the following building block presursors to the drug-monomers were prepared.

TABLE 3

Examples of Building Block Precursors for drug-monomers:

| Ex | Structure/Name | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|
| 1 | 2-Methyl-4,5-bis((prop-2-yn-1-yloxy)methyl)pyridin-3-ol | Clear colourless oil | δ 7.95 (s, 1H), 4.95 (s, 2H), 4.55 (s, 2H), 4.27 (d, J = 2.4 Hz, 2H), 4.12 (d, J = 2.4 Hz, 2H), 2.55 (t, J = 2.4 Hz, 1H), 2.51-2.44 (m, 4H). | δ 150.86, 148.88, 140.53, 127.82, 76.41, 75.28, 67.04, 66.79, 58.35, 57.07, 18.88. | ([M + H]$^+$) 245 |
| 2 | (5-Hydroxy-6-methylpyridine-3,4-diyl)bis(methylene) bis(pent-4-ynoate) | Clear colourless oil | δ 8.13 (s, 1H), 5.27 (s, 2H), 5.23 (s, 2H), 2.68-2.43 (m, 12H), 1.99 (t, J = 2.6 Hz, 1H), 1.94 (t, J = 2.6 Hz, 1H). | δ 174.43, 171.29, 150.76, 150.03, 141.16, 129.00, 82.13, 81.49, 69.63, 69.37, 61.59, 58.30, 33.29, 33.09, 19.40, 14.33, 14.23. | — |
| 3 | (5-Hydroxy-6-methylpyridine-3,4-diyl)bis(methylene) bis(hex-5-ynoate) | — | δ 8.32 (s, 1H), 5.29 (s, 2H), 5.26 (s, 2H), 2.69 (s, 3H), 2.56 (dt, J = 11.5, 7.4 Hz, 4H), 2.27 (ddd, J = 11.9, 6.9, 2.6 Hz, 4H), 1.99 (t, J = 2.6 Hz, 1H), 1.96 (t, J = 2.6 Hz, 1H), 1.86 (m, 4H). | δ 175.9, 172.6, 152.4, 148.1, 135.4, 132.6, 132.5, 83.0, 82.7, 69.9, 69.7, 60.5, 57.6, 32.7, 32.5, 23.4, 23.3, 17.9, 17.8, 16.6. | 358 ([M + H]$^+$). |
| 4 | (5-Hydroxy-6-methylpyridine-3,4-diyl)bis(methylene) bis(hept-6-ynoate | Clear colourless oil | δ 8.11 (s, 1H), 5.20 (d, J = 12.8 Hz, 4H), 2.53 (s, 3H), 2.44-2.33 (m, 4H), 2.20 (tdd, J = 6.9, 4.1, 2.7 Hz, 4H), 1.95 (t, J = 2.6 Hz, 2H), 1.82-1.68 (m, 4H), 1.60-1.45 (m, 4H). | δ 176.14, 172.87, 150.77, 149.98, 141.29, 129.08, 127.28, 83.77, 83.56, 68.90, 68.75, 61.27, 58.00, 33.65, 33.40, 27.78, 27.59, 23.85, 23.66, 19.51, 18.11, 18.05. | ([M + H]$^+$) 386 |
| 5 | (5-Hydroxy-6-methylpyridine-3,4-diyl)bis(methylene) bis(2-methylpent-4-ynoate) | Colourless oil | δ 8.15 (s, 1H), 5.28 (s, 2H), 5.23 (s, 2H), 2.67-2.78 (m, 2H), 2.57 (s, 3H), 2.37-2.55 (m, 4H), 2.02 (t, J = 2.6 Hz, 1H), 1.91 (t, J = 2.5 Hz, 1H), 1.28 (d, J = 7.1 Hz, 3H), 1.26 (d, J = 7.1 Hz, 3H). | — | ([M + H]$^+$) 358.2 |

TABLE 3-continued

Examples of Building Block Precursors for drug-monomers:

| Ex | Structure/Name | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|
| 6 | 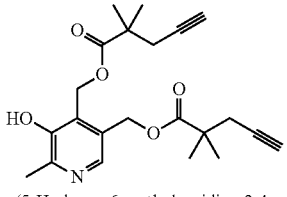<br>(5-Hydroxy-6-methylpyridine-3,4-diyl)bis(methylene) bis(2,2-dimethylpent-4-ynoate) | Colourless oil | δ 8.23 (s, 1H), 5.30 (s, 2H), 5.24 (s, 2H), 2.61 (s, 3H), 2.44 (d, J = 2.7 Hz, 2H), 2.41 (d, J = 2.6 Hz, 2H), 2.04 (m, 1H), 1.87 (t, J = 2.6 Hz, 1H), 1.30 (s, 6H), 1.28 (s, 6H). | — | — |
| 7 | 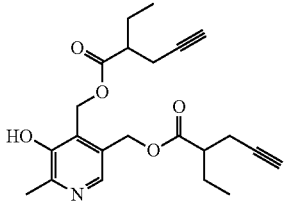 [SMILES: C#CCC(CC)C(=O)OCc1cnc(C)c(O)c1COC(=O)C(CC)CC#C]<br>(5-Hydroxy-6-methylpyridine-3,4-diyl)bis(methylene) bis(2-ethylpent-4-ynoate) | Colourless oil | δ 8.12 (s, 1H), 8.03 (s, 1H), 5.29 (s, 2H), 5.23 (s, 2H), 2.62-2.30 (m, 9H), 1.96 (t, J = 3.3 Hz, 1H), 1.86 (t, J = 2.6 Hz, 1H), 0.90 (t, J = 7.4 Hz, 3H), 0.83 (t, J = 7.5 Hz, 3H). | δ 177.17, 174.10, 150.99, 149.84, 141.94, 128.85, 127.20, 81.33, 80.60, 70.37, 70.12, 61.70, 58.35, 46.09, 45.94, 24.53, 24.49, 20.76, 20.73, 19.79, 11.43, 11.28. | — |
| 8 | 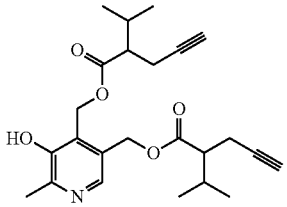 [SMILES: C#CCC(C(=O)OCc1cnc(C)c(O)c1COC(=O)C(CC#C)C(C)C)C(C)C]<br>(5-Hydroxy-6-methylpyridine-3,4-diyl)bis(methylene) bis(2-isopropylpent-4-ynoate) | Colourless oil | δ 8.13 (s, 1H), 8.03 (s, 1H), 5.34-5.19 (m, 4H), 2.54-2.36 (m, 9H), 2.02-1.88 (m, 3H), 1.80 (t, J = 2.1 Hz, 1H), 0.96-0.86 (m, 9H), 0.81 (d, J = 6.8 Hz, 3H). | — | ([M + H]$^+$) 414.0 |
| 9 | 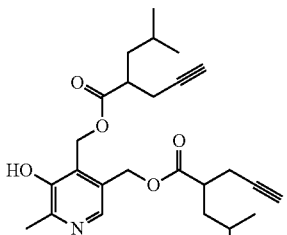<br>(5-Hydroxy-6-methylpyridine-3,4-diyl)bis(methylene) bis(2-isobutylpent-4-ynoate) | Colourless oil | δ 8.12 (s, 1H), 8.01 (s, 1H), 5.29 (s, 2H), 5.22 (m, 2H), 2.69 (m, 2H), 2.52 (s, 3H), 2.48-2.33 (m, 4H), 1.96 (t, J = 2.6 Hz, 1H), 1.84 (m, 1H), 1.70-1.37 (m, 6H), 0.94-0.78 (m, 12H). | — | — |
| 10 | 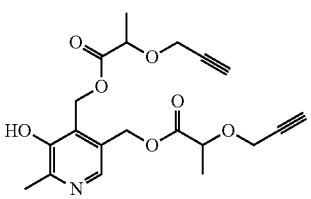 [SMILES: C#CCOC(C)C(=O)OCc1cnc(C)c(O)c1COC(=O)C(C)OCC#C]<br>(5-Hydroxy-6-methylpyridine-3,4-diyl)bis(methylene) bis(2-(prop-2-yn-1-yloxy)propanoate) | Colourless oil | δ 8.14 (s, 1H), 7.85 (s, 1H), 5.32 (s, 2H), 5.27 (m, 2H), 4.32-4.23 (m, 4H), 4.18 (ddd, J = 16.0, 6.1, 2.4 Hz, 2H), 2.53 (s, 3H), 2.43 (t, J = 2.4 Hz, 2.33 (t, J = 2.4 Hz, 1H), 1.44 (d, J = 4.9 Hz, 3H), 1.42 (d, J = 4.9 Hz, 3H). | — | — |

TABLE 3-continued

Examples of Building Block Precursors for drug-monomers:

| Ex | Structure/Name | Appearance | ¹H (CDCl₃) (unless otherwise stated) δ (ppm) | ¹³C (CDCl₃) (unless otherwise stated) δ (ppm) | ESI-MS |
|---|---|---|---|---|---|
| 11 | (5-Hydroxy-6-methylpyridine-3,4-diyl)bis(methylene) bis (2,2-dimethyl-3-(prop-2-yn-1-yloxy)propanoate) | Colourless oil | δ 8.34 (s, 1H), 5.29 (s, 2H), 5.25 (s, 2H), 4.11 (d, J = 2.4 Hz, 2H), 4.06 (d, J = 2.4 Hz, 2H), 3.52 (s, 2H), 3.50 (s, 2H), 2.68 (s, 3H), 2.45 (t, J = 2.4 Hz, 1H), 2.42 (t, J = 2.4 Hz, 1H), 1.23 (s, 6H), 1.22 (s, 6H). | — | — |
| 12 | (5-Hydroxy-6-methylpyridine-3,4-diyl)bis(methylene) bis(4-(prop-2-yn-1-yl)tetrahydro-2H-pyran-4-carboxylate) | Yellow oil | δ 8.14 (s, 1H), 7.78 (s, 1H), 5.34 (s, 2H), 5.26 (s, 2H), 3.78 (m, 4H), 3.45 (m, 4H), 2.54 (s, 3H), 2.45 (dd, J = 8.7, 2.6 Hz, 4H), 2.10 (m, 4H), 2.01 (m, 1H), 1.84 (t, J = 2.6 Hz, 1H), 1.72-1.60 (m, 4H). | δ 177.25, 174.28, 150.83, 149.75, 141.86, 128.77, 127.04, 79.10, 78.36, 72.03, 71.95, 65.04, 64.87, 61.92, 58.63, 44.93, 44.75, 33.25, 33.19, 29.37, 29.30, 19.73. | ([M + H]⁺) 470.0 |
| 13 | (5-Hydroxy-6-methylpyridine-3,4-diyl)bis(methylene) bis(3,3-dimethylpent-4-ynoate) | Colourless semi solid viscous oil | δ 8.12 (s, 1H), 5.27 (s, 2H), 5.21 (s, 2H), 2.57-2.41 (m, 7H), 2.13 (s, 1H), 2.05 (s, 1H), 1.33 (s, 6H), 1.30 (s, 6H). | δ 173.33, 170.34, 150.89, 149.88, 141.90, 128.87, 127.28, 89.89, 89.16, 69.17, 68.81, 61.49, 58.15, 46.94, 46.76, 29.97, 29.86, 29.39, 19.76. | ([M + H]⁺) 386.8 |
| 14 | (5-Hydroxy-6-methylpyridine-3,4-diyl)bis(methylene) bis(3-isopropylpent-4-ynoate) | Colourless oil | δ 8.12 (s, 1H), 5.27 (dd, J = 19.9, 14.1 Hz, 4H), 2.90-2.69 (m, 2H), 2.64-2.40 (m, 7H), 2.09-2.06 (m, 1H), 1.97 (dt, J = 13.3, 6.6 Hz, 1H), 1.82-1.63 (m, 2H), 1.04-0.89 (m, 12H). | δ 174.70, 171.51, 151.03, 149.99, 141.76, 128.96, 84.13, 83.47, 71.47, 71.20, 61.78, 58.43, 38.05, 37.79, 35.09, 35.04, 31.32, 31.25, 20.88, 20.76, 19.71, 18.24, 18.17. | — |
| 15 | (5-hydroxy-6-methylpyridine-3,4-diyl)bis(methylene) bis(3-methylpent-4-ynoate) | Yellow oil | (400 MHz) δ 8.11 (1H), 5.34-5.16 (m, 4H), 3.04-2.85 (m, 2H), 2.57 (m, 2H), 2.50 (s, 3H), 2.45 (m 2H), 2.05 (d, J = 2.4 Hz, 1H), 2.00 (d, J = 2.4 Hz, 1H), 1.19 (ddd, J = 12.8, 9.4, 5.3 Hz, 6H). | (101 MHz) δ 173.89, 170.94, 150.95, 149.95, 141.86, 128.85, 127.25, 86.89, 86.23, 69.54, 69.25, 61.72, 58.33, 41.43, 41.16, 22.73, 22.70, 20.72, 20.64, 19.76. | |

TABLE 3-continued

Examples of Building Block Precursors for drug-monomers:

| Ex | Structure/Name | Appearance | ¹H (CDCl₃) (unless otherwise stated) δ (ppm) | ¹³C (CDCl₃) (unless otherwise stated) δ (ppm) | ESI-MS |
|---|---|---|---|---|---|
| 16 | (5-Hydroxy-6-methylpyridine-3,4-diyl)bis(methylene) di(pent-4-yn-1-yl) bis(carbonate) | Clear colourless oil | δ 8.21 (s, 1H), 5.32 (s, J = 10.6 Hz, 2H), 5.26 (s, J = 10.2 Hz, 2H), 4.28 (dt, J = 14.6, 6.3 Hz, 4H), 2.61 (s, 3H), 2.35-2.24 (m, 4H), 2.01-1.94 (m, 2H), 1.94-1.79 (m, 4H). | — | ([M + H]⁺) 390 |
| 17 | | Colourless oil | ¹H NMR (400 MHz, CDCl₃) δ 8.22 (br s, 1H), 5.47 (s, 2H), 5.36 (s, 2H), 3.30 (s, 6H), 3.28 (s, 6H), 2.81 (d, J = 2.9 Hz, 2H), 2.81 (d, J = 3.0 Hz, 2H), 2.05 (t, J = 2.7 Hz, 1H), 1.89 (t, J = 2.7 Hz, 1H). | — | — |
| 18 | | Colourless oil | ¹H NMR (400 MHz, CDCl₃) δ 8.18 (s, 1H), 5.46 (s, 2H), 5.36 (s, 2H), 3.57-3/46 (m, 8H), 2.75 (m, 4H), 2.53 (s, 3H), 2.05 (td, J = 2.6, 1.2 Hz, 1H), 1.91 (t, J = 2.7 Hz, 1H), 1.18 (s, 6H), 0.70 (s, 6H). | ¹³C NMR (100 MHz, CDCl₃) δ 170.6, 168.4, 150.9, 149.8, 142.2, 128.2, 127.1, 98.4, 98.3, 77.0, 76.4, 73.9, 73.8, 72.1, 72.0, 62.8, 59.6, 38.8, 30.2, 30.1, 29.72, 29.70, 22.7, 22.6, 21.90, 21.87, 19.7. | — |
| 19 | | Yellow oil | ¹H NMR (400 MHz, CDCl₃) δ 8.08 (s, 1H), 5.37 (br s, 1H), 5.19 (s, 2H), 5.16 (s, 2H), 3.99 (dd, J = 5.6, 2.5 Hz, 2H), 2.38 (s, 3H), 2.36 (t, J = 7.5 Hz, 2H), 2.27 (t, J = 2.5 Hz, 1H), 2.20 (td, J = 7.0, 2.6 Hz, 2H), 1.95 (t, J = 2.6 Hz, 1H), 1.75 (m, 2H), 1.54 (m, 2H). | ¹³C NMR (100 MHz, CDCl₃) δ 173.0, 157.9, 151.3, 150.4, 141.6, 129.0, 127.3, 84.0, 78.8, 72.5, 68.9, 61.5, 58.8, 33.8, 31.3, 27.9, 24.0, 19.8, 18.2. | — |
| 20 | | Yellow oil | ¹H NMR (400 MHz, CDCl₃) δ 8.22 (br s, 1H), 8.11 (s, 1H), 5.23 (s, 2H), 5.21 (s, 2H), 4.96 (br s, 1H), 4.00 (m, 2H), 2.52 (s, 3H), 2.41 (t, J = 7.5 Hz, 2H), 2.25 (t, J = 2.5 Hz, 1H), 2.20 (td, J = 7.0, 2.7 Hz, 2H), 1.95 (t, J = 2.7 Hz, 1H), 1.75 (m, 2H), 1.52 (m, 2H). | ¹³C NMR (100 MHz, CDCl₃) δ 176.4, 155.5, 151.1, 150.0, 141.9, 129.2, 127.1, 83.8, 79.5, 72.0, 69.0, 62.4, 58.2, 33.6, 31.1, 27.7, 23.8, 19.8, 18.2. | — |
| 21 | | Colourless oil | ¹H NMR (400 MHz, CDCl₃) δ 8.23 (s, 1H), 5.33 (s, 2H), 5.26 (s, 2H), 4.20 (m, 4H), 2.61 (s, 3H), 2.23 (td, J = 7.0, 2.6 Hz, 4H), 1.95 (m, 2H), 1.80 (m, 4H), 1.61 (m, 4H) | ¹³C NMR (100 MHz, CDCl₃) δ 157.1, 154.8, 151.6, 149.7, 138.4, 130.5, 130.3, 83.7, 83.6, 69.3, 69.2, 69.0, 68.3, 64.1, 60.6, 27.7, 27.6, 24.7, 24.6, 18.13, 18.09, 18.0. | — |
| 22 | 2-(Prop-2-yn-1-yl)pent-4-yn-1-yl 3-hydroxybenzoate | Colourless solid | δ 7.62-7.56 (m, 1H), 7.55 (dd, J = 2.5, 1.5 Hz, 1H), 7.32 (dd, J = 10.2, 5.7 Hz, 1H), 7.07 (ddd, J = 8.1, 2.6, 1.0 Hz, 1H), 5.64 (s, 1H), 4.41 (d, J = 6.1 Hz, 2H), 2.48 (dd, J = 6.5, 2.7 Hz, 4H), 2.37-2.21 (m, 1H), 2.03 (t, J = 2.6 Hz, 2H). | — | — |

TABLE 3-continued

Examples of Building Block Precursors for drug-monomers:

| Ex | Structure/Name | Appearance | ¹H (CDCl₃) (unless otherwise stated) δ (ppm) | ¹³C (CDCl₃) (unless otherwise stated) δ (ppm) | ESI-MS |
|---|---|---|---|---|---|
| 23 | (structure) | Yellow oil | ¹H NMR (400 MHz, CDCl₃) δ 9.00 (s, 1H), 8.09 (s, 1H), 5.27 (s, 1H), 5.20 (s, 4H), 4.96 (s, 1H), 4.05-3.92 (m, 4H), 2.52 (s, 3H), 2.29 (t, J = 2.5 Hz, 1H), 2.27 (t, J = 2.5 Hz, 1H). | — | 332.1 [M + H]⁺ |
| 24 | (structure) | Yellow oil | ¹H NMR (400 MHz, CDCl₃) δ 8.08 (s, 1H), 5.43 (br s, 1H), 5.18 (s, 2H), 5.17 (s, 2H), 3.38-3.31 (m, 4H), 2.51 (s, 3H), 2.43-2.36 (m, 4H), 2.02 (t, J = 2.6 Hz, 1H), 2.00 (t, J = 2.6 Hz, 1H). | ¹³C NMR (100 MHz, CDCl₃) δ 158.4, 155.9, 151.1, 150.6, 141.1, 129.6, 127.7, 81.6, 81.0, 70.6, 70.4, 62.1, 58.5, 40.1, 39.9, 20.0, 19.8, 19.7. | — |
| 25 | (structure) | Colourless oil | ¹H NMR (400 MHz, CDCl₃) δ 8.48 (s, 1H), 7.90 (s, 1H), 4.87 (s, 2H), 4.40 (s, 2H), 3.64 (t, J = 6.4 Hz, 2H), 3.41 (t, J = 6.2 Hz, 2H), 2.46 (s, 3H), 2.25 (td, J = 6.9, 2.7 Hz, 2H), 2.20 (td, J = 6.9, 2.6 Hz, 2H), 1.97 (t, J = 2.7 Hz, 1H), 1.94 (t, J = 2.7 Hz, 1H), 1.85-1.78 (m, 2H), 1.71-1.53 (m, 8H). | ¹³C NMR (100 MHz, CDCl₃) δ 151.1, 148.7, 140.5, 128.2, 127.7, 84.3, 83.9, 71.4, 69.6, 69.1, 69.0, 68.9, 68.7, 28.8, 28.6, 25.4, 25.0, 19.2, 18.33, 18.27. | — |
| 26 | (structure) 3-((2,2-dimethylpent-4-ynoyl)oxy)-2-(((2,2-dimethylpent-4-ynoyl)oxy)methyl)-2-methylpropanoic acid | Pale orange semi-solid | δ 4.33-4.22 (m, 4H), 2.42 (d, J = 2.6 Hz, 4H), 2.00 (t, J = 2.7 Hz, 2H), 1.32 (s, 3H), 1.26 (d, J = 5.1 Hz, 12H). | δ 178.88, 175.92, 80.78, 70.88, 65.45, 46.47, 42.40, 29.61, 24.56, 17.82. | — |
| 27 | (structure) (Z)-7-((1R,5S,6R,7R)-3-butyl-7-((S,E)-3-hydroxy-5-phenylpent-1-en-1-yl)-2,4-dioxa-3-borabicyclo[3.2.1]octan-6-yl)-N-ethylhept-5-enamide | Colourless viscous oil | δ 7.32-7.27 (m, 2H), 7.22-7.15 (m, 3H), 5.61-5.49 (m, 2H), 5.43 (ddd, J = 18.0, 9.7, 4.3 Hz, 2H), 4.34 (s, 1H), 4.12 (s, 1H), 4.09 (dd, J = 12.7, 5.6 Hz, 1H), 3.27 (qd, J = 7.3, 5.7 Hz, 2H), 2.77-2.61 (m, 2H), 2.42 (t, J = 5.6 Hz, 1H), 2.25 (dd, J = 11.3, 4.7 Hz, 2H), 2.12 (ddd, J = 17.1, 10.9, 4.9 Hz, 3H), 1.97 (d, J = 12.9 Hz, 1H), 1.83 (dd, J = 9.2, 6.5 Hz, 4H), 1.68 (dt, J = 15.5, 7.8 Hz, 3H), 1.40-1.24 (m, 4H), 1.12 (t, J = 7.3 Hz, 3H), 0.88 (t, J = 7.1 Hz, 3H), 0.72-0.62 (m, 2H). | | |
| 28 | (structure) 4-nitrophenyl 2-(prop-2-yn-1-yl)pent-4-ynoate | Pale yellow oil | δ 8.28 (d, J = 9.2 Hz, 2H), 7.31 (d, J = 9.2 Hz, 2H), 3.13-3.04 (m, 1H), 2.86-2.72 (m, 4H), 2.12 (t, J = 2.7 Hz, 2H) | δ 170.23, 155.29, 145.60, 125.28, 122.55, 79.78, 71.35, 43.30. | — |

TABLE 3-continued

Examples of Building Block Precursors for drug-monomers:

| Ex | Structure/Name | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|
| 29 | 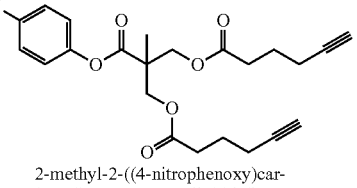<br>2-methyl-2-((4-nitrophenoxy)car-bonyl) propane-1,3-diyl bis(hex-5-ynoate) | Colourless viscous oil | δ 8.29 (d, J = 9.2 Hz, 2H), 7.28 (s, 2H), 4.43-4.35 (m, 4H), 2.51 (t, J = 7.4 Hz, 4H), 2.27 (td, J = 6.9, 2.6 Hz, 4H), 1.98 (t, J = 2.6 Hz, 2H), 1.85 (p, J = 7.1 Hz, 4H), 1.44 (s, 3H). | δ 172.50, 170.66, 155.11, 145.69, 125.36, 122.44, 83.02, 69.49, 65.31, 47.16, 32.65, 23.50, 17.80, 17.76. | — |
| 30 | 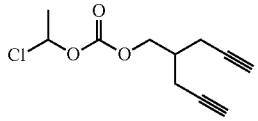<br>1-chloroethyl (2-(prop-2-yn-1-yl)pent-4-yn-1-yl) carbonate | clear colourless liquid | δ 6.43 (q, J = 5.8 Hz, 1H), 4.31 (d, J = 6.1 Hz, 2H), 2.48-2.36 (m, 4H), 2.25-2.14 (m, 1H), 2.03 (t, J = 2.6 Hz, 2H), 1.84 (d, J = 5.8 Hz, 3H). | — | — |
| 31 | 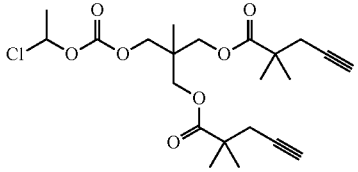 [SMILES: C#CCC(C)(C)C(=O)OCC(C)(COC(=O)OC(C)Cl)COC(=O)C(C)(C)CC#C]<br>2-((((1-chloroethoxy)carbonyl)oxy)methyl)-2-methylpropane-1,3-diyl bis(2,2-dimethylpent-4-ynoate) | Colourless oil | $^1$H NMR (400 MHz, CDCl$_3$) δ 6.40 (q, J = 5.8 Hz, 1H), 4.18 (s, 2H), 4.06 (m, 4H), 2.43 (d, J = 2.6 Hz, 4H), 2.02 (t, J = 2.7 Hz, 2H), 1.83 (d, J = 5.8 Hz, 3H), 1.29 (s, 12H), 1.08 (s, 3H). | $^{13}$C NMR (100 MHz, CDCl$_3$) δ 176.1, 152.9, 84.8, 81.0, 70.9, 70.3, 65.9, 65.9, 42.6, 39.1, 29.8, 25.3, 24.8, 17.1. | — |
| 32 | 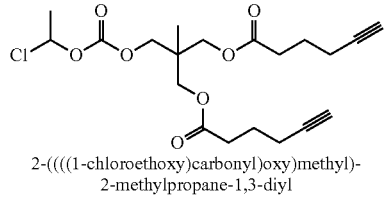<br>2-((((1-chloroethoxy)carbonyl)oxy)methyl)-2-methylpropane-1,3-diyl bis(hex-5-ynoate) | Colourless oil | $^1$H NMR (400 MHz, CDCl$_3$) δ 6.40 (q, J = 5.8 Hz, 1H), 4.15 (s, 2H), 4.03 (m, 4H), 2.48 (t, J = 7.4 Hz, 4H), 2.27 (td, J = 6.9, 2.6 Hz, 4H), 1.98 (t, J = 2.6 Hz, 2H), 1.88-1.81 (m, 7H), 1.05 (s, 3H). | $^{13}$C NMR (100 MHz, CDCl$_3$) δ 172.8, 152.9, 84.9, 83.2, 70.2, 69.5, 65.7, 65.6, 38.7, 32.8 25.3, 23.6, 18.0, 17.1. | — |
| 33 | 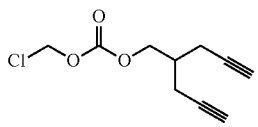<br>chloromethyl (2-(prop-2-yn-1-yl)pent-4-yn-1-yl) carbonate | Colourless oil | $^1$H NMR (400 MHz, CDCl$_3$) δ 5.74 (s, 2H), 4.33 (d, J = 6.1 Hz, 2H), 2.41 (dd, J = 6.5, 2.7 Hz, 4H), 2.21 (m, 1H), 2.03 (t, J = 2.7 Hz, 2H). | — | — |
| 34 | 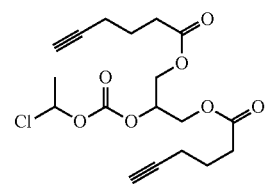 [SMILES: C#CCCCC(=O)OCC(COC(=O)CCCC#C)OC(=O)OC(C)Cl]<br>2-(((1-chloroethoxy)carbonyl)oxy)propane-1,3-diylbis(hex-5-ynoate) | Colourless oil | δ 6.42 (q, J = 5.8 Hz, 1H), 5.19 (ddt, J = 6.7, 5.9, 3.9 Hz, 1H), 4.38 (ddd, J = 12.6, 8.9, 3.9 Hz, 2H), 4.21 (ddd, J = 12.3, 9.5, 6.3 Hz, 2H), 2.50 (td, J = 7.4, 2.5 Hz, 4H), 2.27 (td, J = 6.9, 2.6 Hz, 4H), 1.97 (td, J = 2.6, 0.9 Hz, 2H), 1.91-1.80 (m, 7H). | δ 172.43, 172.39, 152.24, 84.82, 83.03, 82.99, 73.94, 69.34, 61.88, 61.76, 32.49, 32.47, 25.09, 23.36, 23.35, 17.72, 17.68. | — |

Using the above methods and the building blocks prepared in Table 4 the following drug-monomers were prepared.

TABLE 4

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 35 | 2-Methyl-4,5-bis((prop-2-yn-1-yloxy)methyl)pyridin-3-yl (Z)-7-((1R,2R,3R,5S)-3,5-dihydroxy-2-((R)-3-hydroxy-5-phenylpentyl)cyclopentyl)hept-5-enoate | 2 | Clear colourless oil | δ 8.39 (s, 1H), 7.32-7.26 (m, 2H), 7.23-7.14 (m, 3H), 5.48 (tdd, J = 18.0, 10.9, 7.0 Hz, 2H), 4.71 (s, 2H), 4.62 (s, 2H), 4.19 (d, J = 2.4 Hz, 2H), 4.16 (s, 1H), 4.08 (d, J = 2.4 Hz, 2H), 4.00-3.92 (m, 1H), 3.73-3.55 (m, 1H), 2.87-2.73 (m, 1H), 2.71-2.59 (m, 3H), 2.53-2.44 (m, 2H), 2.44-2.31 (m, 4H), 2.31-2.16 (m, 4H), 1.90-1.46 (m, 13H), 1.46-1.21 (m, 2H). | δ 171.30, 152.27, 146.38, 145.20, 142.05, 137.69, 131.31, 129.83, 129.14, 128.44, 128.42, 125.87, 79.27, 79.07, 78.77, 75.38, 74.78, 71.28, 66.48, 62.28, 57.63, 52.98, 51.94, 42.60, 39.13, 35.78, 33.30, 32.14, 29.68, 27.07, 26.68, 24.69, 19.20. | ([M + Na]$^+$) 640 |
| 36 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(pent-4-ynoate) | 2 | Clear colourless oil | δ 8.45 (s, 1H), 7.31-7.26 (m, 2H), 7.22-7.12 (m, 3H), 5.59-5.39 (m, 2H), 5.31 (s, 2H), 5.16 (s, 2H), 4.17 (d, J = 2.0 Hz, 1H), 3.97 (s, 1H), 3.72-3.59 (m, 1H), 2.85-2.72 (m, 1H), 2.72-2.61 (m, 3H), 2.61-2.15 (m, 16H), 2.01-1.95 (m, 2H), 1.92-1.66 (m, 8H), 1.66-1.47 (m, 3H), 1.47-1.21 (m, 2H). | δ 171.36, 171.24, 171.22, 153.04, 147.52, 144.76, 142.02, 129.94, 129.03, 128.45, 128.41, 125.89, 82.10, 78.80, 74.78, 71.31, 69.43, 69.39, 61.45, 57.14, 53.01, 51.91, 42.65, 39.13, 35.81, 33.34, 33.22, 32.98, 32.13, 29.69, 27.07, 26.67, 24.70, 19.56, 14.34, 14.21. | |
| 37 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(hex-5-ynoate) | 2 | colourless viscous oil | δ 8.45 (s, 1H), 7.28 (m, 2H), 7.20-7.16 (m, 3H), 5.48 (m, 2H), 5.28 (s, 2H), 5.13 (s, 2H), 4.18 (s, 1H), 3.96 (m, 1H), 3.66 (m, 1H), 2.79 (ddd, J = 13.6, 9.0, 6.3 Hz, 1H), 2.70-2.63 (m, 3H), 2.48 (t, J = 7.4 Hz, 2H), 2.44-2.34 (m, 6H), 2.27-2.21 (m, 7H), 1.96 (t, J = 2.6 Hz, 2H), 1.89-1.49 (m, 14H), 1.45-1.30 (m, 2H).. | δ 172.7, 172.6, 171.4, 152.9, 147.1, 145.0, 142.2, 136.4, 130.1, 129.1, 128.6, 128.5, 126.0, 83.14, 83.13, 78.9, 74.9, 71.4, 69.6, 61.2, 57.0, 53.1, 52.0, 42.8, 39.3, 35.9, 33.5, 32.8, 32.6, 32.3, 29., 27.2, 26.8, 24.8, 23.51, 23.47, 19.5, 17.91, 17.88 | 730 ([M + H]$^+$). |
| 38 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(hept-6-ynoate) | 2 | Clear colourless oil | δ 8.43 (s, 1H), 7.32-7.26 (m, 2H), 7.23-7.15 (m, 3H), 5.60-5.37 (m, 2H), 5.26 (s, 2H), 5.12 (s, 2H), 4.17 (s, 1H), 3.96 (s, 1H), 3.71-3.59 (m, 1H), 2.85-2.73 (m, 1H), 2.73-2.61 (m, 3H), 2.61-2.13 (m, 17H), 1.94 (td, J = 2.6, 1.9 Hz, 2H), 1.91-1.47 (m, 21H), 1.47-1.23 (m, 2H). | δ 172.82, 171.34, 153.01, 147.74, 144.63, 142.02, 135.50, 129.90, 129.57, 129.06, 128.45, 128.41, 125.88, 83.81, 78.81, 74.77, 71.31, 68.78, 68.76, 61.15, 56.81, 53.44, 53.03, 51.91, 42.66, 39.14, 35.83, 33.57, 33.37, 33.32, 32.14, 29.71, 27.74, 27.71, 27.07, 26.69, 24.72, 23.83, 23.76, 19.71, 18.10. | ([M + Na]$^+$) 780 |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 39 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2-methylpent-4-ynoate) | 2 | Viscous colourless oil | δ 8.46 (s, 1H), 7.31-7.27 (m, 2H), 7.23-7.13 (m, 3H), 5.57-5.39 (m, 2H), 5.30 (m, 2H), 5.15 (m, 2H), 4.17 (br s, 1H), 3.96 (br s, 1H), 3.66 (m, 1H), 2.82-2.58 (m, 6H), 2.53-2.18 (m, 11H), 2.00-1.96 (m, 2H), 1.91-1.50 (m, 11H), 1.05-1.45 (m, 10H). | — | — |
| 40 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2,2-dimethylpent-4-ynoate) | 2 | Viscous colourless oil | δ 8.47 (s, 1H), 7.31-7.27 (m, 2H), 7.22-7.16 (m, 3H), 5.55-5.40 (m, 2H), 5.28 (s, 2H), 5.14 (s, 2H), 4.18 (m, 1H), 3.96 (m, 1H), 3.66 (m, 1H), 2.79 (m, 1H), 2.74-2.63 (m, 3H), 2.45-2.31 (m, 8H), 2.27-2.18 (m, 3H), 2.00-1.97 (m, 2H), 1.90-1.50 (m, 9H), 1.45-1.31 (m, 3H), 1.28 (s, 6H), 1.24 (s, 6H). | δ 176.16, 176.11, 171.34, 152.93, 147.62, 144.74, 142.18, 135.32, 130.07, 129.88, 129.18, 128.58, 128.55, 126.01, 80.73, 78.96, 74.90, 71.47, 71.00, 70.97, 61.65, 57.33, 53.18, 52.05, 42.83, 42.47, 42.45, 39.29, 35.97, 33.51, 32.28, 29.83, 29.72, 27.21, 26.82, 24.84, 24.68, 24.56, 19.90. | ([M + H]$^+$) 758.4 |
| 41 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2-ethylpent-4-ynoate) | 2 | Viscous colourless oil | δ 8.47 (s, 1H), 7.31-7.27 (m, 2H), 7.23-7.16 (m, 3H), 5.56-5.39 (m, 2H), 5.30 (m, 2H), 5.17 (s, 2H), 4.18 (br s, 1H), 3.97 (m, 1H), 3.67 (m, 1H), 2.84-2.62 (m, 4H), 2.58-2.19 (m, 11H), 1.97 (m, 2H), 1.88-1.50 (m, 17H), 1.45-1.24 (m, 3H), 0.89 (q, J = 7.4 Hz, 6H). | δ 173.96, 171.35, 153.01, 147.62, 144.84, 142.18, 135.69, 130.07, 129.21, 128.60, 128.55, 126.03, 81.24, 78.99, 74.92, 71.49, 70.28, 61.39, 57.08, 53.21, 52.06, 46.09, 45.86, 42.87, 39.29, 35.98, 33.51, 32.28, 29.85, 27.22, 26.85, 24.87, 24.52, 24.29, 20.79, 20.63, 19.77, 11.43, 11.35. | — |
| 42 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2-isopropylpent-4-ynoate) | 2 | Viscous colourless oil | δ 8.48 (s, 1H), 7.30-7.27 (m, 2H), 7.21-7.16 (m, 3H), 5.55-5.40 (m, 2H), 5.32 (m, 2H), 5.16 (s, 2H), 4.18 (br s, 1H), 3.96 (m, 1H), 3.67 (m, 1H), 2.83-2.61 (m, 4H), 2.55-2.19 (m, 13H), 1.98-1.47 (m, 17H), 1.45-1.27 (m, 2H), 0.96-0.85 (m, 12H). | δ 173.69, 173.60, 171.33, 153.03, 147.94, 144.72, 142.19, 135.38, 130.05, 129.86, 129.21, 128.59, 128.55, 126.02, 81.63, 78.97, 74.91, 71.47, 70.20, 70.17, 61.27, 56.91, 53.20, 52.06, 51.80, 51.58, 42.84, 39.29, 38.76, 35.98, 33.52, 32.28, 30.25, 30.06, 29.86, 27.21, 26.84, 24.87, 20.18, 20.12, 20.06, 19.92, 19.25, 19.13. | — |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 43 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2-isobutylpent-4-ynoate) | 2 | Viscous colourless oil | δ 8.47 (s, 1H), 7.32-7.27 (m, 2H), 7.23-7.16 (m, 3H), 5.58-5.41 (m, 2H), 5.30 (m, 2H), 5.15 (s, 2H), 4.18 (br s, 1H), 3.96 (m, 1H), 3.67 (m, 1H), 2.84-2.57 (m, 6H), 2.56-2.17 (m, 13H), 1.97 (m, 2H), 1.92-1.29 (m, 19H), 0.88 (m, 12H). | δ 174.41, 174.37, 171.33, 153.05, 147.85, 144.75, 142.18, 135.35, 130.05, 129.79, 129.20, 128.59, 128.55, 126.02, 81.18, 78.98, 74.92, 71.48, 70.42, 70.39, 61.43, 57.13, 53.21, 52.07, 42.96, 42.85, 42.76, 40.80, 40.54, 39.30, 38.76, 35.98, 33.51, 32.28, 29.86, 27.21, 26.84, 26.10, 26.02, 24.88, 22.83, 22.78, 22.30, 22.27, 21.87, 21.70, 19.89. | |
| 44 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2-(prop-2-yn-1-yloxy)propanoate) | 2 | Visocus colourless oil | δ 8.47 (s, 1H), 7.31-7.27 (m, 2H), 7.23-7.15 (m, 3H), 5.57-5.40 (m, 2H), 5.35 (s, 2H), 5.21 (m, 2H), 4.34-4.14 (m, 7H), 3.97 (m, 1H), 3.66 (m, 1H), 2.83-2.61 (m, 4H), 2.52-2.33 (m, 7H), 2.30-2.18 (m, 5H), 1.91-1.48 (m, 10H), 1.45-1.31 (m, 8H). | δ 172.35, 171.45, 153.52, 147.95, 144.79, 142.15, 135.15, 130.07, 129.25, 129.17, 128.59, 128.55, 126.02, 78.97, 78.92, 78.86, 75.53, 75.46, 74.90, 73.12, 73.06, 71.44, 61.73, 57.38, 57.35, 53.19, 52.03, 42.80, 39.28, 35.97, 33.49, 32.27, 29.85, 27.21, 26.82, 24.81, 19.91, 18.58, 18.51. | ([M + H]$^+$) 762.4 |
| 45 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(2,2-dimethyl-3-(prop-2-yn-1-yloxy)propanoate) | 2 | Viscous colourless oil | δ 8.45 (s, 1H), 7.32-7.27 (m, 2H), 7.23-7.17 (m, 3H), 5.55-5.41 (m, 2H), 5.26 (s, 2H), 5.11 (s, 2H), 4.18 (br s, 1H), 4.09 (dd, J = 7.3, 2.4 Hz, 4H), 3.96 (m, 1H), 3.66 (m, 1H), 3.51 (s, 2H), 3.46 (s, 2H), 2.83-2.63 (m, 4H), 2.52 (m, 1H), 2.43-2.35 (m, 5H), 2.33-2.19 (m, 4H), 1.91-1.47 (m, 13H), 1.45-1.24 (m, 3H), 1.21 (s, 6H), 1.16 (s, 6H). | δ 175.89, 171.36, 152.65, 147.25, 144.67, 142.19, 135.43, 130.17, 130.04, 129.24, 128.59, 128.56, 126.02, 79.67, 78.99, 76.62, 76.59, 74.91, 74.71, 74.66, 71.48, 61.52, 58.66, 57.18, 53.22, 52.06, 43.77, 43.73, 42.86, 39.30, 35.98, 33.50, 32.28, 29.86, 27.22, 26.85, 24.86, 22.54, 22.48, 19.85. | — |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 46 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(4-(prop-2-yn-1-yl)tetrahydro-2H-pyran-4-carboxylate) | 2 | Yellow viscous oil | δ 8.49 (s, 1H), 7.31-7.27 (m, 2H), 7.24-7.17 (m, 3H), 5.55-5.40 (m, 2H), 5.34 (s, 2H), 5.19 (s, 2H), 4.16 (br s, 1H), 3.96 (m, 1H), 3.79 (m, 4H), 3.66 (m, 1H), 3.46 (m, 4H), 2.83-2.63 (m, 4H), 2.46-2.17 (m, 13H), 2.14-1.98 (m, 7H), 1.89-1.48 (m, 14H), 1.46-1.28 (m, 2H). | δ 174.13, 174.09, 171.29, 153.18, 147.74, 144.88, 142.18, 135.31, 130.18, 129.76, 129.07, 128.59, 128.55, 126.03, 79.03, 78.99, 78.95, 74.90, 72.15, 72.08, 71.41, 65.02, 64.97, 61.66, 57.30, 53.16, 52.03, 44.82, 44.74, 42.84, 39.29, 35.95, 33.50, 33.27, 33.11, 32.28, 29.82, 29.36, 29.22, 27.24, 26.83, 24.87, 19.86. | ([M + H]$^+$) 841.9 |
| 47 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(3,3-dimethylpent-4-ynoate) | 2 | Pale yellow viscous oil | δ 8.46 (s, 1H), 7.34-7.25 (m, 2H), 7.21-7.10 (m, 3H), 5.55-5.36 (m, 2H), 5.30 (s, 2H), 5.16 (s, 2H), 4.17 (s, 1H), 3.96 (d, J = 2.3 Hz, 1H), 3.71-3.60 (m, 1H), 2.84-2.71 (m, 1H), 2.72-2.59 (m, 3H), 2.52-2.45 (m, 2H), 2.43-2.30 (m, 6H), 2.28-2.16 (m, 3H), 2.14 (t, J = 3.4 Hz, 2H), 1.91-1.35 (m, 15H), 1.33 (s, 6H), 1.31 (m, 6H). | δ 171.43, 170.29, 170.16, 153.06, 147.89, 144.73, 142.17, 135.60, 130.03, 129.77, 129.20, 128.58, 128.54, 126.01, 89.83, 89.78, 78.94, 77.48, 77.16, 76.84, 74.88, 71.45, 68.99, 68.88, 61.28, 56.84, 53.16, 52.04, 46.89, 46.61, 42.82, 39.27, 35.96, 33.49, 32.27, 29.84, 29.75, 29.41, 29.28, 27.19, 26.82, 24.85, 19.83. | ([M + Na]$^+$) 758.7 |
| 48 | (5-(((Z)-7-((1R,2R,3R,5S)-3,5-Dihydroxy-2-((R)-3-hydroxy-5-phenylpentyl)cyclopentyl)hept-5-enoyl)oxy)-6-methylpyridine-3,4-diyl)bis(methylene) bis(3-isopropylpent-4-ynoate) | 2 | Colourless oil | δ 8.46 (s, 1H), 7.28 (m, 2H), 7.24-7.10 (m, 3H), 5.48 (m, 2H), 5.30 (s, 2H), 5.15 (m, 2H), 4.16 (s, 1H), 3.97 (s, 1H), 3.67 (m, 1H), 2.85-2.70 (m, 3H), 2.66 (dd, J = 15.3, 7.6 Hz, 3H), 2.56-2.32 (m, 8H), 2.31-2.15 (m, 4H), 2.07 (m, 2H), 1.92-1.30 (m, 16H), 1.06-0.89 (m, 12H). | δ 171.27, 171.22, 152.94, 147.64, 144.68, 142.01, 135.47, 129.89, 129.59, 129.05, 128.43, 128.39, 125.87, 83.87, 81.97, 81.81, 78.82, 74.77, 71.31, 71.18, 71.09, 61.36, 57.05, 53.06, 51.91, 42.71, 39.14, 37.80, 37.59, 35.82, 34.90, 34.71, 33.36, 32.12, 31.07, 31.01, 29.69, 27.06, 26.68, 24.71, 20.73, 20.70, 19.62, 18.04, 17.94. | ([M + Na]$^+$) 807.8 |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 49 | (5-(((Z)-7-((1R,2R,3R,5S)-3,5-dihydroxy-2-((R)-3-hydroxy-5-phenylpentyl)cyclopentyl)hept-5-enoyl)oxy)-6-methylpyridine-3,4-diyl)bis(methylene) bis(3-methylpent-4-ynoate) | 2 | Pale yellow oil | (400 MHz) δ 8.44 (s, 1H), 7.34-7.23 (m, 2H), 7.23-7.10 (m, 3H), 5.52 (dt, J = 11.0, 7.2 Hz, 1H), 5.43 (dt, J = 10.9, 7.0 Hz, 1H), 5.29 (s, J = 18.8 Hz, 2H), 5.21-5.07 (m, 2H), 4.16 (s, J = 15.6 Hz, 1H), 3.96 (s, 1H), 3.71-3.56 (m, 1H), 3.03-2.81 (m, 2H), 2.83-2.70 (m, 2H), 2.69-2.60 (m, 3H), 2.56-2.32 (m, 9H), 2.31-2.17 (m, 3H), 2.06 (d, J = 2.4 Hz, 2H), 1.98-1.46 (m, 13H), 1.46-1.28 (m, 2H), 1.21 (dd, J = 6.9, 6.2 Hz, 6H). | (101 MHz) δ 171.45, 170.89, 170.83, 153.20, 147.92, 144.78, 142.17, 135.51, 130.06, 129.56, 129.14, 128.55, 128.52, 125.98, 86.87, 86.81, 78.88, 74.82, 71.42, 69.37, 69.31, 61.48, 57.14, 53.08, 52.01, 42.79, 41.35, 41.09, 39.24, 35.94, 33.48, 32.25, 29.81, 27.17, 26.79, 26.16, 24.84, 22.71, 22.56, 20.69, 20.67, 19.81. | — |
| 50 | 2-Methyl-4,5-bis((((pent-4-yn-1-yloxy)carbonyl)oxy)methyl)pyridin-3-yl (Z)-7-((1R,2R,3R,5S)-3,5-dihydroxy-2-((R)-3-hydroxy-5-phenylpentyl)cyclopentyl)hept-5-enoate | 2 | | δ 8.53 (s, 1H), 7.98 (d, J = 8.5 Hz, 1H), 7.56-7.51 (m, 1H), 7.44-7.30 (m, 2H), 7.31-7.21 (m, 5H), 7.22-7.10 (m, 4H), 5.61 (s, 2H), 5.54-5.30 (m, 5H), 4.15 (s, 1H), 4.00-3.91 (m, 1H), 3.72-3.62 (m, 1H), 2.86-2.41 (m, 8H), 2.41-2.34 (m, 5H), 2.33-2.07 (m, 12H), 2.01-1.94 (m, 2H), 1.92-1.67 (m, 13H), 1.67-1.29 (m, 8H). | δ 173.97, 171.46, 154.81, 153.76, 148.01, 142.21, 129.95, 129.62, 129.57, 129.24, 128.54, 128.53, 125.97, 78.93, 78.89, 74.87, 71.44, 69.22, 67.12, 67.00, 64.54, 63.07, 60.38, 53.09, 53.04, 52.03, 42.75, 42.65, 39.24, 39.21, 35.94, 33.74, 33.42, 32.26, 29.78, 27.63, 27.56, 27.15, 27.07, 26.76, 24.97, 24.76, 19.80, 15.33, 15.11, 15.04. | ([M + H]$^+$) 762 |
| 51 | (5-(((Z)-7-((1R,2R,3R,5S)-3,5-dihydroxy-2-((R)-3-hydroxy-5-phenylpentyl)cyclopentyl)hept-5-enoyl)oxy)-6-methylpyridine-3,4-diyl)bis(methylene) bis(2,2-dimethoxypent-4-ynoate) | 2 | Colourless oil | $^1$H NMR (400 MHz, CDCl$_3$) δ 8.51 (s, 1H), 7.30-7.26 (m, 2H), 7.23-7.16 (m, 3H), 5.54-5.40 (m, 4H), 5.29 (s, 2H), 4.17 (br s, 1H), 3.96 (br s, 1H), 3.66 (m, 1H), 3.28 (s, 6H), 3.25 (s, 6H), 2.82-2.75 (m, 5H), 2.73-2.57 (m, 4H), 2.43-2.15 (m, 9H), 2.02 (t, J = 2.7 Hz, 1H), 2.00 (t, J = 2.7 Hz, 1H), 1.89-1.49 (m, 16H), 1.44-1.27 (m, 2H). | $^{13}$C NMR (100 MHz, CDCl$_3$) δ 171.3, 167.5, 153.4, 148.1, 144.7, 142.2, 135.0, 130.1, 129.2, 128.6, 128.5, 126.0, 101.0, 79.0, 76.8, 76.7, 74.9, 72.3, 72.1, 71.5, 62.6, 58.2, 53.2, 52.0, 50.5, 42.8, 39.3, 36.0, 33.5, 32.3, 29.9, 27.2, 26.8, 25.0, 24.8, 20.0. | 821.8 [M + H]$^+$ |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 52 | (5-(((Z)-7-((1R,2R,3R,5S)-3,5-dihydroxy-2-((R)-3-hydroxy-5-phenylpentyl)cyclopentyl)hept-5-enoyl)oxy)-6-methylpyridine-3,4-diyl)bis(methylene) bis(5,5-dimethyl-2-(prop-2-yn-1-yl)-1,3-dioxane-2-carboxylate) | 2 | Colourless oil | $^1$H NMR (400 MHz, CDCl$_3$) δ 8.53 (s, 1H), 7.30-7.26 m, 2H), 7.21-7.14 (m, 3H), 5.53-5.40 (m, 4H), 5.33 (br s, 2H), 4.17 (br s, 1H), 3.96 (br s, 1H), 3.66 (m, 1H), 3.58-3.38 (m, 8H), 2.85-2.61 (m, 8H), 2.48-2.01 (m, 9H), 1.92-1.24 (m, 12H), 1.18 (s, 3H), 1.17 (s, 3H), 0.70 (s, 3H), 0.69 (s, 3H). | $^{13}$C NMR (100 MHz, CDCl$_3$) δ 171.3, 168.5, 168.3, 153.4, 144.8, 142.2, 130.1, 129.5, 129.2, 128.6, 128.6, 126.0, 98.4, 98.3, 79.0, 74.9, 73.8, 73.7, 72.3, 72.1, 71.5, 62.4, 57.8, 53.2, 52.0, 42.9, 39.3, 36.0, 33.5, 32.3, 30.1, 29.9, 29.73, 29.67, 27.2, 26.8, 25.8, 24.8, 22.7, 21.9, 21.8, 19.7. | 901.8 [M + H]$^+$ |
| 53 | 5-((hex-5-ynoyloxy)methyl)-2-methyl-4-(((prop-2-yn-1-ylcarbamoyl)oxy)methyl)pyridin-3-yl (Z)-7-((1R,2R,3R,5S)-3,5-dihydroxy-2-((R)-3-hydroxy-5-phenylpentyl)cyclopentyl)hept-5-enoate | 2 | Yellow oil | $^1$H NMR (400 MHz, CDCl$_3$) δ 8.42 (s, 1H), 7.29-7.25 (m, 2H), 7.19-7.16 (m, 3H), 5.55-5.40 (m, 2H), 5.34 (br s, 1H), 5.26 (s, 2H), 5.12 (s, 2H), 4.16 (br s, 1H), 3.85-4.01 (m, 3H), 3.64 (m, 1H), 2.78 (m, 1H), 2.69-2.61 (m, 3H), 2.44-2.16 (m, 13H), 1.94 (t, J = 2.6 Hz, 1H), 1.88-1.48 (m, 16H), 1.42-1.25 (m, 2H). | $^{13}$C NMR (100 MHz, CDCl$_3$) δ 173.0, 171.5, 155.5, 153.1, 147.8, 144.7, 142.2, 135.7, 130.1, 129.9, 129.2, 128.6, 128.5, 126.0, 84.0, 79.6, 78.9, 74.9, 71.9, 71.4, 68.9, 62.2, 57.1, 53.1, 52.0, 42.7, 39.2, 36.0, 33.5, 32.3, 31.0, 29.8, 27.8, 27.2, 26.8, 24.8, 23.9, 19.8, 18.2. | — |
| 54 | 4-((hept-6-ynoyloxy)methyl)-2-methyl-5-(((prop-2-yn-1-ylcarbamoyl)oxy)methyl)pyridin-3-yl (Z)-7-((1R,2R,3R,5S)-3,5-dihydroxy-2-((R)-3-hydroxy-5-phenylpentyl)cyclopentyl)hept-5-enoate | 2 | Yellow oil | $^1$H NMR (400 MHz, CDCl$_3$) δ 8.42 (s, 1H), 7.30-7.26 (m, 2H), 7.20-7.16 (m, 3H), 5.54-5.41 (m, 2H), 5.35 (br s, 1H), 5.24 (s, 2H), 5.12 (s, 2H), 4.17 (br s, 1H), 3.98-3.80 (m, 3H), 3.66 (m, 1H), 2.78 (m, 1H), 2.72-2.59 (m, 3H), 2.44-2.14 (m, 13H), 1.95 (t, J = 2.7 Hz, 1H), 1.90-1.48 (m, 16H), 1.44-1.28 (m, 2H). | $^{13}$C NMR (100 MHz, CDCl$_3$) δ 173.0, 171.7, 155.4, 153.1, 147.9, 144.9, 142.2, 135.8, 130.1, 129.7, 129.2, 128.6, 128.5, 126.0, 84.0, 79.6, 78.9, 74.8, 72.0, 71.4, 68.9, 61.3, 58.0, 53.0, 52.0, 42.8, 39.2, 35.9, 33.7, 33.5, 32.3, 31.1, 29.7, 27.9, 27.1, 26.8, 24.9, 24.0, 19.8, 18.2. | — |
| 55 | 4,5-bis((((hex-5-yn-1-yloxy)carbonyl)oxy)methyl)-2-methylpyridin-3-yl (Z)-7-((1R,2R,3R,5S)-3,5-dihydroxy-2-((R)-3-hydroxy-5-phenylpentyl)cyclopentyl)hept-5-enoate | 2 | Pale yellow oil | $^1$H NMR (400 MHz, CDCl$_3$) δ 8.46 (s, 1H), 7.31-7.26 (m, 2H), 7.24-7.16 (m, 3H), 5.55-5.41 (m, 2H), 5.32 (s, 2H), 5.18 (s, 2H), 4.21-4.09 (m, 5H), 3.96 (br s, 1H), 3.66 (m, 1H), 2.79 (m, 1H), 2.70-2.65 (m, 3H), 2.45-2.34 (m, 4H), 2.28-2.17 (m, 8H), 1.95 (t, J = 2.5 Hz, 2H), 1.88-1.47 (m, 18H), 1.43-1.23 (m, 4H). | $^{13}$C NMR (100 MHz, CDCl$_3$) δ 171.4, 154.9, 154.9, 153.5, 145.0, 142.2, 130.0, 129.3, 128.59, 128.55, 126.0, 83.81, 83.78, 79.0, 74.9, 71.5, 69.1, 69.0, 68.3, 68.1, 64.4, 60.3, 53.2, 52.1, 42.8, 39.3, 35.9, 33.4, 32.3, 29.8, 27.74, 27.71, 27.2, 26.8, 24.8, 24.7, 24.7, 19.6, 18.1. | — |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 56 | 2-methyl-4,5-bis(((prop-2-yn-1-ylcarbamoyl)oxy)methyl)pyridin-3-yl (Z)-7-((1R,2R,3R,5S)-3,5-dihydroxy-2-((R)-3-hydroxy-5-phenylpentyl)cyclopentyl)hept-5-enoate | 2 | Yellow oil | $^1$H NMR (400 MHz, CDCl$_3$) δ 8.39 (s, 1H), 7.31-7.24 (m, 2H), 7.22-7.14 (m, 3H), 5.80-5.57 (m, 2H), 5.54-5.37 (m, 2H), 5.21 (s, 2H), 5.11 (s, 2H), 4.15 (s, 1H), 4.00-3.82 (m, 5H), 3.64 (m, 1H), 2.75 (m, 1H), 2.69-2.60 (m, 3H), 2.43-2.29 (m, 4H), 2.27-2.12 (m, 5H), 1.89-1.66 (m, 7H), 1.63-1.45 (m, 3H), 1.44-1.30 (m, 2H). | $^{13}$C NMR (100 MHz, CDCl$_3$) δ 171.8, 155.7, 155.6, 153.0, 147.7, 144.7, 142.2, 136.0, 130.1, 129.9, 129.6, 128.51, 128.50, 125.9, 79.72, 79.70, 78.7, 74.7, 71.9, 71.8, 71.3, 62.1, 57.9, 52.8, 51.9, 42.7, 39.1, 35.8, 33.3, 32.2, 30.9, 29.7, 27.1, 26.7, 24.8, 19.6. | 704.4 [M + H]$^+$ |
| 57 | 4,5-bis(((but-3-yn-1-ylcarbamoyl)oxy)methyl)-2-methylpyridin-3-yl (Z)-7-((1R,2R,3R,5S)-3,5-dihydroxy-2-((R)-3-hydroxy-5-phenylpentyl)cyclopentyl) hept-5-enoate | 2 | Yellow oil | $^1$H NMR (400 MHz, CDCl$_3$) δ 8.44 (s, 1H), 7.32-7.27 (m, 2H), 7.21-7.16 (m, 3H), 5.54-5.38 (m, 2H), 5.34-5.20 (m, 3H), 5.12 (s, 2H), 4.17 (br s, 1H), 3.95 (br s, 1H), 3.66 (m, 1H), 3.40-3.22 (m, 4H), 2.78 (m, 1H), 2.76-2.62 (m, 3H), 2.47-1.48 (m, 27H), 1.45-1.25 (m, 2H). | — | — |
| 58 | 4,5-bis((hex-5-yn-1-yloxy)methyl)-2-methylpyridin-3-yl (Z)-7-((1R,2R,3R,5S)-3,5-dihydroxy-2-((R)-3-hydroxy-5-phenyl pentyl) cyclopentyl)hept-5-enoate | 2 | | $^1$H NMR (400 MHz, CDCl$_3$) δ 8.37 (s, 1H), 7.30-7.26 (m, 2H), 7.22-7.15 (m, 3H), 5.56-5.42 (m, 2H), 4.58 (s, 2H), 4.47 (s, 2H), 4.17 (br s, 1H), 3.97 (br s, 1H), 3.65 (m, 1H), 3.50 (t, J = 6.3 Hz, 2H), 3.38 (t, J = 6.3 Hz, 2H), 2.79 (m, 1H), 2.70-2.61 (m, 3H), 2.46 (br s, 1H), 2.39-2.32 (m, 4H), 2.28-2.14 (m, 8H), 1.96-1.93 (m, 2H), 1.89-1.49 (m, 19H), 1.45-1.28 (m, 2H). | $^{13}$C NMR (100 MHz, CDCl$_3$) δ 171.4, 152.1, 147.0, 144.9, 142.2, 137.3, 131.7, 129.9, 129.3, 128.59, 128.55, 126.0, 84.3, 78.9, 75.0, 71.44, 70.41, 70.3, 68.74, 68.69, 68.2, 64.0, 53.2, 52.1, 42.8, 39.3, 36.0, 33.5, 32.3, 29.8, 28.8, 27.2, 26.9, 25.3, 25.2, 24.9, 19.8, 18.3. | |
| 59 | 2-(Prop-2-yn-1-yl)pent-4-yn-1-yl 3-(((Z)-7-((1R,2R,3R,5S)-3,5-Dihydroxy-2-((R)-3-hydroxy-5-phenylpentyl)cyclopentyl)hept-5-enoyl)oxy)benzoate | 2 | Colourless oil | δ 8.27-8.21 (m, 1H), 8.10-8.06 (m, 1H), 7.79 (t, J = 7.9 Hz, 1H), 7.66-7.61 (m, 2H), 7.52 (dd, J = 10.1, 4.3 Hz, 3H), 5.82 (ddt, J = 33.9, 10.8, 7.2 Hz, 2H), 4.75 (d, J = 6.1 Hz, 2H), 4.51 (s, 1H), 4.29 (s, 1H), 4.05-3.88 (m, 1H), 3.17-3.06 (m, 1H), 3.05-2.89 (m, 4H), 2.81 (dd, J = 6.4, 2.6 Hz, 4H), 2.77-2.52 (m, 6H), 2.37 (dd, J = 4.7, 2.1 Hz, 2H), 2.27-1.79 (m, 12H), 1.80-1.62 (m, 2H). | δ 172.17, 165.64, 150.87, 142.20, 131.67, 129.97, 129.63, 129.38, 128.57, 128.54, 127.12, 126.67, 126.00, 123.01, 80.98, 78.97, 74.94, 71.48, 70.76, 66.23, 53.15, 52.03, 42.77, 39.24, 36.59, 35.94, 33.77, 32.25, 29.83, 27.23, 26.71, 24.85, 20.21. | ([M + Na]$^+$) 636.9 |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 60 | 2-(Prop-2-yn-1-yl)pent-4-yn-1-yl 4-(((Z)-7-((1R,2R,3R,5S)-3,5-dihydroxy-2-((R)-3-hydroxy-5-phenylpentyl)cyclopentyl)hept-5-enoyl)oxy)benzoate | 2 | colourless viscous oil | δ 8.06 (m, 2H), 7.28 (m, 2H), 7.20-7.15 (m, 5H), 5.48 (m, 2H), 4.40 (d, J = 6.1 Hz, 2H), 4.17 (s, 1H), 3.96 (s, 1H), 3.65 (m, 1H), 2.78 (ddd, J = 13.5, 9.1, 6.3 Hz, 1H), 2.67 (m, 1H), 2.60 (t, J = 7.3 Hz, 2H), 2.47 (dd, J = 6.5, 2.6 Hz, 4H), 2.41-2.21 (m, 5H), 2.03 (t, J = 2.6 Hz, 2H), 1.88-1.67 (m, 7H), 1.64-1.48 (m, 3H), 1.44-1.31 (m, 2H). | δ 171.9, 165.7, 154.6, 142.1, 131.4, 129.9, 129.4, 128.6, 128.5, 127.7, 126.0, 121.8, 81.0, 79.0, 75.0, 71.5, 70.7, 66.0, 53.1, 52.1, 42.7, 39.2, 36.6, 35.9, 33.9, 32.3, 29.8, 27.2, 26.7, 24.8, 20.2. | 615 ([M + H]$^+$). |
| 61 | (Z)-2-(Prop-2-yn-1-yl)pent-4-yn-1-yl 7-((1R,2R,3R,5S)-3,5-dihydroxy-2-((R)-3-hydroxy-5-phenylpentyl)cyclopentyl)hept-5-enoate | 2 | Clear colourless viscous oil | δ 7.33-7.24 (m, 2H), 7.24-7.14 (m, 3H), 5.56-5.32 (m, 2H), 4.23-4.06 (m, 3H), 4.01-3.88 (m, 1H), 3.73-3.60 (m, 1H), 2.88-2.58 (m, 3H), 2.44-2.27 (m, 8H), 2.25-2.05 (m, 4H), 2.01 (t, J = 2.7 Hz, 2H), 1.90-1.84 (m, 2H), 1.84-1.46 (m, 9H), 1.46-1.18 (m, 2H). | δ 173.79, 142.20, 129.63, 129.57, 128.56, 128.55, 125.98, 81.04, 78.94, 74.88, 71.45, 70.63, 65.28, 53.06, 52.03, 42.68, 39.22, 36.38, 35.94, 33.70, 32.26, 29.79, 27.09, 26.76, 24.96, 20.00. | 540 ([M + 2Na]$^+$). |
| 62 | (Z)-2-(Prop-2-yn-1-yl)pent-4-yn-1-yl 7-((1R,2R,3R,5S)-3,5-dihydroxy-2-((R,E)-3-hydroxy-4-(3-(trifluoromethyl)phenoxy)but-1-en-1-yl)cyclopentyl)hept-5-enoate | 2 | clear colourless viscous oil | δ 7.44-7.36 (m, 1H), 7.25-7.20 (m, 1H), 7.18-7.12 (m, 1H), 7.12-7.06 (m, 1H), 5.83-5.61 (m, 2H), 5.50-5.32 (m, 2H), 4.63-4.47 (m, 1H), 4.26-4.17 (m, 1H), 4.15 (d, J = 6.2 Hz, 2H), 4.07-3.90 (m, 3H), 2.78-2.46 (m, 2H), 2.46-2.25 (m, 8H), 2.25-2.04 (m, 11H), 2.01 (t, J = 2.6 Hz, 2H), 1.87-1.77 (m, 1H), 1.77-1.48 (m, 4H). | δ 173.80, 158.77, 135.25, 133.27, 31.91, 130.22, 129.87, 129.43, 129.20, 122.67, 118.22, 118.03 (q, J$_{C-F}$ = 3.8 Hz), 111.62 (q, J$_{C-F}$ = 3.7 Hz), 78.25, 73.23, 72.23, 70.85, 70.64, 65.31, 56.20, 50.68, 43.10, 36.38, 33.63, 31.07, 26.74, 25.81, 24.87, 20.00. | 608 ([M + 2Na]$^+$). |
| 63 | 2-(((Z)-7-((1R,2R,3R,5S)-3,5-Dihydroxy-2-((R)-3-hydroxy-5-phenylpentyl)cyclopentyl)hept-5-enoyl)oxy)propane-1,3-diyl bis(hex-5-ynoate) | 2 | clear colourless oil | δ 7.35-7.24 (m, 2H), 7.24-7.12 (m, 3H), 5.53-5.32 (m, 2H), 5.32-5.16 (m, 1H), 4.37-4.23 (m, 2H), 4.23-4.08 (m, 3H), 3.93 (t, J = 8.6 Hz, 1H), 3.67 (m, 1H), 2.86-2.74 (m, 1H), 2.74-2.59 (m, 2H), 2.47 (tt, J = 7.4, 3.7 Hz, 4H), 2.43-2.03 (m, 12H), 1.98 (t, J = 2.6 Hz, 2H), 1.91-1.45 (m, 13H), 1.45-1.17 (m, 3H). | δ 173.33, 172.66, 172.27, 142.12, 129.62, 129.27, 128.42, 125.83, 83.08, 78.72, 74.62, 71.28, 69.40, 69.38, 69.08, 68.94, 62.26, 62.18, 52.81, 51.81, 42.56, 39.07, 35.78, 33.53, 33.38, 32.78, 32.60, 32.12, 29.62, 26.93, 26.56, 26.53, 24.77, 24.73, 23.50, 23.44, 17.77, 17.74. | 698 ([M + 2Na]$^+$). |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 64 | 2-((((Z)-7-((1R,2R,3R,5S)-3,5-Dihydroxy-2-((R)-3-hydroxy-5-phenylpentyl)cyclopentyl)hept-5-enoyl)oxy)methyl)-2-methylpropane-1,3-diyl bis(hex-5-ynoate) | 2 | clear colourless oil | δ 7.32-7.25 (m, 2H), 7.23-7.10 (m, 3H), 5.57-5.27 (m, 2H), 4.16 (bs, 1H), 4.08-3.88 (m, 7H), 3.71-3.61 (m, 1H), 2.87-2.73 (m, 1H), 2.73-2.58 (m, 1H), 2.51-2.42 (m, 4H), 2.40-2.03 (m, 12H), 1.98 (t, J = 2.6 Hz, 2H), 1.91-1.46 (m, 12H), 1.46-1.23 (m, 2H), 1.02 (s, 3H). | δ 173.63, 172.98, 142.20, 129.70, 129.44, 128.54, 128.53, 125.97, 83.16, 78.92, 74.84, 71.41, 69.50, 65.88, 65.81, 53.05, 51.99, 42.68, 39.22, 38.47, 35.93, 33.68, 32.83, 32.25, 29.78, 27.09, 26.75, 24.93, 23.58, 17.91, 17.26. | 703 ([M + 2Na]$^+$). |
| 65 | 1-((((2-(prop-2-yn-1-yl)pent-4-yn-1-yl)oxy)carbonyl)oxy)ethyl (Z)-7-((1R,2R,3R,5S)-3,5-dihydroxy-2-((R)-3-hydroxy-5-phenylpentyl)cyclopentyl)hept-5-enoate | 10A | colourless viscous oil | δ 7.30-7.27 (m, 2H), 7.23-7.17 (m, 3H), 6.76 (q, J = 5.4 Hz, 1H), 5.51-5.35 (m, 2H), 4.25 (d, J = 6.2 Hz, 2H), 4.16 (m, 1H), 3.95 (m, 1H), 3.67 (m, 1H), 2.80 (m, 1H), 2.68 (m, 1H), 2.41-2.09 (m, 11H), 2.02 (t, J = 2.6 Hz, 2H), 1.87 (t, J = 3.0 Hz, 2H), 1.82-1.55 (m, 8H), 1.51 (d, J = 5.4 Hz, 3H), 1.43-1.31 (m, 2H). | — | 605.3 [M + Na]$^+$ |
| 66 | 2-(((((1-(((Z)-7-((1R,2R,3R,5S)-3,5-dihydroxy-2-((R)-3-hydroxy-5-phenylpentyl)cyclopentyl)hept-5-enoyl)oxy)ethoxy)carbonyl)oxy)methyl)-2-methylpropane-1,3-diyl bis(2,2-dimethylpent-4-ynoate) | 10A | Colourless oil | $^1$H NMR (400 MHz, CDCl$_3$) δ 7.32-7.26 (m, 2H), 7.21-7.16 (m, 3H), 6.73 (q, J = 5.4 Hz, 1H), 5.50-5.35 (m, 2H), 4.17 (br s, 1H), 4.12 (s, 2H), 4.04 (s, 4H), 3.95 (br s, 1H), 3.67 (m, 1H), 2.84-2.64 (m, 2H), 2.43 (d, J = 2.6 Hz, 1H), 2.40-2.10 (m, 6H), 2.02 (t, J = 2.6 Hz, 2H), 1.91-1.53 (m, 16H), 1.50 (d, J = 5.4 Hz, 3H), 1.43-1.32 (m, 2H), 1.28 (s, 12H), 1.07 (s, 3H). | $^{13}$C NMR (100 MHz, CDCl$_3$) δ 176.0, 171.7, 152.9, 142.1, 129.6, 129.3, 128.4, 128.4, 125.9, 91.5, 80.8, 78.8, 74.8, 71.3, 70.8, 69.7, 65.8, 53.0, 51.9, 42.6, 42.5, 39.1, 38.9, 35.8, 33.34, 33.30, 32.1, 29.7, 29.6, 27.0, 26.48, 26.45, 24.6, 24.4, 19.5, 16.9. | 818.8 [M + Na]$^+$ |
| 67 | 2-(((((1-(((Z)-7-((1R,2R,3R,5S)-3,5-dihydroxy-2-((R)-3-hydroxy-5-phenylpentyl)cyclopentyl)hept-5-enoyl)oxy)ethoxy)carbonyl)oxy)methyl)-2-methylpropane-1,3-diylbis(hex-5-ynoate) | 10A | Colourless oil | $^1$H NMR (400 MHz, CDCl$_3$) δ 7.30-7.26 (m, 2H), 7.24-7.18 (m, 3H), 6.74 (q, J = 5.4 Hz, 1H), 4.16 (br s, 1H), 4.10 (s, 2H), 4.01 (m, 4H), 3.95 (br s, 1H), 3.67 (m, 1H), 2.83-2.64 (m, 2H), 2.47 (t, J = 7.4 Hz, 4H), 2.38-2.00 (m, 15H), 1.98 (t, J = 2.6 Hz, 2H), 1.87-1.54 (m, 14H), 1.51 (d, J = 5.4 Hz, 3H), 1.42-1.25 (m, 2H), 1.03 (s, 3H). | $^{13}$C NMR (100 MHz, CDCl$_3$) δ 172.9, 171.8, 153.1, 142.2, 129.8, 129.7, 129.5, 128.57, 128.55, 126.0, 91.7, 83.2, 79.0, 75.0, 71.5, 69.7, 69.5, 65.7, 53.2, 52.0, 42.7, 39.3, 38.7, 36.0, 33.50, 33.46, 32.8, 32.3, 29.8, 27.2, 26.63, 26.60, 24.59, 24.58, 23.6, 19.7, 18.0, 17.1. | 790.8 [M + Na]$^+$ |

TABLE 4-continued

Examples of DRUG-MONOMERS:

| Ex | Structure/Name | Method | Appearance | $^1$H (CDCl$_3$) (unless otherwise stated) δ (ppm) | $^{13}$C (CDCl$_3$) (unless otherwise stated) δ (ppm) | ESI-MS |
|---|---|---|---|---|---|---|
| 68 | ((((2-(prop-2-yn-1-yl)pent-4-yn-1-yl)oxy)carbonyl)oxy)methyl (Z)-7-((1R,2R,3R,5S)-3,5-dihydroxy-2-((R)-3-hydroxy-5-phenylpentyl)cyclopentyl)hept-5-enoate | 10A | — | $^1$H NMR (400 MHz, CDCl$_3$) δ 7.33-7.27 (m, 2H), 7.24-7.19 (m, 3H), 5.78 (s, 2H), 5.53-5.37 (m, 2H), 4.31 (d, J = 6.1 Hz, 2H), 4.19 (br s, 1H), 3.98 (br s, 1H), 3.70 (m, 1H), 2.86-2.67 (m, 2H), 2.44-2.11 (m, 11H), 2.05 (t, J = 2.6 Hz, 2H), 1.95-1.51 (m, 13H), 1.45-1.33 (m, 2H). | — | 568.9 [M + H]$^+$ |
| 69 | 2-(((1-(tert-butylamino)-3-((4-morpholino-1,2,5-thiadiazol-3-yl)oxy)propan-2-yl)oxy)carbonyl)-2-methylpropane-1,3-diyl bis(2,2-dimethylpent-4-ynoate) | 6 | Colourless oil | δ 5.29-5.20 (m, 1H), 4.61 (d, J = 4.3 Hz, 2H), 4.35-4.18 (m, 4H), 3.79 (t, J = 4.8 Hz, 4H), 3.56-3.43 (m, 4H), 2.84 (d, J = 5.0 Hz, 2H), 2.39 (t, J = 2.4 Hz, 4H), 2.00 (t, J = 2.6 Hz, 2H), 1.23 (s, 3H), 1.22 (dt, J = 66.6, 32.3 Hz, 12H), 1.09 (s, 9H). | δ 175.92, 175.87, 172.19, 158.45, 149.98, 80.64, 73.26, 70.96, 69.99, 66.63, 65.43, 65.40, 47.99, 46.80, 42.68, 42.44, 29.66, 28.96, 24.66, 24.63, 18.07. | ([M + H]$^+$) 648.8 |
| 70 | 2-(((1-(4-(2-(cyclopropylmethoxy)ethyl)phenoxy)-3-(isopropylamino)propan-2-yl)oxy)carbonyl)-2-methylpropane-1,3-diyl bis(2,2-dimethylpent-4-ynoate) | 6 | Colourless oil | δ 7.12 (d, J = 8.6 Hz, 2H), 6.81 (d, J = 8.6 Hz, 2H), 5.26-5.18 (m, 1H), 4.34-4.20 (m, 4H), 4.11 (dd, J = 4.8, 1.6 Hz, 2H), 3.60 (t, J = 7.4 Hz, 2H), 3.27 (d, J = 6.9 Hz, 2H), 2.92 (t, J = 5.9 Hz, 2H), 2.86-2.75 (m, 3H), 2.38 (d, J = 2.6 Hz, 4H), 1.99 (td, J = 2.6, 0.7 Hz, 2H), 1.25 (d, J = 13.5 Hz, 15H), 1.04 (d, J = 6.2 Hz, 7H), 0.56-0.47 (m, 2H), 0.22-0.15 (m, 2H). | δ 175.98, 175.95, 157.10, 131.83, 130.02, 114.68, 80.84, 75.76, 73.22, 71.92, 70.90, 67.48, 65.57, 53.56, 48.92, 47.14, 46.83, 42.42, 35.61, 29.64, 24.66, 24.62, 22.99, 22.89, 18.05, 10.76. | ([M + H]$^+$) 639.9 |
| 71 | (S)-1-(tert-butylamino)-3-((4-morpholino-1,2,5-thiadiazol-3-yl)oxy)propan-2-yl2-(prop-2-yn-1-yl)pent-4-ynoate | 6 | clear colourless oil | δ 5.40-5.25 (m, 1H), 4.66-4.57 (m, 2H), 3.87-3.73 (m, 4H), 3.57-3.41 (m, 4H), 2.85 (t, J = 9.5 Hz, 2H), 2.82-2.72 (m, 1H), 2.72-2.53 (m, 4H), 2.02-1.91 (m, 2H), 1.53-1.44 (m, 2H), 1.09 (s, 9H). | δ 171.86, 153.52, 149.93, 80.45, 80.41, 73.09, 70.91, 70.80, 70.25, 66.67, 50.92, 47.98, 43.28, 42.84, 28.89, 20.16, 20.04. | 435.3 ([M + H]$^+$). |

TABLE 4-continued

Examples of DRUG-MONOMERS:

| Ex | Structure/Name | Method | Appearance | ¹H (CDCl₃) (unless otherwise stated) δ (ppm) | ¹³C (CDCl₃) (unless otherwise stated) δ (ppm) | ESI-MS |
|---|---|---|---|---|---|---|
| 72 | (S)-N-(3-(4-(2-(cyclopropylmethoxy)eth-yl)phenoxy)-2-hydroxypropyl)-N-isopropyl-2-(prop-2-yn-1-yl)pent-4-ynamide | 6 | Colourless oil | (400 MHz, CDCl3) δ 7.17-7.10 (m, 2H), 6.86-6.80 (m, 2H), 5.21 (d, 1H), 4.36 (m, 1H), 4.10-3.94 (m, 2H), 3.91-3.74 (m, 1H), 3.68-3.56 (m, 3H), 3.55-3.41 (m, 1H), 3.35-3.15 (m, 3H), 2.93-2.75 (m, 2H), 2.63-2.40 (m, 4H), 2.10-1.93 (m, 2H), 1.37-1.17 (m, 6H), 1.12-0.97 (m, 1H), 0.57-0.47 (m, 2H), 0.27-0.10 (m, 2H). | (101 MHz, CDCl3) δ 175.63, 157.04, 131.59, 130.01, 114.39, 81.42, 81.02, 75.77, 72.12, 71.93, 70.62, 70.41, 69.75, 49.56, 46.72, 40.54, 35.59, 22.34, 21.92, 21.51, 21.38, 10.75, 3.12. | M + H 426.3 |
| 73 | (S)-2-(((1-(tert-butylamino)-3-((4-morpholino-1,2,5-thiadiazol-3-yl)oxy)propan-2-yl)oxy)carbonyl)-2-methylpropane-1,3-diyl bis(hex-5-ynoate) | 6 | Golden yellow oil | (400 MHz, CDCl3) δ 5.28 (s, 1H), 4.68-4.52 (m, 2H), 4.35-4.14 (m, 4H), 3.79 (t, J = 4.8 Hz, 4H), 3.62-3.37 (m, 4H), 2.85 (s, 2H), 2.54-2.36 (m, 4H), 2.31-2.18 (m, 4H), 2.00-1.92 (m, 2H), 1.87-1.67 (m, 4H), 1.30-1.18 (m, 3H), 1.17-0.98 (m, 9H). | (101 MHz, CDCl3) δ 172.63, 172.25, 153.45, 149.90, 83.14, 70.06, 69.50, 69.48, 66.65, 65.43, 65.35, 48.02, 46.67, 42.71, 32.74, 28.63, 23.57, 17.98, 17.91 | M⁺ 620.8 |
| 74 | (S,E)-1-((1R,2R,3S,5R)-2-((Z)-7-(ethylamino)-7-oxohept-2-en-1-yl)-3,5-dihydroxycyclopentyl)-5-phenylpent-1-en-3-yl 2-(prop-2-yn-1-yl)pent-4-ynoate | 5 | Pale yellow viscous oil | δ 7.29 (d, J = 7.1 Hz, 2H), 7.22-7.15 (m, 3H), 5.78 (s, 1H), 5.62 (dd, J = 15.3, 8.6 Hz, 1H), 5.52 (dd, J = 15.4, 6.8 Hz, 1H), 5.44-5.27 (m, 3H), 4.17 (d, J = 3.8 Hz, 1H), 4.00-3.93 (m, 1H), 3.31-3.21 (m, 2H), 2.77 (dt, J = 13.0, 6.5 Hz, 1H), 2.72-2.60 (m, 6H), 2.35 (ddd, J = 17.0, 11.1, 6.0 Hz, 2H), 2.14 (dd, J = 12.2, 7.1 Hz, 3H), 2.09-1.98 (m, 5H), 1.97-1.88 (m, 1H), 1.82 (d, J = 14.5 Hz, 1H), 1.73-1.63 (m, 2H), 1.50 (ddd, J = 14.3, 9.8, 4.4 Hz, 1H), 1.12 (t, J = 7.3 Hz, 3H). | δ 173.26, 171.77, 141.40, 135.87, 129.98, 129.27, 129.19, 128.57, 128.48, 126.13, 80.28, 78.26, 75.04, 73.11, 70.85, 56.06, 50.82, 43.35, 43.04, 36.30, 35.94, 34.48, 31.64, 26.79, 25.84, 25.70, 20.10, 14.94. | ([M + Na]⁺) 556.0 |

TABLE 4-continued

Examples of DRUG-MONOMERS:

| Ex | Structure/Name | Method | Appearance | ¹H (CDCl₃) (unless otherwise stated) δ (ppm) | ¹³C (CDCl₃) (unless otherwise stated) δ (ppm) | ESI-MS |
|---|---|---|---|---|---|---|
| 75 | 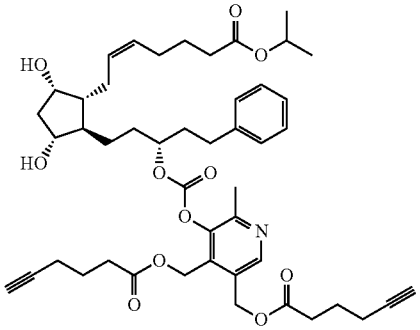 [SMILES: C#CCCCC(=O)OCc1cnc(C)c(OC(=O)O[C@@H](CCc2ccccc2)CC[C@@H]2[C@@H](C/C=C\CCCC(=O)OC(C)C)[C@@H](O)C[C@H]2O)c1COC(=O)CCCC#C]<br>(5-(((((R)-1-((1R,2R,3S,5R)-3,5-dihydroxy-2-((Z)-7-isopropoxy-7-oxohept-2-en-1-yl)cyclopentyl)-5-phenylpentan-3-yl)oxy)carbonyl)oxy)-6-methylpyridine-3,4-diyl)bis(methylene) bis(hex-5-ynoate) | 11 & 12 | — | ¹H NMR (400 MHz, CDCl₃) δ 8.47 (s, 1H), 7.33-7.27 (m, 2H), 7.22-7.20 (m, 3H), 5.48-5.38 (m, 2H), 5.30 (s, 2H), 5.20 (s, 2H), 5.00 (hept, J = 6.3 Hz, 1H), 4.87 (m, 1H), 4.19 (br s, 1H), 3.95 (br s, 1H), 2.84-2.68 (m, 2H), 2.62 (d, J = 7.1 Hz, 1H) 2.51-2.46 (m, 5H), 2.43-2.33 (m, 4H), 2.30-2.04 (m, 10H), 2.01-1.65 (m, 13H), 1.46-1.29 (m, 2H), 1.22 (d, J = 6.3 Hz, 6H). | ¹³C NMR (100 MHz, CDCl₃) δ 173.6, 172.7, 172.5, 153.2, 152.7, 148.2, 144.9, 141.1, 135.8, 130.0, 129.7, 129.3, 128.7, 128.5, 126.4, 83.2, 83.1, 80.7, 78.9, 74.8, 69.52, 69.50, 67.8, 61.3, 56.9, 53.1, 51.8, 42.7, 35.9, 34.2, 32.8, 32.6, 31.7, 29.4, 27.1, 26.8, 25.1, 23.54, 23.45, 22.0, 19.6, 17.93, 17.85. | — |

Using the procedures described above the following monomers shown in Table 5 may be prepared.

TABLE 5

| Example | Drug | Linking Point | Linkage | Alkyne/azide precursor | Production Method | Monomer |
|---|---|---|---|---|---|---|
| 76 | LTP | 1-COOH | Ester | (structure) | Method 2 | (structure) |
| 77 | LTP | 1-COOH | Ester | (structure) | Method 2 | (structure) |
| 78 | LTP | 1-COOH | Ester | (structure) | Method 2 | (structure) |

TABLE 5-continued

| Example | Drug | Linking Point | Linkage | Alkyne/azide precursor | Production Method | Monomer |
|---|---|---|---|---|---|---|
| 79 | LTP | 1-COOH | Ester | | Method 2 | |
| 80 | LTP | 1-COOH | Ester | | Method 2 | |
| 81 | LTP | 1-COOH | Ester | | Method 2 | |

TABLE 5-continued

| Example | Drug | Linking Point | Linkage | Alkyne/azide precursor | Production Method | Monomer |
|---|---|---|---|---|---|---|
| 82 | LTP | 1-COOH | Ester | | Method 2 | |
| 83 | LTP | 1-COOH | Ester | | Method 2 | |
| 84 | TVP | 1-COOH | Ester | | Method 2 | |

TABLE 5-continued

| Example | Drug | Linking Point | Linkage | Alkyne/azide precursor | Production Method | Monomer |
|---|---|---|---|---|---|---|
| 85 | TAF | 1-COOH | Ester | | Method 2 | |
| 86 | BIM (free acid) | 1-COOH | Ester | | Method 2 | |
| 87 | TVP | 1-COOH | Ester | | Method 2 | |

TABLE 5-continued

| Example | Drug | Linking Point | Linkage | Alkyne/azide precursor | Production Method | Monomer |
|---|---|---|---|---|---|---|
| 88 | TAF | 1-COOH | Ester | | Method 2 | |
| 89 | BIM (free acid) | 1-COOH | Ester | | Method 2 | |

TABLE 5-continued
| Example | Drug | Linking Point | Linkage | Alkyne/azide precursor | Production Method | Monomer |
|---|---|---|---|---|---|---|
| 90 | LTP | 1-COOH | Ester | 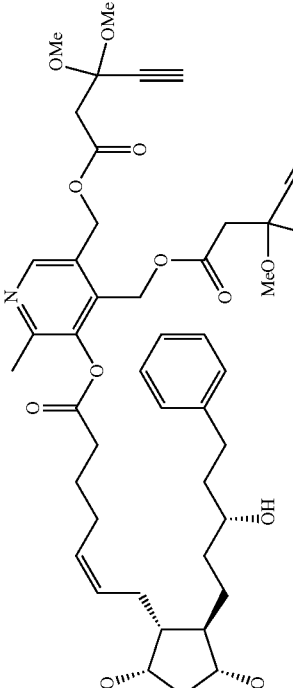 | Method 2 | 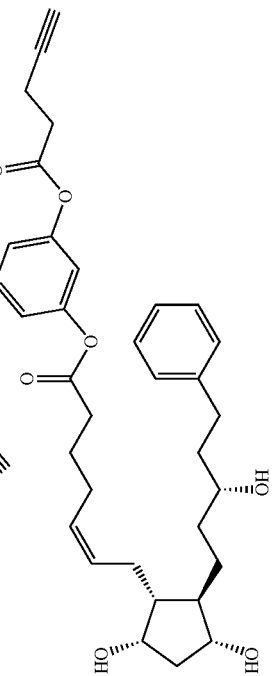 |
| 91 | LTP | 1-COOH | Ester | 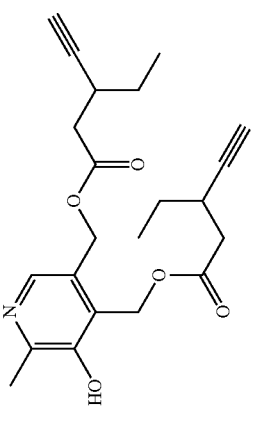 | Method 2 | 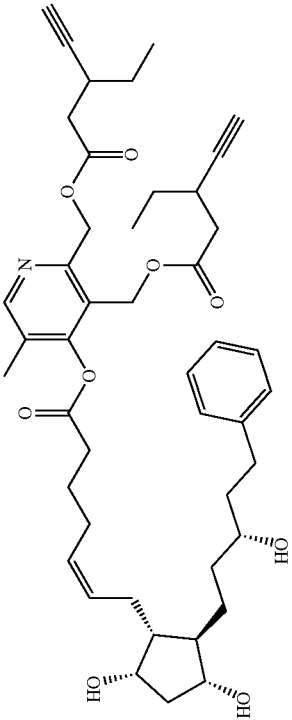 |
| 92 | LTP | 1-COOH | Ester | 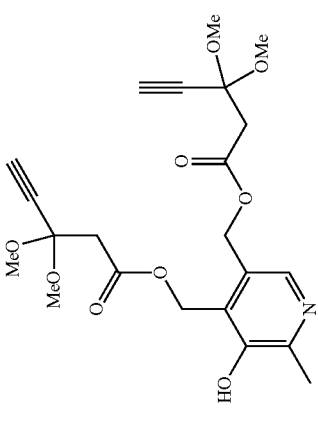 | Method 2 | 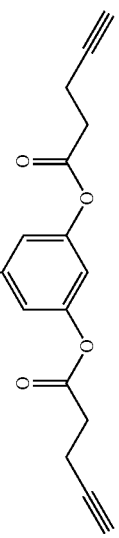 |

TABLE 5-continued

| Example | Drug | Linking Point | Linkage | Alkyne/azide precursor | Production Method | Monomer |
|---|---|---|---|---|---|---|
| 93 | TVP | 1-COOH | Ester | [structure] | Method 2 | [structure] |
| 94 | TVP | 1-COOH | Ester | [structure] | Method 10A | [structure] |
| 95 | TAF | 1-COOH | Ester | [structure] | Method 10A | [structure] |

TABLE 5-continued

| Example | Drug | Linking Point | Linkage | Alkyne/azide precursor | Production Method | Monomer |
|---|---|---|---|---|---|---|
| 96 | BIM | 1-COOH | Ester | | Method 10A | |
| 97 | LTP | 1-COOH | Ester | | Method 10A | |
| 98 | LTP | 1-COOH | Ester | | Method 10A | |

TABLE 5-continued

| Example | Drug | Linking Point | Linkage | Alkyne/azide precursor | Production Method | Monomer |
|---|---|---|---|---|---|---|
| 99 | LTP | 1-COOH | Ester | | Method 10A | |
| 100 | LTP | 1-COOH | Ester | | Method 10A | |
| 101 | LTP | 1-COOH | Ester | | Method 10A | |

TABLE 5-continued
| Example | Drug | Linking Point | Linkage | Alkyne/azide precursor | Production Method | Monomer |
|---|---|---|---|---|---|---|
| 102 | LTP | 1-COOH | Ester | 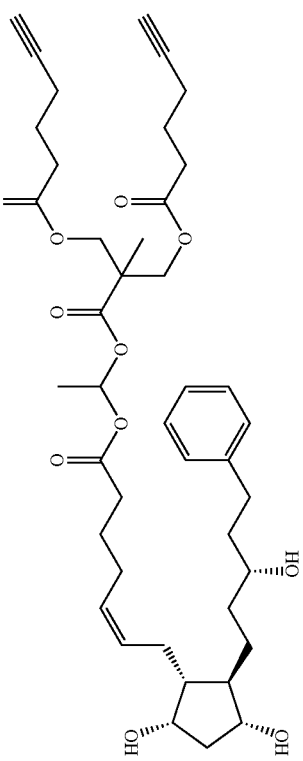 | Method 10A | 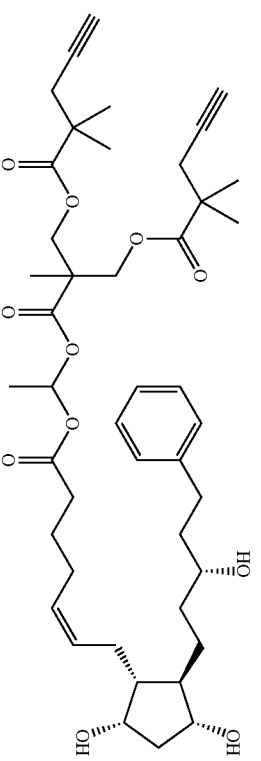 |
| 103 | LTP | 1-COOH | Ester | 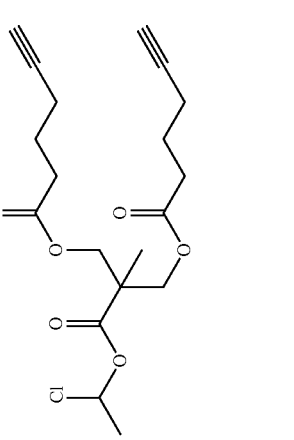 | Method 10A | 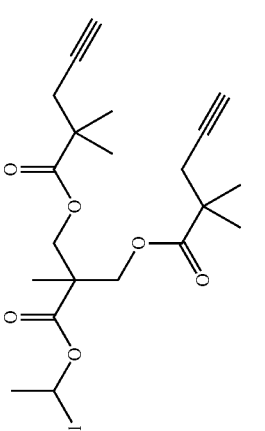 |
| 104 | LTP | 1-COOH | Ester | 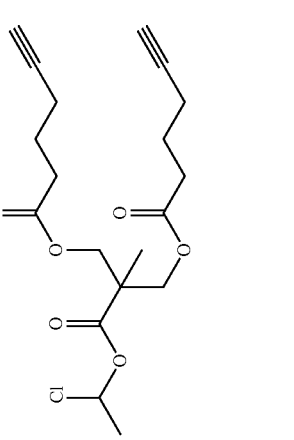 | Method 10A | 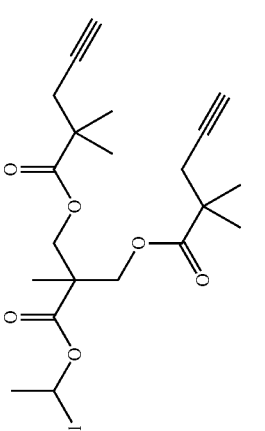 |

TABLE 5-continued

| Example | Drug | Linking Point | Linkage | Alkyne/azide precursor | Production Method | Monomer |
|---|---|---|---|---|---|---|
| 105 | LTP | 1-COOH | Ester | [structure] | Method 10A | [structure] |
| 106 | LTP | 1-COOH | Ester | [structure] | Method 2 | [structure] |
| 107 | BET | 1-COOH | Ester | [structure] | Method 6 | [structure] |

TABLE 5-continued
| Example | Drug | Linking Point | Linkage | Alkyne/azide precursor | Production Method | Monomer |
|---|---|---|---|---|---|---|
| 108 | LTP | 1-COOH | Ester | 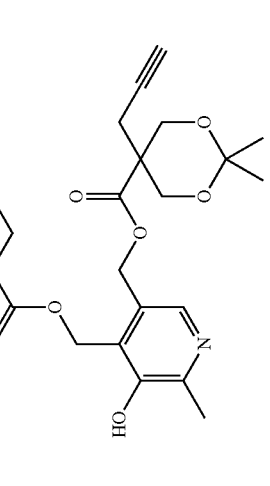 | Method 2 | 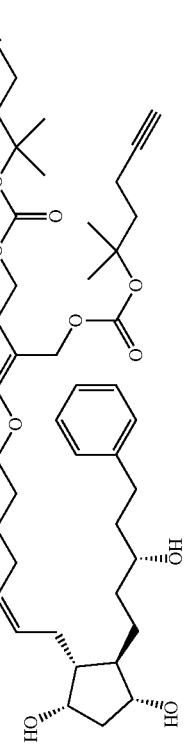 |
| 109 | LTP | 1-COOH | Ester | 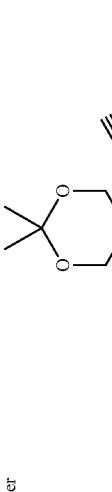 | Method 2 | 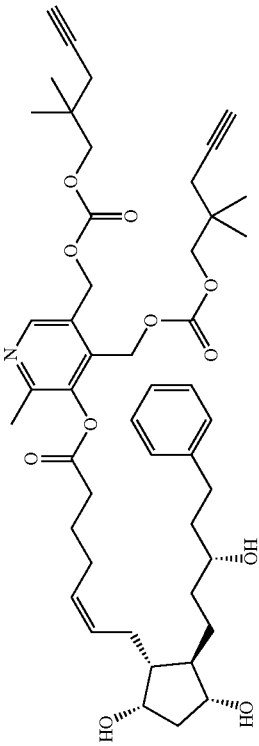 |
| 110 | LTP | 1-COOH | Ester | 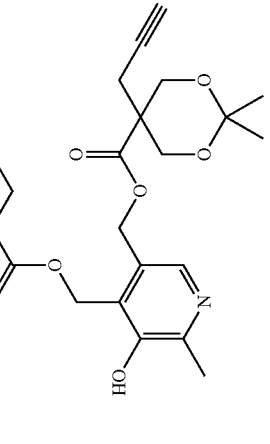 | Method 2 | 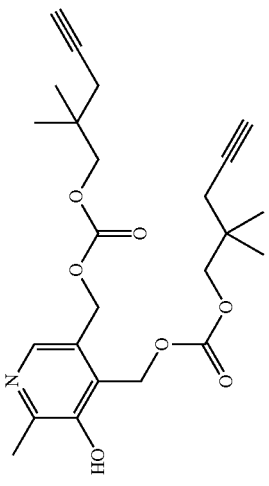 |

TABLE 5-continued
| Example | Drug | Linking Point | Linkage | Alkyne/azide precursor | Production Method | Monomer |
|---|---|---|---|---|---|---|
| 111 | LTP | 1-COOH | Ester | 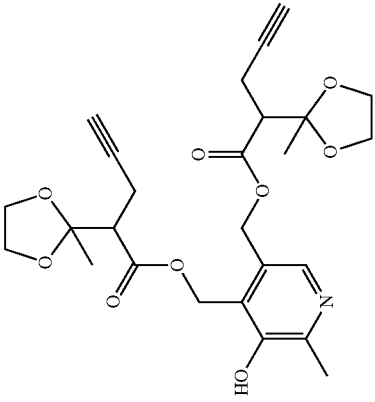 | Method 2 | 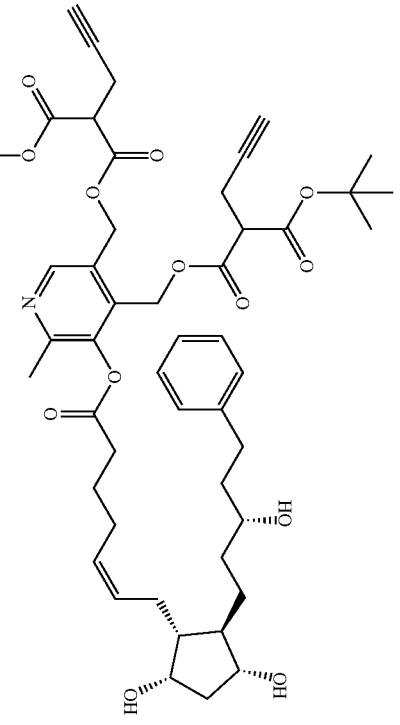 |
| 112 | LTP | 1-COOH | Ester | 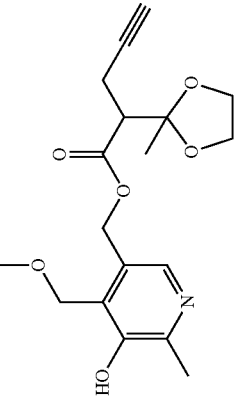 | Method 2 | 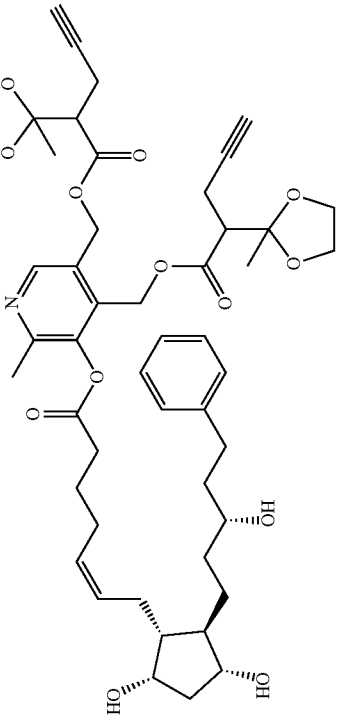 |

TABLE 5-continued

| Example | Drug | Linking Point | Linkage | Alkyne/azide precursor | Production Method | Monomer |
|---|---|---|---|---|---|---|
| 113 | LTP | 1-COOH | Ester | | Method 2 | |
| 114 | LTP | 1-COOH | Ester | | Method 2 | |

TABLE 5-continued

| Example | Drug | Linking Point | Linkage | Alkyne/azide precursor | Production Method | Monomer |
|---|---|---|---|---|---|---|
| 115 | LTP | 1-COOH | Ester | | Method 2 | |
| 116 | LTP | 1-COOH | Ester | | Method 2 | |
| 117 | LTP | 1-COOH | Ester | | Method 2 | |

TABLE 5-continued

| Example | Drug | Linking Point | Linkage | Alkyne/azide precursor | Production Method | Monomer |
|---|---|---|---|---|---|---|
| 118 | LTP | 1-COOH | Ester | | Method 2 | |
| 119 | LTP | 1-COOH | Ester | | Method 2 | |
| 120 | LTP | 1-COOH | Ester | | Method 2 | |

LTP = latanoprost; TVP = travoprost; TAF = tafluprost; BIM = bimatoprost; TIM = timolol; BET = betaxolol Preparation of Drug-Polymer Conjugates Method 17: General Method A: For the Preparation of PEG Azide Co-Monomers: Esters Illustrated Using Example 132

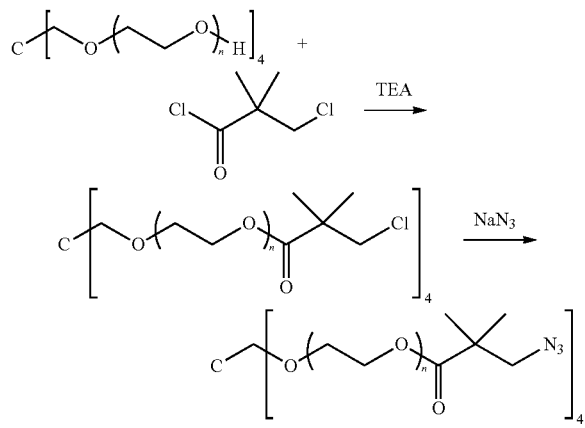

4-arm PEG$_{2000}$-OH (5 g, 2.5 mmol), TEA (3.1 mL, 4.4 eq) and DCM (50 mL) were introduced into a round-bottom flask equipped with a rubber septum and a magnetic stirrer bar and placed under a nitrogen atmosphere. The solution was stirred and cooled to 0° C. in an ice bath. A mixture of 3-chloro-2,2-dimethylpropionyl chloride (2.6 mL, 8 eq) in 10 mL of DCM was added dropwise with a syringe equipped with a needle. The solution was allowed to warm to room temperature and stirred overnight. After filtration, DCM was removed under vacuum and the product was purified by flash chromatography (EtOAc: [DCM/MeOH 95/5] 100:0->0:100) to give the product (5.14 g, 83%) which was was analysed by MALDI-ToF mass spectrometry ($M_n$=2458.3 g·mol$^{-1}$, $M_w$=2474.8 g·mol$^{-1}$, Đ=1.007).

C-(PEG-OCO-C(CH$_3$)$_2$—CH$_2$—Cl)$_4$ (5.135, 2.09 mmol), NaN$_3$ (5.43 g, 40 eq) and DMF (75 mL) were introduced into a round-bottom flask equipped with a rubber septum and a magnetic bar. The solution was stirred for 24 h at 50° C. The solvent was evaporated and the polymer was purified by flash chromatography (EtOAc: Acetone 100:0->0:100) and dried under vacuum to give the product (Example 132) (3.48 g, 67%).\ MALDI-ToF mass spectrometry (Mn=2439.7 g·mol$^{-1}$, Mw=2451.7 g·mol$^{-1}$, Đ=1.005). $^1$H NMR (C—(CH$_2$—CH$_2$—O)—CO—C(CH$_3$)$_2$—CH$_2$—N$_3$)$_4$: 1.30 ppm (6H, (CH$_3$)$_2$; 3.4 ppm-3.8 ppm (44H, —CH$_2$—CH$_2$—O); 4.28 ppm (—CH$_2$—N$_3$)). Overall yield=56%.

Method 18: General Method B for the Preparation of PEG Azide Co-Monomers: Esters Illustrated Using Example 128

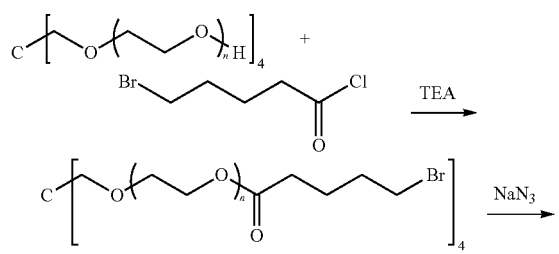

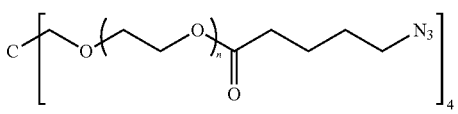

4-arm PEG$_{2000}$-OH (5.0 g, 2.5 mmol), TEA (2.23 g, 3.1 ml, 22 mmol, 8.8 eq) and DCM (50 mL) were introduced in to a round-bottom flask equipped with a stir bar and placed under nitrogen. The solution was stirred and cooled to 0° C. A mixture of 5-bromovaleryl chloride (3.99 g, 2.68 ml, 20.0 mmol, 8 eq) in 10 mL of DCM was added dropwise. The solution was stirred overnight and allowed to warm to room temperature. After filtration, 30 mL of brine was added to the mixture and the aqueous phase was washed three times with DCM (3×100 ml). The organic phases were combined, dried (MgSO$_4$) and under vacuum. The product was purified by column chromatography (EtOAc: Hex=40:60 to 100:0).

C-(PEG-Br)$_4$, (4.36 g. 1.64 mmol), NaN$_3$ (4.27 g, 65.7 mmol and DMF (50 mL) were introduced in to a round-bottom flask. The solution was stirred for 24 h at room temperature. The solvent was evaporated, the mixture solubilised in acetone and filtered. The acetone was evaporated, brine (50 mL) was added and the mixture was washed with ethyl acetate (3×50 mL). The organic phases were combined, dried over MgSO$_4$ and dried under vacuum.

Method 19: General Method C for the Preparation of PEG Azide Co-Monomers: Carbamate Illustrated Using Example 137

4-arm PEG$_{2000}$-carbamate tetraazide co-monomer

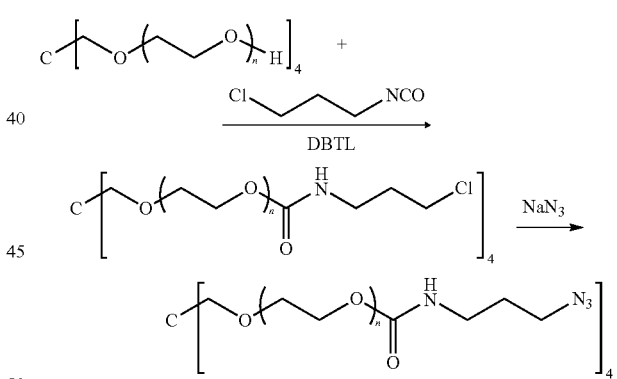

4-arm PEG$_{2000}$-OH (6 g, 3 mmol), dibutyltin dilaurate (0.19 g, 0.3 mmol) and dichloromethane (18 mL) were introduced in to a RBF equipped with a septum and a magnetic bar. 3-Chloropropyl isocyanate (2.15 g, 18.0 mmol) was added dropwise and the mixture was stirred for 24 h at room temperature. The solvent was evaporated and the product analysed by $^1$H NMR and MALDI-TOF spectroscopies.

4-arm PEG$_{2000}$-OCONH—C$_3$H$_6$—Br (4.56 g, 3.91 mmol), NaN$_3$ (10.2, 157 mmol) and DMF (120 mL) were introduced into a round-bottom flask. The solution was stirred for 48 h at 50° C. The solvent was evaporated, the mixture solubilised in EtOAc (50 mL) and filtered, washed with brine (25 mL), dried over NaSO$_4$ and the solvent removed under vacuum. The product was purified by flash chromatography (EtOAc:Hex=40:60 to 100:0 then Acetone 100).

Method 20: General Method for the Preparation of PEG Azide Co-Monomers: Amide
Illustrated Using Example 135; Amide

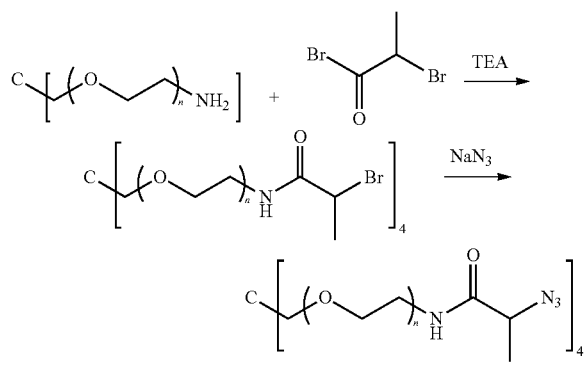

4arm amino-PEG (2.5 g, 1.25 mmol), TEA (1.53 mL, 11 mmol, 8.8 eq) and DCM (28 mL) were introduced in a two-neck round-bottom flask equipped with a pressure equalizing addition funnel and placed under nitrogen. The solution was stirred and cooled down to 0° C. Then, a mixture of 2-bromopropionyl bromide (1.05 mL, 10 mmol, 8 eq) in 2 mL of DCM was added dropwise through the dropping funnel. The solution was stirred overnight and allowed to warm up to room temperature. The mixture was dried, solubilised in 50 mL EtOAc, filtered and washed with brine (25 mL). The aqueous phase was washed twice with EtOAc, the organic phases were combined and dried over $MgSO_4$ and then under vacuum. MALDI-ToF: Mn=2437.4 g/mol; Mw=2440.7 g/mol; Đ=1.001.

(Br—CONH-PEG-)$_4$-C (0.792 g, 0.325 mmol), $NaN_3$ (0.845 g, 1.3 mmol, 40 eq) and DMF (10 mL) were introduced to a round-bottom flask. The solution was stirred during 24 h at room temperature. The solvent was evaporated, the mixture solubilised in 50 mL of ethyl acetate, filtered, washed with brine (25 mL), dried over $NaSO_4$ and under vacuum. MALDI-ToF: Mn=2185.5 g/mol; Mw=2191.6 g/mol; Đ=1.002.

Using the above methods the following polymers in Table 6 were prepared.

TABLE 6

| Ex. | Structure | PEG used | MALDI-ToF |
|---|---|---|---|
| 121 | 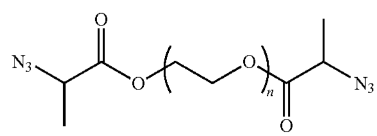 | PEG400 | $M_n$ = 659.0 g/mol<br>$M_w$ = 672.0 g/mol<br>Đ = 1.02 |
| 122 | 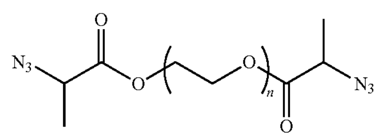 | PEG1000 | $M_n$ = 1256.4 g/mol<br>$M_w$ = 1278.5 g/mol<br>Đ = 1.002 |
| 123 | 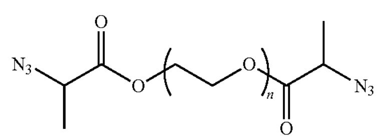 | PEG3000 | $M_n$ = 3186.4 g/mol<br>$M_w$ = 3205.8 g/mol<br>Đ = 1.01 |
| 124 | 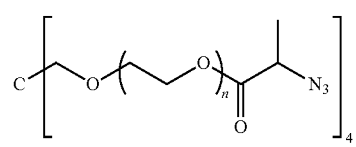 | PEG2000<br>4arm | $M_n$ = 2266.4 g/mol<br>$M_w$ = 2315.8 g/mol<br>Đ = 1.02 |
| 125 | 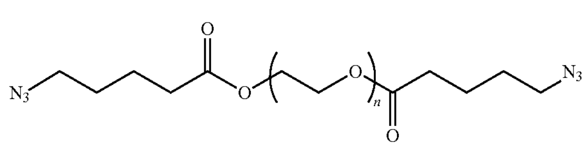 | PEG400 | $M_n$ = 599.1 g/mol<br>$M_w$ = 605.1 g/mol<br>Đ = 1.01 |
| 126 | 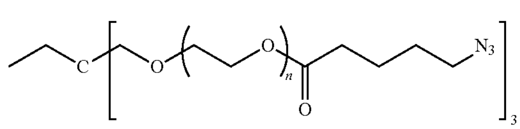 | PEG1000<br>3arm | $M_n$ = 1361.8 g/mol<br>$M_w$ = 1375.4 g/mol<br>Đ = 1.01 |
| 127 | 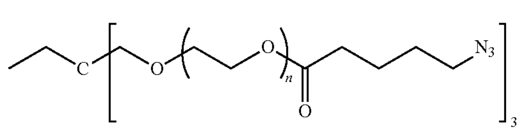 | PEG450<br>3arm | — |

TABLE 6-continued

| Ex. | Structure | PEG used | MALDI-ToF |
|---|---|---|---|
| 128 | 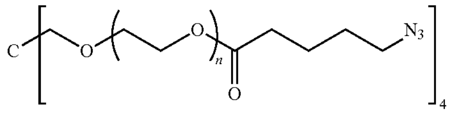 | PEG2000 4arm | $M_n$ = 2351.5 g/mol $M_w$ = 2372.1 g/mol Đ = 1.008 |
| 129 | 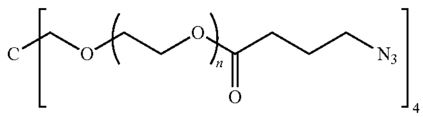 | PEG2000 4arm | $M_n$ = 2420.0 g/mol $M_w$ = 2439.7 g/mol Đ = 1.008 |
| 130 | 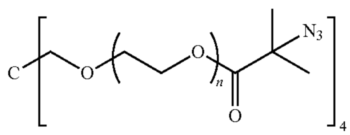 | PEG2000 4arm | $M_n$ = 2350.4 g/mol $M_w$ = 2368.9 g/mol Đ = 1.008 |
| 131 | 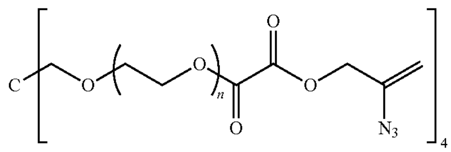 | PEG2000 4arm | $M_n$ = 2395.0 g/mol $M_w$ = 2409.8 g/mol Đ = 1.006 |
| 132 | 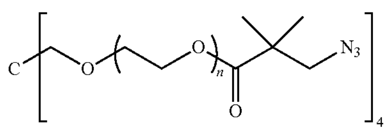 | PEG2000 4arm | $M_n$ = 2439.7 g/mol $M_w$ = 2451.7 g/mol Đ = 1.005 |
| 133 | 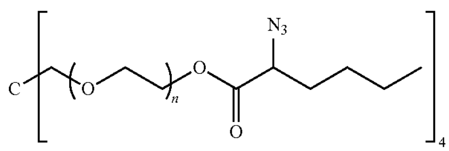 | PEG2000 4arm | $M_n$ = 2480.3 g/mol $M_w$ = 2490.0 g/mol Đ = 1.004 |
| 134 | 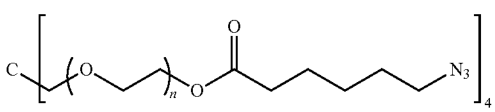 | PEG2000 4arm | $M_n$ = 2436 g/mol $M_w$ = 2474 g/mol Đ = 1.016 |
| 135 | 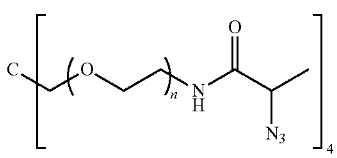 | PEG2000 4arm | $M_n$ = 2202.1 g/mol $M_w$ = 2208.3 g/mol Đ = 1.003 |
| 136 | 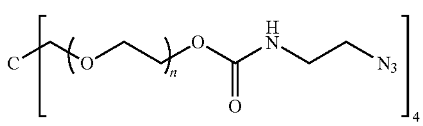 | PEG2000 4arm | $M_n$ = 2438.1 g/mol $M_w$ = 2458.1 g/mol Đ = 1.008 |
| 137 | 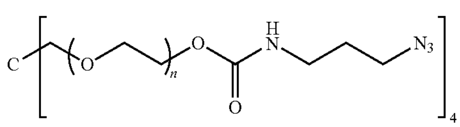 | PEG2000 4arm | $M_n$ = 2525.9 g/mol $M_w$ = 2535.1 g/mol Đ = 1.003 |
| 138 | 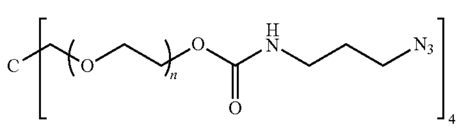 | PEG800 | $M_n$ = 1217.9 g/mol $M_w$ = 1222.1 g/mol Đ = 1.003 |
| 139 | 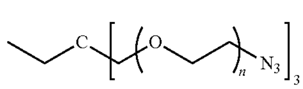 | PEG450 3arm | $M_n$ = 664.2 g/mol $M_w$ = 677.1 g/mol Đ = 1.02 |

TABLE 6-continued

| Ex. | Structure | PEG used | MALDI-ToF |
|---|---|---|---|
| 140 | 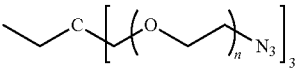 | PEG1000 3arm | |

Comonomers shown in Table 7 may be prepared in accordance with the same general procedure.

TABLE 7

| Ex. | Structure | PEG used |
|---|---|---|
| 141 | 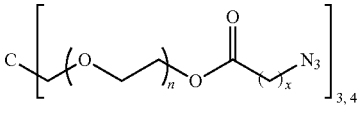<br>with x = 6 to 12 | PEG2000<br>PEG1000<br>PEG800<br>PEG450 |
| 142 | 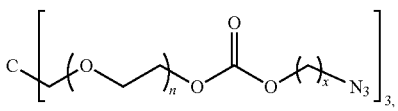<br>with x = 1 to 12 | PEG2000<br>PEG1000<br>PEG800<br>PEG450 |
| 143 | 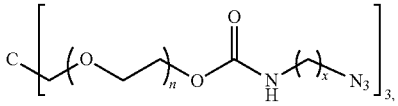<br>with x = 1, 4 to 12 | PEG2000<br>PEG1000<br>PEG800<br>PEG450 |
| 144 | 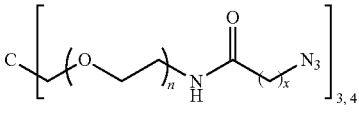<br>with x = 1 to 12 | PEG2000<br>PEG1000<br>PEG800<br>PEG450 |
| 145 | 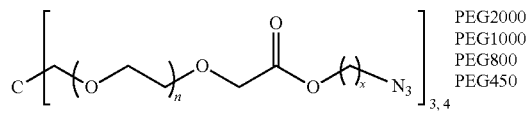<br>with x = 1 to 12 | PEG2000<br>PEG1000<br>PEG800<br>PEG450 |
| 146 | 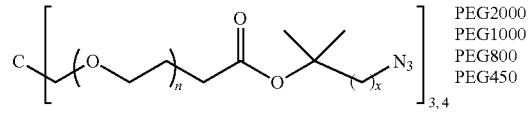<br>with x = 1 to 12 | PEG2000<br>PEG1000<br>PEG800<br>PEG450 |
| 147 | 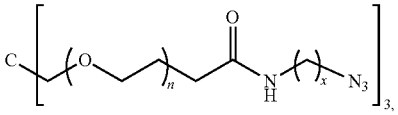<br>with x = 1 to 12 | PEG2000<br>PEG1000<br>PEG800<br>PEG450 |

Polymer Synthesis Linear Polytriazole Synthesis

Method 21: Copper (II)

The dialkyne-drug-monomer (1.0 eq), a diazide co-monomer (1.0 eq) and sodium ascorbate (0.45 eq) were placed into a vial fitted with a stirrer bar and then sealed with a Suba-Seal®. Anhydrous DMF pre-purged with $N_2$ or argon was introduced into the vial and the mixture was stirred to form a clear solution under constant flow of inert atmosphere. An amount of catalyst stock solution (CuBr2 (14.2 mg) and PMDETA (11.0 mg) in 2 mL of DMF) was added into the mixture to give 0.15 eq of $CuBr_2$ and 0.15 eq. PMDETA in the final reaction mixture. The solution was stirred for 24 hours at room temperature under constant flow of $N_2$. At the end of the reaction, the solution was diluted with THF and passed through a column of neutral alumina. The column was washed further with THF followed by DCM to collect the remaining polymers. The solution was then concentrated to around 1 mL and then precipitated into diethyl ether to give the desired polymer upon drying in vacuo.

Method 22: Copper (I)

The dialkyne-drug-monomer (1 eq) and diazide co-monomer (1 eq) were placed into a 4 mL vial fitted with a stirrer bar and then sealed with a Suba-Seal®. 0.5 mL of toluene pre-purged with $N_2$ was introduced into the vial and the mixture was stirred to form a clear solution under constant flow of $N_2$. 0.2 mL of CuBr (0.15 eq) and PMDETA (0.15 eq) stock solution (20 mg/mL in toluene, stirred for 30 minutes under $N_2$ prior to use) was subsequently added into the reaction mixture and the solution was stirred for 24 hours, at room T under constant flow of $N_2$. At the end of the reaction, the solution was diluted with 3 mL of THF and passed through a column of neutral alumina. The column was washed further with 20 mL of THF to ensure all polymer were collected. The solution was then concentrated to around 1 mL and then precipitated into 40 mL of diethyl ether and dried in vacuo.

Method 23: Ruthenium Catalysed Click Reaction

The dialkyne-drug-monomer (1 eq), diazide comonomer (1 eq), and DMF were introduced into vial with a stirrer bar and then sealed with a Suba-Seal®. The solution was purged for 10 minutes with Argon before 14.7 mg of Cp*RuCl(PPh$_3$)$_2$ was added and the reaction heated at 35° C. under Argon for 24 hours. The reaction mixture was added dropwise to ethyl ether to precipitate the product before being dried in vacuo overnight.

Cross Linked Polytriazole Synthesis

Method 24: Cross-Linked or Hyper-Branched Hydrogel

The dialkyne-drug-monomer (1 eq), a tetra-azide co-monomer (0.5 eq) or a tri-azide co-monomer (0.66 eq), Na ascorbate (0.45 eq) and DMF were introduced into a vial equipped with a magnetic stirrer bar. Catalyst stock solution (CuBr2 (14.2 mg) and PMDETA (11.0 mg) in 2 mL of DMF) was added into the mixture to give 0.15 eq of CuBr2 and 0.15 eq. PMDETA (in the final reaction mixture. The vial was sealed with a rubber septum, stirred at room temperature under nitrogen for 24 h. The resulting gel was dialysed in acetonitrile (3×1 L) and dried under high vacuum.

Method 25: Cross-Linked Rods and Bulk Gels Synthesis

The dialkyne-drug-monomer (1 eq), a tetra-azide co-monomer (0.5 eq) or a triazide co-monomer (0.66 eq), Na ascorbate (0.45 eq) and DMF were introduced into a vial equipped with a magnetic stirrer bar and PTFE tubes (0=0.35 mm, I=10 mm, 100 tubes). Catalyst stock solution (CuBr$_2$ (14.2 mg) and PMDETA (11.0 mg) in 2 mL of DMF) was added into the mixture to give 0.15 eq. of CuBr$_2$ and 0.15 eq. PMDETA in the final reaction mixture. The vial was sealed with a rubber septum, and degassing cycle (5 times nitrogen/vacuum cycles) were done to remove the bubbles trapped inside the tubes. The solution was subsequently stirred at room temperature under nitrogen for 24 h during which time gels formed. The tubes were separated from the bulk gels and soaked in isopropanol for minimum 16 hours and the rods were pushed out from the tubes using 0.305 mm stylet/wire. The resulting rods were washed in acetonitrile (3×250 mL) and the bulk gels with 3×1 L acetonitrile for 24 hours and dried under high vacuum.

Method 26: Cross-Linked or Hyper-Branched Hydrogel-Ruthenium Catalysed

Dialkyne-drug-monomer ((1 eq.), tetra-azide comonomer (0.5 eq), and DMF were introduced into a vial with a stirrer bar and then sealed with a Suba-Seal®. The mixture was then purged with Argon for 5 minutes before Cp*RuCl(PPh$_3$)$_2$ catalyst was added. The mixture was heated at 35° C. under Argon for 24 hours—before the temperature was raised to 50° C. for a second 24 hours. The resulting gel was dialysed in acetonitrile (3×1 L) and dried in vacuo overnight.

Method 27: Cross-Linked Rods and Bulk Gels Synthesis Containing 2 Different Cross-Linkers The dialkyne-drug-monomer (1 eq), a tetra-azide co-monomer 1 (0.25 eq) and another tetra-azide co-monomer 2 (0.25 eq), Na ascorbate (0.45 eq) and DMF were introduced into a vial equipped with a magnetic stirrer bar and PTFE tubes (Ø=0.35 mm, l=10 mm, 100 tubes). Catalyst stock solution (CuBr2 (14.2 mg) and PMDETA (11.0 mg) in 2 mL of DMF) was added into the mixture to give 0.15 eq. of CuBr2 and 0.15 eq. PMDETA in the final reaction mixture. The vial was sealed with a rubber septum, and degassing cycle (5 times nitrogen/vacuum cycles) were done to remove the bubbles trapped inside the tubes. The solution was subsequently stirred at room temperature under nitrogen for 24 h to form gels. The tubes were separated from the bulk gels and soaked in isopropanol for minimum 16 hours and the rods were pushed out from the tubes using 0.305 mm stylet/wire. The resulting rods were washed in acetonitrile (3×250 mL) and the bulk gels with 3×1 L acetonitrile for 24 hours and dried under high vacuum.

Method 28: Cross-Linked or Hyper-Branched Hydrogel Containing Two Different Drug-Monomers Dialkyne-drug-monomer (1) (0.5 eq), and dialkyne-drug-monomer (2) (0.5 eq), a tetra-azide co-monomer (0.5 eq) or a tri-azide co-monomer (0.66 eq), Na ascorbate (0.45 eq) and DMF (were introduced in a vial equipped with a magnetic stirring bar. Catalyst stock solution (CuBr2 (14.2 mg) and PMDETA (11.0 mg) in 2 mL of DMF) was added into the mixture to give 0.15 eq of CuBr2 and 0.15 eq. PMDETA in the final reaction mixture. The vial was sealed with a rubber septum, stirred at room temperature under nitrogen for 24 h. The gel was dialysed in acetonitrile (3×1 L) and dried under high vacuum.

Method 29: Polymer Conjugate Prepared with Diazide-Drug-Monomer.

The diazide-drug-monomer (1 eq.) and a dialkyne co-monomer (1 eq.) are dissolved in the solvent of choice. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred vigorously overnight at room temperature until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1$H NMR and $^{13}$C NMR and GPC.

Method 30: Linear Click Polymer Conjugate Prepared with Dialkyne-Drug-Monomer with Additives.

The dialkyne-drug-monomer and diazide co-monomer 1 and co-monomer 2 are dissolved in the solvent of choice while keeping an equimolar ratio between the number of alkyne units and azide units. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred overnight under argon atmosphere and at room temperature for 24 hours. The reaction mixture is then passed through a column of basic alumina to remove the CuBr$_2$ catalyst, and then concentrated in vacuo before being precipitated several times in excess of diethyl ether to afford the desired polymer a solid. The drug-polymerconjugates are analysed by $^1$H NMR and GPC.

Method 31: Polymer Conjugate Prepared with Alkyne-Azide-Drug-Agent Conjugate Monomer (Drug Monomer Only)

The alkyne-azide drug-monomer (1 eq.) is dissolved in the solvent of choice. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1$H NMR and $^{13}$C NMR and GPC.

Method 32: Polymer Conjugate Prepared with Alkyne-Azide-Drug-Monomer (and Co-Monomer)

The alkyne-azide-drug-monomer (1 eq.) and an alkyne-azide co-monomer (1 eq.) are dissolved in the solvent of choice. The solution is purged with argon for 30 minutes before copper (II) bromide (CuBr$_2$) (0.05 mol eq.), PMDETA (0.05 mol eq.) and sodium ascorbate (0.15 mol eq.) are added into the solution. The heterogeneous mixture is stirred vigorously overnight until complete consumption of starting materials, as indicated by TLC. The mixture is diluted with water and any precipitate that forms is collected. Purification of the product by precipitation from DMF and further purification on Sephadex LH-20 gives the title drug-polymer conjugate. The drug-polymer conjugates are analysed by IR, $^1$H NMR and $^{13}$C NMR and GPC.

Using the above methods the following polymers in Table 8 were prepared.

TABLE 8

Examples of Click Polymers

| Example | Drug | Drug-monomer 1 (mg) | Drug-monomer 2 (mg) | Co-Monomer 1 (mg) | Co-Monomer 2 (mg) | Production Method (solvent) | Characterisation |
|---|---|---|---|---|---|---|---|
| 148 | LTP | Example 63 (82.9) | — | PEG400diN₃ (61.5) | — | 21 (DMF) | Mw = 21.3 kDa, PDI = 1.51 solid |
| 149 | LTP | Example 37 (68.2) | — | PEG400diN₃ (45.2) | — | 21 (DMF) | Mw = 21.5 kDa, PDI = 1.51 solid |
| 150 | LTP | Example 65 (73.7) | — | Example 128 (156.4) | — | 24/25 (DMF) | NA |
| 151 | LTP | Example 65 (157.4) | — | Example 131 (327.2) | — | 24/25 (DMF) | NA |
| 152 | LTP | Example 37 (91.2) | — | Example 135 (151.4) | — | 24/25 (DMF) | NA |
| 153 | LTP | Example 37 (92.3) | — | Example 136 (156.0) | — | 24/25 (DMF) | NA |
| 154 | LTP | Example 37 (92.0) | — | ((N3-PEG300)3-C—Et) (92.2) | — | 24/25 (DMF) | NA |
| 155 | LTP | Example 37 (264.8) | — | (N3-PEG500)4-C (363.5) | — | 24/25 (DMF) | NA |
| 156 | LTP | Example 37 (175.4) | — | Example 128 (302.2) | — | 24/25 (DMF) | NA |
| 157 | LTP | Example 37 (93.6) | — | Example 137 (160.1) | — | 24/25 (DMF) | NA |
| 158 | LTP | Example 35 (89.6) | — | Example 128 (167.9) | — | 24/25 (DMF) | NA |
| 159 | LTP | Example 56 (66.9) | (Example 38) (23.1) | (N3-PEG500)4-C (126.8) | — | 28 (DMF) | NA |
| 160 | LTP | Example 38 (94.3) | — | (N3-PEG500)4-C (131.2) | — | 24/25 (DMF) | NA |
| 161 | LTP | Example 38 (96.4) | — | Example 128 (158.6) | — | 24/25 (DMF) | NA |
| 162 | LTP | Example 38 (95.8) | — | Example 137 (158.7) | — | 24/25 (DMF) | NA |
| 163 | LTP | Example 38 (48.0) | Example 56 (44.6) | (N3-PEG500)4-C (126.8) | — | 28 (DMF) | NA |
| 164 | LTP | Example 38 (24.3) | (Example 56) (66.6) | (N3-PEG500)4-C (127.8) | — | 28 (DMF) | NA |
| 165 | LTP | Example 38 (55.7) | (Example 56) (36.6) | (N3-PEG500)4-C (126.4) | — | 28 (DMF) | NA |
| 166 | LTP | Example 38 (69.9) | Example 56 (22.7) | (N3-PEG500)4-C (127) | — | 28 (DMF) | NA |
| 167 | LTP | Example 36 (91.8) | — | (N3-PEG500)4-C (128.5) | — | 24/25 (DMF) | NA |
| 168 | LTP | Example 36 (89.2) | — | Example 128 (156.5) | — | 24/25 (DMF) | NA |
| 169 | LTP | Example 44 (98.0) | — | (N3-PEG500)4-C (127.8) | — | 24/25 (DMF) | NA |
| 170 | LTP | Example 40 (75.4) | — | (N3-PEG500)4-C (99.1) | — | 24/25 (DMF) | NA |
| 171 | LTP | Example 40 (86.5) | — | Example 137 (143.0) | — | 24/25 (DMF) | NA |
| 172 | LTP | Example 39 (104.6) | — | (N3-PEG500)4-C (144.5) | — | 24/25 (DMF) | NA |
| 173 | LTP | Example 39 (93.2) | — | Example 138 (160.9) | — | 24/25 (DMF) | NA |
| 174 | LTP | Example 39 (92.5) | — | (N3-PEG200-)4-C (58.8) | — | 24/25 (DMF) | NA |
| 175 | LTP | Example 53 (109.1) | — | (N3-PEG500)4-C (149.3) | — | 24/25 (DMF) | NA |
| 176 | LTP | Example 41 (143.9) | — | (N3-PEG500)4-C (191.8) | — | 24/25 (DMF) | NA |
| 177 | LTP | Example 42 (149.6) | — | (N3-PEG500)4-C (193.8) | — | 24/25 (DMF) | NA |
| 178 | LTP | Example 59 (79.0) | — | (N3-PEG500)4-C (126.6) | — | 24/25 (DMF) | NA |
| 179 | LTP | Example 43 (103.6) | — | (N3-PEG500)4-C (129.4) | — | 24/25 (DMF) | NA |
| 180 | LTP | Example 48) (104.1) | — | (N3-PEG500)4-C (132.7) | — | 24/25 (DMF) | NA |
| 181 | LTP | Example 46 (107.5) | — | (N3-PEG500)4-C (127.5) | — | 24/25 (DMF) | NA |
| 182 | LTP | Example 45 (66.6) | — | (N3-PEG500)4-C (81.6) | — | 24/25 (DMF) | NA |

TABLE 8-continued

Examples of Click Polymers

| Example | Drug | Drug-monomer 1 (mg) | Drug-monomer 2 (mg) | Co-Monomer 1 (mg) | Co-Monomer 2 (mg) | Production Method (solvent) | Characterisation |
|---|---|---|---|---|---|---|---|
| 183 | LTP | Example 46 (107.5) | — | (N3-PEG500)4-C (127.5) | — | 24/25 (DMF) | N/A Cross-linked hydrogel |
| 184 | LTP | Example 65 (157.7) | — | Example 131 (327.2) | — | 24/25 (DMF) | N/A Cross-linked hydrogel |
| 185 | LTP | Example 65 (157.3) | — | Example 130 (321.6) | — | 24/25 (DMF) | N/A Cross-linked hydrogel |
| 186 | LTP | Example 47 (97.3) | — | (N3-PEG500)4-C (128.7) | — | 24/25 (DMF) | N/A Cross-linked hydrogel |
| 187 | LTP | Example 51 (90.0) | — | (N3-PEG500)4-C (108.4) | — | 24/25 (DMF) | N/A Cross-linked hydrogel |
| 188 | LTP | Example 49 (96.0) | — | (N3-PEG500)4-C (126.0) | — | 24/25 (DMF) | N/A Cross-linked hydrogel |
| 189 | LTP | Example 54 (93.2) | — | (N3-PEG500)4-C (127.2) | — | 24/25 (DMF) | N/A Cross-linked hydrogel |
| 190 | LTP | Example 65 (211.4) | — | (Example 129) (439.1) | — | 24/25 (DMF) | N/A Cross-linked hydrogel |
| 191 | LTP | Example 39 (242.2) | — | (N3-PEG500)4-C (365.8) | — | 24/25 (DMF) | N/A Cross-linked hydrogel |
| 192 | LTP | Example 65 (105.8) | — | (Example 133) (224.9) | — | 24/25 (DMF) | N/A Cross-linked hydrogel |
| 193 | LTP | Example 65 (105.7) | — | (Example 128) (106.9) | Example 137 (113.4) | 27 | N/A Cross-linked hydrogel |
| 194 | LTP | Example 65 (105.8) | — | Example 124 (205.8) | — | 24/25 (DMF) | N/A Cross-linked hydrogel |
| 195 | LTP | Example 52 (135.7) | — | (N3-PEG500)4-C (150) | — | 24/25 (DMF) | N/A Cross-linked hydrogel |
| 196 | LTP | Example 67 (139.7) | — | (N3-PEG500)4-C (182.1) | — | 24/25 (DMF) | N/A Cross-linked hydrogel |
| 197 | LTP | Example 40 (205.2) | — | 4-arm PEG800 azide (124.2) | — | 24/25 (DMF) | N/A Cross-linked hydrogel |
| 198 | LTP | Example 65 (106.6) | — | (N3-PEG500)4-C (91.4) | Example 128 (108.0) | 27 | N/A Cross-linked hydrogel |
| 199 | LTP | Example 65 (122.6) | — |  | Example 134 (255.6) | 24/25 (DMF) | N/A Cross-linked hydrogel |
| 200 | LTP | Example 65 (122.3) | — | (N3-PEG500)4-C (105.9) | Example 134 (128.0) | 27 | N/A Cross-linked hydrogel |
| 201 | LTP | Example 65 (122.5) | — | Example 137 (132.0) | Example 134 (128.0) | 27 | N/A Cross-linked hydrogel |
| 202 | LTP | Example 66 (105.9) | — | (N3-PEG500)4-C (133.3) | — | 24/25 (DMF) | N/A Cross-linked hydrogel |
| 203 | LTP | Example 40) (71.4) | — | PEG2000 diazide (187.3) | — | 21 | Mn = 19.1 kDa<br>Mw = 34.4 kDa<br>Đ = 1.80<br>$^1$H NMR:<br>Ltp: 47.3%,<br>PEG = 52.7%<br>solid |
| 204 | LTP | Example 40 (75.6) | — | PEG5000 diazide (500.3) | — | 21 (DMF) | Mn = 35.7 kDa<br>Mw = 64.3 kDa<br>Đ = 1.80<br>$^1$H NMR:<br>Ltp: 40%,<br>PEG = 60%<br>solid |

TABLE 8-continued

Examples of Click Polymers

| Example | Drug | Drug-monomer 1 (mg) | Drug-monomer 2 (mg) | Co-Monomer 1 (mg) | Co-Monomer 2 (mg) | Production Method (solvent) | Characterisation |
|---|---|---|---|---|---|---|---|
| 205 | BET | Example 72 (78.8) | — | Example 128 (217.7) | — | 24/25 (DMF) | N/A Cross-linked hydrogel |
| 206 | BET | Example 72 (78.8) | — | Example 129 (217.7) | — | 24/25 (DMF) | N/A Cross-linked hydrogel |
| 207 | BIM | Example 74 (87.9) | — | Example 129 (198.8) | — | 24/25 (DMF) | N/A Cross-linked hydrogel |
| 208 | BIM | Example 74 (61.1) | — | (N3-PEG500)4-C (114.8) | — | 24/25 (DMF) | N/A Cross-linked hydrogel |
| 209 | TIM | Example 73 (117.1) | — | (N3-PEG500)4-C (188.6) | — | 24/25 (DMF) | N/A Cross-linked hydrogel |
| 210 | LTP | Example 65 | — | Example 137 | — | 24/25 (DMF) | N/A Cross-linked hydrogel |
| 211 | LTP | Example 65 | — | Example 138 | — | 24/25 (DMF) | N/A Cross-linked hydrogel |
| 212 | LTP | Example 65 | — | Example 138 | — | 24/25 (DMF) | N/A Cross-linked hydrogel |
| 213 | LTP | Example 65 | — | (N3-PEG500)4-C | — | 24/25 (DMF) | N/A Cross-linked hydrogel |
| 214 | LTP | Example 40 (142.2) | — | (N3-PEG1250)8-C (468.7) | — | 24/25 (DMF) | N/A Cross-linked hydrogel |
| 215 | LTP | Example 40 (142.2) | — | PEG1000diN$_3$ (187.4) | — | 21 | Mw = 66.9 kDa PDI = 3.09 |
| 216 | LTP | Example 40 (142.0) | — | PEG400diN3 (102.5) | — | 23 (DMF) | Mw = 8.3 kDa PDI = 1.64 |
| 217 | LTP | Example 40 (142.0) | — | (N3-PEG500)4-C (188.7) | — | 26 (DMF) | NA |
| 218 | LTP | Example 55 (88.0) | — | (N3-PEG500)4-C (111.7) | — | 24/25 (DMF) | N/A Cross-linked hydrogel |
| 219 | TIM | Example 71 (186.7) | — | Example 128 (505.7) | — | 24/25 (DMF) | N/A Cross-linked hydrogel |
| 220 | LTP | Example 65 (52.9) | Example 40 (68.8) | (N3-PEG500)4-C (181.3) | — | 28 | N/A Cross-linked hydrogel |
| 221 | LTP | Example 60 (12.1) | — | (N3-PEG500)4-C (162.4) | (alkyne-PEG$_{500}$-)4-C (149.0) | 27 | N/A Cross-linked hydrogel |
| 222 | LTP | Example 60 (401.1) | — | (N3-PEG500)4-C (664.1) | — | 24/25 (DMF) | N/A Cross-linked hydrogel |
| 223 | LTP | Example 60 (204.5) | — | Example 135 (370.8) | — | 24/25 (DMF) | N/A Cross-linked hydrogel |
| 224 | LTP | Example 60 (202.1) | — | Example 124 (371.1) | — | 24/25 (DMF) | N/A Cross-linked hydrogel |
| 225 | LTP | CAS 1627102-25-3 (1 eq) | — | (N3-PEG500)4-C (0.5 eq) | — | 24/25 (DMF) | N/A Cross-linked hydrogel ross-linked |
| 226 | LTP | CAS 1627102-25-3 (1 eq) | — | Example 135 (0.5 eq) | — | 24/25 (DMF) | N/A Cross-linked hydrogel |
| 227 | LTP | Example 75 (1eq) | — | (N3-PEG500)4-C (0.5 eq) | — | 24/25 (DMF) | N/A Cross-linked hydrogel |
| 228 | LTP | Example 75 (1 eq) | — | Example 135 (0.56 eq) | — | 24/25 (DMF) | N/A Cross-linked hydrogel |

TABLE 8-continued

Examples of Click Polymers

| Example | Drug | Drug-monomer 1 (mg) | Drug-monomer 2 (mg) | Co-Monomer 1 (mg) | Co-Monomer 2 (mg) | Production Method (solvent) | Characterisation |
|---|---|---|---|---|---|---|---|
| 229 | LTP | Example 35 (283.3) | — | (N3-PEG500)4-C (462.6) | — | 24/25 | N/A Cross-linked hydrogel |
| 230 | LTP | Example 58 (107.0) | — | (N3-PEG500)4-C (133.5) | — | 24/25 | N/A Cross-linked hydrogel |
| 231 | LTP | Example 56 (250.9) | — | (N3-PEG500)4-C (361.4) | — | 24/25 | N/A Cross-linked hydrogel |
| 232 | LTP | Example 56 (250.9) | — | Example 128 (453.1) | — | 24/25 | N/A Cross-linked hydrogel |
| 233 | LTP | Example 40 (100.2) | — | (N3-PEG500)4-C (132.2) | — | 24/25 | N/A Cross-linked hydrogel |
| 234 | LTP | Example 56 (250.9) | — | Example 137 (459.4) | — | 24/25 | N/A Cross-linked hydrogel |
| 235 | LTP | Example 35 (111.5) | — | Example 137 (226.0) | — | 24/25 | N/A Cross-linked hydrogel |
| 236 | LTP | Example 35 (112.0) | — | Example 124 (205.0) | — | 24/25 | N/A Cross-linked hydrogel |
| 237 | LTP | Example 35 (112.9) | — | Example 136 (223.0) | — | 24/25 | N/A Cross-linked hydrogel |
| 238 | LTP | Example 35 (90.9) | — | Example 135 (165.0) | — | 24/25 | N/A Cross-linked hydrogel |
| 239 | LTP/TIM | Example 63 (52.5) | CAS 1627102-47-9 (37.3) | PEG400diN3 (77.8) | — | 21 | Mw = 18.0 kDa, PDI = 1.42 |

Using the above methods the following polymers may also be prepared.

| Example | Drug | Drug-monomer conjugate | Co-Monomer 1 | Co-Monomer 2 | Method of Synthesis |
|---|---|---|---|---|---|
| 240 | BIM | Example 86 | (N3-PEG500)4-C | — | 24/25 |
| 241 | TAF | Example 85 | (N3-PEG500)4-C | — | 24/25 |
| 242 | TVP | Example 84 | (N3-PEG500)4-C | — | 24/25 |
| 243 | BIM | Example 86 | Example 137 | — | 24/25 |
| 244 | TAF | Example 85 | Example 137 | — | 24/25 |
| 245 | TVP | Example 84 | Example 137 | — | 24/25 |
| 246 | LTP | Example 36 | (N3-PEG200)4-C | — | 24/25 |
| 247 | LTP | Example 36 | (N3-PEG150)3-C | — | 24/25 |
| 248 | LTP | Example 36 | Example 137 | — | 24/25 |
| 249 | LTP | Example 51 | (N3-PEG200)4-C | — | 24/25 |
| 250 | LTP | Example 51 | (N3-PEG150)3-C | — | 24/25 |
| 251 | LTP | Example 51 | Example 137 | — | 24/25 |
| 252 | LTP | Example 39 | (N3-PEG200)4-C | — | 24/25 |
| 253 | LTP | Example 39 | (N3-PEG150)3-C | — | 24/25 |
| 254 | LTP | Example 39 | Example 137 | — | 24/25 |
| 255 | LTP | Example 50 | Example 137 | — | 24/25 |
| 256 | LTP | Example 50 | (N3-PEG200)4-C | — | 24/25 |
| 257 | LTP | Example 50 | (N3-PEG150)3-C | — | 24/25 |
| 258 | BIM | Example 74 | Example 128 | — | 24/25 |
| 259 | BIM | Example 74 | Example 134 | — | 24/25 |
| 260 | LTP | Example 75 | (N3-PEG150)3-C | — | 24/25 |
| 261 | LTP | Example 75 | Example 137 | — | 24/25 |
| 262 | LTP | Example 44 | Example 128 | — | 24/25 |
| 263 | LTP | Example 44 | Example 134 | — | 24/25 |
| 264 | LTP | Example 44 | Example 137 | — | 24/25 |
| 265 | LTP | Example 44 | (N3-PEG200)4-C | — | 24/25 |
| 266 | LTP | Example 36 | Example 128 | — | 24/25 |
| 267 | LTP | Example 36 | Example 134 | — | 24/25 |
| 268 | LTP | Example 36 | Example 137 | — | 24/25 |
| 269 | LTP | Example 36 | (N3-PEG200)4-C | — | 24/25 |
| 270 | LTP | Example 49 | Example 128 | — | 24/25 |
| 271 | LTP | Example 49 | Example 134 | — | 24/25 |
| 272 | LTP | Example 49 | Example 137 | — | 24/25 |
| 273 | LTP | Example 49 | (N3-PEG200)4-C | — | 24/25 |
| 274 | LTP | Example 37 | Example 128 | — | 24/25 |
| 275 | LTP | Example 37 | Example 134 | — | 24/25 |
| 276 | LTP | Example 37 | Example 137 | — | 24/25 |
| 277 | LTP | Example 37 | (N3-PEG200)4-C | — | 24/25 |
| 278 | LTP | Example 38 | Example 128 | — | 24/25 |
| 279 | LTP | Example 38 | Example 134 | — | 24/25 |
| 280 | LTP | Example 38 | Example 137 | — | 24/25 |
| 281 | LTP | Example 38 | (N3-PEG200)4-C | — | 24/25 |

Drug Release Method

Polymer samples were tested for in vitro drug release following guidelines recommended by the International Organisation of Standardisation. The samples were placed onto a wire mesh folded into an M shape and suspended in isotonic phosphate buffer (IPB) pH 7.4 or pH 8.4 (Table 1), and stirred at 37° C. or 55° C. Aliquots of the receptor solution were collected at pre-determined time points until the drug was depleted from the polymer.

In-Vitro Release Sample Preparation 15 mL of isotonic phosphate buffer (pH 7.4) was added to approximately 10 mg of bulk polymer material and allowed to stir in a 37° C. water bath in the absence of light. 100 μL aliquots of each sample were removed at defined time points. 100 μL of isotonic phosphate buffer was replaced back into each sample after each aliquot removal. The amount of drug in the aliquots was quantified by reverse phase high performance liquid chromatography (HPLC) coupled with UV detection. Analytes were separated on a C18 column with a solvent mixture as outlined for each drug class in Table 9 below.

TABLE 9

| Assay | Column | Mobile Phase | Flow rate (mL/min) | Wavelength (nm) | Retention time (min) |
|---|---|---|---|---|---|
| 1: Latanoprost free acid: | Kinetex ® XB C18 150 × 4.6 mm; 5 µm, 100 Å | Acetonitrile:water 38:62 pH 3.0 (adjusted with phosphoric acid) | 1.0 | 210 | 7.0 |
| 2: Bimatoprost | Kinetex ® EVO C18 150 × 4.6 mm; 5 µm, 100 Å | Acetonitrile:0.1% TEA in water 37:63 pH 6.0 (adjusted with acetic acid) | 1.0 | 210 | 20.0 |
| 3. Timolol | C18 | Acetonitrile:0.6% TEA in water adjusted to pH 3 with phosphoric acid 17:83 | 1 mL/min | 296 nm | 10 |
| 4. Betaxolol | C18 | Acetonitrile: 0.05M Na2HPO4•12H2O, pH 3.0 10-60% | 1 mL/min | 280 nm | 24 |

Degradation Sample Preparation

In Vitro Degradation of Cross-Linked Polymers

A degradation sample consists of three to four rods of cross-linked polymer (total polymer mass=0.5 to 1.1 mg) wrapped in a stainless-steel mesh, placed in an amber glass vial filled with 15 mL of isotonic phosphate buffer (pH 7.4) and equipped with a stir bar and a PTFE/silicone septum screw cap. The initial mass of both mesh and rods is recorded.

Ten to twelve of these samples were placed in a thermostatted water bath at either 37° C. or 55° C., equipped with a multi-stirring plate. The samples are stirred at 300 rpm at the required temperature and a sample is removed at predetermined time points. The polymer is removed from the sample and the mesh with the rods was washed twice with milliQ water and dried under vacuum. The rods were weighed. When rods could not be removed from the mesh (rods stuck), the mesh with rods was weighed. In addition, the drug concentration of the buffer was measured by HPLC.

The amount of drug release from samples undergoing biodegradation was also determined. 100 µL aliquots of each sample were removed at defined time points. The amount of drug in the aliquots was quantified by reverse phase high performance liquid chromatography (HPLC) coupled with UV detection, as outlined below.

In Vitro Degradation of Linear Polymers

A degradation sample consists of carefully weighed polymer (~10 mgs) placed in an 8 mL vial filled with 5 mL of isotonic phosphate buffer (pH 7.4) and equipped with a stir bar and a PTFE/silicone septum screw cap. Four to five samples of each polymer were placed in a thermostatted water bath at either 37° C. or 55° C., equipped with a multi-stirring plate. The samples are stirred at 300 rpm at the required temperature and a sample is removed at predetermined time points. 100 µL aliquots were removed from each sample and the amount of drug in the aliquots was quantified by reverse phase high performance liquid chromatography (HPLC) coupled with UV detection, as outlined below. The remaining solution was dried in a freeze dryer for 72 hours. Gel permeation chromatography (GPC) analysis was done on each sample to analyse the molecular weight of the polymer.

GPC Analysis:

Gel permeation chromatography (GPC) analysis of the polymer samples was performed on Shimadzu liquid chromatography system equipped with a Shimadzu RID-10A differential refractive index detector (A=633 nm) and Shimadzu SPD-20A ultraviolet detector connected to a 5.0 µm bead-size guard column (50×7.8 mm) followed by three Shodex KF-805 L columns (300×8 mm, bead size: 10 µm, pore size maximum: 5000 Å) in series operating at 40° C. The eluent was N,N-dimethylacetamide (HPLC grade, with 0.03% w/v LiBr) and running at 1 mL/min. A molecular weight calibration curve was produced using polystyrene standards with narrow molecular weights distribution ranging from 500 to 2×10$^6$ Da.

The amount of drug release from samples undergoing biodegradation was also determined. 100 µL aliquots of each sample were removed at defined time points. The amount of drug in the aliquots was quantified by reverse phase high performance liquid chromatography (HPLC) coupled with UV detection, as outlined in Table 10 below.

TABLE 10

Drug release from polymers.

| | | Release study | |
|---|---|---|---|
| Example no. | Buffer pH for release study | Drug | Rate [µg/10 mg/24 hrs] |
| 210 | 7.4 | Latanoprost free acid | 11.73 |
| 150 | 7.4 | Latanoprost free acid | 7.52 |
| 211 | 7.4 | Latanoprost free acid | 2.61 |
| 212 | 7.4 | Latanoprost free acid | 3.18 |
| 155 | 7.4 | Latanoprost free acid | 14.96 |
| 229 | 7.4 | Latanoprost free acid | 3.37 |
| 156 | 7.4 | Latanoprost free acid | 9.33 |
| 232 | 7.4 | Latanoprost free acid | 5.49 |
| 160 | 7.4 | Latanoprost free acid | 13.18 |
| 161 | 7.4 | Latanoprost free acid | 5.57 |

TABLE 10-continued

Drug release from polymers.

| | | Release study | |
|---|---|---|---|
| Example no. | Buffer pH for release study | Drug | Rate [μg/10 mg/24 hrs] |
| 162 | 7.4 | Latanoprost free acid | 6.40 |
| 230 | 7.4 | Latanoprost free acid | 1.62 |
| 173 | 7.4 | Latanoprost free acid | 10.57 |
| 170 | 7.4 | Latanoprost free acid | 6.95 |
| 164 | 7.4 | Latanoprost free acid | 9.14 |
| 166 | 7.4 | Latanoprost free acid | 11.99 |
| 163 | 7.4 | Latanoprost free acid | 8.88 |
| 231 | 7.4 | Latanoprost free acid | 7.52 |
| 196 | 7.4 | Latanoprost free acid | 9.73 |
| 214 | 7.4 (55.0° C.) | Latanoprost free acid | 40.57 |
| 191 | 7.4 | Latanoprost free acid | 14.78 |
| 192 | 7.4 | Latanoprost free acid | 28.23 |
| 233 | 7.4 | Latanoprost free acid | 6.76 |
| 177 | 7.4 | Latanoprost free acid | 6.30 |
| 179 | 7.4 | Latanoprost free acid | 4.85 |
| 195 | 7.4 | Latanoprost free acid | 18.93 |
| 180 | 7.4 | Latanoprost free acid | 6.83 |
| 181 | 7.4 | Latanoprost free acid | 9.53 |
| 186 | 7.4 | Latanoprost free acid | 8.95 |
| 221 | 7.4 | Latanoprost free acid | 7.01 |
| 222 | 7.4 | Latanoprost free acid | 36.23 |
| 223 | 7.4 | Latanoprost free acid | 15.09 |
| 224 | 7.4 | Latanoprost free acid | 137.13 |
| 193 | 7.4 | Latanoprost free acid | 10.35 |
| 199 | 7.4 | Latanoprost free acid | 7.39 |
| 200 | 7.4 | Latanoprost free acid | 12.09 |
| 201 | 7.4 | Latanoprost free acid | 10.24 |

Pupil Response Method
Dog IOP and Pupil Size Study Method

The in vivo performance of select drug polymer conjugates were studied in purpose bred dogs (*Canis lupus familiaris*), homozygous for the G661R missense mutation in ADAMTS10, and therefore affected with primary angle glaucoma.

The needle containing a rod-shaped implant of the selected conjugate was inserted into the anterior chamber at the limbus by penetrating the conjunctiva, sclera and cornea. The needle was moved as far as possible into the anterior chamber so that its tip was close to the inferior iridocorneal angle. The implant was expelled from the needle and placed into the inferior iridocorneal angle by moving a stylet inside the needle towards the needle tip. The needle was then removed from the anterior chamber and the conjunctiva around the injection site held off with forceps for 1-2 minutes to minimize leakage of aqueous humour.

The measurement of diurnal intraocular pressure (IOP) was performed by means of a rebound tonometer (TONOVET™; Icare Finland Oy, Vantaa, Finland) on awake, unsedated dogs. IOP measurements taken at 8 am, 12 μm, and 4 μm and the mean of all measurements was also calculated in order to determine the mean diurnal IOP.

Pupil diameter was measured by means of Jameson™ calipers. Pupil sizes were assessed at the same time points as IOP measurements (08:00, 12:00, and 16:00) and immediately following the tonometry. The room light was turned off, and a red LED headlight used to visualize the fundic reflection for outline of the pupil by retroillumination. Pupil sizes for measurements at 8 am, 12 μm, and 4 μm were used to calculate the average pupil size.

Rabbit Biodegradation Study

The in vivo implant biodegradation of select drug polymer conjugates were studied in New Zealand White albino rabbits or Dutch Belted pigmented rabbits.

The needle containing a rod-shaped implant of the selected conjugate was inserted into the anterior chamber at the limbus by penetrating the conjunctiva, sclera and cornea. The needle was moved as far as possible to the centre of the anterior chamber. The implant was expelled from the needle and placed onto the cornea by moving a stylet inside the needle towards the needle tip. The needle was then removed from the anterior chamber and the conjunctiva around the injection site held off with forceps for 1-2 minutes to minimize leakage of aqueous humour.

At designated time points implants were excised from the eye, washed twice with MilliQ water, dried to constant weight and weighed on a 6-figure balance. The measured weight was compared to the weight of the implant prior to implant administration to a rabbit eye to determine the % weight loss.

Discussion of Drawings

Referring to the drawings the figures show specific examples of the drug polymer conjugate and demonstrate the effect of variation in the monomer components and the presence of biodegradable groups such as formula II.

Figure 1:
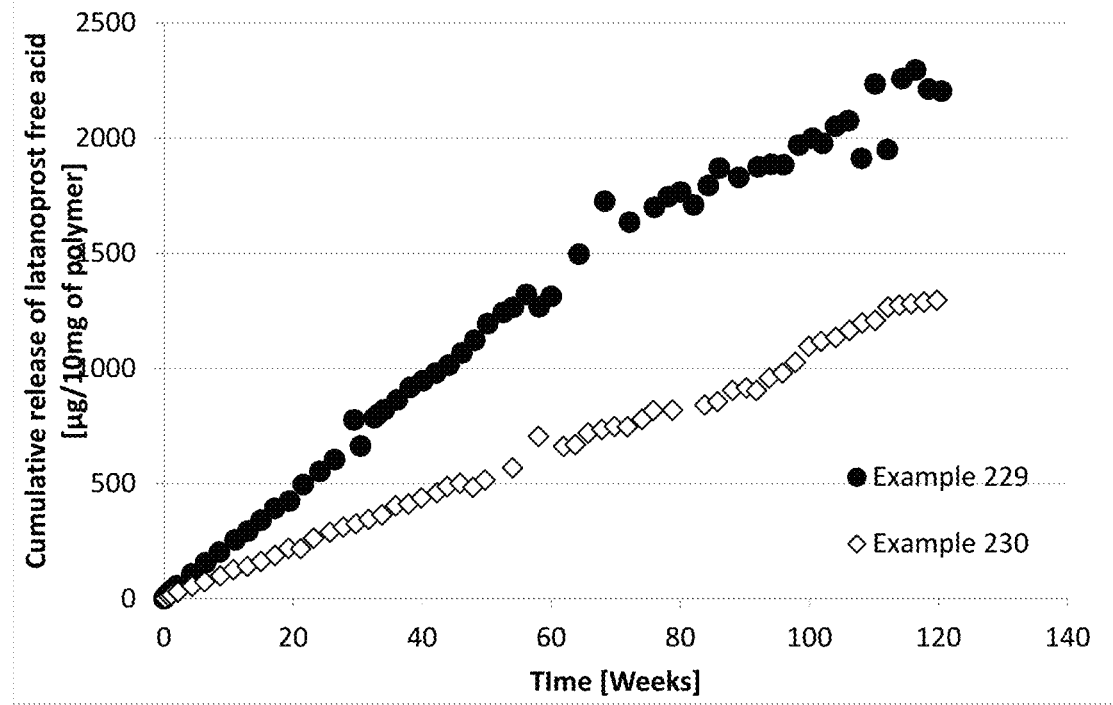
FIG. 1 is a graph having two plots showing the cumulative release (μg/10 mg) of latanoprost free acid with time exposed to isotonic phosphate buffer (pH 7.4) at 37.0° C. from drug-polymer conjugates of Example 229 and 230 with a common linker (L), common co-monomer but a different Q-X moiety.

In FIG. 1 the plots show the cumulative release (μg/10 mg) of latanoprost free acid with time exposed to isotonic phosphate buffer (pH 7.4) at 37.0° C. from drug-polymer conjugates with a common linker (L), common co-monomer but a different Q-X moiety. Example 229 has a shorter methylene chain within the Q-X moiety than Example 230. In both cases the rate of drug release is shown to be the preferred near zero-order profile to provide a product that delivers a constant daily dose for the entire treatment period. Release of latanoprost free acid is more rapid with Example 229 that Example 230, showing that changes to chemistry around an aryl ester linker (L) can be used to vary rate of drug release.

Drug-polymer conjugates of Example 229 and Example 230 were produced and each are a product of the respective drug monomers, Example 1 and Example 58, and 4-arm PEG500 azide,

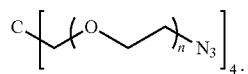

Example 1 and Example 58 both involve latanoprost free acid attached through an aryl ester to pyridoxine but with an ether Q-X functionality with increasing methylene chain length within Q-X.

TABLE 11

| Drug Monomer Example | Example 1 | Example 58 |
|---|---|---|
| Structure | (structure with LtpFA, pyridine, propargyl ether) | (structure with LtpFA, pyridine, hexynyl ether) |

In both cases release there is no biodegradable moiety within the polymer of the construct, hence drug release is solely a function of hydrolysis of the linker (L) to release latanoprost free acid. A biodegradable polymer is not required to provide effective drug release. Example 229 has a shorter methylene chain within the Q-X moiety than Example 230. Release of latanoprost free acid is more rapid with Example 229 that Example 230, showing that changes to chemistry around an aryl ester linker (L) can be used to vary rate of drug release.

Figure 2:
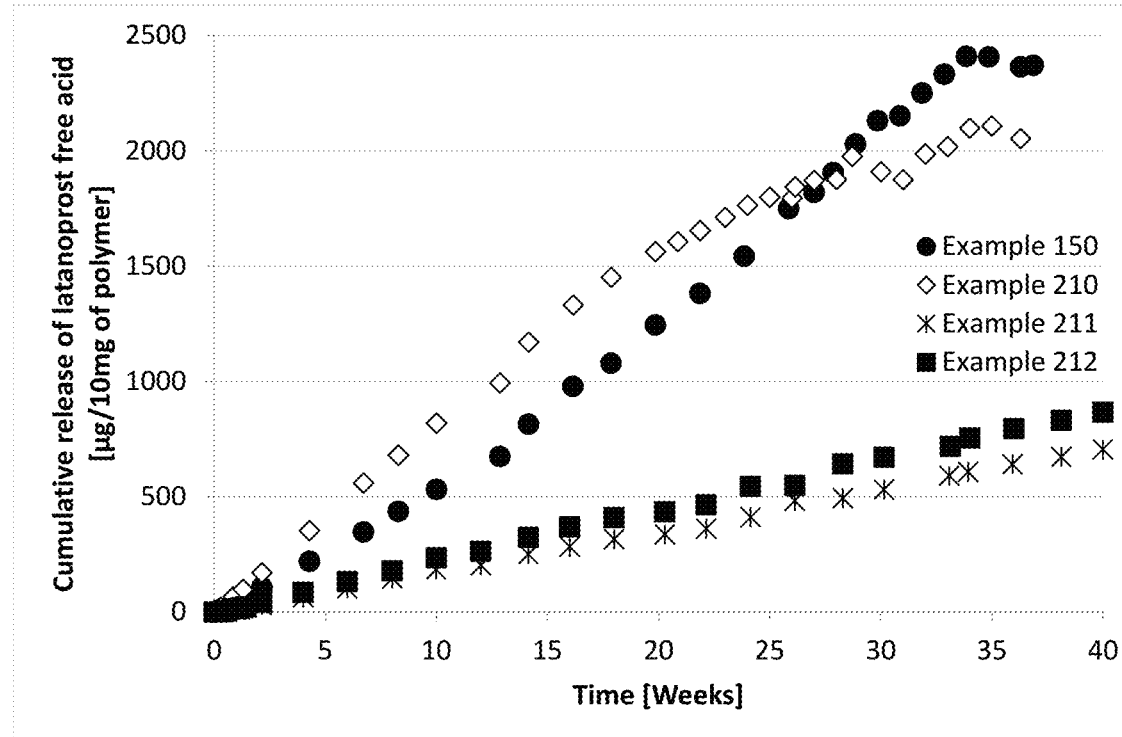
FIG. 2 is a graph having four plots showing the cumulative release (μg/10 mg) of latanoprost free acid with time exposed to isotonic phosphate buffer (pH 7.4) at 37.0° C. from drug-polymer conjugates 150, 210, 211, and 212 with linker (L) but varying in comonomer, cross link density or Q-X.

In FIG. 2 plots show the cumulative release (μg/10 mg) of latanoprost free acid with time exposed to isotonic phosphate buffer (pH 7.4) at 37.0° C. from drug-polymer conjugates with linker (L) common to the Example drug-polymer conjugates but different co-monomers. Example 150 and Example 210 have proportionally greater PEG content with respect to drug-monomer compared with Example 211 and Example 212, showing that PEG content can be used to vary rate of drug release even with different polymer chemistry. Example 150 and Example 210 use the same PEG content but different Q-X components in the drug monomer, an ester and carbamate respectively, showing that in the case of an acyloxyalkylacyl linker (L) is the predominant determinant of rate of drug release rather than changes to chemistry of Q-X. Example 211 and Example 212 have the same chemical composition but with Example 212 of higher cross-linking density, showing that cross-linking density does not have a significant effect on rate of drug release.

Drug-polymer conjugates of Example 150, Example 210, Example 211 and Example 212 were produced. The composition of all 4 examples are derived from a common latanoprost free acid drug monomer, Example 65:

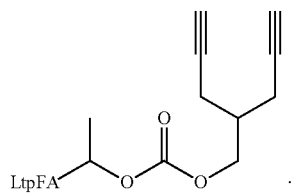

Example 211 and Example 212 are both compositions of a stoichiometric product of Example 65 and a common 4-arm PEG200 azide

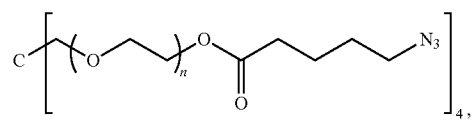

co-monomer. Example 211 was produced with the reactants at a 0.09M concentration and Example 212 with the reactants at a concentration of 0.18M to ensure Example 212 has a higher cross-linking density. Example 150 is a composition of a stoichiometric product of Example 65 and the co-monomer 4-arm PEG500 ester azide,

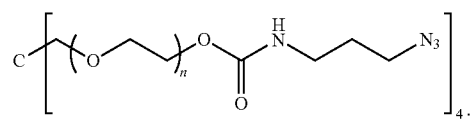

whereas, Example 210 is a composition of a stoichiometric product of Example 65 and the co-monomer 4-arm PEG500 carbamate azide, In all cases the rate of drug release is shown (FIG. 2) to be zero-order to provide a product that delivers a constant daily dose for the entire treatment period. The actual dose per day can be selected by controlling the weight of product administered. Example 150 and Example 210 use the same PEG content but different Q-X components in the drug monomer, an ester and carbamate respectively, showing that in the case of an acyloxyalkylacyl linker (L) is the predominant determinant of rate of drug release rather than changes to chemistry of Q-X. Example 150 and Example 210 have proportionally greater PEG content with respect to drug-monomer compared with Example 211 and Example 212, showing that PEG content can be used to vary rate of drug release even with different polymer chemistry. Example 211 and Example 212 have the same chemical composition but with Example 212 of higher cross-linking density, showing that cross-linking density does not have a significant effect on rate of drug release.

Figure 3:
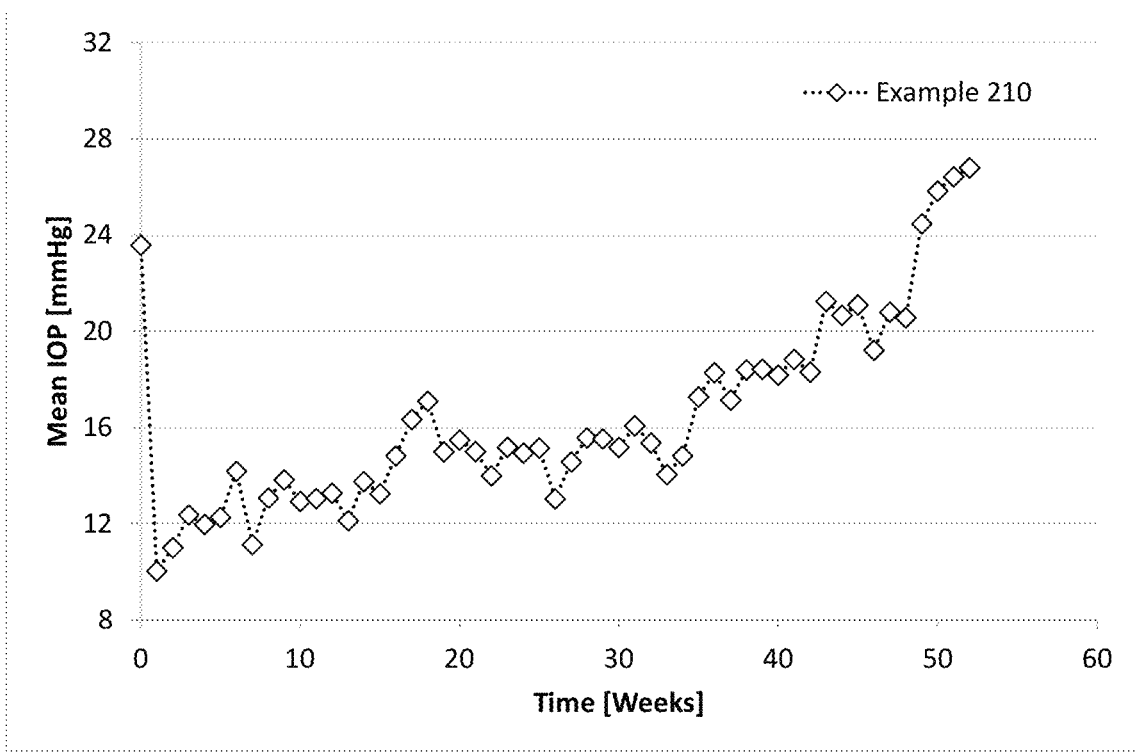
FIG. 3 is a graph showing the intraocular pressure (IOP) lowering effect (mmHg) in dog eyes treated with a rod-shaped ocular implant comprised of Example 210.

In FIG. 3 the plot shows the intraocular pressure (IOP) lowering effect (mmHg) in dog eyes treated with a rod-shaped ocular implant comprised of Example Example 210. These results demonstrate therapeutic levels of drug (latanoprost free acid) are released. In this case the treatment period is determined by the chemistry of the linker (L) as drug is depleted from the polymer prior to significant implant mass loss (or implant biodegradation).

Rod-shaped implants of Example 210 were produced suitable for administration to dogs with a 27 G needle. The implant was administered to the eye of the dog by means of an administration device fitted with a 27 G needle that housed the implant. The needle was injected into the anterior chamber of the eye then the implant expelled from the needle by moving a stylet down the barrel of the needle towards the eye chamber. IOP (mmHg) was measured weekly by means of a rebound tonometer. Dog eyes respond to a prostaglandin analogue with a lowering of IOP. Therapeutic concentrations of the prostaglandin analogue, latanoprost free acid, was shown to be released during the near-zero order release period as indicated by an IOP lowering effect of 30% (refer FIG. 1). The IOP was shown to diminish after about 37 weeks, which coincides with depletion of the latanoprost free acid from the material following an extended period of drug release (refer FIG. 1). Such a result demonstrates that the chemistry of the linker (L) can be used to vary the treatment period of the product.

Figure 4A:
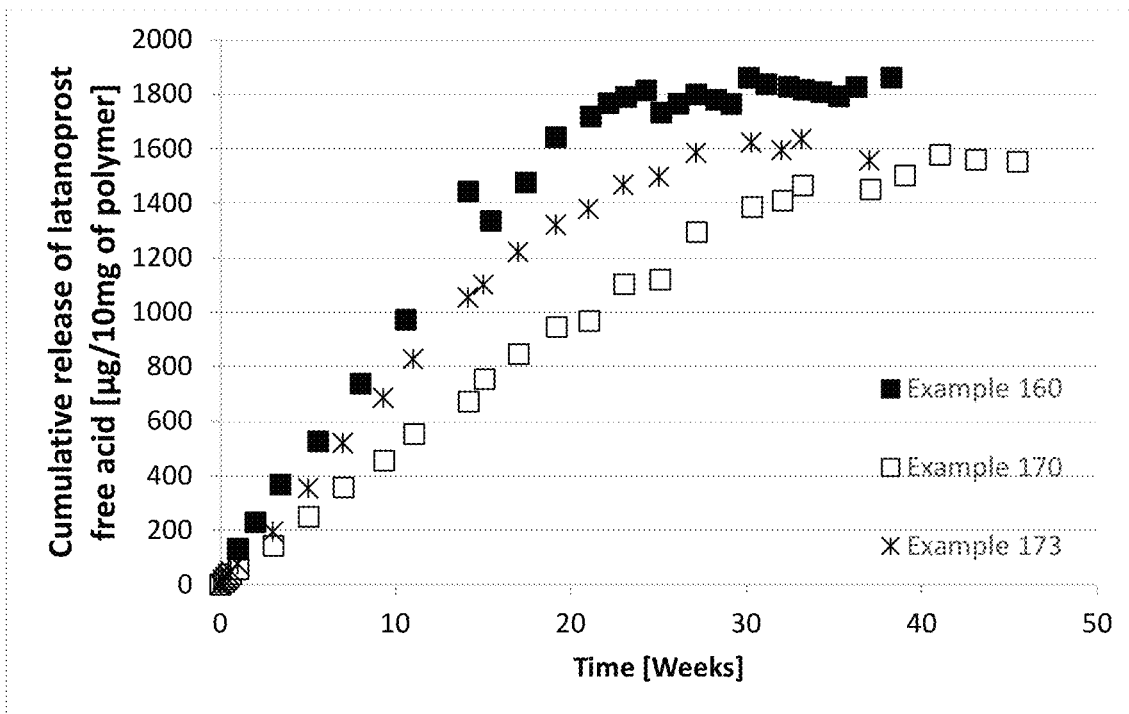
FIGS. 4A and 4B include two graphs relating to polymer drug composites of Example 160, 170 and 173 showing.
Figure 4B:
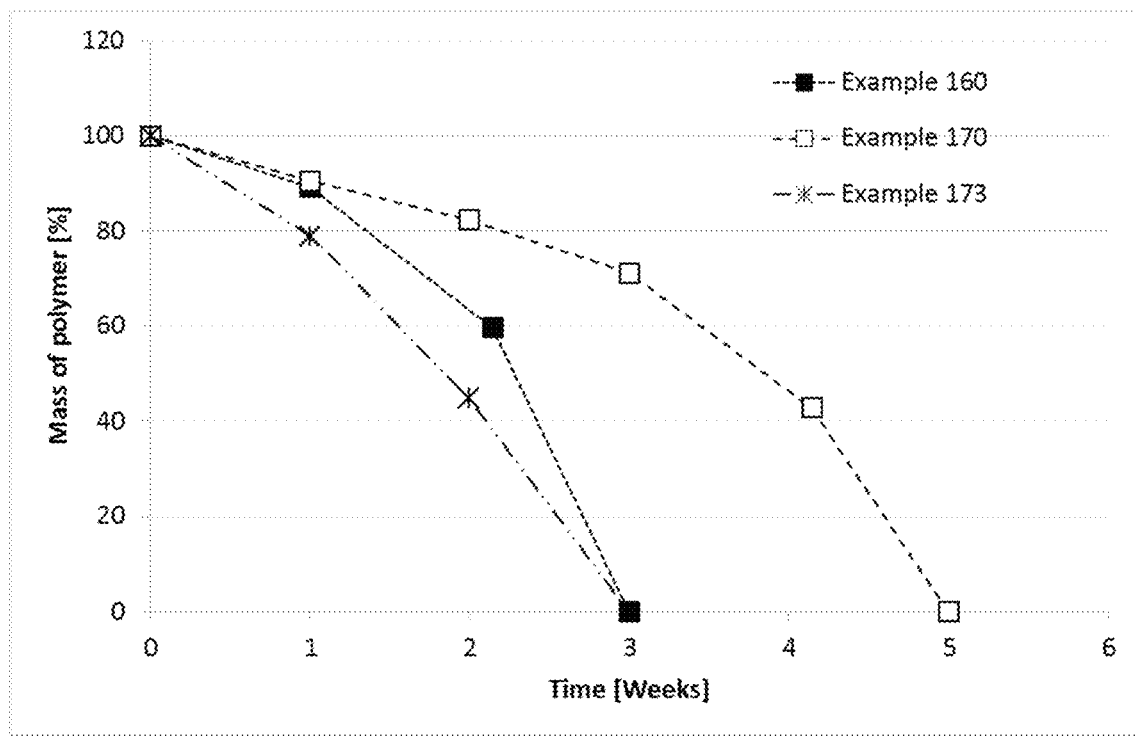

In FIGS. 4A and 4B the plots showing a). cumulative release (μg/10 mg) of latanoprost free acid (FIG. 4A), and b). % mass loss with time exposed to isotonic phosphate buffer (pH 7.4) (FIG. 4B) at 37.0° C. and 55.0° C., respectively, from drug-polymer conjugates, Example 160, Example 173 and Example 170, with a common linker (L), common co-monomer but different Q-X moieties. The release rates do not vary significantly with changes to the Q-X moiety of the drug monomer, whereas, the period until complete mass loss does vary. Furthermore, the mass loss is non-linear with very little loss initially but accelerating after a lag period. Such a profile allows a product to be produced to ensure very little mass loss during its treatment period with rapid mass loss after the treatment period. The rate of drug release is shown to be the preferred near zero-order profile to provide a product that delivers a constant daily dose for the entire treatment period.

Drug-polymer conjugates of Example 160, Example 173 and Example 170 were produced. Each of Example 160, Example 173 and Example 170 are a product of the respective drug monomers, Example 38, Example 39 and Example 40, and 4-arm PEG500 azide,

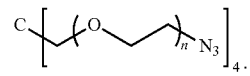

Example 38, Example 39 and Example 40 all involve latanoprost free acid attached through an aryl ester to pyridoxine but with an ester Q-X functionality with increasing steric hindrance.

TABLE 12

| Drug Monomer Example | Example 38 |
|---|---|
| Structure | (structure shown) |

| Drug Monomer Example | Example 39 |
|---|---|
| Structure | (structure shown) |

| Drug Monomer Example | Example 40 |
|---|---|
| Structure | (structure shown) |

The release rates do not vary significantly with changes to the Q-X moiety of the drug monomer, whereas, the period until complete mass loss does vary (refer FIG. 3). Furthermore, the mass loss is non-linear with very little loss initially but accelerating after a lag period. Such a profile allows a product to be produced to ensure very little mass loss during its treatment period with rapid mass loss after the treatment period.

Figure 5:
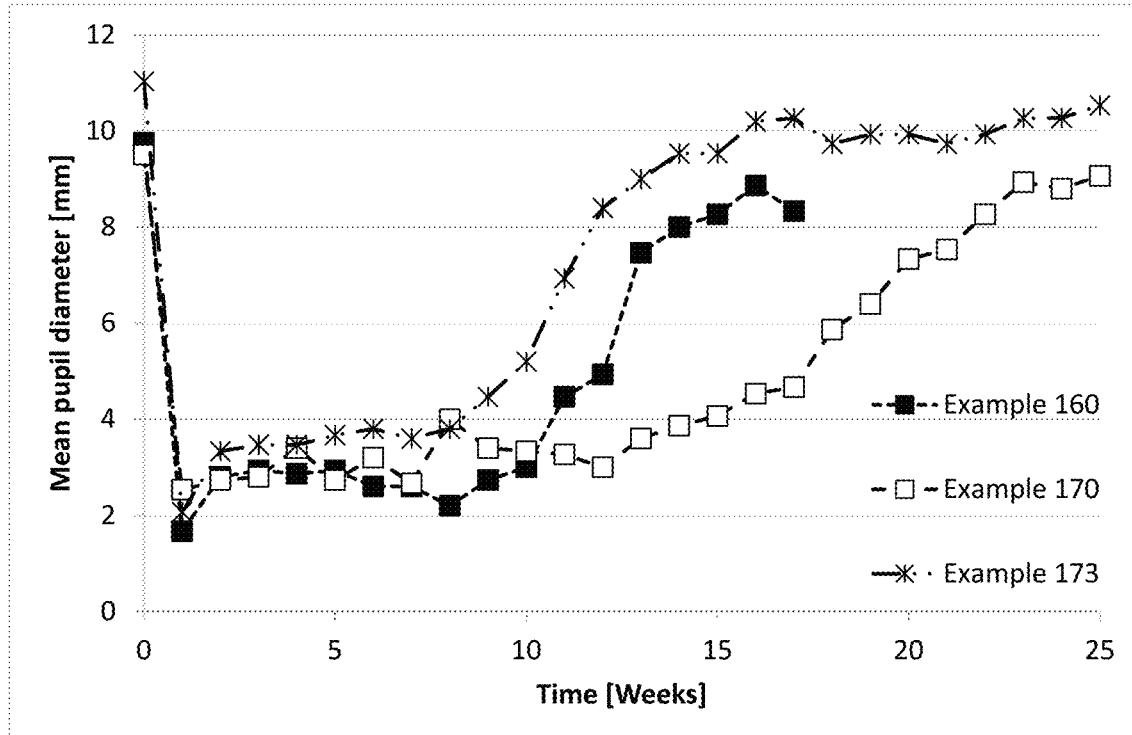
FIG. 5 is a graph having three plots showing the miotic pupil response (mm) with time in dog eyes treated with a rod-shaped ocular implant comprised of Example Example 160, Example 173 and Example 170.

In FIG. 5 the plots show the miotic pupil response (mm) in dog eyes treated with a rod-shaped ocular implant comprised of Example Example 160, Example 173 and Example 170. These results demonstrate therapeutic levels of drug (latanoprost free acid) are released. In this case the treatment period is determined by the biodegradation chemistry of Formula II, as complete implant mass loss (or implant biodegradation) occurs prior to any significant depletion of latanoprost free acid attached through the linker (L). The rate of drug release is shown to be the preferred near zero-order profile to provide a constant daily dose for the entire treatment period. Rod-shaped implants of Example 160, Example 173 and Example 170 were produced suitable for administration to dogs with a 27 G needle. The implant was administered to the eye of the dog by means of an administration device fitted with a 27 G needle that housed the implant. The needle was injected into the anterior chamber of the eye then the implant expelled from the needle by moving a stylet down the barrel of the needle towards the eye chamber. Pupil size (mm) was measured weekly by means of Vernier™ calipers. Dog pupils show a miotic response to a prostaglandin analogue. The pupil response was measured weekly following administration (refer FIG. 2). In all three cases therapeutic concentrations of the prostaglandin analogue, latanoprost free acid, was shown to be released during the near-zero order release period as indicated by a pupil size less than 4 mm. The pupil response was shown to diminish at about 8 weeks, 11 weeks and 15 weeks, for Example 160, Example 173 and Example 170, respectively, which coincides with significant mass loss of each implant (refer FIG. 3). Such a result demonstrates that the chemistry of the Q-X moiety can be used to vary the treatment period of the product.

Figure 6:
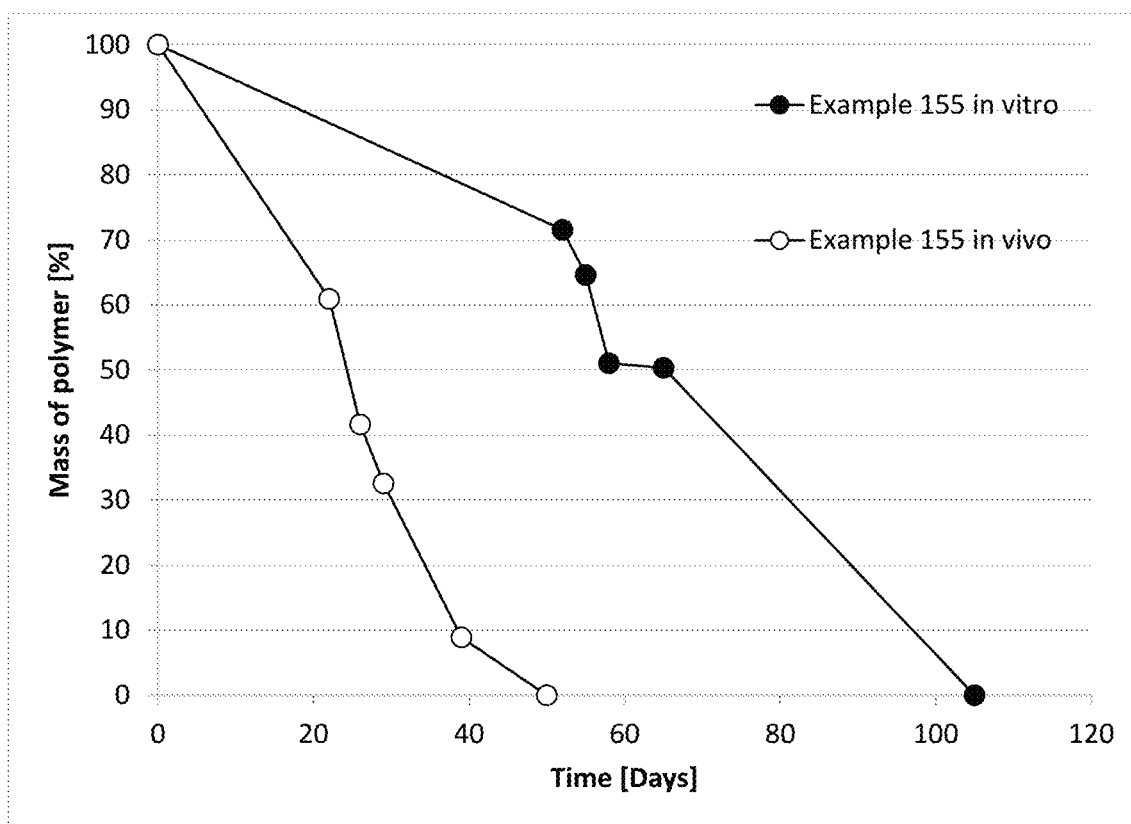
FIG. 6 is a graph with two plots plot showing % mass loss with time exposed to isotonic phosphate buffer (pH 7.4) at 37.0° C. in vitro and rabbit aqueous humour in vivo from drug-polymer conjugates, Example 155.

In FIG. 6 the plots show the % mass loss with time exposed to isotonic phosphate buffer (pH 7.4) at 37.0° C. in vitro and rabbit aqueous humour in vivo from drug-polymer conjugates, Example 155. Example 155 has an ester moiety in the polymer chain, which is susceptible to aqueous hydrolysis. The study confirms that the in vitro exposure to isotonic phosphate buffer (pH 7.4) is a reliable predictor of in vivo performance.

Figure 7A:
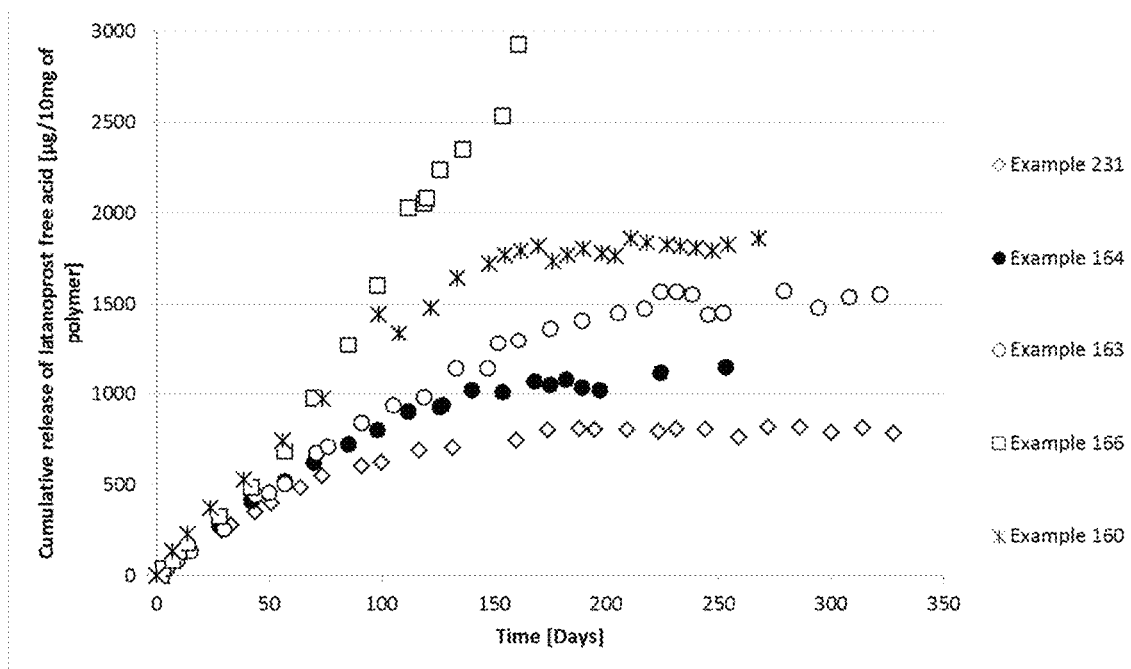
FIG. 7A and FIG. 7B include two graphs each including five plots showing: a)
Figure 7B:
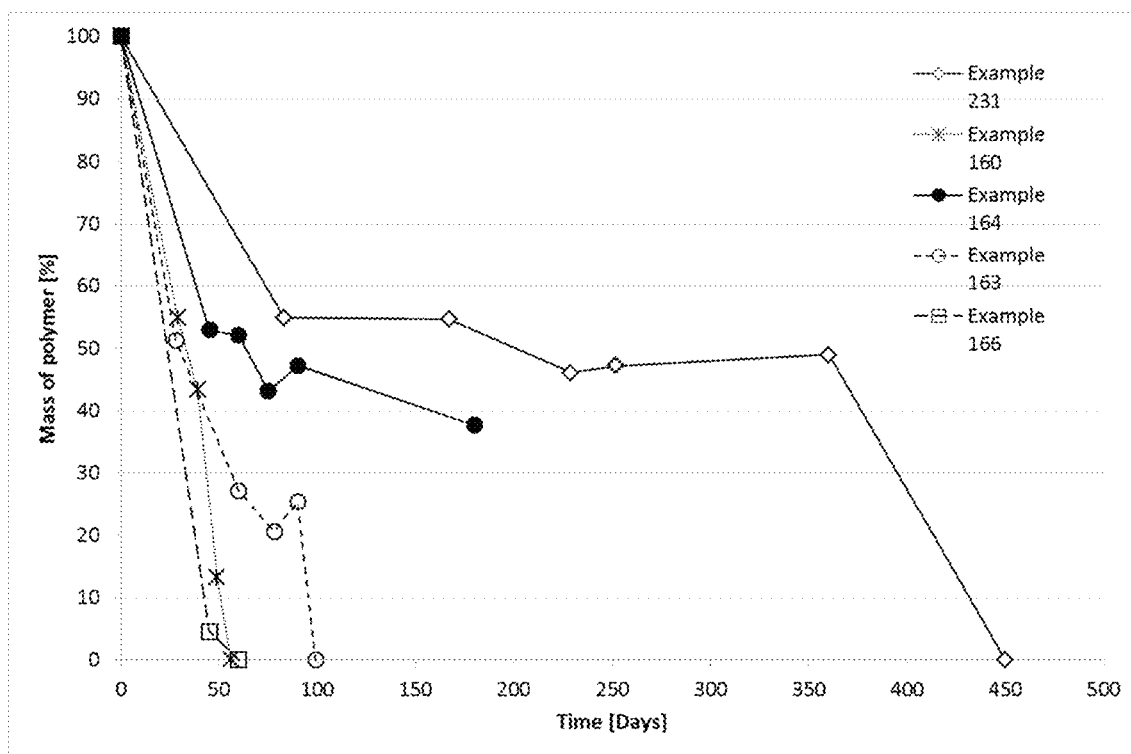

In FIGS. 7A and 7B the plots show a) cumulative release (μg/10 mg) of latanoprost free acid (FIG. 7A), and b) % mass loss with time exposed to rabbit aqueous humour in vivo (FIG. 7B) from drug-polymer conjugates, Example 160, Example 164, Example 163, Example 166 and Example 231. The polymer conjugates represent a series of constructs with varying stoichiometry between two drug monomers, Example 38, which has an ester moiety within Q-X and Example 56, which has a carbamate moiety within Q-X. The ester moiety provides higher susceptibility to biodegradation than the carbamate. Example 231 is derived solely from Example 56, Example 160 is derived solely from Example 38, whereas, Example 164, Example 163 and Example 166 have stoichiometric ratios of Example 38:Example 56 of 0.75:0.25, 0.5:0.5, 0.25:0.75, respectively. The % mass loss in vivo is more rapid with constructs that have higher ester content within Q-X. Similarly, the release rate of latanoprost free acid from the common aryl ester drug linkage was also more rapid with higher ester content in Q-X. Drug-polymer conjugates of Example 160, Example 164, Example 163, Example 166 and Example 231 were produced to study the biodegradation performance of drug polymer conjugates of the invention. The polymer conjugates are a product of one or both drug monomers, Example 38 and Example 56, with 4-arm PEG500 azide co-monomer,

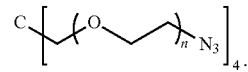

Example 231 is derived solely from Example 56, Example 160 is derived solely from Example 38, whereas, Example 164, Example 163 and Example 166 have stoichiometric ratios of Example 38:Example 56 of 0.75:0.25, 0.5:0.5, 0.25:0.75, respectively. The following table outlines the structure of the drug monomer used to produce the constructs and their stoichiometric proportions in each construct.

TABLE 13

Example 56

| Drug Monomer Structure | |
|---|---|
| Example 160 | 0 |
| Example 164 | 0.75 |
| Example 163 | 0.5 |

TABLE 13-continued

| | |
|---|---|
| Example 166 | 0.25 |
| Example 231 | 1.0 |
| Drug Monomer Structure | Example 38 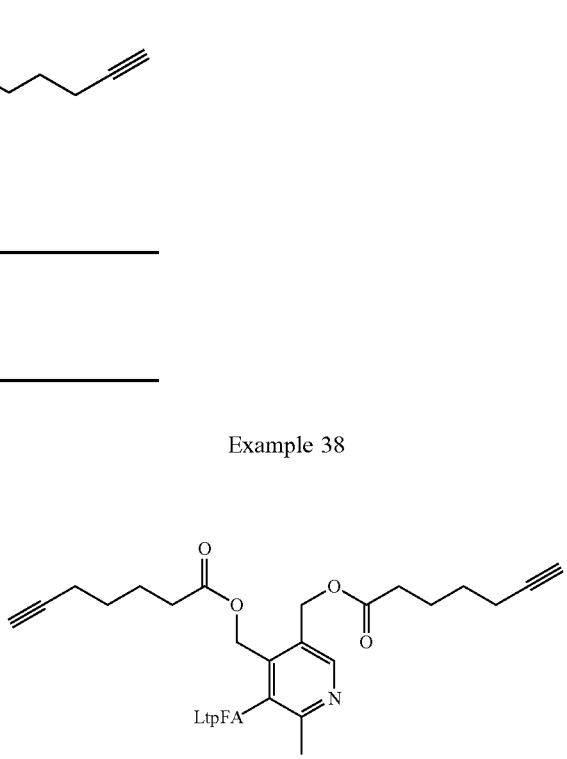 |
| Example 160 | 1.0 |
| Example 164 | 0.25 |
| Example 163 | 0.5 |
| Example 166 | 0.75 |
| Example 231 | 0 |

The series are effectively a mix of ester and carbamate Q-X moieties to control in vivo biodegradation. The ester moiety providing higher susceptibility to biodegradation than the carbamate. The % mass loss in vivo is more rapid with constructs that have higher ester content within Q-X (refer FIG. 7). Similarly, the release rate of latanoprost free acid from the common aryl ester drug linkage was also more rapid with higher ester content in Q-X.

Figure 8A:
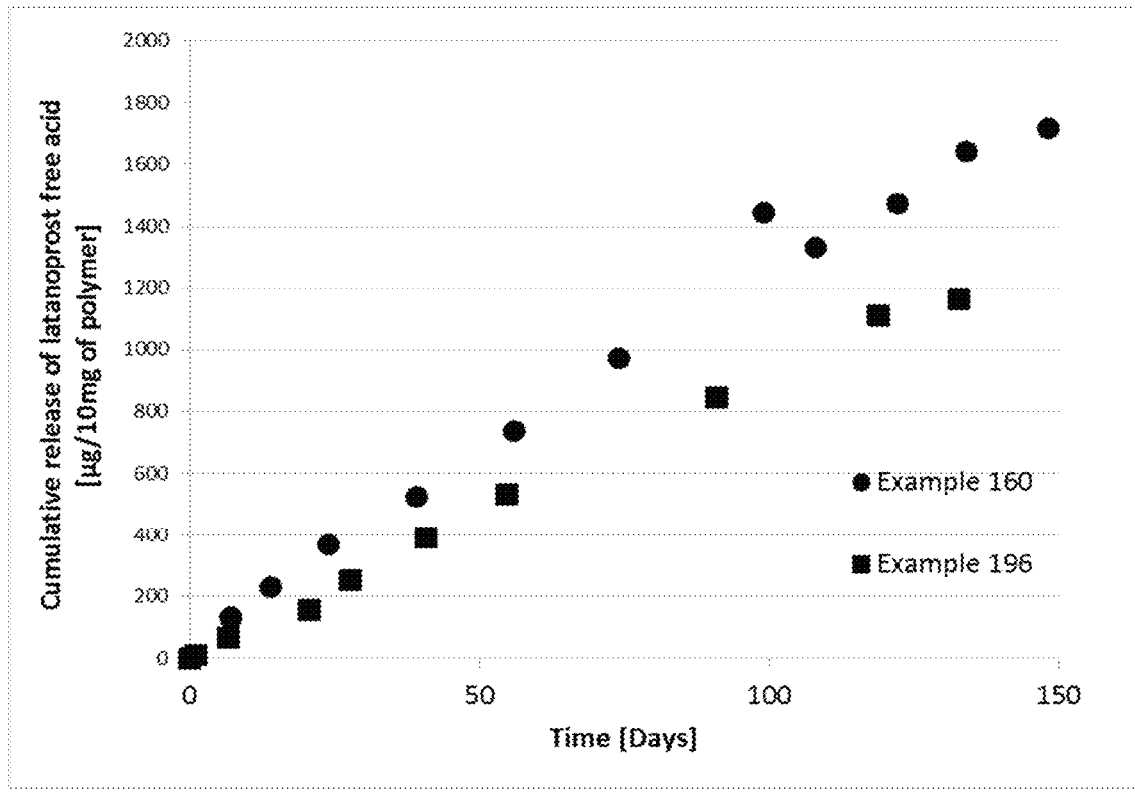
FIG. 8A and FIG. 8B include two graphs each with two plots showing.
Figure 8B:
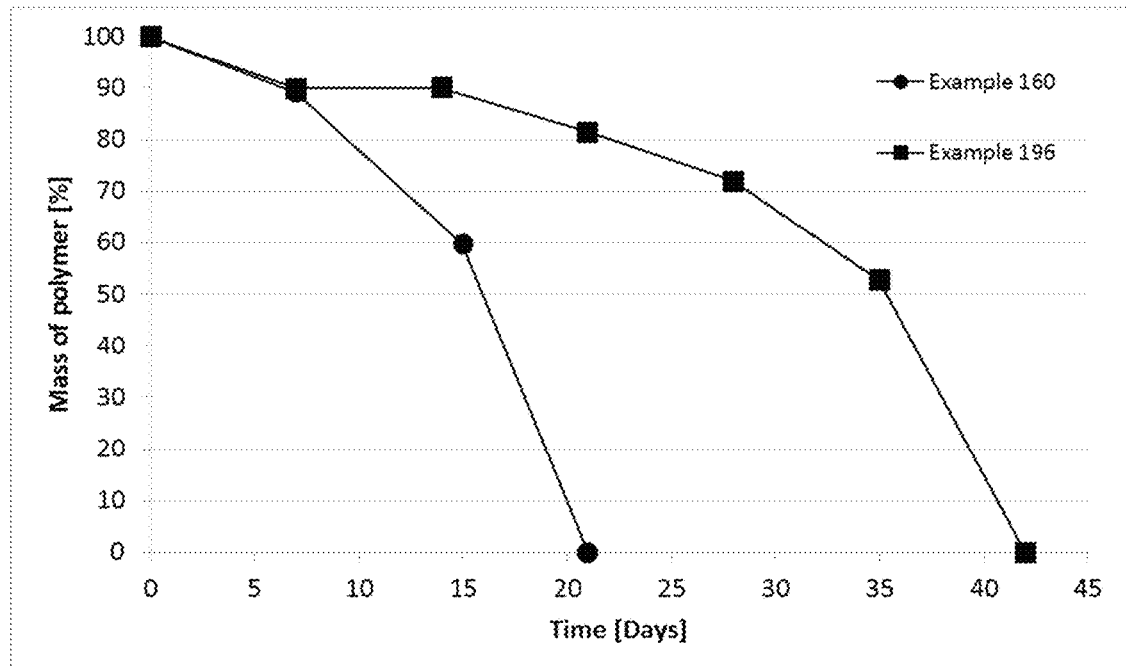

In FIGS. 8A and 8B the plots show a). cumulative release (µg/10 mg) of latanoprost free acid (FIG. 8A), and b). % mass loss with time exposed to isotonic phosphate buffer (pH 7.4) at 37.0° C. and 55.0° C., respectively (FIG. 8B), from drug-polymer conjugate Examples, Example 160 and Example 196. Example 160 is a construct where latanoprost free acid is attached to the polymer by an aryl heteroaryl ester linkage (L) to pyridoxine and Example 196 is a construct where latanoprost free acid is attached to the polymer by an acyloxyalkylacyl ester linkage (L). Both constructs use an ester biodegradation moiety as part of Q-X. The rate of drug release is shown to be the preferred near zero-order profile for both constructs to provide a product that delivers a constant daily dose for the entire treatment period. The release rates do not vary significantly between the pyridoxine system and the acyloxyalkylacyl ester system, whereas, the period until complete mass is greater with the acyloxyalkylacyl ester system, Example 196.

Drug-polymer conjugates of Example 160 and Example 196 were produced. Example 160 is a product of drug monomer, Example 38, where latanoprost free acid is attached to the polymer by an aryl heteroaryl ester linkage (L), and 4-arm PEG500 azide co-monomer. Example 196 is a product of drug monomer, Example 67, where latanoprost free acid is attached to the polymer by an acyloxyalkylacyl ester linkage (L), and 4-arm PEG500 azide co-monomer. Both constructs use an n-alkyl ester biodegradation moiety as part of Q-X. No biodegradation moiety is present in the co-monomer.

Following are the structures of the latanoprost free acid drug monomers used in each construct:

Example 38

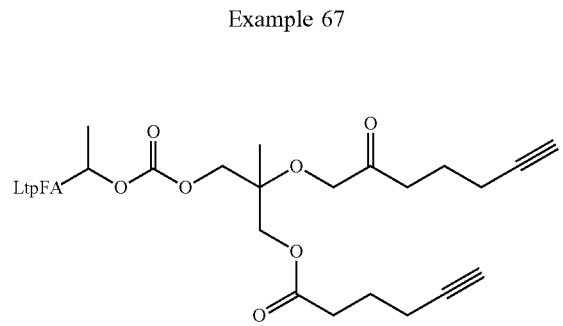

Example 67

The release rates do not vary significantly between the pyridoxine system and the acyloxyalkylacyl ester system, whereas, the period until complete mass is greater with the acyloxyalkylacyl ester system, Example 196.

Figure 9:
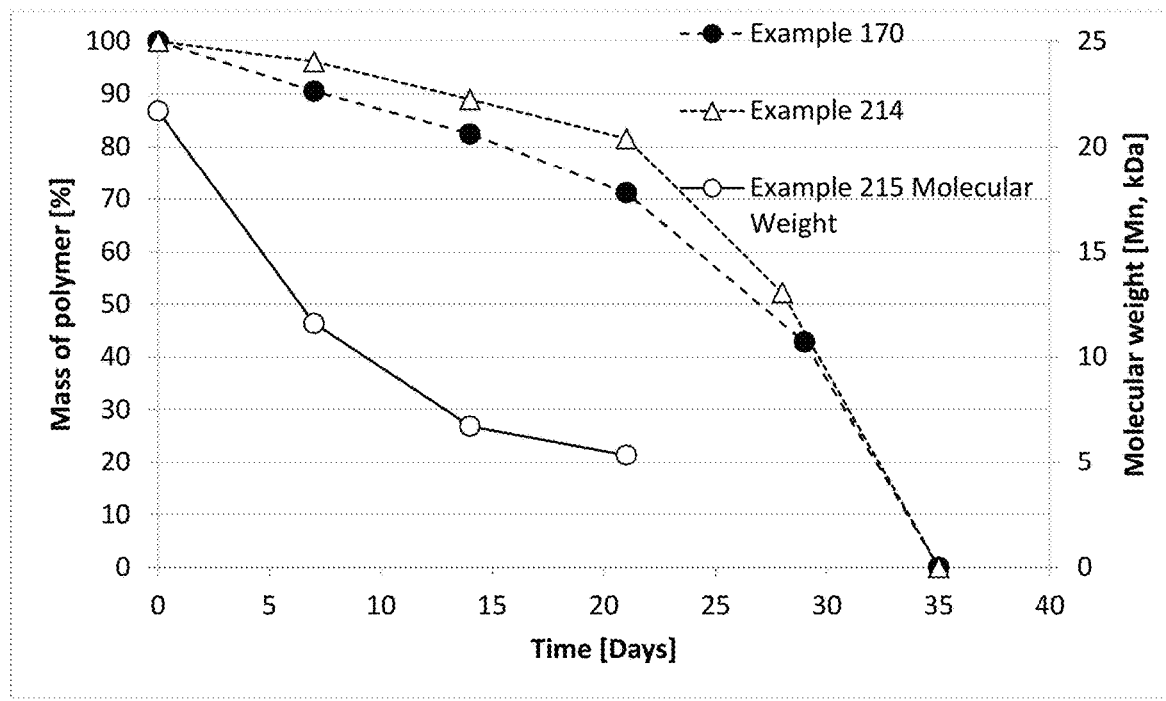
FIG. 9 is a graph with three plots showing % mass loss for Example 215, Example 170 and Example 214 with time exposed to isotonic phosphate buffer (pH 7.4) at 55.0° C.

In FIG. 9 the plots show the % mass loss for Example 170 and Example 214 with time exposed to isotonic phosphate buffer (pH 7.4) at 55.0° C. Example 215, Example 170 and Example 214 are a product of a common drug monomer, Example 40, where latanoprost free acid is linked to the polymer with a heteroaryl ester linkage (L) and a PEG1000 diazide, 4-arm PEG500 azide and 8-arm PEG500 azide, respectively. The constructs have a common gem-dimethyl ester biodegradation moiety in different polymer architectures. Example 215's molecular weight is observed to decrease after immediate exposure to an aqueous environment, confirming hydrolysis of the gem-dimethyl ester. However, no significant mass loss of Example 170 and Example 214 is observed until after a long lag phase, despite the fact they have the same biodegradation moiety. It is postulated that degradation of individual ester moieties occurs at the same rat but no loss of mass is observed with Example 170 and Example 214 because of the cross-linked network. Such a profile allows a product to be produced to ensure very little mass loss during its treatment period with rapid mass loss after the treatment period.

Drug-polymer conjugates of Example 215, Example 170 and Example 214 show the importance of the cross-linked architecture for achieving the optimum mass loss profile (biodegradation profile). All three constructs are a product of drug monomer, Example 40.

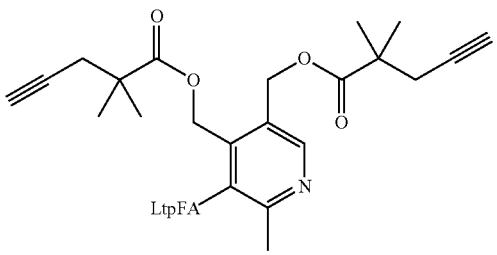

In the case of Example 215, a PEG1000 diazide is used as the co-monomer to produce a linear polymer. In the case of Example 170 and Example 214, a 4-arm PEG500 azide or 8-arm PEG1250 azide is used as the co-monomer, respectively, to produce a polymer with a cross-linked architecture. No biodegradation chemistry is introduced by the co-monomer, hence, the same gem-dimethyl ester Q-X moiety provides a biodegradation chemistry common to all three constructs. The fact Example 170 and Example 214 result in insoluble polymers confirm their cross-linked architecture. Example 215 is a polymer freely soluble in water and polar organic solvents.

Example 215's molecular weight is observed to decrease after immediate exposure to an aqueous environment, confirming hydrolysis of the gem-dimethyl ester. However, no significant mass loss of Example 170 and Example 214 is observed until after a long lag phase, despite the fact they have the same biodegradation moiety (refer FIG. 9). It is postulated that degradation of individual ester moieties occurs at the same rat but no loss of mass is observed with Example 170 and Example 214 because of the cross-linked network. Such a profile allows a product to be produced to ensure very little mass loss during its treatment period with rapid mass loss after the treatment period.

Figure 10:
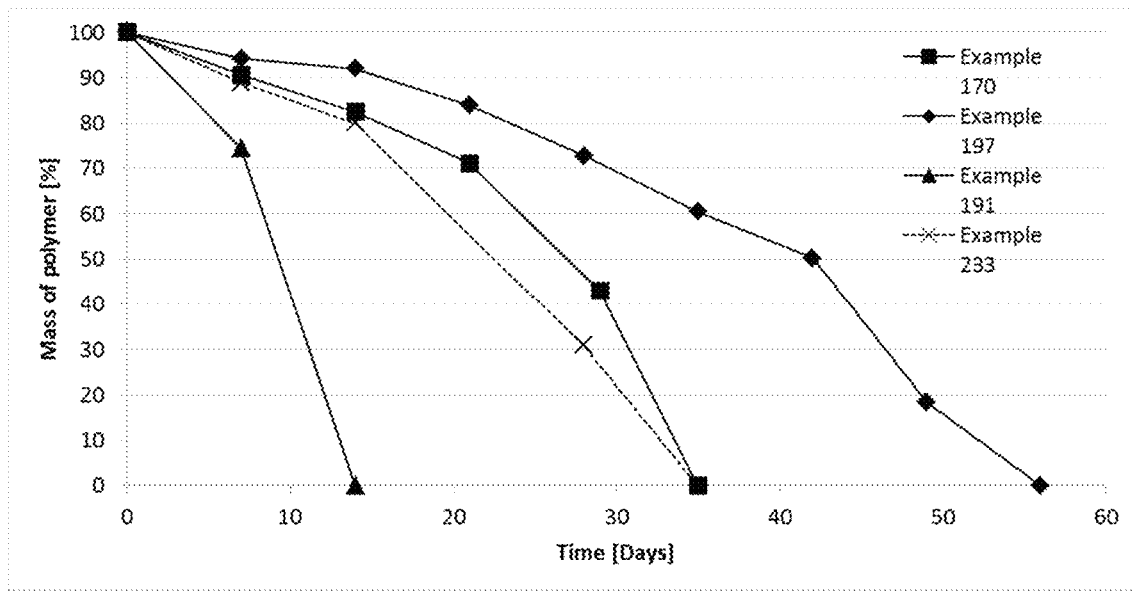
FIG. 10 includes 4 plots showing the % mass loss with time exposed to isotonic phosphate buffer (pH 7.4) at 55.0° C. from drug-polymer conjugates of Examples 170, Example 197, Example 191 and Example 233.

In FIG. 10 the plots show the % mass loss with time exposed to isotonic phosphate buffer (pH 7.4) at 55.0° C. from drug-polymer conjugates with a common linker (L), common Formula IV chemistry and common cross-linked architecture. Example 197, Example 170 and Example 191 have different PEG content of 37, 57 and 60 wt %, respectively. Example 233 has a high cross-link density compared with Example 170. Results show that the character and rate of mass loss can be varied with PEG content but not cross-linking density.

Drug-polymer conjugates of Example 191, Example 170, Example 233 and Example 197 were produced to show the importance of PEG content and cross-linking density for achieving the optimum mass loss profile (biodegradation profile). All four constructs are a product of drug monomer, Example 40.

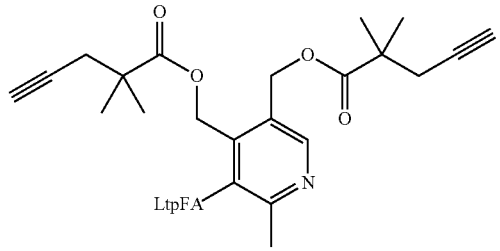

In the case of Example 197, a 4-arm PEG200 azide co-monomer is used to produce the polymer. For both Example 170 and Example 191, a 4-arm PEG500 azide is used to produce the polymer. In the case of Example 170, stoichiometric amounts of the co-monomer are used, whereas, with Example 191 an excess of co-monomer was used. Such combinations should ensure that Example 191 had an excess of PEG content compared with Example 170, and in turn Example 170 would have a greater PEG content compared with Example 197. Such an outcome is confirmed by the faster mass loss (shorter biodegradation period) seen with Example 191 compared with Example 170 and Example 170's faster mass loss compared with Example 197.

Example 233 was produced by reacting the respective monomers, Example 40 and 4-arm PEG500 azide at higher concentrations than used to produce Example 170 to achieve a product with the same chemistry but a higher cross-link density. It is clear from the similar mass loss profiles when exposed to isotonic phosphate buffer (pH 7.4) at 55° C. that cross-link density has no effect of the mass loss profile.

Figure 11A:
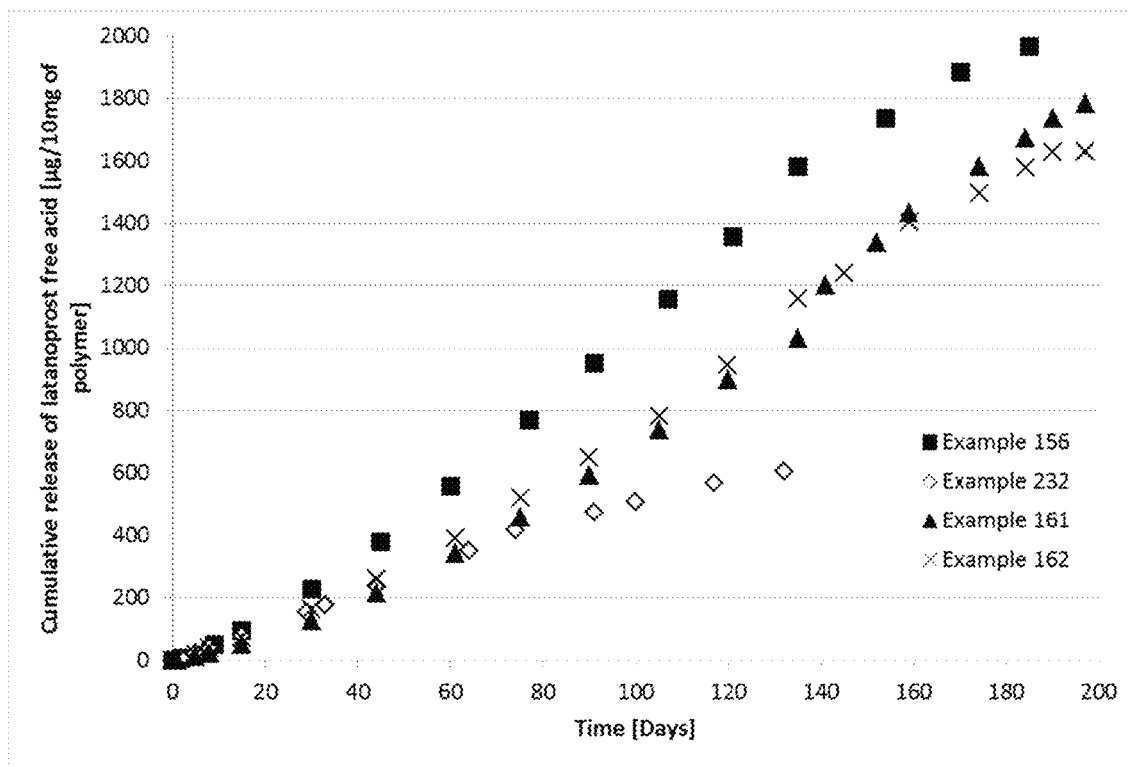
FIG. 11A and FIG. 11B are two graphs each including four plots showing
Figure 11B:
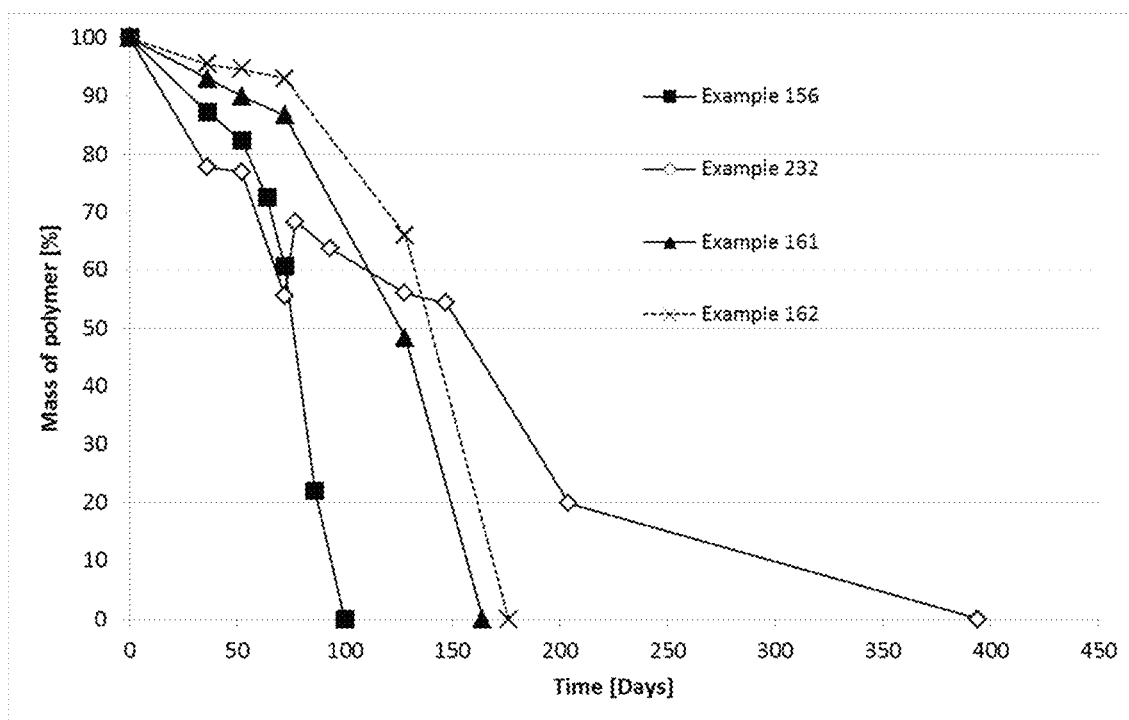

In FIGS. 11A and 11B the plots show a). cumulative release (μg/10 mg) of latanoprost free acid (FIG. 11A), and b). % mass loss with time exposed to isotonic phosphate buffer (pH 7.4) at 37.0° C. (FIG. 11B) from preferred Examples drug-polymer conjugates. Example 156, Example 232, Example 161 and Example 162 are all derived from a common a heteroaryl ester linkage (L) but variation with the biodegradation moiety within Q-X and variation with the biodegradation moiety in Formula VI of the co-monomer. The constructs show a variation on the period to complete mass loss. The mass loss is a preferred non-linear profile with a predicted period until complete mass loss in a mammalian eye of a preferred period of between 20 weeks and 45 weeks. The rate of drug release is shown to be the preferred near zero-order profile to provide a product that delivers a constant daily dose for the entire treatment period. Correspondingly, the constructs also show variation to the rate of release of latanoprost free acid that predict a preferred treatment period of between 20 weeks and 45 weeks.

Figure 12A:
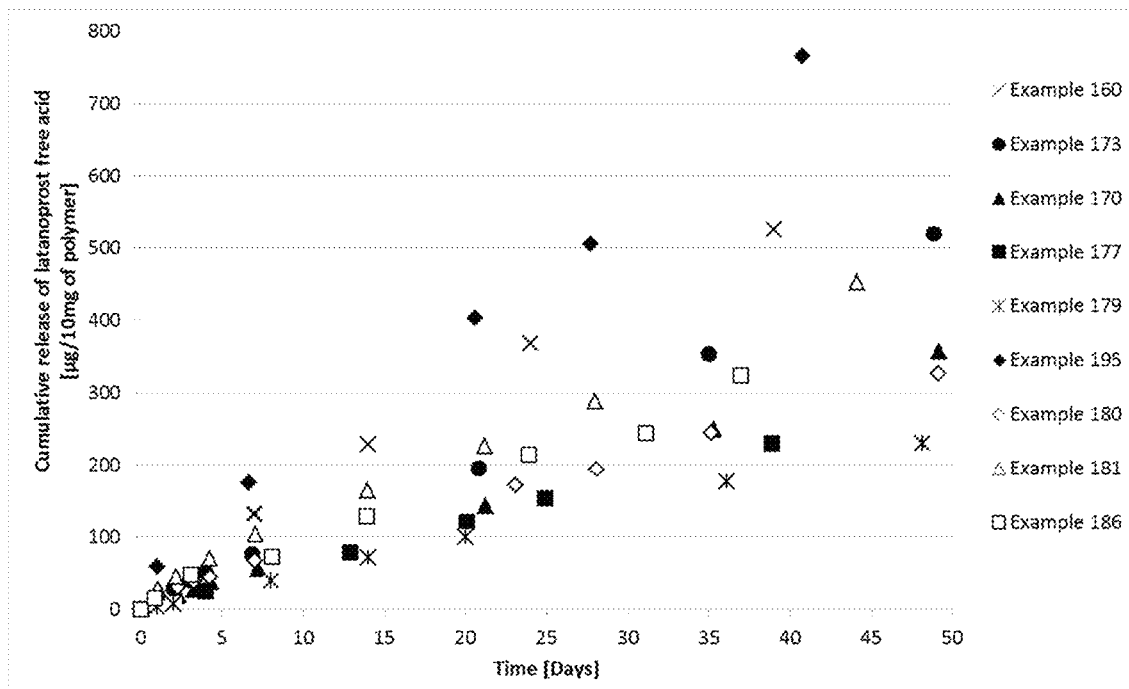
FIG. 12A and FIG. 12B are two graphs, each including nine plots, showing
Figure 12B:
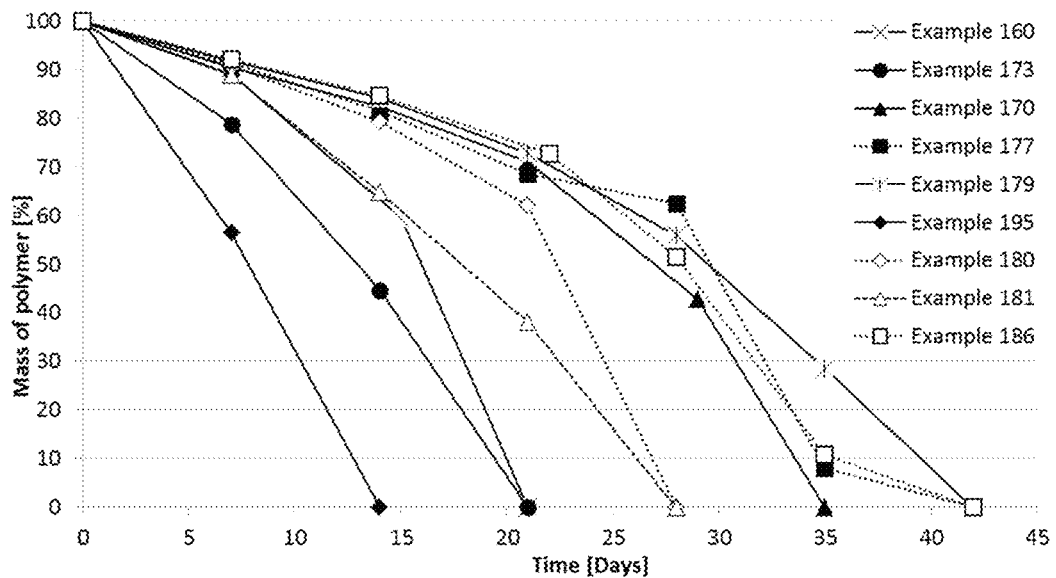

In FIGS. 12A and 12B the plots show a). cumulative release (μg/10 mg) of latanoprost free acid (FIG. 12A), and b). % mass loss with time exposed to isotonic phosphate buffer (pH 7.4) (FIG. 12B) at 37.0° C. and 55.0° C., respectively, from preferred Examples drug-polymer conjugates. Example 160, Example 173, Example 170, Example 177, Example 179, Example 195, Example 180, Example 181 and Example 186 are all derived from a common a heteroaryl ester linkage (L) but variation with an ester biodegradation moiety within Q-X. All constructs were derived from a common 4-arm PEG500 azide co-monomer. Variations to the ester biodegradation moiety involve different R-groups α or β to the carbonyl of the ester with increasing degrees of hindrance. The constructs show a variation on the period to complete mass loss. The mass loss is a preferred non-linear profile with a predicted period until complete mass loss in a mammalian eye of a preferred treatment period of between 20 weeks and 45 weeks. The rate of drug release is shown to be the preferred near zero-order profile to provide a product that delivers a constant daily dose for the entire treatment period. Correspondingly, the constructs also show variation to the rate of release of latanoprost free acid that predict a preferred treatment period of between 20 weeks and 45 weeks.

Figure 13:
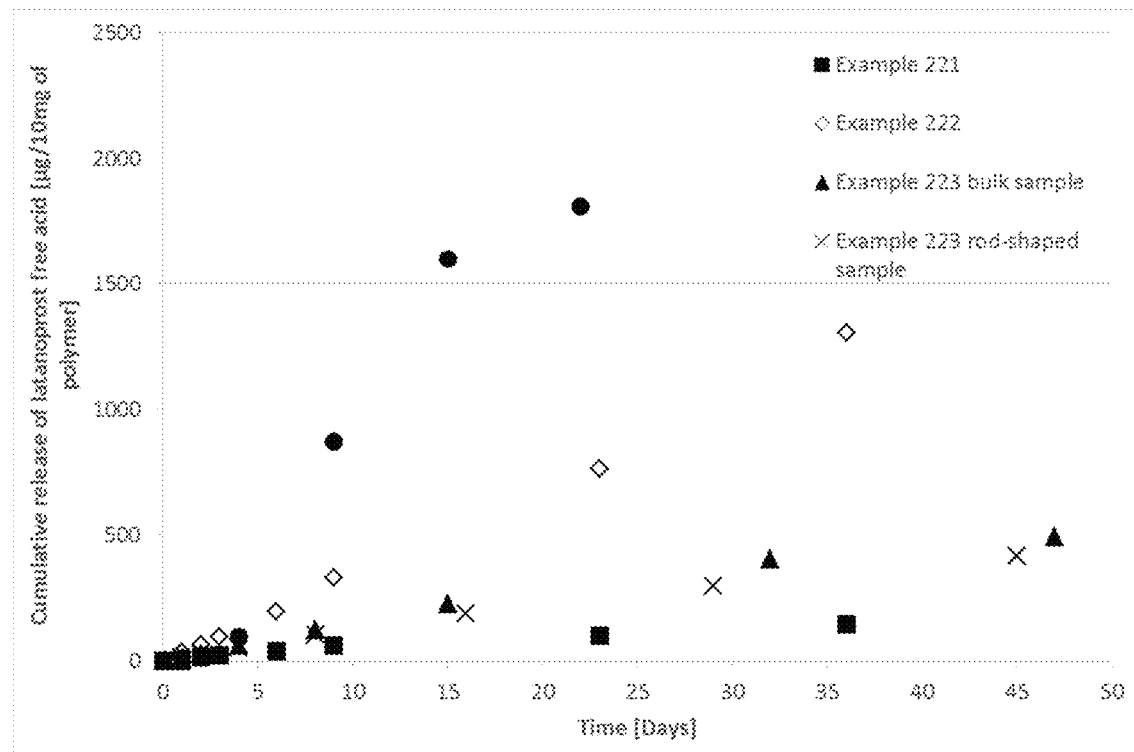
FIG. 13 is a graph having four plots showing cumulative release (μg/10 mg) of latanoprost free acid with time exposed to isotonic phosphate buffer (pH 7.4) at 37.0° C.

In FIG. 13 the plots show the cumulative release (µg/10 mg) of latanoprost free acid with time exposed to isotonic phosphate buffer (pH 7.4) at 37.0° C. from Example drug-polymer conjugates with a common linkage (L). Example 221, Example 222, Example 223, PAP141112-5 and Example 224 are all derived from a common an aryl ester linkage (L) but variation in the chemistry of Q-X and variation with the biodegradation moiety in Formula VI of the co-monomer. In all cases the rate of drug release is shown to be the preferred near zero-order profile to provide a product that delivers a constant daily dose for the entire treatment period. The actual dose per day can be selected by controlling the weight of product administered. The constructs provide a selection of rates of release of latanoprost free acid, which in turn can be used to select different treatment periods.

Drug-polymer conjugates of Example 221, Example 222, Example 223, PAP141112-5 and Example 224 were produced. The constructs were all derived from a common drug monomer with an aryl ester linkage (L):

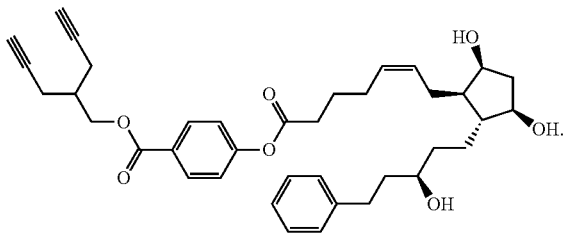 [SMILES: C#CCC(CC#C)COC(=O)c1ccc(OC(=O)CCC/C=C\C[C@@H]2[C@@H](CC[C@@H](O)CCc3ccccc3)[C@H](O)C[C@@H]2O)cc1]

Following are the structures of the co-monomers used in each construct:

Example 221

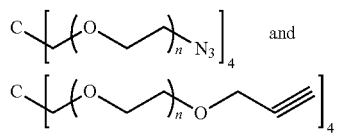

Example 222

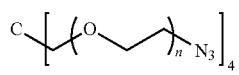

Example 223

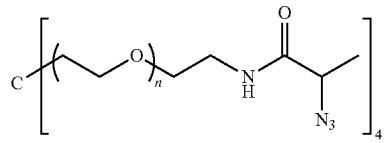

Example 224

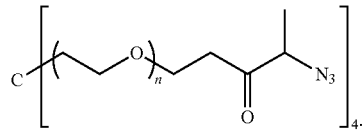

For each construct the composition comprises an equal molar ratio of each of the co-monomers in stoichiometric amounts with the drug monomer. In the case of Example 223 a 10 mg bulk sample and a approximately 300 µg a rod-shaped sample was studied. The drug release rates of the two samples of Example 223 are the same despite their different geometries.

In all cases the rate of drug release is shown to be the preferred near zero-order profile to provide a product that delivers a constant daily dose for the entire treatment period. The actual dose per day can be selected by controlling the weight of product administered. The constructs provide a selection of rates of release of latanoprost free acid, which in turn can be used to select different treatment periods.

In FIGS. 14A and 14B the plots show a). cumulative release (µg/10 mg) of latanoprost free acid (FIG. 14A), and b). % mass loss with time exposed to isotonic phosphate buffer (pH 7.4) (FIG. 14B) at 37.0° C. and 55.0° C., respectively, from preferred Examples drug-polymer conjugates. Example 170 uses a heteroaryl ester linkage (L) with a gem dimethyl ester biodegradation moiety within Q-X. Example 193, Example 199, Example 200 and Example 201 use a common acyloxyalkylacyl ester linkage (L), but use different 4-arm PEG azide co-monomers with different biodegradation moieties. The release rates do not vary significantly with changes to the linkage or co-monomer, whereas, the period until complete mass loss does vary. Furthermore, the mass loss is a preferred non-linear profile with a predicted period until complete mass loss in a mammalian eye of a preferred period of between 20 weeks and 45 weeks. The rate of drug release is shown to be the preferred near zero-order profile to provide a product that delivers a constant daily dose for the entire treatment period. Correspondingly, the constructs also show variation to the rate of release of latanoprost free acid that predict a preferred treatment period of between 20 weeks and 45 weeks.

Drug-polymer conjugates of Example 160, Example 193, Example 199, Example 200 and Example 201 were produced. The composition of Example 160 is a product of the latanoprost free acid drug monomer, Example 40:

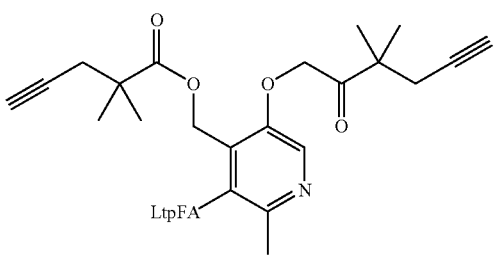

and 4-arm PEG500 azide.

The composition of the 4 examples Example 193, Example 199, Example 200 and Example 201 are derived from a common latanoprost free acid drug monomer, Example 65:

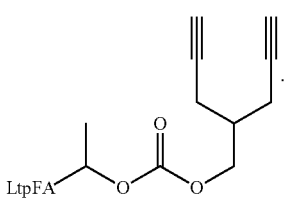

Following are the structures of the co-monomers used in each construct:

Example 193

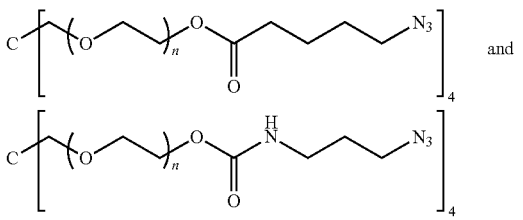

Example 199

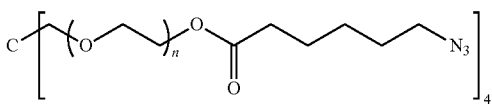

Example 200

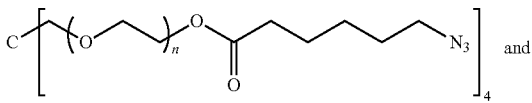

-continued

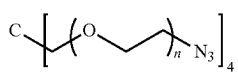

Example 201

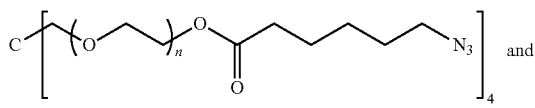

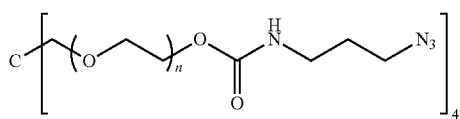

For each construct the composition comprises an equal molar ratio of each of the co-monomers in stoichiometric amounts with the drug monomer, Example 65.

In all cases the rate of drug release (FIG. 12A) is shown to be zero-order to provide a product that delivers a constant daily dose for the entire treatment period and that the release rates do not vary significantly with changes to the chemistry of the polymer from use of the different co-monomers. Furthermore, the mass loss is a preferred non-linear profile with a predicted period until complete mass loss in a mammalian eye of a preferred period of between 20 weeks and 45 weeks. Such a profile allows a product to be produced to provide a preferred effective treatment period of between 20 and 45 weeks.

In FIG. 15 the plots show cumulative release (μg/10 mg) of latanoprost free acid and timolol with time exposed to isotonic phosphate buffer (pH 7.4) at 37.0° C. from Example 239, demonstrating that polymer drug conjugates with more than one drug can be produced and release therapeutic levels of each drug.

Example 239 is derived from a product of the monomers, Example 63

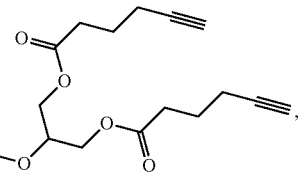

Timolol carbonate dialkyne (CAS 1627102-47-9)

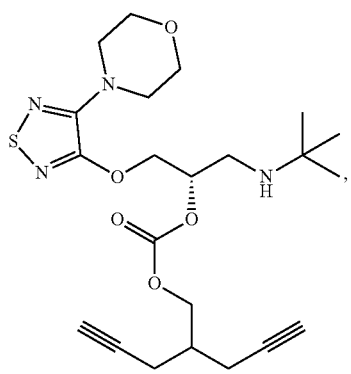 [SMILES: C#CCC(CC#C)COC(=O)O[C@@H](CNC(C)(C)C)COc1nsnc1N1CCOCC1]

and PEG diazide MW400.

The invention claimed is:

1. A drug-polymer conjugate, which is a copolymer of (i) at least one monomer of Formula (I):

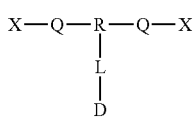
(I)

where:
X may be the same or different at each occurrence and represents a terminal functional group comprising an alkyne or an azide;
R is selected from the group consisting of linear or branched hydrocarbon, optionally substituted aryl and optionally substituted heteroaryl;
D is a releasable drug selected from a prostaglandin analogue according to Formula Xb:

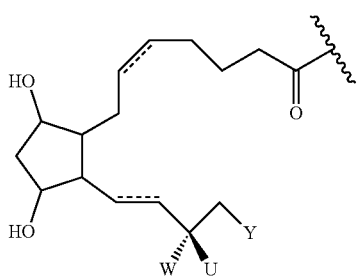
(Xb)

wherein:
⁓⁓⁓ represents the point of attachment of the prostaglandin analogue to linker group L;
----- represents a double or single bond;
Y is optionally substituted $C_4$ to $C_{10}$ hydrocarbyl or optionally substituted $C_4$ to $C_{10}$ hydrocarbyloxy; and
W is hydroxy and U is hydrogen, or W and U are both fluoro, or W and U together form oxo;
L is a linker group;
wherein the drug D is conjugated to the polymer backbone via an ester linkage formed between the drug D and the linker group L;
Q is independently selected at each occurrence and may be present or absent;

wherein when present, Q represents a linking group and is selected from the group consisting of:

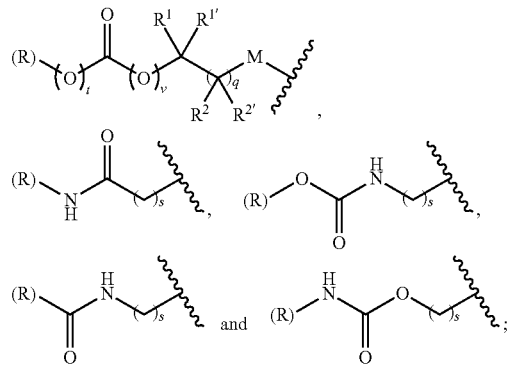

wherein
(R) indicates the end of the group attached to the group R and the opposite end is attached to (X);
each of t and v are independently 0 or 1 and at least one of t and v is 1;
$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and
M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;
q is 0 or 1;
s is from 0 to 10;
and
(ii) at least one co-monomer of Formula (IIIa):

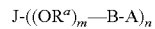
(IIIa)

wherein
A may be the same or different at each occurrence and represents a group comprising a terminal functional group comprising an alkyne or an azide functionality, wherein the alkyne or azide functionality in the terminal functional group is complementary to the alkyne or azide functionality in a terminal functional group X present on a monomer of formula (I);
J represents a bond, oxygen or linking functional group,
$R^a$ is selected from ethylene, propylene, butylene and mixtures thereof;
m is 1 to 300;
n is 3 to 8;
B is a bond, oxygen, the group of formula -MOC(O)N(H)M'-, -MOC(O)OM'—, MC(O)NHM'-, the group formula selected from (VIa), (VIb), (VIc) and (VId):

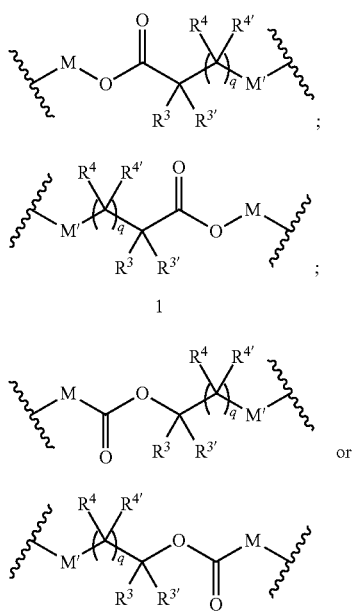

(VIa)

(VIb)

(VIc) or (VId)

wherein M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N(R$^{w'}$)-($C_1$ to $C_{10}$ straight or branched chain aliphatic) and an amine linking group comprising $C_1$ to $C_{10}$ straight or branched chain aliphatic interrupted by the group N(R$^{w'}$) wherein IV' is selected from hydrogen and $C_1$ to $C_4$ alkyl;

q is 0 or 1; and wherein in the monomers of formula, (VIa), (VIb), (VIc) and (VId) the groups $R^3$, $R^{3'}$, $R^4$ and $R^{4'}$ are independently selected from the group consisting of hydrogen, alkyl, alkoxy, alkoxy-alkyl, amino, alkyl amino, dialkylamino, amino-alkyl, alkylamino-alkyl, dialkylamino-alkyl wherein one of the pairs of $R^3$, $R^{3'}$, $R^4$, $R^{4'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl; and wherein at least one of the groups Q in the monomer of formula (I) and B in the co-monomer of formula (Ma) comprise at least one substituent selected from the group consisting of $R^1$, $R^{1'}$, $R^2$, $R^{2'}$, $R^3$, $R^{3'}$, $R^4$ and $R^{4'}$ which is present and is not hydrogen.

2. The drug-polymer conjugate of claim 1, wherein the monomer of formula I is of formula (IV):

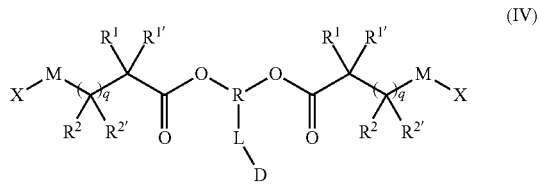

(IV)

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N(R$^w$)—($C_1$ to $C_{10}$ straight or branched chain aliphatic) and an amine linking group comprising $C_1$ to $C_{10}$ straight or branched chain aliphatic interrupted by the group N(R$^w$) wherein R$^w$ is selected from hydrogen and $C_1$ to $C_4$ alkyl;

X is a terminal functional group comprising an alkyne or an azide;

R is selected from the group consisting of optionally substituted linear or branched hydrocarbon, optionally substituted aryl and optionally substituted heteroaryl;

L is the linker group; and

D is a releasable drug selected from a prostaglandin analogue of formula (Xb):

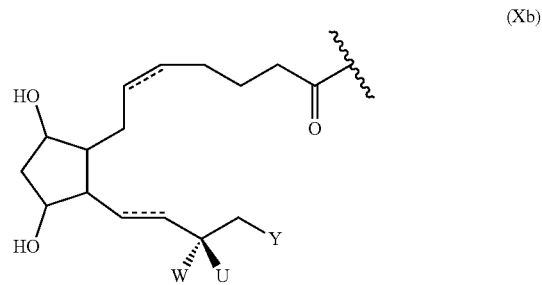

(Xb)

wherein:

~~~~ represents the point of attachment of the prostaglandin analogue to linker group L;

----- represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo;

wherein the prostaglandin analogue D is conjugated to the polymer backbone via an ester in which the acid residue is the 1-position acid of the prostaglandin and the alcohol portion of the ester is provided by the linker group;

$R^1$, $R^{1'}$, $R^2$, $R^{2'}$, are independently selected from the group consisting of hydrogen, alkyl, alkoxy, alkoxy-alkyl, amino, alkyl amino, dialkylamino, amino-alkyl, alkylamino-alkyl, dialkylamino-alkyl and wherein one of the pairs of $R^1$, $R^{1'}$ and $R^2$, $R^{2'}$ may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl; and q is 0 or 1.

3. The drug-polymer conjugate of claim 2, wherein at least one of $R^1$, $R^{1'}$, $R^2$ and $R^{2'}$ is other than hydrogen.

4. The drug-polymer conjugate of claim 1, wherein in the monomer of formula Ma the group B is a bond, oxygen, the group of formula -MOC(O)N(H)M'- or the group formula (VIa)

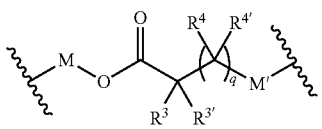

(VIa)

wherein

M and M' are independently selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1;

wherein in the monomers of formula (IV) and (III) the groups $R^1$, $R^{1'}$, $R^2$, $R^{2'}$, $R^3$, $R^{3'}$, $R^4$ and $R^{4'}$ are independently selected from the group consisting of hydrogen, alkyl, alkoxy, alkoxy-alkyl and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and one of the pairs of $R^3$, $R^{3'}$ and $R^4$, $R^{4'}$, may between the members of the pair form a carbocycle or heterocycle of 3 to 6 constituent ring members wherein the heterocycle may comprise from 1 to 3 constituent oxygen heteroatom ring members.

5. The drug-polymer conjugate of claim 1, wherein the polymer backbone comprises a plurality of biodegradable groups of formula (II):

wherein:

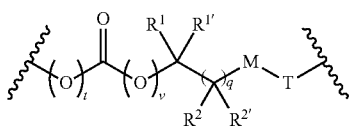

(II)

each of t and v are independently 0 or 1 and at least one of t and v is 1;

$R^1$, $R^{1'}$, $R^2$ and $R^{2'}$ are independently selected from the group consisting of hydrogen, alkyl, alkoxy and alkoxyalkyl, and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent oxygen heteroatom ring members; and at least one of $R^1$, $R^{1'}$, $R^2$ and $R^{2'}$ is not hydrogen;

wherein M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

q is 0 or 1; and

T is a triazole moiety.

6. The drug-polymer conjugate of claim 5, wherein one of t and v is 1 and the other is 0.

7. The drug-polymer conjugate of claim 1, which is a polymer network comprising network segments of formula (XXX):

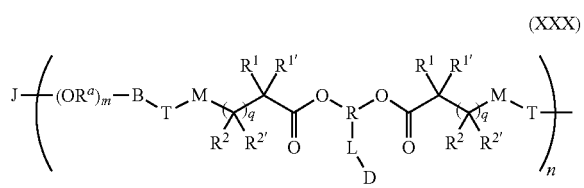

(XXX)

wherein groups J, R, $R^a$, $R^1$, $R^{1'}$, $R^2$, $R^{2'}$, B, M, R, L and D and the integers m, q and n are as therein defined and T is a triazole moiety.

8. The drug-polymer conjugate of claim 1, wherein J is a hydrocarbon of formula:

$C_zH_{2z+2-n}$ wherein z is from 1 to 8 and n is from 3 to 8.

9. The drug-polymer conjugate of any one of claim 1, wherein n is from 3 to 8 and J is selected from the group consisting of:

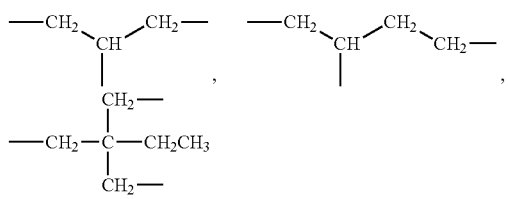

wherein n is 3; and

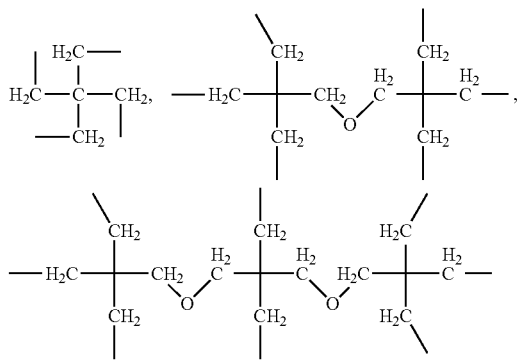

wherein n is from 4, 6 or 8.

10. The drug-polymer conjugate of claim 1, wherein formula Ma is of formula (IIIa-1) or (IIIa-2)

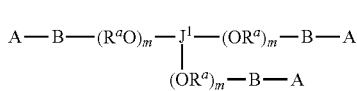
(IIIa-1)

wherein $J^1$ is of formula $C_zH_{2z-1}$ (straight or branched chain) and wherein z is an integer from 3 to 8; and

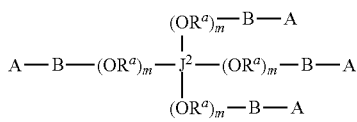
(IIIa-2)

wherein $J^2$ is of formula $C_zH_{2z-2}$ (straight or branched chain) and wherein z is an integer from 3 to 8.

11. The drug-polymer conjugate of claim 1, wherein R is selected from the group consisting of straight and branched chain hydrocarbon of from 1 to 12 carbon atoms,

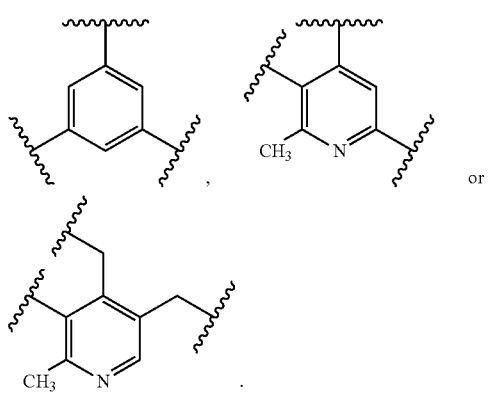

12. The drug-polymer conjugate of claim 1, wherein L is of a formula selected from the group consisting of:

(R) —O-(D);

(R) —OC(O)—Ar-0-(D);

(R) —NHC(O)—Ar—O-(D);

(R) —C(O)O—$C_{1-12}$alkylene-O-(D);

(R) —OC(O)O—$C_{1-12}$alkylene-O-(D); and (R) —OC(O)—$C_1$-$C_{12}$alkylene-O-(D)

wherein:

(R) indicates the end of the linker group bonded to the R group in the polymer backbone and (D) indicates the end of the linker group bonded to the releasable drug selected from prostaglandin analogues of formula (Xb).

13. The drug-polymer conjugate of claim 1, wherein the releasable drug D is a prostaglandin analogue selected from the group consisting of:

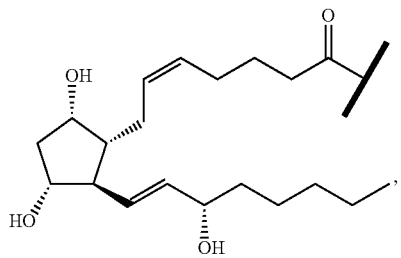

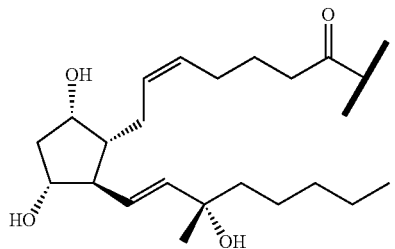

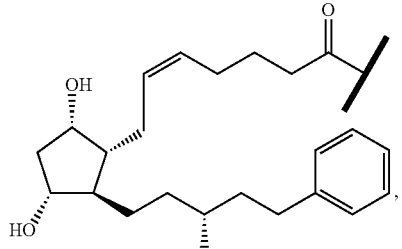

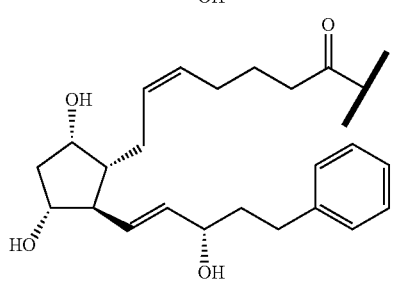

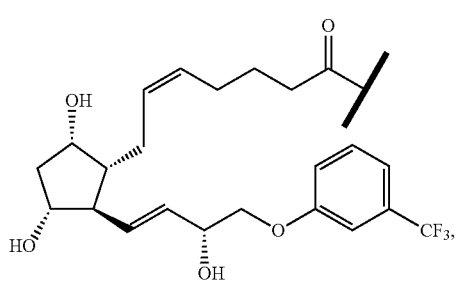

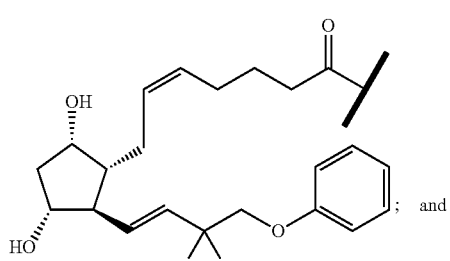

; and

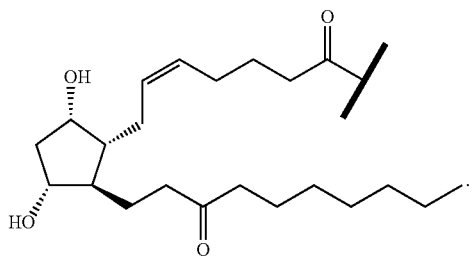

14. The drug-polymer conjugate of claim 1, wherein the drug is a prostaglandin analogue is of formula

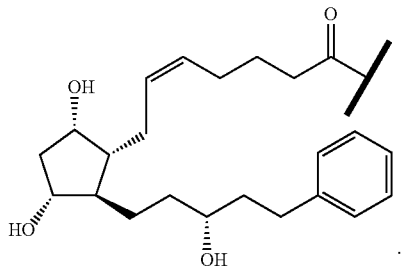

15. The drug-polymer conjugate of claim 1, wherein the monomer of formula (I) is of formula (IVc)

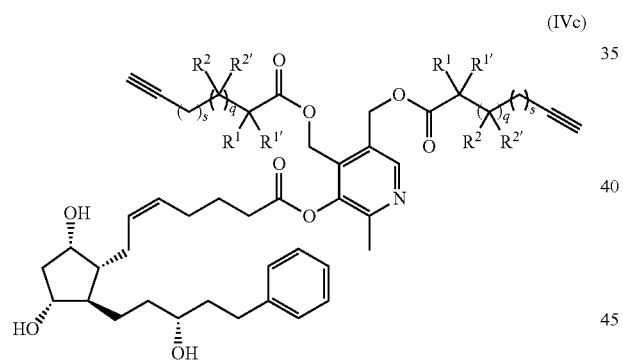

(IVc)

wherein the groups $R^1$, $R^{1'}$, $R^2$ and $R^{2'}$ are independently selected from the group consisting of hydrogen, $C_1$ to $C_6$ alkyl, $C_1$ to $C_6$ alkoxy and $C_1$ to $C_6$ alkoxy-($C_1$ to $C_6$ alkyl); and wherein one of the pairs of $R^1$, $R^{1'}$ and $R^2$, $R^{2'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may be substituted by $C_1$ to $C_6$ alkyl; and wherein at least one of $R^1$, $R^{1'}$, $R^2$ and $R^{2'}$ is other than hydrogen;

s is from 0 to 6;

q is 0 or 1.

16. The drug-polymer conjugate of claim 1, wherein the monomer of formula (I) is of formula selected from the group consisting of:

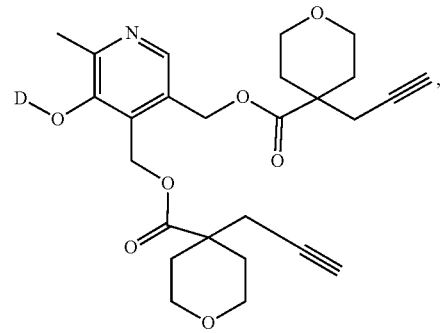

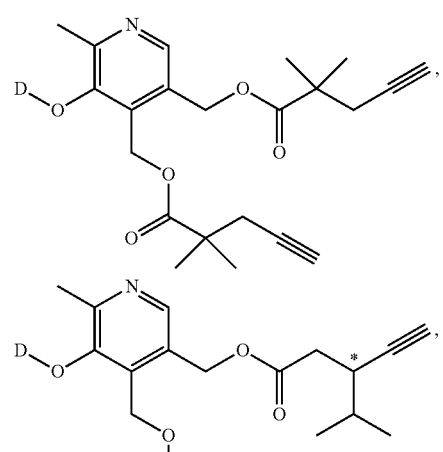

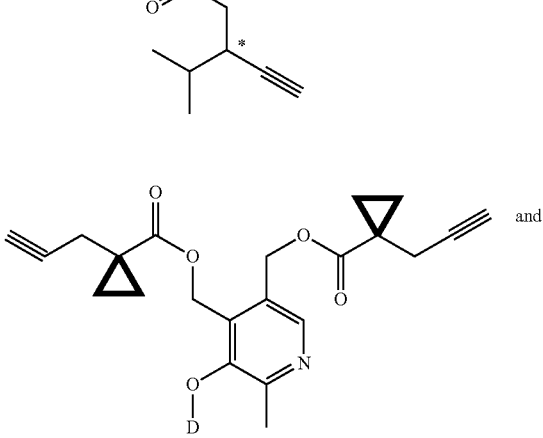

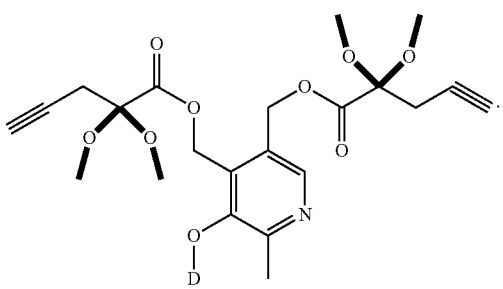

17. The drug polymer conjugate of claim 1, wherein the monomer of formula (I) comprises

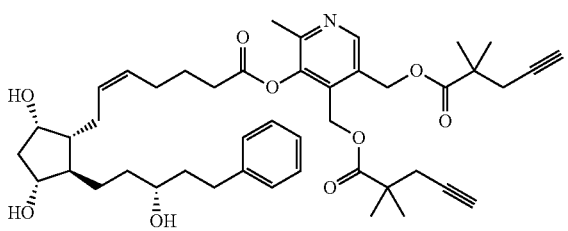 [SMILES: C#CCC(C)(C)C(=O)OCc1cnc(C)c(OC(=O)CCC/C=C\C[C@@H]2[C@@H](CC[C@@H](O)CCc3ccccc3)[C@H](O)C[C@@H]2O)c1COC(=O)C(C)(C)CC#C]

and the co-monomer of formula III comprises formula (IIIa-2)

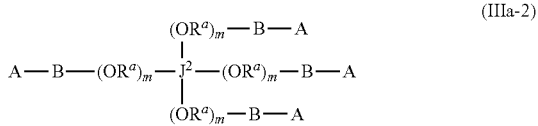

wherein $R^a$ is ethylene;

m is 1 to 300;

$J^2$ is of formula $C_zH_{2z-2}$, straight or branched chain, and wherein z is an integer from 3 to 8;

A is azide; and

B is a bond.

18. A drug-polymer drug conjugate of claim 1, wherein the linker group L is of formula selected from:

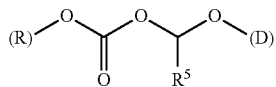

wherein $R^5$ is selected from the group consisting of hydrogen and $C_1$ to $C_6$ alkyl.

19. A drug-polymer conjugate of claim 1, wherein the monomer of formula (I) is of formula (IVc)

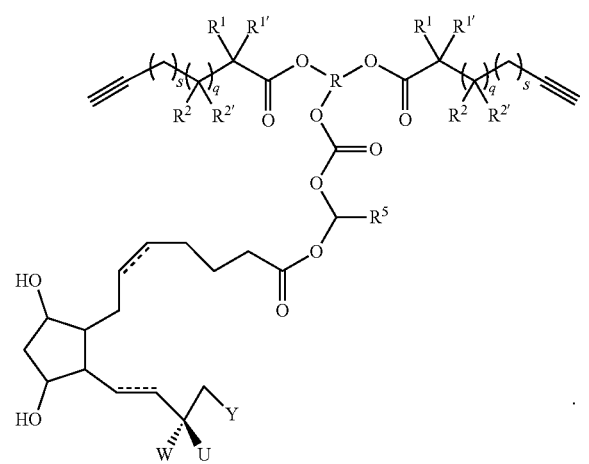

20. A monomer of formula (IV):

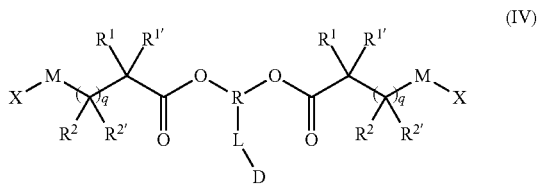

wherein

M is selected from the group consisting of a bond, optionally substituted $C_1$ to $C_{10}$ straight or branched chain aliphatic, the group —O—($C_1$ to $C_{10}$ straight or branched chain aliphatic), an ether linking group comprising $C_1$ to $C_{10}$ straight or branched chain aliphatic interrupted by a oxygen (—O—), the group —N($R^w$)—($C_1$ to $C_{10}$ straight or branched chain aliphatic) and an amine linking group comprising $C_1$ to $C_{10}$ straight or branched chain aliphatic interrupted by the group N($R^w$) wherein $R^w$ is selected from hydrogen and $C_1$ to $C_4$ alkyl;

X is a terminal functional group comprising an alkyne or an azide;

R is selected from the group consisting of optionally substituted linear or branched hydrocarbon, optionally substituted aryl and optionally substituted heteroaryl;

L is a linker group; and

D is a releasable drug selected from a prostaglandin analogue of formula (Xb);

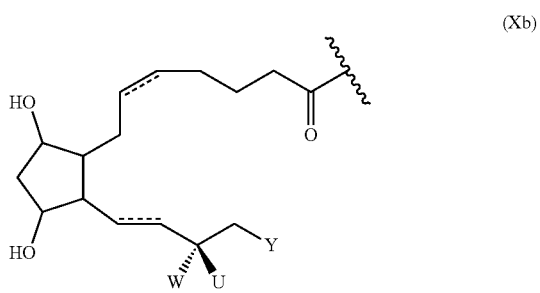

wherein:

- ⁓⁓⁓ represents the point of attachment of the prostaglandin analogue to linker group L;
- ----- represents a double or single bond;

Y is optionally substituted $C_4$ to $C_{10}$ hydrocarbyl or optionally substituted $C_4$ to $C_{10}$ hydrocarbyloxy;

W is hydroxy and U is hydrogen, or W and U are both fluoro, or W and U together form oxo;

wherein the drug D is conjugated to the polymer backbone via an ester linkage formed between the drug D and the linker L;

$R^1, R^{1'}, R^2, R^{2'}$, are independently selected from the group consisting of hydrogen, alkyl, alkoxy, alkoxy-alkyl, amino, alkyl amino, dialkylamino, amino-alkyl, alkylamino-alkyl, dialkylamino-alkyl and wherein one of the pairs of $R^1, R^{1'}$ and $R^2, R^{2'}$, may between the members of the pair form a carbocycle or heterocycle of 3 to 6 constituent ring members wherein the heterocycle may comprise from 1 to 3 constituent heteroatom ring members selected from oxygen and nitrogen which nitrogen may optionally be substituted by $C_1$ to $C_6$ alkyl; and q is 0 or 1; and wherein at least one of $R^1$, $R^{1'}$, $R^2$ and $R^{2'}$ is other than hydrogen.

* * * * *

UNITED STATES PATENT AND TRADEMARK OFFICE
CERTIFICATE OF CORRECTION

PATENT NO. : 11,787,906 B2
APPLICATION NO. : 16/493252
DATED : October 17, 2023
INVENTOR(S) : Birkett et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 833 days.

Signed and Sealed this
Twelfth Day of November, 2024

Katherine Kelly Vidal
*Director of the United States Patent and Trademark Office*